United States Patent
Orwat et al.

(10) Patent No.: US 11,306,081 B2
(45) Date of Patent: Apr. 19, 2022

(54) PHENYLACETAMIDES AS INHIBITORS OF ROCK

(71) Applicant: BRISTOL-MYERS SQUIBB COMPANY, Princeton, NJ (US)

(72) Inventors: Michael J. Orwat, New Hope, PA (US); Donald J. P. Pinto, Churchville, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 93 days.

(21) Appl. No.: 16/629,736

(22) PCT Filed: Jul. 11, 2018

(86) PCT No.: PCT/US2018/041559
§ 371 (c)(1),
(2) Date: Jan. 9, 2020

(87) PCT Pub. No.: WO2019/014300
PCT Pub. Date: Jan. 17, 2019

(65) Prior Publication Data
US 2021/0147407 A1 May 20, 2021

Related U.S. Application Data

(60) Provisional application No. 62/531,624, filed on Jul. 12, 2017.

(51) Int. Cl.
| | | |
|---|---|---|
| C07D 417/14 | (2006.01) | |
| C07D 401/12 | (2006.01) | |
| C07D 405/14 | (2006.01) | |
| C07D 413/12 | (2006.01) | |
| C07D 417/12 | (2006.01) | |
| C07D 471/04 | (2006.01) | |
| C07D 513/04 | (2006.01) | |
| C07F 9/6558 | (2006.01) | |
| C07F 9/6561 | (2006.01) | |

(52) U.S. Cl.
CPC ......... *C07D 417/14* (2013.01); *C07D 401/12* (2013.01); *C07D 405/14* (2013.01); *C07D 413/12* (2013.01); *C07D 417/12* (2013.01); *C07D 471/04* (2013.01); *C07D 513/04* (2013.01); *C07F 9/6561* (2013.01); *C07F 9/65583* (2013.01)

(58) Field of Classification Search
CPC .. C07D 417/14; C07D 513/04; C07D 401/12; C07D 405/14; C07D 413/12; C07D 471/12; C07D 471/04; C07F 9/6561; C07F 9/65583
USPC .......................................................... 514/81
See application file for complete search history.

(56) References Cited

FOREIGN PATENT DOCUMENTS

| | | |
|---|---|---|
| WO | WO2004041813 A1 | 5/2004 |
| WO | WO2010032875 A2 | 3/2010 |
| WO | WO2014113620 A2 | 7/2014 |
| WO | WO2014134388 A1 | 9/2014 |
| WO | WO2014134391 A1 | 9/2014 |
| WO | WO2015002915 A1 | 1/2015 |
| WO | WO2015002926 A1 | 1/2015 |
| WO | WO2016010950 A1 | 1/2016 |
| WO | WO2016028971 A1 | 2/2016 |
| WO | WO2016112236 A1 | 7/2016 |
| WO | WO2016144936 A1 | 9/2016 |
| WO | WO2017123860 A1 | 7/2017 |
| WO | WO2017205709 A1 | 11/2017 |
| WO | WO2018009622 A1 | 1/2018 |
| WO | WO2018009625 A1 | 1/2018 |
| WO | WO2018009627 A1 | 1/2018 |
| WO | WO2018102325 A1 | 6/2018 |
| WO | WO2019014303 A1 | 1/2019 |
| WO | WO2019014304 A1 | 1/2019 |
| WO | WO2019014308 A1 | 1/2019 |
| WO | WO2019089868 A1 | 5/2019 |

OTHER PUBLICATIONS

CAS Registry 1292639-60-1 Entered STN: May 10, 2011Benzeneacetic acid, 4-([3-(aminocarbonyl) -2-pyridinylJ oxy}.

*Primary Examiner* — Kahsay Habte
(74) *Attorney, Agent, or Firm* — Hong Liu

(57) ABSTRACT

The present invention provides compounds of Formula (I): Formula (I) or stereoisomers, tautomers, or pharmaceutically acceptable salts thereof, wherein all the variables are as defined herein. These compounds are selective ROCK inhibitors. This invention also relates to pharmaceutical compositions comprising these compounds and methods of treating cardiovascular, smooth muscle, oncologic, neuropathologic, autoimmune, fibrotic, and/or inflammatory disorders using the same.

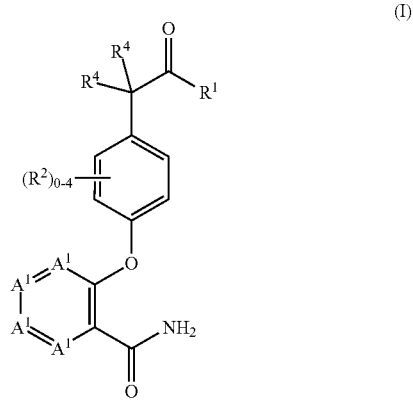

(I)

14 Claims, No Drawings
Specification includes a Sequence Listing.

SEQUENCE LISTING

<160> NUMBER OF SEQ ID NOS: 1

<210> SEQ ID NO 1
<211> LENGTH: 11
<212> TYPE: PRT
<213> ORGANISM: Artificial Sequence

```
<220> FEATURE:
<223> OTHER INFORMATION: Synthesized Peptide
<220> FEATURE:
<221> NAME/KEY: MISC_FEATURE
<223> OTHER INFORMATION: FITC-AHA at N Terminus attached at A1 - A11
<220> FEATURE:
<221> NAME/KEY: MISC_FEATURE
<223> OTHER INFORMATION: OH at C Terminus attached at A1 - A11

<400> SEQUENCE: 1

Ala Lys Arg Arg Arg Leu Ser Ser Leu Arg Ala
1               5                   10
```

PHENYLACETAMIDES AS INHIBITORS OF ROCK

CROSS REFERENCE TO RELATED APPLICATIONS

This application is a 371 application of PCT/US2018/041559, filed Jul. 11, 2018, which is entitled to priority pursuant to 35 U.S.C. § 119(e) to U.S. provisional patent application No. 62/531,624, filed Jul. 12, 2017, which is incorporated herein in its entirety.

FIELD OF THE INVENTION

The present invention relates generally to novel phenylacetamides and their analogues thereof, which are inhibitors of Rho kinases, compositions containing them, and methods of using them, for example, for the treatment or prophylaxis of disorders associated with aberrant Rho kinase activity.

BACKGROUND OF THE INVENTION

Rho-Kinase (ROCK) is a member of the serine-threonine protein kinase family. ROCK exists in two isoforms, ROCK1 and ROCK2 (Ishizaki, T. et al., *EMBO J.*, 15:1885-1893 (1996)). ROCK has been identified as an effector molecule of RhoA, a small GTP-binding protein (G protein) that plays a key role in multiple cellular signaling pathways. ROCK and RhoA are ubiquitously expressed across tissues. The RhoA/ROCK signaling pathway is involved in a number of cellular functions, such as ACTIN® organization, cell adhesion, cell migration, and cytokinesis (Riento, K. et al., *Nat. Rev. Mol. Cell Biol.*, 4:446-456 (2003)). It is also directly involved in regulating smooth muscle contraction (Somlyo, A. P., *Nature*, 389:908-911 (1997)). Upon activation of its receptor, RhoA is activated, and, in turn, it activates ROCK. Activated ROCK phosphorylates the myosin-binding subunit of myosin light chain phosphatase, which inhibits activity of the phosphatase and leads to contraction. Contraction of the smooth muscle in the vasculature increases blood pressure, leading to hypertension.

There is considerable evidence in the literature that the Rho A/ROCK signaling pathway plays an important role in signal transduction initiated by several vasoactive factors, for example angiotensin II (Yamakawa, T. et al., *Hypertension*, 35:313-318 (2000)), urotensin II (Sauzeau, V. et al., *Circ. Res.*, 88:1102-1104 (2001)), endothelin-1 (Tangkijvanich, P. et al., *Hepatology*, 33:74-80 (2001)), serotonin (Shimokawa, H., *Jpn. Circ. J.*, 64:1-12 (2000)), norepinephrine (Martinez, M. C. et al., *Am. J. Physiol.*, 279:H1228-H1238 (2000)) and platelet-derived growth factor (PDGF) (Kishi, H. et al., *J. Biochem.*, 128:719-722 (2000)). Many of these factors are implicated in the pathogenesis of cardiovascular disease.

Additional studies in the literature, some using the known ROCK inhibitors fasudil (Asano, T. et al., *J. Pharmacol. Exp. Ther.*, 241:1033-1040 (1987)) or Y-27632 (Uehata, M. et al., *Nature*, 389:990-994 (1997)) further illustrate the link between ROCK and cardiovascular disease. For example, ROCK expression and activity have been shown to be elevated in spontaneously hypertensive rats, suggesting a link to the development of hypertension in these animals (Mukai, Y. et al., *FASEB J.*, 15:1062-1064 (2001)). The ROCK inhibitor Y-27632 (Uehata, M. et al., Nature, ibid.) was shown to significantly decrease blood pressure in three rat models of hypertension, including the spontaneously hypertensive rat, renal hypertensive rat and deoxycortisone acetate salt hypertensive rat models, while having only a minor effect on blood pressure in control rats. This reinforces the link between ROCK and hypertension.

Other studies suggest a link between ROCK and atherosclerosis. For example, gene transfer of a dominant negative form of ROCK suppressed neointimal formation following balloon injury in porcine femoral arteries (Eto, Y. et al., *Am. J. Physiol. Heart Circ. Physiol.*, 278:H1744-H1750 (2000)). In a similar model, ROCK inhibitor Y-27632 also inhibited neointimal formation in rats (Sawada, N. et al., *Circulation*, 101:2030-2033 (2000)). In a porcine model of IL-1 beta-induced coronary stenosis, long term treatment with the ROCK inhibitor fasudil was shown to progressively reduce coronary stenosis, as well as promote a regression of coronary constrictive remodeling (Shimokawa, H. et al., *Cardiovascular Res.*, 51:169-177 (2001)).

Additional investigations suggest that a ROCK inhibitor would be useful in treating other cardiovascular diseases. For example, in a rat stroke model, fasudil was shown to reduce both the infarct size and neurologic deficit (Toshima, Y., Stroke, 31:2245-2250 (2000)). The ROCK inhibitor Y-27632 was shown to improve ventricular hypertrophy, fibrosis and function in a model of congestive heart failure in Dahl salt-sensitive rats (Kobayashi, N. et al., *Cardiovascular Res.*, 55:757-767 (2002)).

Other animal or clinical studies have implicated ROCK in additional diseases including coronary vasospasm (Shimokawa, H. et al., *Cardiovasc. Res.*, 43:1029-1039 (1999)), cerebral vasospasm (Sato, M. et al., *Circ. Res.*, 87:195-200 (2000)), ischemia/reperfusion injury (Yada, T. et al., *J. Am. Coll. Cardiol.*, 45:599-607 (2005)), pulmonary hypertension (Fukumoto, Y. et al., *Heart*, 91:391-392 (2005)), angina (Shimokawa, H. et al., *J. Cardiovasc. Pharmacol.*, 39:319-327 (2002)), renal disease (Satoh, S. et al., *Eur. J. Pharmacol.*, 455:169-174 (2002)) and erectile dysfunction (Gonzalez-Cadavid, N. F. et al., *Endocrine*, 23:167-176 (2004)).

In another study, it has been demonstrated that inhibition of the RhoA/ROCK signaling pathway allows formation of multiple competing lamellipodia that disrupt the productive migration of monocytes (Worthylake, R. A. et al., *J. Biol. Chem.*, 278:13578-13584 (2003)). It has also been reported that small molecule inhibitors of Rho Kinase are capable of inhibiting MCP-1 mediated chemotaxis in vitro (Iijima, H., *Bioorg. Med. Chem.*, 15:1022-1033 (2007)). Due to the dependence of immune cell migration upon the RhoA/ROCK signaling pathway one would anticipate inhibition of Rho Kinase should also provide benefit for diseases such as rheumatoid arthritis, psoriasis, and inflammatory bowel disease.

The above studies provide evidence for a link between ROCK and cardiovascular diseases including hypertension, atherosclerosis, restenosis, stroke, heart failure, coronary vasospasm, cerebral vasospasm, ischemia/reperfusion injury, pulmonary hypertension and angina, as well as renal disease and erectile dysfunction. Given the demonstrated effect of ROCK on smooth muscle, ROCK inhibitors may also be useful in other diseases involving smooth muscle hyper-reactivity, including asthma and glaucoma (Shimokawa, H. et al., *Arterioscler. Thromb. Vasc. Biol.*, 25:1767-1775 (2005)). Furthermore, Rho-kinase has been indicated as a drug target for the treatment of various other diseases, including airway inflammation and hyperresponsiveness (Henry, P. J. et al., *Pulm. Pharmacol Ther.*, 18:67-74 (2005)), cancer (Rattan, R. et al., *J. Neurosci. Res.*, 83:243-255 (2006); Lepley, D. et al., *Cancer Res.*, 65:3788-3795 (2005)), fibrotic diseases (Jiang, C. et al., *Int. J. Mol.*

Sci., 13:8293-8307 (2012); Zhou, L. et al., *Am. J. Nephrol.,* 34:468-475 (2011)), as well as neurological disorders, such as spinal-cord injury, Alzheimer's disease, multiple sclerosis, stroke and neuropathic pain (Mueller, B. K. et al., *Nat. Rev. Drug Disc.,* 4:387-398 (2005); Sun, X. et al., *J. Neuroimmunol.,* 180:126-134 (2006)).

There remains an unmet medical need for new drugs to treat cardiovascular disease. In the 2012 update of Heart Disease and Stroke Statistics from the American Heart Association (*Circulation,* 125:e2-e220 (2012)), it was reported that cardiovascular disease accounted for 32.8% of all deaths in the U.S., with coronary heart disease accounting for ~1 in 6 deaths overall in the U.S.. Contributing to these numbers, it was found that ~33.5% of the adult U.S. population was hypertensive, and it was estimated that in 2010~6.6 million U.S. adults would have heart failure. Therefore, despite the number of medications available to treat cardiovascular diseases (CVD), including diuretics, beta blockers, angiotensin converting enzyme inhibitors, angiotensin blockers and calcium channel blockers, CVD remains poorly controlled or resistant to current medication for many patients.

There are many reports of ROCK inhibitors under investigation (see, for example, US 2012/0122842 A1, US 2010/0041645 A1, US 2008/0161297 A1, and Hu, E. et al., *Exp. Opin. Ther. Targets,* 9:715-736 (2005)). Reports also include WO2014/113620, WO 2014/134388, WO 2014/134391, WO2015/002915, WO2015/002926, WO2016/010950, WO2016/028971, WO2016/112236, and WO2016/144936, all of which are assigned to the present applicant. However, fasudil is the only marketed ROCK inhibitor at this time. An i.v. formulation was approved in Japan for treatment of cerebral vasospasm. Thus, there remains a need for new therapeutics, including ROCK inhibitors, for the treatment of cardiovascular diseases, cancer, neurological diseases, renal diseases, fibrotic diseases, bronchial asthma, erectile dysfunction, and glaucoma.

SUMMARY OF THE INVENTION

The present invention provides novel phenylacetamides, their analogues, including stereoisomers, tautomers, pharmaceutically acceptable salts, or solvates thereof, which are useful as selective inhibitors of Rho kinases.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of conditions associated with aberrant ROCK activity.

The compounds of the present invention may be used in therapy.

The compounds of the present invention may be used for the manufacture of a medicament for the treatment and/or prophylaxis of a condition associated with aberrant ROCK activity.

In another aspect, the present invention is directed to a method of treating a cardiovascular or related disease which method comprises administering to a patient in need of such treatment a compound of the present invention as described above. Examples of such diseases that may be treated include, for example, hypertension, atherosclerosis, restenosis, stroke, heart failure, renal failure, coronary artery disease, peripheral artery disease, coronary vasospasm, cerebral vasospasm, ischemia/reperfusion injury, pulmonary hypertension, angina, erectile dysfunction and renal disease.

In another aspect, the present invention is directed to a method of treating diseases involving smooth muscle hyper reactivity including asthma, erectile dysfunction and glaucoma, which method comprises administering to a patient in need of such treatment a compound of the present invention as described above.

In another aspect, the present invention is directed to a method of treating diseases mediated at least partially by Rho kinase including fibrotic diseases, oncology, spinal-cord injury, Alzheimer's disease, multiple sclerosis, stroke, neuropathic pain, rheumatoid arthritis, psoriasis and inflammatory bowel disease, which method comprises administering to a patient in need of such treatment a compound of the present invention as described above.

In yet additional aspects, the present invention is directed at pharmaceutical compositions comprising the above-mentioned compounds, processes for preparing the above-mentioned compounds and intermediates used in these processes.

The compounds of the invention can be used alone, in combination with other compounds of the present invention, or in combination with one or more, preferably one to two other agent(s).

These and other features of the invention will be set forth in expanded form as the disclosure continues.

DETAILED DESCRIPTION OF THE INVENTION

I. Compounds of the Invention

In one aspect, the present invention provides, inter alia, compounds of Formula (I):

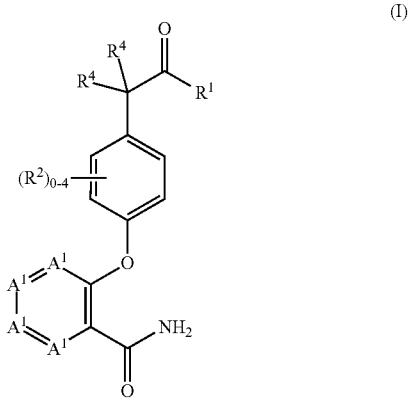

or stereoisomers, tautomers, pharmaceutically acceptable salts, solvates, or prodrugs thereof, wherein $A^1$, at each occurrence, is independently selected from $CR^3$ and N; provided that $A^1$ is not all $CR^3$ and that no more than two A variables are N;

$R^1$ is selected from —OH and $NR^5R^5$;

$R^2$, at each occurrence, is independently selected from halogen, $C_{1-6}$ alkyl, $C_{1-4}$ alkoxy, $C_{1-4}$ alkylthio, $C_{1-4}$ haloalkyl, —OH, —CH$_2$OH, —OCH$_2$F, —OCHF$_2$, —OCF$_3$, CN, —NH$_2$, —NH($C_{1-4}$ alkyl), —N($C_{1-4}$ alkyl)$_2$, —C$_2$H, —CH$_2$CO$_2$H, —C$_2$($C_{1-4}$ alkyl), —CO($C_{1-4}$ alkyl), —CH$_2$NH$_2$, —CONH$_2$, —CONH(C$_{1-4}$ alkyl), —CON(C$_{1-4}$ alkyl)$_2$, —OCH$_2$CO$_2$H, —NHCO(C$_{1-4}$ alkyl), —NHCO$_2$(C$_{1-4}$ alkyl), —NHSO$_2$(C$_{1-4}$ alkyl), —SO$_2$NH$_2$, —C(=NH)NH$_2$, carbocycle, and heterocycle, wherein said alkyl, alkoxy, alkylthio, haloalkyl, carbocycle, and heterocycle are substituted with 0-4 R$^9$;

R$^3$, at each occurrence, is independently selected from H, halogen, C$_{1-6}$ alkyl, C$_{1-4}$ alkoxy, C$_{1-4}$ alkylthio, C$_{1-4}$ haloalkyl, —CH$_2$OH, —OCH$_2$F, —OCHF$_2$, —OCF$_3$, CN, —NH$_2$, —NH(C$_{1-4}$ alkyl), —N(C$_{1-4}$ alkyl)$_2$, —CO$_2$H, —CH$_2$CO$_2$H, —C$_2$(C$_{1-4}$ alkyl), —CO(C$_{1-4}$ alkyl), —CH$_2$NH$_2$, —CONH$_2$, —CONH(C$_{1-4}$ alkyl), —CON(C$_{1-4}$ alkyl)$_2$, —OCH$_2$CO$_2$H, —NHCO(C$_{1-4}$ alkyl), —NHCO$_2$(C$_{1-4}$ alkyl), —NHSO$_2$(C$_{1-4}$ alkyl), —SO$_2$NH$_2$, —C(=NH)NH$_2$, carbocycle, and heterocycle, wherein said alkyl, alkoxy, alkylthio, haloalkyl, carbocycle, and heterocycle are substituted with 0-4 R$^9$;

R$^4$, at each occurrence, is independently selected from H, F and C$_{1-4}$ alkyl;

R$^5$, at each occurrence, is independently selected from H, —(CR$^6$R$^6$)$_n$—C$_{3-10}$ carbocycle, and —(CR$^6$R$^6$)$_n$— 4-15 membered heterocycle comprising carbon atoms and 1-4 heteroatoms selected from N, NR$^8$, O, and S(O)$_p$, wherein said alkyl, carbocycle and heterocycle are substituted with 1-4 R$^7$;

alternatively, R$^5$ and R$^5$ are taken together with the nitrogen atom to which they are attached to form 4- to 15-membered heterocycle substituted with 1-4 R$^7$;

R$^6$, at each occurrence, is independently selected from H and C$_{1-4}$ alkyl;

R$^7$, at each occurrence, is independently selected from H, =O, NO$_2$, halogen, C$_{1-4}$ alkyl, C$_{1-4}$ alkoxy, CN, OH, CF$_3$, —(CH$_2$)$_n$—CO$_2$H, —(CH$_2$)$_n$—CO$_2$(C$_{1-4}$ alkyl), —(CH$_2$)$_n$—NR$^8$R$^8$, —NHCO(C$_{1-4}$ alkyl), —NHCOCF$_3$, —NHCO$_2$(C$_{1-4}$ alkyl), —NHCO$_2$(CH$_2$)$_2$O(C$_{1-4}$ alkyl), —NHCO$_2$(CH$_2$)$_3$O(C$_{1-4}$ alkyl), —NHCO$_2$(CH$_2$)$_2$OH, —NHCO$_2$(CH$_2$)$_2$NH$_2$, —NHCO$_2$(CH$_2$)$_2$N(C$_{1-4}$ alkyl)$_2$, —NHCO$_2$CH$_2$CO$_2$H, —CH$_2$NHCO$_2$(C$_{1-4}$ alkyl), —NHC(O)NR$^8$R$^8$, —NHSO$_2$(C$_{1-4}$ alkyl), —SO$_2$NH$_2$, —SO$_2$NH(C$_{1-4}$ alkyl), —SO$_2$N(C$_{1-4}$ alkyl)$_2$, —SO$_2$NH(CH$_2$)$_2$OH, —SO$_2$NH(CH$_2$)$_2$O(C$_{1-4}$ alkyl), —(CH$_2$)$_n$—CONR$^8$R$^8$, —O(CH$_2$)$_n$-carbocycle, —O(CH$_2$)$_n$-heterocycle, —NHCO-carbocycle, —NHCO-heterocycle, —(CH$_2$)$_n$-carbocycle, and —(CH$_2$)$_n$-heterocycle comprising carbon atoms and 1-4 heteroatoms selected from N, NR$^8$, O, and S(O)$_p$, wherein said alkyl, alkenyl, alkynyl, alkoxyl, carbocycle, and heterocycle are substituted with 0-4 R$^9$;

R$^8$, at each occurrence, is independently selected from H, C$_{1-4}$ alkyl, C$_{2-4}$ alkenyl, C$_{2-4}$ alkynyl, —(CH$_2$)$_n$—C(O)C$_{1-4}$ alkyl, —(CH$_2$)$_n$—C(O)carbocycle, —(CH$_2$)$_n$—C(O)heterocycle, —(CH$_2$)$_n$—C(O)NR$^a$R$^a$, —(CH$_2$)$_n$—C(O)O-alkyl, —(CH$_2$)$_n$—C(O)O-carbocycle, —(CH$_2$)$_n$—C(O)O-heterocycle, —(CH$_2$)$_n$—SO$_2$alkyl, —(CH$_2$)$_n$ SO$_2$carbocycle, —(CH$_2$)$_n$—SO$_2$heterocycle, —(CH$_2$)$_n$—SO$_2$NR$^a$R$^a$, —(CH$_2$)$_n$-carbocycle, and —(CH$_2$)$_n$-heterocycle, wherein said alkyl, carbocycle, and heterocycle are substituted with 0-4 R$^9$;

alternatively, R$^1$ and R$^8$ are taken together with the nitrogen atom to which they are attached to form 4- to 10-membered heterocycle substituted with 0-4 R$^9$;

R$^9$, at each occurrence, is independently selected from halogen, OH, NO$_2$, CHF$_2$, CF$_3$, C$_{1-4}$ alkyl, C$_{1-4}$ alkoxy, CH$_2$OH, CO(C$_{1-4}$ alkyl), CO$_2$H, CO$_2$(C$_{1-4}$ alkyl), —(CH$_2$)$_n$NR$^a$R$^a$, —(CH$_2$)$_n$CONR$^a$R$^a$, —O(CH$_2$)$_n$carbocycle, —O(CH$_2$)$_n$heterocycle, —O(CH$_2$)$_n$NR$^a$R$^a$, —(CR$^{10}$R$^{10}$)$_n$— 4-10 membered heterocycle, wherein said alkyl, alkoxyl, carbocycle, and heterocycle are substituted with 0-4 R$^b$;

R$^{10}$ is selected from H and C$_{1-4}$ alkyl;

R$^a$, at each occurrence, is independently selected from H, C$_{1-4}$ alkyl, —(CH$_2$)$_n$OH, CO(C$_{1-4}$ alkyl), COCF$_3$, CO$_2$(C$_{1-4}$ alkyl), —CONH$_2$, —CONH—C$_{1-4}$ alkylene-CO$_2$(C$_{1-4}$ alkyl), C$_{1-4}$ alkylene-CO$_2$(C$_{1-4}$ alkyl), R$^c$, CO$_2$R$^c$, and CONHR$^c$; alternatively, R$^a$ and R$^a$ are taken together with the nitrogen atom to which they are attached to form 4- to 10-membered heterocycle, wherein said alkyl, alkylene, and heterocycle are substituted with 0-4 R$^b$;

R$^b$, at each occurrence, is independently selected from =O, OH, halogen, C$_{1-4}$ alkyl, C$_{1-4}$ alkoxy, OCF$_3$, NH$_2$, NO$_2$, N(C$_{1-4}$ alkyl)$_2$, CO(C$_{1-4}$ alkyl), CO(C$_{1-4}$ haloalkyl), CO$_2$(C$_{1-4}$ alkyl), CONH$_2$, —CONH(C$_{1-4}$ alkyl), —CON(C$_{1-4}$ alkyl)$_2$, —CONH—C$_{1-4}$ alkylene-O(C$_{1-4}$ alkyl), —CONH—C$_{1-4}$ alkylene-N(C$_{1-4}$ alkyl)$_2$, —CONH—C$_{1-4}$ alkylene-N (C$_{1-4}$ alkyl)$_2$, —C$_{1-4}$ alkylene-O—P(O)(OH)$_2$, —NHCO$_2$(C$_{1-4}$ alkyl), —R$^c$, COR$^c$, CO$_2$R$^c$, and CONHR$^c$;

R$^c$, at each occurrence, is independently selected from —(CH$_2$)$_n$—C$_{3-6}$ cycloalkyl, —(CH$_2$)$_n$-phenyl, and —(CH$_2$)$_n$-5- to 6-membered heterocycle containing carbon atoms and 1-4 heteroatoms selected from the group consisting of: N, NH, N(C$_{1-4}$ alkyl), 0, and S(O)$_p$; wherein each ring moiety is substituted with 0-2 R$^d$;

R$^d$, at each occurrence, is independently selected from =O, halogen, —OH, C$_{1-4}$ alkyl, NH$_2$, NH(C$_{1-4}$ alkyl), N(C$_{1-4}$ alkyl)$_2$, C$_{1-4}$ alkoxy, and —NHCO(C$_{1-4}$ alkyl), and heterocycle containing carbon atoms and 1-4 heteroatoms selected from the group consisting of: N, NH, N(C$_{1-4}$ alkyl), O, and S(O)$_p$;

n, at each occurrence, is independently selected from 0, 1, 2, 3, and 4; and p, at each occurrence, is independently selected from 0, 1, and 2.

In another aspect, the present invention provides compounds of Formula (II):

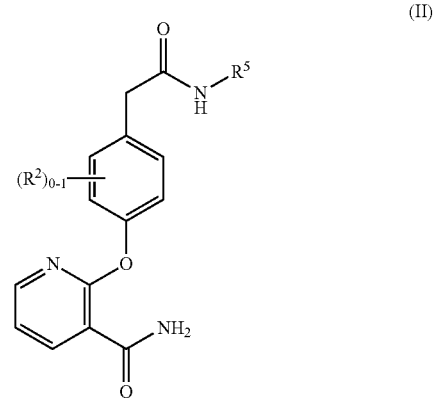

or stereoisomers, tautomers, pharmaceutically acceptable salts, solvates, or prodrugs thereof, wherein R$^2$ is independently selected from halogen and C$_{1-6}$ alkyl;

R$^5$ is a 4-15 membered heterocycle comprising carbon atoms and 1-4 heteroatoms selected from N, NR$^8$, O, and S(O)$_p$, wherein said heterocycle is substituted with 1-4 R$^7$;

R$^7$, at each occurrence, is independently selected from H, =O, NO$_2$, halogen, C$_{1-4}$ alkyl, C$_{1-4}$ alkoxy, CN, OH, CF$_3$, —(CH$_2$)$_n$—CO$_2$H, —(CH$_2$)$_n$—CO$_2$(C$_{1-4}$ alkyl), —(CH$_2$)$_n$—NR$^8$R$^8$, —NHCO(C$_{1-4}$ alkyl), —NHCOCF$_3$, —NHCO$_2$(C$_{1-4}$ alkyl), —NHCO$_2$(CH$_2$)$_2$O(C$_{1-4}$ alkyl), —NHCO$_2$(CH$_2$)$_3$O(C$_{1-4}$ alkyl), —NHCO$_2$(CH$_2$)$_2$OH, —NHCO$_2$(CH$_2$)$_2$NH$_2$, —NHCO$_2$(CH$_2$)$_2$N(C$_{1-4}$ alkyl)$_2$, —NHCO$_2$CH$_2$CO$_2$H, —CH$_2$NHCO$_2$(C$_{1-4}$ alkyl), —NHC(O)NR$^8$R$^8$, —NHSO$_2$(C$_{1-4}$ alkyl), —SO$_2$NH$_2$, —SO$_2$NH(C$_{1-4}$ alkyl), —SO$_2$N(C$_{1-4}$ alkyl)$_2$, —SO$_2$NH(CH$_2$)$_2$OH, —SO$_2$NH(CH$_2$)$_2$O(C$_{1-4}$ alkyl), —(CH$_2$)$_n$—CONR$^8$R$^8$, —O(CH$_2$)$_n$-carbocycle, —O(CH$_2$)$_n$-heterocycle, —NHCO-carbocycle, —NHCO-heterocycle, —(CH$_2$)$_n$-carbocycle, and —(CH$_2$)$_n$-heterocycle comprising carbon atoms and 1-4 heteroatoms selected from N, NR$^8$, O, and S(O)$_p$, wherein said alkyl, alkenyl, alkynyl, alkoxy, carbocycle, and heterocycle are substituted with 0-4 R$^9$;

R$^8$, at each occurrence, is independently selected from H, C$_{1-4}$ alkyl, C(O)C$_{1-4}$alkyl, —(CH$_2$)$_n$ C(O)NR$^a$R$^a$, C(O)O-alkyl, SO$_2$alkyl, SO$_2$NR$^a$R$^a$, —(CH$_2$)$_n$-carbocycle, and —(CH$_2$)$_n$-heterocycle, wherein said alkyl, carbocycle, and heterocycle are substituted with 0-4 R$^9$;

R$^9$, at each occurrence, is independently selected from halogen, OH, NO$_2$, CHF$_2$, CF$_3$, C$_{1-4}$ alkyl, C$_{1-4}$ alkoxy, CH$_2$OH, CO$_2$H, CO$_2$(C$_{1-4}$ alkyl), CONH$_2$, —(CH$_2$)$_n$NR$^a$R$^a$, —(CH$_2$)$_n$CONR$^a$R$^a$, —O(CH$_2$)$_n$heterocycle, —O(CH$_2$)$_{(2-4)}$NR$^a$R$^a$, —(CH$_2$)$_n$— 4-10 membered heterocycle, wherein said alkyl, alkoxyl, carbocycle, and heterocycle are substituted with 0-4 R$^b$;

R$^a$, at each occurrence, is independently selected from H, C$_{1-4}$ alkyl, —(CH$_2$)$_n$OH, CO(C$_{1-4}$ alkyl), COCF$_3$, CO$_2$(C$_{1-4}$ alkyl), —CONH$_2$, —CONH—C$_{1-4}$ alkylene-CO$_2$(C$_{1-4}$ alkyl), C$_{1-4}$ alkylene-CO$_2$(C$_{1-4}$ alkyl), R$^c$, CO$_2$R$^c$, and CONHR$^c$; alternatively, R$^a$ and R$^a$ are taken together with the nitrogen atom to which they are attached to form 4- to 10-membered heterocycle, wherein said alkyl, alkylene, and heterocycle are substituted with 0-4 R$^b$;

R$^b$, at each occurrence, is independently selected from =O, halogen, C$_{1-4}$ alkyl, C$_{1-4}$ alkoxy, OCF$_3$, NH$_2$, NO$_2$, N(C$_{1-4}$ alkyl)$_2$, CO(C$_{1-4}$ alkyl), CO(C$_{1-4}$ haloalkyl), CO$_2$(C$_{1-4}$ alkyl), CONH$_2$, —CONH(C$_{1-4}$ alkyl), —CON(C$_{1-4}$ alkyl)$_2$, —CONH—C$_{1-4}$ alkylene-O(C$_{1-4}$ alkyl), —CONH—C$_{1-4}$ alkylene-N(C$_{1-4}$ alkyl)$_2$, —CONH—C$_{1-4}$ alkylene-N (C$_{1-4}$ alkyl)$_2$, —C$_{1-4}$ alkylene-O—P(O)(OH)$_2$, —NHCO$_2$(C$_{1-4}$ alkyl), —R$^c$, COR$^c$, CO$_2$R$^c$, and CONHR$^c$;

R$^c$, at each occurrence, is independently selected from —(CH$_2$)$_n$—C$_{3-6}$ cycloalkyl, —(CH$_2$)$_n$-phenyl, and —(CH$_2$)$_n$-5- to 6-membered heterocycle containing carbon atoms and 1-4 heteroatoms selected from the group consisting of N, NH, N(C$_{1-4}$ alkyl), O, and S(O)$_p$; wherein each ring moiety is substituted with 0-2 R$^d$;

R$^d$, at each occurrence, is independently selected from =O, halogen, —OH, C$_{1-4}$ alkyl, NH$_2$, NH(C$_{1-4}$ alkyl), N(C$_{1-4}$ alkyl)$_2$, C$_{1-4}$ alkoxy, and —NHCO(C$_{1-4}$ alkyl), and heterocycle containing carbon atoms and 1-4 heteroatoms selected from the group consisting of N, NH, N(C$_{1-4}$ alkyl), O, and S(O)$_p$;

n, at each occurrence, is independently selected from 0, 1, 2, 3, and 4;

p, at each occurrence, is independently selected from 0, 1, and 2.

In another aspect, the present invention provides compounds of Formula (II) or stereoisomers, tautomers, pharmaceutically acceptable salts, solvates, or prodrugs thereof, wherein R$^2$ is independently selected from F, Cl, and Br;

R$^5$ is selected from

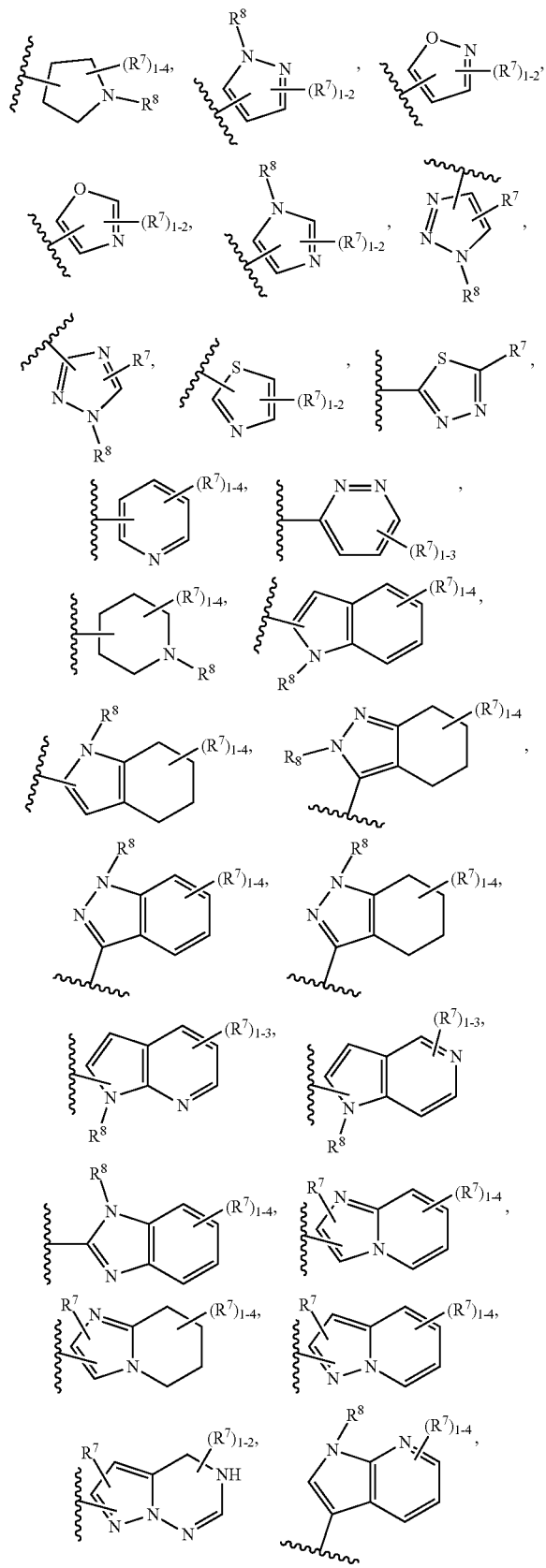

-continued

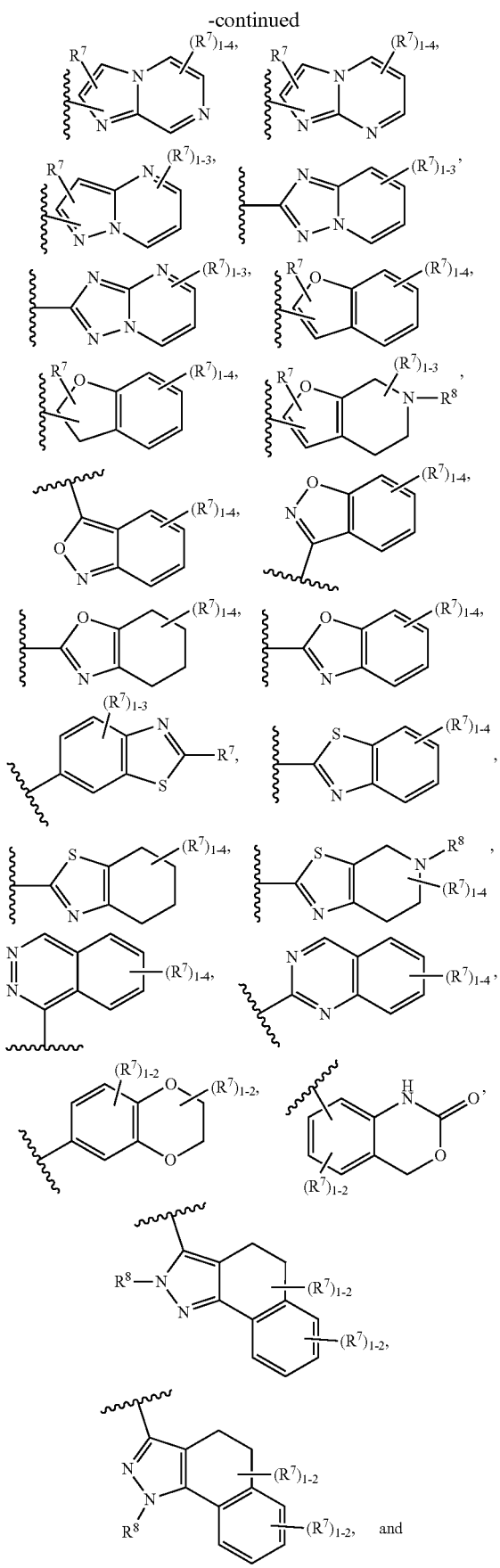

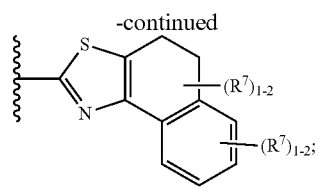

-continued

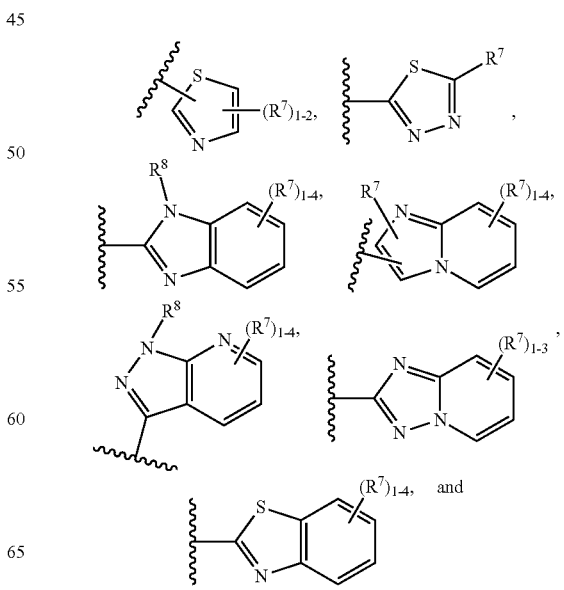

$R^7$, at each occurrence, is independently selected from H, =O, halogen, $C_{1-4}$ alkyl, $C_{1-4}$ alkoxy, CN, OH, $CF_3$, —$(CH_2)_n$—$CO_2H$, —$(CH_2)_n$—$CO_2(C_{1-4}$ alkyl), —$(CH_2)_n$—$NR^8R^8$, —NHCO($C_{1-4}$ alkyl), —NHCOCF$_3$, —NHCO$_2(C_{1-4}$ alkyl), —NHCO$_2(CH_2)_2O(C_{1-4}$ alkyl), —NHCO$_2(CH_2)_3O(C_{1-4}$ alkyl), —NHCO$_2(CH_2)_2OH$, —NHCO$_2(CH_2)_2NH_2$, —NHCO$_2(CH_2)_2N(C_{1-4}$ alkyl)$_2$, —NHCO$_2CH_2CO_2H$, —CH$_2$NHCO$_2(C_{1-4}$ alkyl), —NHC(O)NR$^8$R$^8$, —NHSO$_2(C_{1-4}$ alkyl), —SO$_2$NH$_2$, —SO$_2$NH($C_{1-4}$ alkyl), —SO$_2$N($C_{1-4}$ alkyl)$_2$, —SO$_2$NH(CH$_2$)$_2$OH, —SO$_2$NH(CH$_2$)$_2$O($C_{1-4}$ alkyl), —(CH$_2$)$_n$—CONR$^8$R$^8$, —O(CH$_2$)$_n$-carbocycle, —O(CH$_2$)$_n$-heterocycle, —NHCO-carbocycle, —NHCO-heterocycle, —(CH$_2$)$_n$-carbocycle, and —(CH$_2$)$_n$-heterocycle comprising carbon atoms and 1-4 heteroatoms selected from N, NR$^8$, O, and S(O)$_p$, wherein said alkyl, alkenyl, alkynyl, alkoxy, carbocycle, and heterocycle are substituted with 0-4 R$^9$;

$R^8$, at each occurrence, is independently selected from H, $C_{1-4}$ alkyl, —(CH$_2$)$_n$-carbocycle, and —(CH$_2$)$_n$-heterocycle, wherein said alkyl, carbocycle, and heterocycle are substituted with 0-4 R$^9$;

$R^9$, at each occurrence, is independently selected from halogen, OH, NO$_2$, CHF$_2$, CF$_3$, $C_{1-4}$ alkyl, $C_{1-4}$ alkoxy, CH$_2$OH, CO$_2$H, CO$_2$(C$_{1-4}$ alkyl), CONH$_2$, —(CH$_2$)$_n$NH$_2$, —(CH$_2$)$_n$CONH$_2$, —O(CH$_2$)$_n$heterocycle, —O(CH$_2$)$_{(2-4)}$NH$_2$, —(CH$_2$)$_n$— 4-10 membered heterocycle; and other variables are as defined in Formula (II) above.

In another aspect, the present invention provides compounds of Formula (II) or stereoisomers, tautomers, pharmaceutically acceptable salts, solvates, or prodrugs thereof, wherein $R^2$ is independently selected from F and Cl;

$R^5$ is selected from

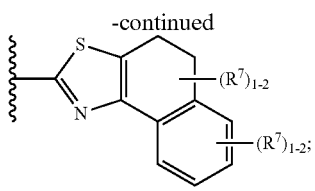

R⁷, at each occurrence, is independently selected from H, halogen, $C_{1-4}$ alkyl, $C_{1-4}$ alkoxy, a carbocycle, and a heterocycle comprising carbon atoms and 1-4 heteroatoms selected from N, NR⁸, O, and $S(O)_p$, wherein said alkyl, alkenyl, alkynyl, alkoxy, carbocycle, and heterocycle are substituted with 0-4 R⁹;

R⁸, at each occurrence, is independently selected from H, $C_{1-4}$ alkyl, and $-(CH_2)_n-C_{3-6}$cycloalkyl;

R⁹, at each occurrence, is independently selected from halogen, OH, $CHF_2$, $CF_3$, $C_{1-4}$ alkyl, $C_{1-4}$ alkoxy, $CH_2OH$, $CO_2H$, $CO_2(C_{1-4}$ alkyl), and $CONH_2$; and other variables are as defined in Formula (II) above.

In another aspect, the present invention provides compounds of Formula (II) or stereoisomers, tautomers, pharmaceutically acceptable salts, solvates, or prodrugs thereof, wherein R⁷, at each occurrence, is independently selected from H, F, Cl, Br, Me, Et, OMe, OEt, $OCH_2C(CH_2)_{20}H$,

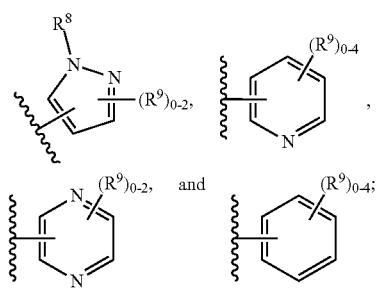

R⁹, at each occurrence, is independently selected from F, Cl, Br, OH, $CHF_2$, $CF_3$, $C_{1-4}$ alkyl, and $C_{1-4}$ alkoxy; and other variables are as defined in Formula (II) above.

In another aspect, the present invention provides compounds of Formula (I), or stereoisomers, tautomers, pharmaceutically acceptable salts, solvates, or prodrugs thereof, wherein R⁵ and R⁵ are taken together with the nitrogen atom to which they are attached to form

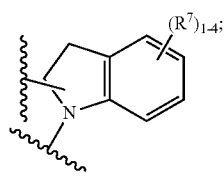

and

R⁷ is selected from H, CN, $C_{1-4}$ alkyl substituted with 0-4 R⁹, $C_{1-4}$ alkoxy substituted with 0-4 R⁹; and R⁹ is selected from halogen, OH, $C_{3-6}$ cycloalkyl, phenyl, and heterocycle.

In another aspect, the present invention provides compounds of Formula (III):

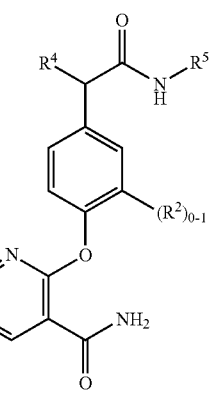

or stereoisomers, tautomers, pharmaceutically acceptable salts, solvates, or prodrugs thereof, wherein
R² is selected from F, Cl, Br, and $OC_{1-4}$ alkyl;
R⁴ is selected from H and $C_{1-4}$ alkyl;
R⁵ is selected from

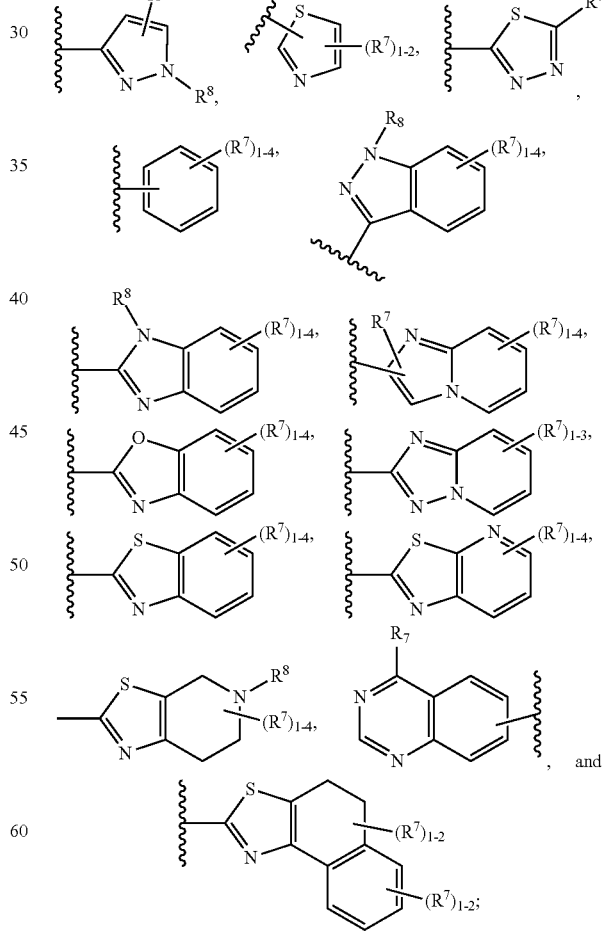

R⁷, at each occurrence, is independently selected from H, =O, $NO_2$, halogen, $C_{1-4}$ alkyl, $C_{1-4}$ alkoxy, CN, OH, $CF_3$, —(CH₂)ₙ—CO(C₁₋₄ alkyl), —(CH₂)ₙ—CO₂H, —(CH₂)ₙ—CO₂(C₁₋₄ alkyl), —(CH₂)ₙ—NR⁸R⁸, —NHCO(C₁₋₄ alkyl), —NHCOCF₃, —NHCO₂(C₁₋₄ alkyl), —NHCO₂(CH₂)₂O(C₁₋₄ alkyl), —NHCO₂(CH₂)₃O(C₁₋₄ alkyl), —NHCO₂(CH₂)₂OH, —NHCO₂(CH₂)₂NH₂, —NHCO₂(CH₂)₂N(C₁₋₄ alkyl)₂, —NHCO₂CH₂CO₂H, —CH₂NHCO₂(C₁₋₄ alkyl), —NHC(O)NR⁸R⁸, —NHSO₂(C₁₋₄ alkyl), —P(=O)(C₁₋₃ alkyl)₂, —SO₂C₁₋₄ alkyl, —SO₂NH₂, —SO₂NH(C₁₋₄ alkyl), —SO₂N(C₁₋₄ alkyl)₂, —SO₂NH(CH₂)₂OH, —SO₂NH(CH₂)₂O(C₁₋₄ alkyl), —(CH₂)ₙ—CONR⁸R⁸, —O(CH₂)ₙ-carbocycle, —O(CH₂)ₙ-heterocycle, —NHCO-carbocycle, —NHCO-heterocycle, —CO-carbocycle, —CO-heterocycle, —(CH₂)ₙ-carbocycle, and —(CH₂)ₙ-heterocycle comprising carbon atoms and 1-4 heteroatoms selected from N, NR⁸, O, and S(O)ₚ, wherein said alkyl, alkenyl, alkynyl, alkoxyl, carbocycle, and heterocycle are substituted with 0-4 R⁹;

R⁸, at each occurrence, is independently selected from H, C₁₋₄ alkyl, C₂₋₄ alkenyl, C₂₋₄ alkynyl, —(CH₂)ₙ—C(O)C₁₋₄ alkyl, —(CH₂)ₙ—C(O)carbocycle, —(CH₂)ₙ—C(O)heterocycle, —(CH₂)ₙ—C(O)NRᵃRᵃ, —(CH₂)ₙ—C(O)O-alkyl, —(CH₂)ₙ—C(O)O-carbocycle, —(CH₂)ₙ—C(O)O-heterocycle, —(CH₂)ₙ—SO₂alkyl, —(CH₂)ₙ SO₂carbocycle, —(CH₂)ₙ—SO₂heterocycle, —(CH₂)ₙ—SO₂NRᵃRᵃ, —(CH₂)ₙ-carbocycle, and —(CH₂)ₙ-heterocycle, wherein said alkyl, carbocycle, and heterocycle are substituted with 0-4 R⁹;

alternatively, R¹ and R⁸ are taken together with the nitrogen atom to which they are attached to form 4- to 10-membered heterocycle substituted with 0-4 R⁹;

R⁹, at each occurrence, is independently selected from halogen, OH, NO₂, CHF₂, CN, CF₃, C₁₋₄ alkyl, C₁₋₄ alkoxy, CH₂OH, CO(C₁₋₄ alkyl), CO₂H, CO₂(C₁₋₄ alkyl), —(CH₂)ₙNRᵃRᵃ, —(CH₂)ₙCONRᵃRᵃ, —O(CH₂)ₙcarbocycle, —O(CH₂)ₙheterocycle, —O(CH₂)ₙNRᵃRᵃ, NRᵃCO₂(C₁₋₄ alkyl), S(O)ₚC₁₋₄ alkyl, —(CR¹⁰R¹⁰)ₙ-carbocycle, —(CR¹⁰R¹⁰)ₙ— 4-10 membered heterocycle, wherein said alkyl, alkoxyl, carbocycle, and heterocycle are substituted with 0-4 Rᵇ;

R¹⁰ is selected from H and C₁₋₄ alkyl;

Rᵃ, at each occurrence, is independently selected from H, C₁₋₄ alkyl, —(CH₂)ₙOH, CO(C₁₋₄ alkyl), COCF₃, CO₂(C₁₋₄ alkyl), —CONH₂, —CONH—C₁₋₄ alkylene-CO₂(C₁₋₄ alkyl), C₁₋₄ alkylene-CO₂(C₁₋₄ alkyl), Rᶜ, CO₂Rᶜ, and CONHRᶜ; alternatively, Rᵃ and Rᵃ are taken together with the nitrogen atom to which they are attached to form 4- to 10-membered heterocycle, wherein said alkyl, alkylene, and heterocycle are substituted with 0-4 Rᵇ;

Rᵇ, at each occurrence, is independently selected from =O, OH, halogen, C₁₋₄ alkyl, C₁₋₄ alkoxy, OCF₃, NH₂, NO₂, N(C₁₋₄ alkyl)₂, CO(C₁₋₄ alkyl), CO(C₁₋₄ haloalkyl), CO₂(C₁₋₄ alkyl), CONH₂, —CONH(C₁₋₄ alkyl), —CON(C₁₋₄ alkyl)₂, —CONH—C₁₋₄ alkylene-O(C₁₋₄ alkyl), —CONH—C₁₋₄ alkylene-N(C₁₋₄ alkyl)₂, —CONH—C₁₋₄ alkylene-N (C₁₋₄ alkyl)₂, —C₁₋₄ alkylene-O—P(O)(OH)₂, —NHCO₂(C₁₋₄ alkyl), —Rᶜ, CORᶜ, CO₂Rᶜ, and CONHRᶜ;

Rᶜ, at each occurrence, is independently selected from —(CH₂)ₙ—C₃₋₆ cycloalkyl, —(CH₂)ₙ-phenyl, and —(CH₂)ₙ-5- to 6-membered heterocycle containing carbon atoms and 1-4 heteroatoms selected from the group consisting of N, NH, N(C₁₋₄ alkyl), 0, and S(O)ₚ; wherein each ring moiety is substituted with 0-2 Rᵈ;

Rᵈ, at each occurrence, is independently selected from =O, halogen, —OH, C₁₋₄ alkyl, NH₂, NH(C₁₋₄ alkyl), N(C₁₋₄ alkyl)₂, C₁₋₄ alkoxy, and —NHCO(C₁₋₄ alkyl), and heterocycle containing carbon atoms and 1-4 heteroatoms selected from the group consisting of N, NH, N(C₁₋₄ alkyl), 0, and S(O)ₚ;

n, at each occurrence, is independently selected from 0, 1, 2, 3, and 4; and p, at each occurrence, is independently selected from 0, 1, and 2.

In another aspect, the present invention provides compounds of Formula (III), or stereoisomers, tautomers, pharmaceutically acceptable salts, solvates, or prodrugs thereof, wherein R² is selected from F, Cl, and OCH₃;

R⁵ is selected from

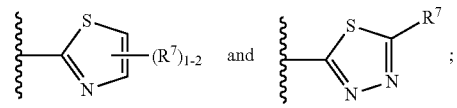

R⁷ is selected from H, C₁₋₃alkyl substituted with halogen,

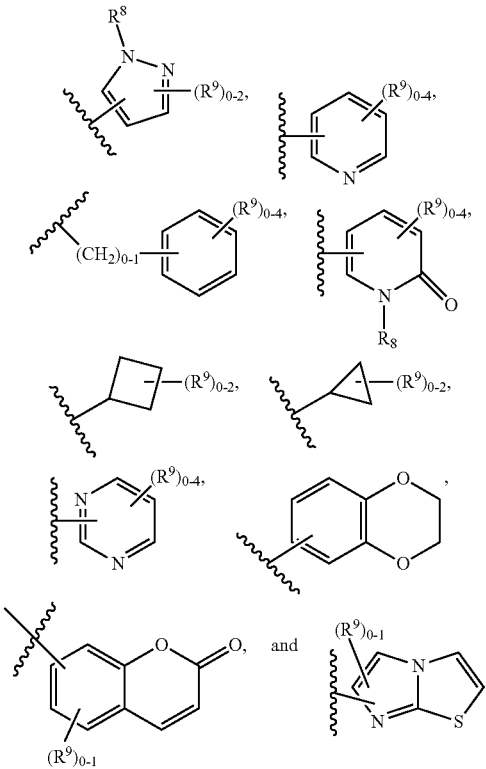

R⁸ is selected from H and C₁₋₃alkyl optionally substituted with halogen;

R⁹ is selected from F, Cl, CN, C₁₋₄ alkyl substituted with 0-2 Rᵇ, C₁₋₃ alkoxy, C₃₋₆ cycloalkyl, NHCO₂(C₁₋₄ alkyl), SO₂C₁₋₃ alkyl, and

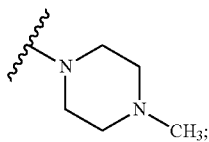

and

Rᵇ, at each occurrence, is independently selected from OH and halogen.

In another aspect, the present invention provides compounds of Formula (III), or stereoisomers, tautomers, pharmaceutically acceptable salts, solvates, or prodrugs thereof, wherein $R^2$ is independently selected from F, Cl, and $OCH_3$;

$R^5$ is selected from

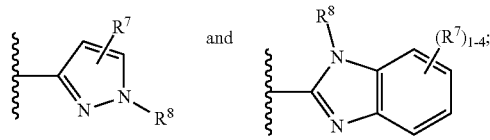

$R^7$ is selected from H, F, Cl, Br, $C_{1-3}$ alkyl substituted with 0-4 $R^9$, $C_{1-3}$ alkoxy substituted with 0-4 $R^9$, CN, $CO_2C_{1-4}$ alkyl, $P(=O)(C_{1-3}$ alkyl$)_2$, $SO_2C_{1-4}$ alkyl,

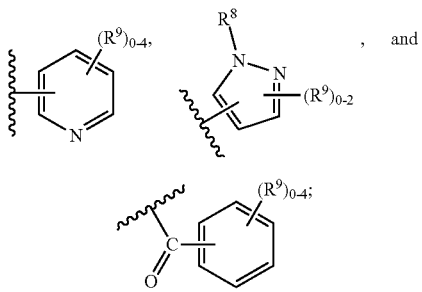

$R^8$ is selected from H and $C_{1-3}$ alkyl substituted with 0-4 $R^9$;

$R^9$ is selected from halogen, OH, CN, $C_{1-3}$ alkyl substituted with 0-4 $R^b$, $C_{1-3}$ alkoxy substituted with 0-4 $R^b$, $CO_2(C_{1-4}$ alkyl), $CONH_2$, $NHCO_2(C_{1-3}$ alkyl), $C_{3-6}$ cycloalkyl, phenyl, and heterocycle; and $R^b$, at each occurrence, is independently selected from OH and halogen.

In another aspect, the present invention provides compounds of Formula (III), or stereoisomers, tautomers, pharmaceutically acceptable salts, solvates, or prodrugs thereof, wherein $R^2$ is independently selected from F, Cl, and $OCH_3$;

$R^5$ is selected from

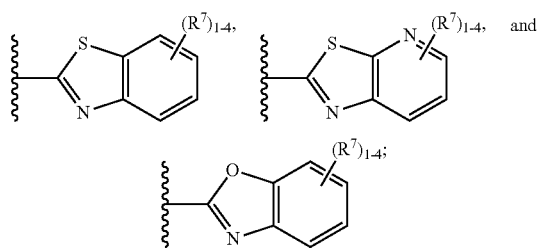

$R^7$ is selected from H, CN, $C_{1-3}$ alkyl substituted with 0-4 $R^9$, $C_{1-3}$ alkoxy substituted with 0-4 $R^9$, $CO_2C_{1-4}$ alkyl, $CONH_2$, $P(=O)(C_{1-3}$ alkyl$)_2$, $SO_2C_{1-3}$ alkyl,

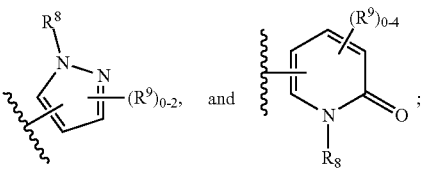

$R^8$ is selected from H and $C_{1-3}$ alkyl substituted with 0-4 $R^9$;

$R^9$ is selected from halogen, OH, CN, $C_{1-3}$ alkyl substituted with 0-4 $R^b$, $C_{1-3}$ alkoxy substituted with 0-4 $R^b$, $CO_2(C_{1-4}$ alkyl), $CONH_2$, $NHCO_2(C_{1-3}$ alkyl), $C_{3-6}$ cycloalkyl, phenyl, and heterocycle; and $R^b$, at each occurrence, is independently selected from OH and halogen.

In another aspect, the present invention provides compounds of Formula (III), or stereoisomers, tautomers, pharmaceutically acceptable salts, solvates, or prodrugs thereof, wherein $R^2$ is selected from F, Cl, and $OCH_3$;

$R^5$ is

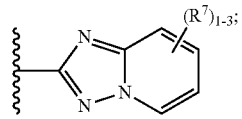

$R^7$ is selected from H, F, Cl, Br, CN, $C_{1-3}$ alkyl substituted with 0-4 $R^9$, $C_{1-3}$ alkoxy substituted with 0-4 $R^9$, $CO_2C_{1-4}$ alkyl, $CONH_2$, $P(=O)(C_{1-3}$ alkyl$)_2$, $SO_2C_{1-3}$ alkyl, and

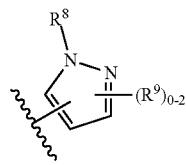

and $R^8$ is selected from H and $C_{1-3}$ alkyl substituted with 0-4 $R^9$;

$R^9$ is selected from halogen, OH, CN, $C_{1-3}$ alkyl substituted with 0-4 $R^b$, $C_{1-3}$ alkoxy substituted with 0-4 $R^b$, $CO_2(C_{1-4}$ alkyl), $CONH_2$, $NHCO_2(C_{1-3}$ alkyl), $C_{3-6}$ cycloalkyl, phenyl, and heterocycle; and $R^b$, at each occurrence, is independently selected from OH and halogen.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements (including individual variable definitions) of an embodiment are meant to be combined with any and all other elements from any of the embodiments to describe additional embodiments.

For example, in one non-limiting embodiment of Formula (II), $R^5$ is

$R^7$ is selected from H and $C_{1-4}$ alkoxy optionally substituted with OH.

In another non-limiting embodiment of Formula (II), $R^5$ is

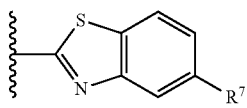

$R^7$ is selected from H and $C_{1-4}$ alkoxy optionally substituted with OH,

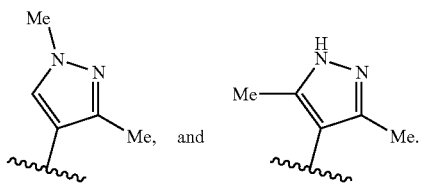 [SMILES: *c1cn(C)nc1C ; *c1c(C)n[nH]c1C]

In another non-limiting embodiment of Formula (II), $R^5$ is

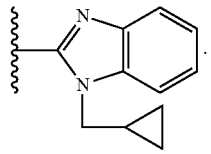 [SMILES: *c1nc2ccccc2n1CC1CC1]

In another non-limiting embodiment of Formula (II), $R^5$ is

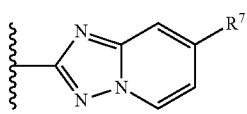

$R^7$ is selected from H and $C_{1-4}$ alkoxy optionally substituted with OH.

In another non-limiting embodiment of Formula (II), $R^5$ is

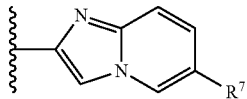

$R^7$ is selected from H and halogen.

In another non-limiting embodiment of Formula (II), $R^5$ is

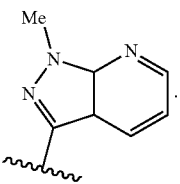 [SMILES: *C1=NN(C)C2N=CC=CC12]

In another non-limiting embodiment of Formula (II), $R^5$ is

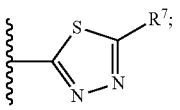

$R^7$ is selected from H, $C_{1-4}$ alkyl

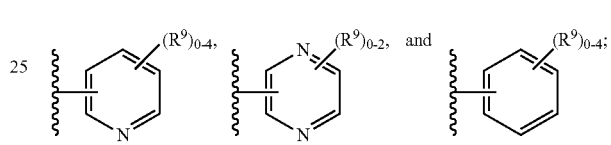

and $R^9$ is halogen.

In another non-limiting embodiment of Formula (III), $R^5$ is

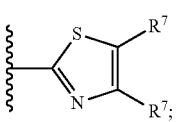

one $R^7$ is

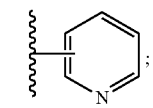

the other is $C_{3-6}$ cycloalkyl.

In another non-limiting embodiment of Formula (III), $R^5$ is

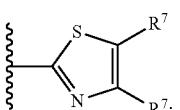

one $R^7$ is $CH_3$, the other is

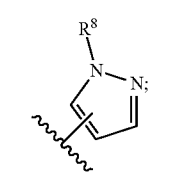

$R^8$ is $CH_3$.

In another non-limiting embodiment of Formula (III), $R^5$ is

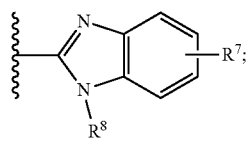

$R^7$ is selected from F, $CF_3$ and

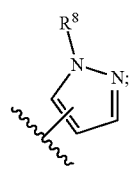

$R^8$ is selected from $CH_3$, $CF_2$ and $CH_2$-cyclopropyl.

In another non-limiting embodiment of Formula (III), $R^5$ is

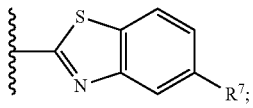

$R^7$ is

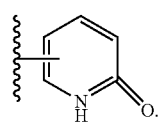

In another non-limiting embodiment of Formula (III), $R^5$ is

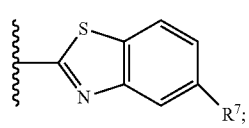

$R^7$ is

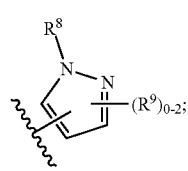

$R^8$ is selected from H, $CH_3$, $CD_3$, and $CHF_2$; $R^9$ is selected from $CH_3$, $CF_3$, and cyclopropyl.

In another non-limiting embodiment of Formula (III), $R^5$ is

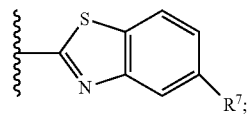

$R^7$ is $C_{1-4}$ alkoxy optionally substituted with OH.

In another non-limiting embodiment of Formula (III), $R^2$ is selected from F and Cl $R^5$ is

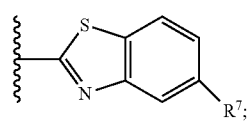

$R^7$ is $C_{1-4}$ alkoxy optionally substituted with OH.

In another non-limiting embodiment of Formula (III), $R^2$ is selected from F, Cl, and Br; $R^5$ is selected from

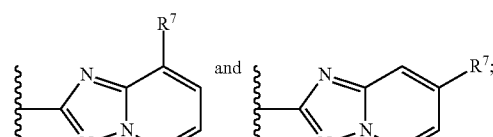

$R^7$ is $C_{1-4}$ alkoxy optionally substituted with phenyl.

In another non-limiting embodiment of Formula (III), $R^2$ is Cl; $R^5$ is

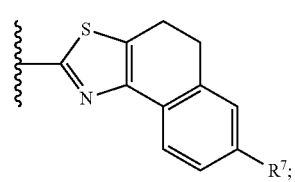

$R^7$ is $C_{1-4}$ alkoxy.

In another aspect, the present invention provides a compound selected from any subset list of compounds exemplified in the present application.

In another embodiment, the compounds of the present invention have ROCK $IC_{50}$ values $\leq 10$ µM.

In another embodiment, the compounds of the present invention have ROCK $IC_{50}$ values $\leq 1$ µM.

In another embodiment, the compounds of the present invention have ROCK $IC_{50}$ values $\leq 0.1$ µM.

In another embodiment, the compounds of the present invention have ROCK $IC_{50}$ values $\leq 0.05$ µM.

In another embodiment, the compounds of the present invention have ROCK $IC_{50}$ values $\leq 0.01$ µM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate, thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition further comprising additional therapeutic agent(s).

In another embodiment, the present invention provides a method for the treatment and/or prophylaxis of a condition associated with aberrant ROCK activity comprising administering to a patient in need of such treatment and/or prophylaxis a therapeutically effective amount of at least one of the compounds of the present invention or a stereoisomer, a tautomer, a pharmaceutically acceptable salt, or a solvate thereof. As used herein, the term "patient" encompasses all mammalian species.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" covers the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a patient that has not yet presented with a clinical disease state, whereas secondary prevention is defined as preventing a second occurrence of the same or similar clinical disease state. In another embodiment, the present invention provides a combined preparation of a compound of the present invention and additional therapeutic agent(s) for simultaneous, separate or sequential use in therapy.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The term "stereoisomer" refers to isomers of identical constitution that differ in the arrangement of their atoms in space. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity.

The symbols "R" and "S" represent the configuration of substituents around a chiral carbon atom(s). The isomeric descriptors "R" and "S" are used as described herein for indicating atom configuration(s) relative to a core molecule and are intended to be used as defined in the literature (IUPAC Recommendations 1996, *Pure and Applied Chemistry*, 68:2193-2222 (1996)).

The term "chiral" refers to the structural characteristic of a molecule that makes it impossible to superimpose it on its mirror image. The term "homochiral" refers to a state of enantiomeric purity. The term "optical activity" refers to the degree to which a homochiral molecule or nonracemic mixture of chiral molecules rotates a plane of polarized light.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_1$-$C_6$ alkyl" denotes alkyl having 1 to 6 carbon atoms.

Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro (F), chloro (Cl), bromo (Br), and iodo (I). "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle" or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 13th Edition, John Wiley & Sons, Inc., New York (1997). "$C_6$ or $C_{10}$ aryl" or "$C_{6-10}$ aryl" refers to phenyl and naphthyl. Unless otherwise specified, "aryl", "$C_6$ or $C_{10}$ aryl" or "$C_{6-10}$ aryl" or "aromatic residue" may be unsubstituted or substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

The term "benzyl", as used herein, refers to a methyl group on which one of the hydrogen atoms is replaced by a phenyl group, wherein said phenyl group may optionally be substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

As used herein, the term "heterocycle" or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N—O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and S(O)$_p$, wherein p is 0, 1 or 2).

Bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counterion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology,* 112:309-396, Academic Press (1985);

b) Bundgaard, H., Chapter-5, "Design and Application of Prodrugs", Krosgaard-Larsen, P. et al., eds., *A Textbook of Drug Design and Development*, pp. 113-191, Harwood Academic Publishers (1991);

c) Bundgaard, H., *Adv. Drug Deliv. Rev.,* 8:1-38 (1992);

d) Bundgaard, H. et al., *J. Pharm. Sci.,* 77:285 (1988); and e) Kakeya, N. et al., *Chem. Pharm. Bull.,* 32:692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Deuterium has one proton and one neutron in its nucleus and that has twice the mass of ordinary hydrogen. Deuterium can be represented by symbols such as "$^2$H" or "D". The term "deuterated" herein, by itself or used to modify a compound or group, refers to replacement of one or more hydrogen atom(s), which is attached to carbon(s), with a deuterium atom. Isotopes of carbon include $^{13}C$ and $^{14}C$.

Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "saturated" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1H$" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me Methyl
Et Ethyl
Pr Propyl
i-Pr Isopropyl
Bu Butyl
i-Bu Isobutyl
t-Bu tert-butyl
Ph Phenyl
Bn Benzyl
Boc tert-butyloxycarbonyl
AcOH or HOAc acetic acid
$AlCl_3$ aluminum chloride
AIBN Azobisisobutyronitrile
$BBr_3$ boron tribromide
$BCl_3$ boron trichloride
BEMP 2-tert-butylimino-2-diethylamino-1,3-dimethylperhydro-1,3,2-diazaphosphorine
BOP reagent benzotriazol-1-yloxytris(dimethylamino)phosphonium hexafluorophosphate
Boc2O Di-tert-butyl dicarbonate
Burgess reagent 1-methoxy-N-triethylammoniosulfonyl-methanimidate
CBz Carbobenzyloxy
$CH_2Cl_2$ Dichloromethane
$CH_3CN$ or CAN Acetonitrile
$CDCl_3$ deutero-chloroform
$CHCl_3$ Chloroform
mCPBA or m-CPBA meta-chloroperbenzoic acid
$Cs_2CO_3$ cesium carbonate
$Cu(OAc)_2$ copper (II) acetate
$Cy_2NMe$ N-cyclohexyl-N-methylcyclohexanamine
DBU 1,8-diazabicyclo[5.4.0]undec-7-ene
DCE 1,2 dichloroethane
DCM dichloromethane
DEA diethylamine
Dess-Martin 1,1,1-tris(acetyloxy)-1,1-dihydro-1,2-beniziodoxol-3-(1H)-one
DIC or DIPCDI diisopropylcarbodiimide
DIEA, DIPEA or diisopropylethylamine Hunig's base
DMAP 4-dimethylaminopyridine
DME 1,2-dimethoxyethane
DMF dimethyl formamide
DMSO dimethyl sulfoxide
cDNA complimentary DNA
Dppp (R)-(+)-1,2-bis(diphenylphosphino)propane
DuPhos (+)-1,2-bis((2S,5S)-2,5-diethylphospholano)benzene
EDC N-(3-dimthylaminopropyl)-N'-ethylcarbodiimide
EDCI N-(3-dimthylaminopropyl)-N'-ethylcarbodiimide hydrochloride
EDTA ethylenediaminetetraacetic acid
(S,S)-EtDuPhosRh(I) (+)-1,2-bis((2S,5S)-2,5-diethylphospholano)benzene(1,5-cyclooctadiene)rhodium(I) trifluoromethanesulfonate
$Et_3N$ or TEA triethylamine
EtOAc ethyl acetate
$Et_2O$ diethyl ether
EtOH Ethanol
G3 precatalyst Buchwald G3 (3d gen.) catalyst
GMF glass microfiber filter
Grubbs (II) (1,3-bis(2,4,6-trimethylphenyl)-2-imidazolidinylidene)dichloro (phenylmethylene)(triycyclohexylphosphine)ruthenium
HCl hydrochloric acid
HATU O-(7-azabenzotriazol-1-yl)-N,N,N',N'-tetramethyluronium hexafluorophosphate
HEPES 4-(2-hydroxyethyl)piperaxine-1-ethanesulfonic acid
Hex Hexane
HOBt or HOBT 1-hydroxybenzotriazole
$H_2SO_4$ sulfuric acid
$K_2CO_3$ potassium carbonate
KOAc potassium acetate
$K_3PO_4$ potassium phosphate
LAH lithium aluminum hydride
LG leaving group LiGH lithium hydroxide
MeOH Methanol
MgSO$_4$ magnesium sulfate
MsOH or MSA methylsulfonic acid
NaCl sodium chloride
NaH sodium hydride
NaHCO$_3$ sodium bicarbonate
Na$_2$CO$_3$ sodium carbonate
NaOH sodium hydroxide
Na$_2$SO$_3$ sodium sulfite
Na$_2$SO$_4$ sodium sulfate
NBS N-bromosuccinimide
NCS N-chlorosuccinimide
NH$_3$ Ammonia
NH$_4$Cl ammonium chloride
NH$_4$OH ammonium hydroxide
OTf triflate or trifluoromethanesulfonate
Pd$_2$(dba)$_3$ tris(dibenzylideneacetone)dipalladium(O)
Pd(OAc)$_2$ palladium(II) acetate
Pd/C palladium on carbon
Pd(dppf)Cl$_2$ [1,1'-bis(diphenylphosphino)-ferrocene]dichloropalladium(II)
Ph$_3$PCl$_2$ triphenylphosphine dichloride
PG protecting group
POCl$_3$ phosphorus oxychloride
i-PrOH or IPA isopropanol
PS polystyrene
SEM-Cl 2-(trimethysilyl)ethoxymethyl chloride
SiO$_2$ silica oxide
SnCl$_2$ tin(II) chloride
TBAI tetra-n-butylammonium iodide
TEA triethylamine
TFA trifluoroacetic acid
THF tetrahydrofuran
TMSCHN$_2$ trimethylsilyldiazomethane
T3P propane phosphonic acid anhydride
TRIS tris (hydroxymethyl) aminomethane The compounds of the present invention can be prepared in a number of ways known to one skilled in the art of organic synthesis.

IV. Biology

In Vitro Assays

The effectiveness of compounds of the present invention as ROCK inhibitors can be determined in a 30 μL assay containing 20 mM HEPES, pH 7.5, 20 mM MgCl$_2$, 0.015% Brij-35, 4 mM DTT, 5 μM ATP and 1.5 μM peptide substrate (FITC-AHA-AKRRRLSSLRA-OH) (SEQ ID No. 1). Compounds were dissolved in DMSO so that the final concentration of DMSO was <2%, and the reaction was initiated with Rho kinase variants. After incubation, the reaction was terminated by the addition of EDTA and the phosphorylated and non-phosphorylated peptides separated using a LABCHIP® 3000 Reader (Caliper Life Sciences). Controls consisted of assays that did not contain compound, and backgrounds consisted of assays that contained enzyme and substrate but had EDTA from the beginning of the reaction to inhibit kinase activity. Compounds were tested in dose-response format, and the inhibition of kinase activity was calculated at each concentration of compound. The inhibition data were fit using a curve-fitting program to determine the IC$_{50}$; i.e., the concentration of compound required to inhibit 50% of kinase activity.

Representative Examples were tested in the ROCK assay described above and found having ROCK inhibitory activity. A range of ROCK inhibitory activity (IC$_{50}$ values) of ≤50 μM (50000 nM) was observed. Table A below lists the ROCK IC$_{50}$ values measured for the following examples.

TABLE A

| Example No. | ROCK2 IC$_{50}$ (nM) |
| --- | --- |
| 001 | 10 |
| 002 | 35 |
| 003 | 20 |
| 004 | 3 |
| 005 | 10 |
| 006 | 18 |
| 007 | 14 |
| 008 | 7 |
| 009 | 35 |
| 010 | 159 |
| 011 | 150 |
| 012 | 38 |
| 013 | 21 |
| 014 | 96 |
| 015 | 31 |
| 016 | 87 |
| 017 | 404 |
| 018 | 245 |
| 019 | 49 |
| 020 | 106 |
| 021 | 53 |
| 022 | 41 |
| 023 | 4 |
| 024 | 8 |
| 025 | 23 |
| 026 | 8 |
| 027 | 5 |
| 028 | 30 |
| 029 | 9 |
| 030 | 8 |
| 031 | 8 |
| 032 | 89 |
| 033 | 7 |
| 034 | 8 |
| 035 | 10 |
| 036 | 48 |
| 037 | 34 |
| 038 | 30 |
| 039 | 183 |
| 040 | 99 |
| 041 | 175 |
| 042 | 471 |
| 043 | 69.6 |
| 044 | 24 |
| 045 | 21 |
| 046 | 22 |
| 047 | 84 |
| 048 | 112 |
| 049 | 194 |
| 050 | 175 |
| 051 | 145 |
| 052 | 177 |
| 053 | 21 |
| 054 | 364 |
| 055 | 1111 |
| 056 | 1086 |
| 057 | 186 |
| 058 | 419 |
| 059 | 98 |
| 060 | 87 |
| 061 | 506 |
| 062 | 863 |
| 063 | 339 |
| 064 | 423 |
| 065 | 109 |
| 066 | 830 |
| 067 | 89 |
| 068 | 600 |
| 069 | 558 |
| 070 | 57 |
| 071 | 621 |
| 072 | 147 |
| 073 | 244 |
| 074 | 1104 |

TABLE A-continued

| Example No. | ROCK2 IC$_{50}$ (nM) |
|---|---|
| 075 | 534 |
| 076 | 332 |
| 077 | 42 |
| 078 | 96 |
| 079 | 181 |
| 080 | 15 |
| 081 | 59 |
| 082 | 6 |
| 083 | 106 |
| 084 | 947 |
| 085 | 176 |
| 086 | 137 |
| 087 | 47 |
| 088 | 126 |
| −089 | 14 |
| 090 | 419 |
| 091 | 874 |
| 092 | 361 |
| 093 | 213 |
| 094 | 15 |
| 095 | 113 |
| 096 | 110 |
| 097 | 336 |
| 098 | 31 |
| 099 | 583 |
| 100 | 191 |
| 101 | 261 |
| 102 | 12 |
| 103 | 17 |
| 104 | 7 |
| 105 | 15 |
| 106 | 262 |
| 107 | 29 |
| 108 | 40 |
| 109 | 74 |
| 110 | 36 |
| 111 | 37 |
| 112 | 6 |
| 113 | 58 |
| 114 | 162 |
| 115 | 8 |
| 116 | 8 |
| 117 | 139 |
| 118 | 650 |
| 119 | 6 |
| 120 | 23 |
| 121 | 45 |
| 122 | 97 |
| 123 | 18 |
| 124 | 68.5 |
| 125 | 12 |
| 126 | 82 |
| 127 | 127 |
| 128 | 301 |
| 129 | 69 |
| 130 | 23 |
| 131 | 129 |
| 132 | 129 |
| 133 | 198 |
| 134 | 44 |
| 135 | 25 |
| 136 | 11 |
| 137 | 13 |
| 138 | 39 |
| 139 | 25 |
| 140 | 93 |
| 141 | 34 |
| 142 | 72 |
| 143 | 6 |
| 144 | 5 |
| 145 | 132.6 |
| 146 | 132 |
| 147 | 1390 |
| 148 | 147 |
| 149 | 1234 |
| 150 | 465 |
| 151 | 44 |
| 152 | 55 |
| 153 | 218 |
| 154 | 42 |
| 155 | 1928 |
| 156 | 3456 |
| 157 | 804 |
| 158 | 1722 |
| 159 | 2176 |
| 160 | 39 |
| 161 | 16 |
| 162 | 47 |
| 163 | 16 |
| 164 | 12 |
| 165 | 26 |
| 166 | 24 |
| 167 | 25 |
| 168 | 18 |
| 169 | 13 |
| 170 | 31 |
| 171 | 3 |
| 172 | 7 |
| 173 | 8 |
| 174 | 10 |
| 175 | 44 |
| 176 | 16 |
| 177 | 7 |
| 178 | 14 |

V. Pharmaceutical Compositions, Formulations and Combinations

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the patient to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 18th Edition (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the disorder.

By way of general guidance, the daily oral dosage of each active ingredient, when used for the indicated effects, will range between about 0.001 to about 1000 mg/kg of body weight, preferably between about 0.01 to about 100 mg/kg of body weight per day, and most preferably between about 0.1 to about 20 mg/kg/day. Intravenously, the most preferred doses will range from about 0.001 to about 10 mg/kg/minute during a constant rate infusion. Compounds of this invention may be administered in a single daily dose, or the total daily dosage may be administered in divided doses of two, three, or four times daily.

Compounds of this invention can also be administered by parenteral administration (e.g., intra-venous, intra-arterial, intramuscularly, or subcutaneously. When administered intra-venous or intra-arterial, the dose can be given continuously or intermittent. Furthermore, formulation can be developed for intramuscularly and subcutaneous delivery that ensure a gradual release of the active pharmaceutical ingredient.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the inhibition of ROCK. Such compounds may be provided in a commercial kit, for example, for use in pharmaceutical research involving ROCK. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a cardiovascular and/or inflammatory disorder (as defined previously). In another embodiment, the package insert states that the pharmaceutical composition can be used in combination (as defined previously) with a second therapeutic agent to treat cardiovascular and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof. The following Examples have been prepared, isolated and characterized using the methods disclosed herein.

VI. General Synthesis Including Schemes

Examples of compounds of the present invention prepared by methods described in the general schemes are given in the intermediates and examples section set out hereinafter. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al., (*Protective Groups in Organic Synthesis*, 4th Edition, Wiley-Interscience (2006)).

Compounds of this invention can be prepared by aryl or heteroaryl halide (A) displacement by a 2-(4-hydroxyphenyl)acetic acid (B) followed by standard coupling of 2-(4-((3-carbamoylpyridin-2-yl)oxy)phenyl)acetic acid (C) with bicyclic or monocyclic-heterocyclic amines (D or F) using such coupling agents as BOP. The amides (E or G) with halogen substitutents at R7 can be further elaborated through Suzuki cross coupling methodologies known in the art.

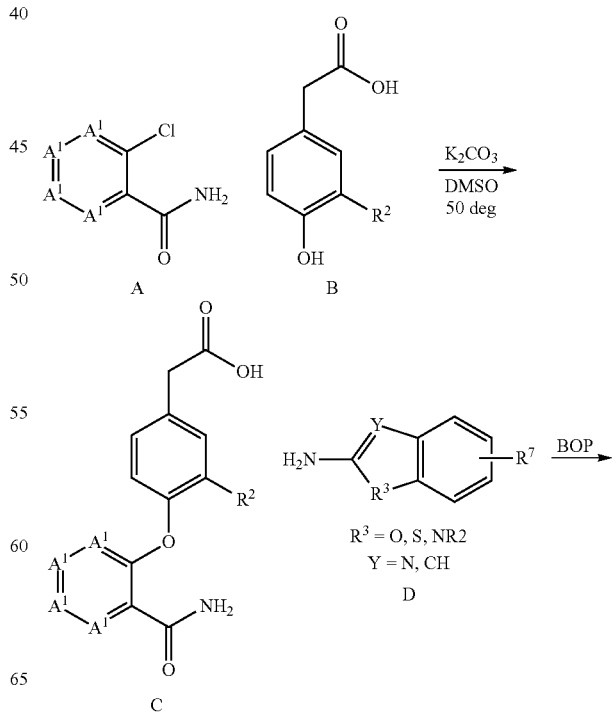

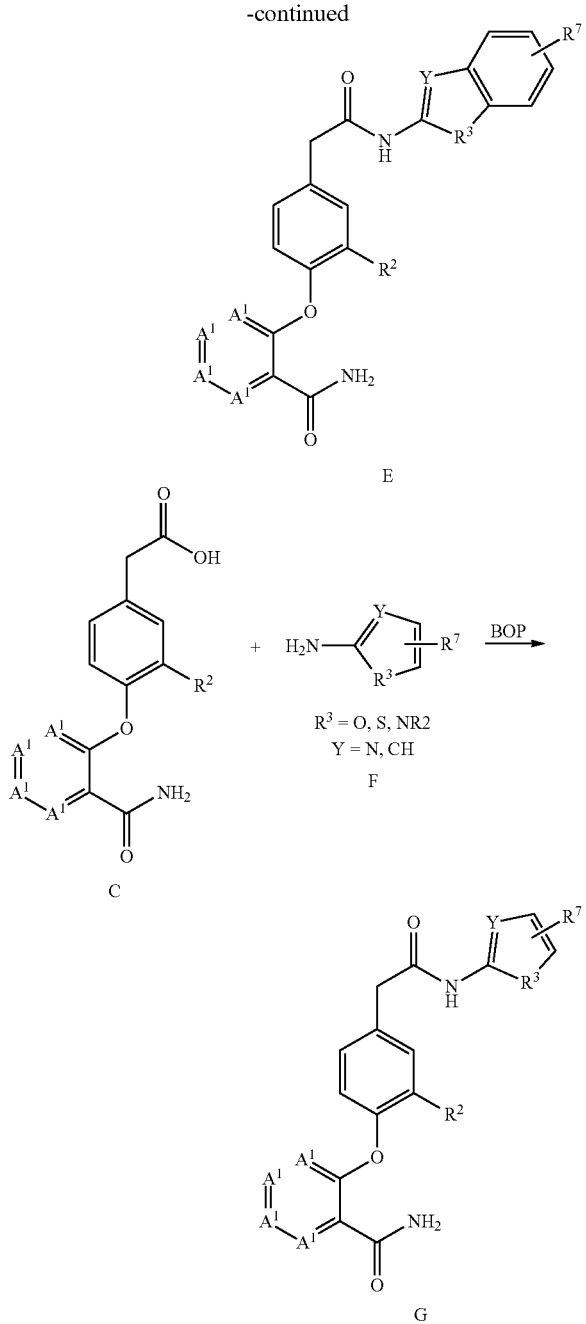

Purification of intermediates and final products was carried out via either normal or reverse phase chromatography. Normal phase chromatography was carried out using pre-packed SiO$_2$ cartridges eluting with either gradients of hexanes and EtOAc, DCM and MeOH unless otherwise indicated. Reverse phase preparative HPLC was carried out using C18 columns eluting with gradients of Solvent A (90% water, 10% MeOH, 0.1% TFA) and Solvent B (10% water, 90% MeOH, 0.1% TFA, UV 220 nm) or with gradients of Solvent A (90% water, 10% CH$_3$CN, 0.1% TFA) and Solvent B (10% water, 90% CH$_3$CN, 0.1% TFA, UV 220 nm) or with gradients of Solvent A (98% water, 2% CH$_3$CN, 0.05% TFA) and Solvent B (98% CH$_3$CN, 2% water, 0.05% TFA, UV 220 nm) (or) Sunfire Prep C18 OBD 5u 30×100 mm, 25 min gradient from 0-100% B. A=H$_2$O/CH$_3$CN/TFA 90:10:0.1. B=CH$_3$CN/H$_2$O/TFA 90:10:0.1

Unless otherwise stated, analysis of final products was carried out by reverse phase analytical HPLC.

Method A: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Method B: Waters Acquity UPLC BEH C18, 2.1×50 mm, 1.7-μm particles; Mobile Phase A: 5:95 acetonitrile:water with 0.1% TFA; Mobile Phase B: 95:5 acetonitrile:water with 0.1% TFA; Temperature: 50° C.; Gradient: 0-100% B over 3 minutes, then a 0.75-minute hold at 100% B; Flow: 1.11 mL/min.

Method C SunFire (4.6×150 mm) (15 min gradient—95:5 H$_2$O/acetonitrile—to 95:5 acetonitrile/H$_2$O −0.05% TFA).

Intermediate 1. 2-(4-((3-cyanopyridin-2-yl)oxy)-3-fluorophenyl)acetic Acid

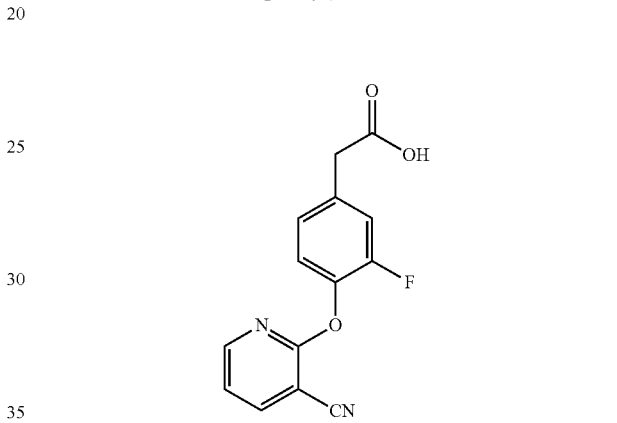

To 2-chloronicotinonitrile (0.489 g, 3.53 mmol) in DMSO (5 mL) was added 2-(3-fluoro-4-hydroxyphenyl)acetic acid (0.6 g, 4 mmol) and K$_2$CO$_3$ (1.072 g, 7.760 mmol) and the reaction mixture was heated to 60° C. for 14 h. The reaction mixture was allowed to cool to room temperature, quenched by the addition of 1N HCl and the resultant solid was filtered and dried under vacuum to afford (0.9 g, 90% yield) of Intermediate 1 as a tan solid. $^1$H NMR (400 MHz, CD$_3$OD) δ 8.32 (dd, J=5.0, 1.9 Hz, 1H), 8.25 (dd, J=7.7, 2.0 Hz, 1H), 7.35-7.23 (m, 3H), 7.23-7.10 (m, 1H), 3.70 (s, 2H). LCMS m/z=273.0 (M+H).$^+$ Intermediate 2. 2-(4-((3-cyanopyridin-2-yl)oxy)-3-fluorophenyl)acetyl Chloride

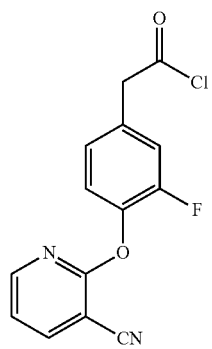 [SMILES: N#Cc1cccnc1Oc1ccc(CC(=O)Cl)cc1F]

To a suspension of intermediate 1 (1.6 g, 5.9 mmol) in DCE (11.7 mL) was added SOCl$_2$ (4.29 ml, 58.8 mmol) and the reaction mixture was heated to 50° C. The reaction mixture turned clear and was stirred for 1 h. Evaporation of the solvents in vacuum afforded the 2-(4-((3-cyanopyridin-2-yl)oxy)-3-fluorophenyl)acetyl chloride (1.71 g, 100%) as a white solid. LCMS m/z=286.9 (M+H)$^+$ for methyl ester.

Intermediate 3. 2-(4-((3-cyanopyridin-2-yl)oxy)phenyl)acetic Acid, HCl

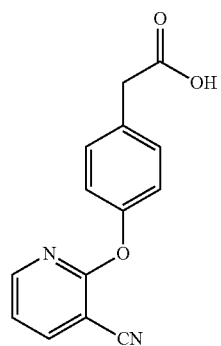 [SMILES: N#Cc1cccnc1Oc1ccc(CC(=O)O)cc1]

2-(4-((3-Cyanopyridin-2-yl)oxy)phenyl)acetic acid, HCl (14.7 g, 99% yield), a brown solid; was prepared as described for intermediate 1, substituting 2-(4-hydroxyphenyl)acetic acid for 2-(3-fluoro-4-hydroxyphenyl)acetic acid $^1$H NMR (400 MHz, DMSO-d$_6$) δ 12.39 (br s, 1H), 8.88-8.18 (m, 2H), 7.42-7.29 (m, 3H), 7.23-7.15 (m, 2H), 2.63 (s, 2H). LCMS m/z=255.1 (M+H).$^+$ Intermediate 4. 2-(3-chloro-4-((3-cyanopyridin-2-yl)oxy)phenyl)acetic Acid

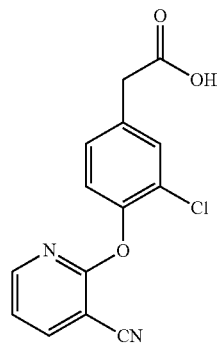 [SMILES: N#Cc1cccnc1Oc1ccc(CC(=O)O)cc1Cl]

2-(3-Chloro-4-((3-cyanopyridin-2-yl)oxy)phenyl)acetic acid (1.5 g, 97% yield) was prepared as described for intermediate 1, substituting 2-(3-chloro-4-hydroxyphenyl)acetic acid for 2-(3-fluoro-4-hydroxyphenyl)acetic acid $^1$H NMR (400 MHz, CD$_3$OD) δ 8.35-8.20 (m, 2H), 7.52 (d, J=2.0 Hz, 1H), 7.40-7.33 (m, 1H), 7.32-7.21 (m, 2H), 3.70 (s, 2H). LCMS(ESI) m/z: 289-290.9 (M+H).$^+$ Intermediate 5. 2-(4-((3-carbamoylpyridin-2-yl)oxy)-3-fluorophenyl)acetic Acid, HCl

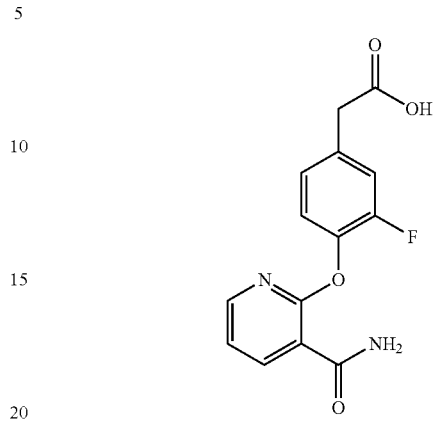

Intermediate 1 (3 g, 10 mmol) was dissolved in DMSO (55.1 mL), then K$_2$CO$_3$ (6.09 g, 44.1 mmol) was added. The reaction mixture was cooled slightly in a water bath (not freezing DMSO). To the reaction mixture was added hydrogen peroxide (30% wt. aq) (11.26 ml, 110.0 mmol) dropwise over 5 min (slight exotherm), and the reaction mixture was stirred at room temperature. After 72 h, conc. HCl was carefully added and the resultant white solid was filtered, washed with excess water and dried under vacuum to afford (2.86 g, 79.0% yield) of Intermediate 5. $^1$H NMR (400 MHz, DMSO-d$_6$) δ 12.46 (br s, 1H), 8.47-8.09 (m, 2H), 7.81 (br d, J=8.1 Hz, 2H), 7.40-7.23 (m, 3H), 7.16 (dd, J=8.1, 1.3 Hz, 1H), 3.66 (s, 2H). LCMS m/z=291.1 (M+H).$^+$ Intermediate 6. 2-(4-((3-carbamoylpyridin-2-yl)oxy)phenyl)acetic Acid, HCl

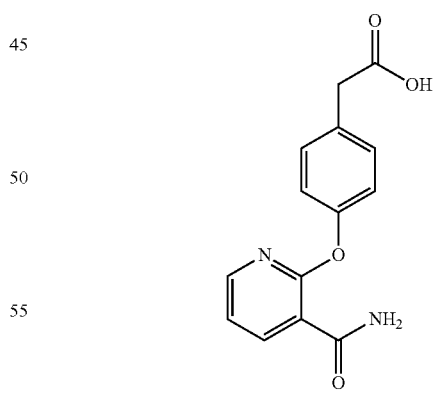

2-(4-((3-Carbamoylpyridin-2-yl)oxy)phenyl)acetic acid, HCl (1.3 g, 87% yield), a pale yellow solid, was prepared in a similar manner as intermediate 5. $^1$H NMR (500 MHz, DMSO-d$_6$) δ 8.26-8.11 (m, 2H), 7.78 (br. s., 1H), 7.75 (br. s., 1H), 7.36-7.27 (m, 2H), 7.22 (dd, J=7.4, 4.7 Hz, 1H), 7.16-7.05 (m, 2H), 3.48-3.32 (m, 1H), 2.59-2.52 (m, 2H). LCMS m/z=273.1 (M+H).$^+$ Intermediate 7 2-(3-chloro-4-((3-cyanopyridin-2-yl)oxy)phenyl)acetic Acid, HCl

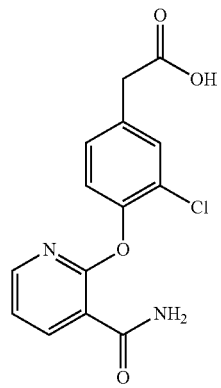 [SMILES: NC(=O)c1cccnc1Oc1ccc(CC(=O)O)cc1Cl]

2-(3-Chloro-4-((3-cyanopyridin-2-yl)oxy)phenyl)acetic acid, HCl (0.45 g, 100% yield), a white solid, was prepared as described for intermediate 5, substituting 2-(3-chloro-4-((3-cyanopyridin-2-yl)oxy)phenyl)acetic acid for 2-(4-((3-cyanopyridin-2-yl)oxy)-3-fluorophenyl)acetic acid. $^1$H NMR (400 MHz, DMSO-d$_6$) δ 12.48 (br s, 1H), 8.40-8.03 (m, 2H), 7.97-7.69 (m, 2H), 7.49 (d, J=2.0 Hz, 1H), 7.44-6.89 (m, 3H), 3.32 (s, 2H). LCMS m/z: 306.9 (M+H).$^+$ Intermediate 8. 2-(4-(2-((5-bromobenzo[d]thiazol-2-yl)amino)-2-oxoethyl)-2-fluorophenoxy)nicotinamide, HCl

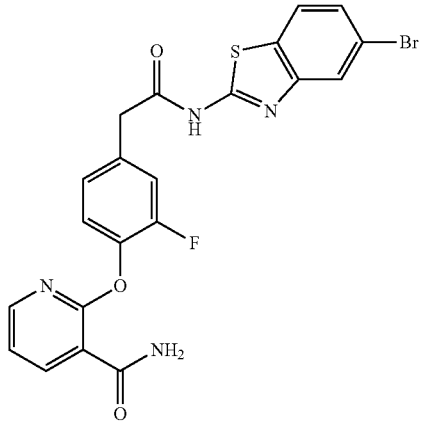 [SMILES: NC(=O)c1cccnc1Oc1ccc(CC(=O)Nc2nc3cc(Br)ccc3s2)cc1F]

Step 1. To a suspension of intermediate 1 (0.35 g, 1.3 mmol) in DCE (4 mL) was added SOCl$_2$ (0.925 mL, 12.7 mmol) and the reaction mixture was heated to 50° C. The reaction turned clear and was stirred for 1 h. The solvents were removed under reduced pressure and to the resultant solid was added 5-bromobenzo[d]thiazol-2-amine (0.32 g, 1.4 mmol), THF (3 mL) and DIEA (0.66 mL, 3.8 mmol). After 24 h, the solvents were evaporated under reduced pressure and the residue was purified via silica gel chromatography eluting with DCM/0-100% ethyl acetate to afford (0.385 g, 62.9% yield) of N-(5-bromobenzo[d]thiazol-2-yl)-2-(4-((3-cyanopyridin-2-yl)oxy)-3-fluorophenyl)acetamide as a yellow solid. $^1$H NMR (400 MHz, CDCl$_3$) δ 9.06 (br s, 1H), 8.34 (dd, J=4.8, 2.0 Hz, 1H), 8.07 (dd, J=7.7, 2.0 Hz, 1H), 7.93 (d, J=1.8 Hz, 1H), 7.72 (d, J=8.6 Hz, 1H), 7.55-7.46 (m, 1H), 7.51-7.45 (m, 1H), 7.36 (t, J=8.0 Hz, 1H), 7.28-7.14 (m, 2H), 3.92 (s, 2H). LCMS m/z=484.9 (M+H).$^+$ Step 2. N-(5-bromobenzo[d]thiazol-2-yl)-2-(4-((3-cyanopyridin-2-yl)oxy)-3-fluorophenyl)acetamide (0.38 g, 0.78 mmol) was dissolved in DMSO (3.93 mL), then K$_2$CO$_3$ (0.435 g, 3.14 mmol) was added. The reaction mixture was cooled slightly in a water bath and 30% hydrogen peroxide (0.80 mL, 7.9 mmol) was added dropwise over 5 min (slight exotherm), and the reaction mixture was stirred at room temperature for 14 h. The reaction mixture was quenched by the careful addition of HCl and the resultant solid was filtered and dried under vacuum to afford (0.45 g, 106% yield) of Intermediate 8 as a tan solid. $^1$H NMR (400 MHz, DMSO-d$_6$) δ 12.82 (br s, 1H), 8.29-8.14 (m, 2H), 7.98 (dd, J=5.2, 3.2 Hz, 2H), 7.82 (br s, 1H), 7.80 (br s, 1H), 7.53-7.46 (m, 1H), 7.42-7.33 (m, 2H), 7.25 (dd, J=7.4, 5.0 Hz, 2H), 3.93 (s, 2H). LCMS m/z=500.9-501.9 (M+H).$^+$ Example 1. 2-(2-fluoro-4-(2-((7-methoxy-4,5-dihydronaphtho[1,2-d]thiazol-2-yl)amino)-2-oxoethyl)phenoxy)nicotinamide

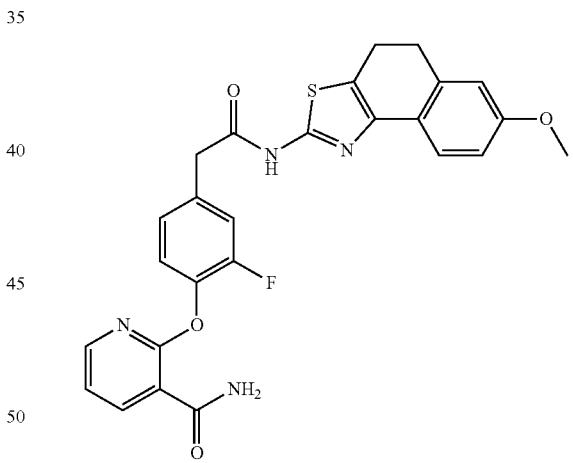

In a vial, to a mixture of intermediate 5 (0.02 g, 0.07 mmol), 7-methoxy-4,5-dihydronaphtho[1,2-d]thiazol-2-amine (0.02 g, 0.07 mmol) was added BOP (0.030 g, 0.069 mmol), DMF (0.3 mL), and DIEA (0.060 ml, 0.35 mmol). After 72 h, the reaction mixture was filtered and subjected to reverse phase HPLC purification to afford Example 1 (4.4 mg, 9.9%). $^1$H NMR (500 MHz, DMSO-d$_6$) δ 8.34-8.04 (m, 2H), 7.85-7.81 (m, 1H), 7.80-7.73 (m, 1H), 7.58 (d, J=8.2 Hz, 1H), 7.42-7.29 (m, 2H), 7.27-7.12 (m, 2H), 6.91-6.79 (m, 2H), 3.83 (s, 2H), 3.33 (br s, 1H), 3.02-2.93 (m, 2H), 2.92-2.84 (m, 2H), 3.77 (s, 3H). LCMS m/z=505.0 (M+H)$^+$; HPLC purity >96% with retention time 1.81 min. [method A]

Example 2. 2-(4-(2-((5-methoxybenzo[d]thiazol-2-yl)amino)-2-oxoethyl)phenoxy) Nicotinamide

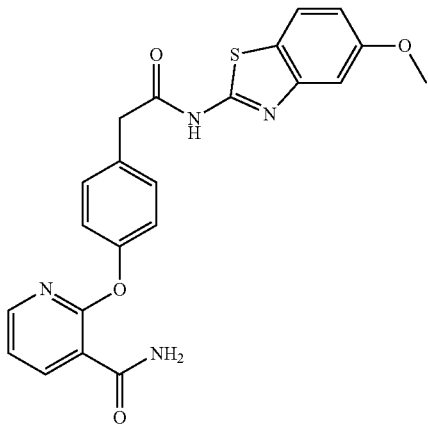 [SMILES: COc1ccc2sc(NC(=O)Cc3ccc(Oc4ncccc4C(N)=O)cc3)nc2c1]

To a mixture of intermediate 6 (20 mg, 0.065 mmol), 5-methoxybenzo[d]thiazol-2-amine (11.68 mg, 0.06500 mmol), was added DMF (0.3 mL), a DMF (0.5 mL) solution containing BOP (28.7 mg, 0.0650 mmol) and DIEA (0.057 mL, 0.32 mmol) were added. After 24 h, the reaction mixture was filtered and subjected to reverse phase HPLC purification to afford Example 2 (1.6 mg, 4.2% yield), $^1$H NMR (500 MHz, DMSO-$d_6$) δ $^1$H NMR (500 MHz, DMSO-$d_6$) δ 12.58 (br s, 1H), 8.29-8.00 (m, 2H), 7.82 (br d, J=8.5 Hz, 1H), 7.79 (br s, 1H), 7.75 (br s, 1H), 7.40 (br d, J=8.2 Hz, 2H), 7.28 (s, 1H), 7.21 (br dd, J=7.3, 4.9 Hz, 1H), 7.16 (br d, J=8.2 Hz, 2H), 6.94 (dd, J=8.5, 1.8 Hz, 1H), 3.86 (s, 2H) 3.82 (s, 3H). LCMS m/z=434.9 (M+H)$^+$; HPLC purity >94% with retention time 1.52 min. [method B]

Example 3. 2-(2-fluoro-4-(2-((5-(2-hydroxy-2-methylpropoxy)benzo[d]thiazol-2-yl)amino)-2-oxoethyl)phenoxy)nicotinamide

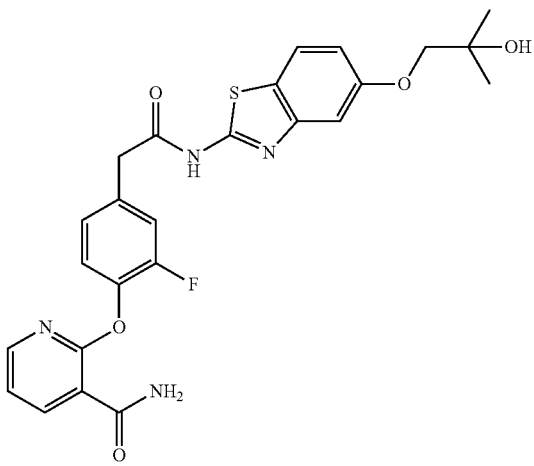 [SMILES: CC(C)(O)COc1ccc2sc(NC(=O)Cc3ccc(Oc4ncccc4C(N)=O)c(F)c3)nc2c1]

Step 1. 2-Aminobenzo[d]thiazol-5-ol (0.066 g, 0.40 mmol) was suspended in MeCN (4.5 mL), then 2,2-dimethyloxirane (0.35 ml, 4.0 mmol), $K_2CO_3$ (0.220 g, 1.59 mmol) and water (0.300 mL) were added. The reaction mixture was stirred under microwave irradiation at 120° C. for 30 min. The reaction mixture was diluted with MeOH, concentrated under reduced pressure and purified by silica gel chromatography using DCM/0-15% MeOH as eluents to afford (73 mg, 77% yield) 1-((2-aminobenzo[d]thiazol-5-yl)oxy)-2-methylpropan-2-ol as a clear oil. $^1$H NMR (400 MHz, CDCl$_3$) δ 7.47 (d, J=8.8 Hz, 1H), 7.14 (d, J=2.4 Hz, 1H), 6.82 (dd, J=8.6, 2.4 Hz, 1H), 5.34 (d, J=7.7 Hz, 2H), 3.85 (s, 2H), 3.52 (s, 1H), 1.41-1.37 (m, 6H). LCMS m/z=238.9 (M+H).$^+$ Step 2. In a vial, to intermediate 5 (12.18 mg, 0.04200 mmol) and 1-((2-aminobenzo[d]thiazol-5-yl)oxy)-2-methylpropan-2-ol (10 mg, 0.042 mmol) was added DMF (0.3 mL), BOP (18.56 mg, 0.04200 mmol) and DIEA (0.037 ml, 0.21 mmol). The reaction mixture was stirred at room temperature for 72 h. The reaction mixture was filtered and subjected to reverse phase HPLC purification to afford Example 3 (1.5 mg, 5.4% yield). $^1$H NMR (500 MHz, DMSO-$d_6$) δ 8.30-8.11 (m, 2H), 7.84 (br s, 1H), 7.82 (br s, 1H), 7.79 (br d, J=8.7 Hz, 1H), 7.47-7.30 (m, 2H), 7.30-7.17 (m, 3H), 6.93 (br d, J=8.8 Hz, 1H), 3.86 (s, 2H), 3.78 (s, 2H), 2.55 (s, 1H), 1.83 (br s, 1H), 1.23 (s, 6H). LCMS m/z=511.0 (M+H)+; HPLC purity >94% with retention time 1.45 min. [method B]

Example 4. 2-(4-(2-((5-(1,3-dimethyl-1H-pyrazol-4-yl)benzo[d]thiazol-2-yl)amino)-2-oxoethyl)-2-fluorophenoxy)nicotinamide

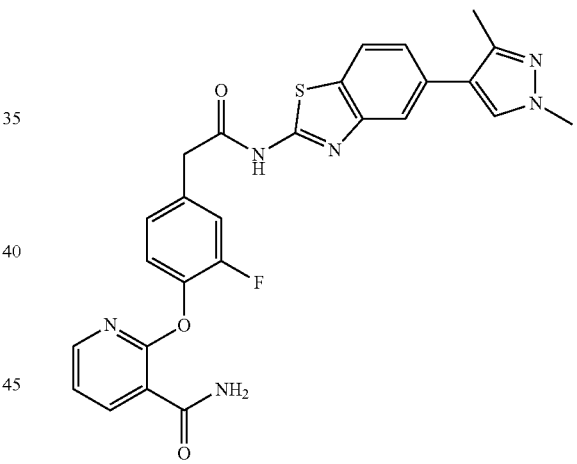

To a vial was added intermediate 8 (25 mg, 0.050 mmol), 1,3-dimethyl-4-(4,4,5,5-tetramethyl-1,3,2-dioxaborolan-2-yl)-1H-pyrazole (16.61 mg, 0.07500 mmol), 3M potassium phosphate tribasic (83 μl, 0.25 mmol) and DMF (1.5 mL). The reaction mixture was degassed with N$_2$, and chloro(2-dicyclohexylphosphino-2',4',6'-tri-i-propyl-1,1'-biphenyl)(2'-amino-1,1'-biphenyl-2-yl) palladium (II) (3.92 mg, 4.99 μmol) was added and the reaction mixture was heated to 70° C. After 1 h, the reaction mixture was allowed to cool to room temperature, filtered and subjected to reverse phase HPLC purification to afford Example 4 (4.4 mg, 14% yield). $^1$H NMR (500 MHz, DMSO-$d_6$) δ 8.21 (br d, J=7.5 Hz, 1H), 8.20-8.16 (m, 1H), 7.95 (d, J=8.2 Hz, 1H), 7.92 (s, 1H), 7.75 (s, 1H), 7.72 (br s, 1H), 7.66 (br s, 1H), 7.37 (br t, J=8.2 Hz, 3H), 7.25 (br dd, J=7.3, 4.4 Hz, 2H), 3.92 (s, 2H), 3.81 (s, 3H), 2.34 (s, 3H), 1.02 (m, 1H). LCMS m/z=517.1 (M+H).$^+$ HPLC purity >98% with retention time 1.41 min. [method B]

Examples 5 and 6 were Prepared as Described Following the General Procedure for Example 4

| Ex # | Structure | Name | HNMR | LCMS (M + H)+ | HPLC retention time (min) |
|---|---|---|---|---|---|
| 5 | 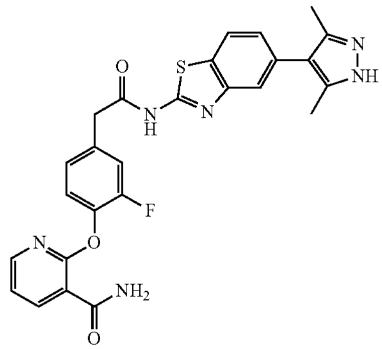 [SMILES: Cc1n[nH]c(C)c1-c1ccc2sc(NC(=O)Cc3ccc(Oc4ncccc4C(N)=O)c(F)c3)nc2c1] | 2-(4-(2-((5-(3,5-dimethyl-1H-pyrazol-4-yl)benzo[d]thiazol-2-yl)amino)-2-oxoethyl)-2-fluorophenoxy)nicotinamide | $^1$H NMR (500 MHz, DMSO-$d_6$) δ 8.30-8.04 (m, 2H), 7.97 (d, J = 8.2 Hz, 1H), 7.88 (br s, 1H), 7.76 (br s, 1H), 7.61 (s, 1H), 7.51-7.29 (m, 2H), 7.28-7.13 (m, 3H), 3.91 (s, 2H), 3.77 (br s, 1H), 2.98 (s, 1H), 2.21 (s, 6H). | 517.2 | 1.23 Method B |
| 6 | 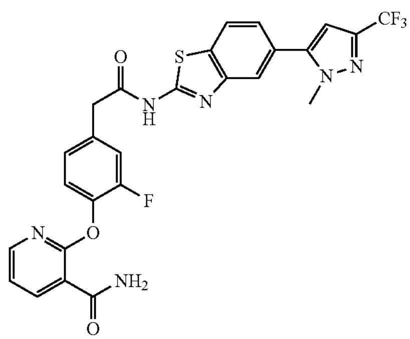 [SMILES: Cn1nc(C(F)(F)F)cc1-c1ccc2sc(NC(=O)Cc3ccc(Oc4ncccc4C(N)=O)c(F)c3)nc2c1] | 2-(2-fluoro-4-(2-((5-(1-methyl-3-(trifluoromethyl)-1H-pyrazol-5-yl)benzo[d]thiazol-2-yl)amino)-2-oxoethyl)phenoxy)nicotinamide | $^1$H NMR (500 MHz, DMSO-$d_6$) δ 12.65 (br s, 1H), 8.22 (dd, J = 7.4, 1.8 Hz, 1H), 8.19 (dd, J = 4.8, 1.7 Hz, 1H), 8.14 (d, J = 8.2 Hz, 1H), 7.96 (s, 1H), 7.72 (br s, 1H), 7.66 (br s, 1H), 7.51 (dd, J = 8.1, 1.2 Hz, 1H), 7.43-7.32 (m, 2H), 7.30-7.17 (m, 2H), 6.94 (s, 1H), 3.97 (s, 3H), 3.94 (s, 2H) | 571.1 | 1.89 Method A |

Example 7. 2-(2-chloro-4-(2-((1-(cyclopropylmethyl)-1H-benzo[d]imidazol-2-yl)amino)-2-oxoethyl)phenoxy)nicotinamide

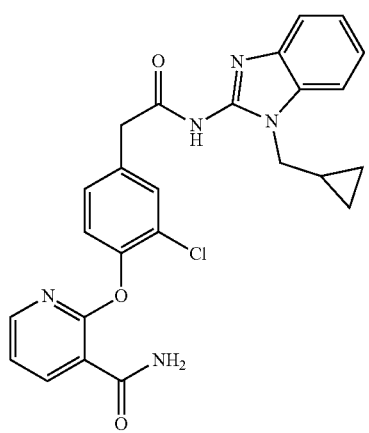 [SMILES: NC(=O)c1cccnc1Oc1ccc(CC(=O)Nc2nc3ccccc3n2CC2CC2)cc1Cl]

Step 1. To commercially available N-(cyclopropylmethyl)benzene-1,2-diamine (0.18 g, 1.1 mmol) in MeOH (4 mL)/H$_2$O (1 mL) was added cyanic bromide (0.17 g, 1.7 mmol). After stirring 24 h, the reaction mixture was concentrated under reduced pressure and treated with con. NH$_4$OH. The solid precipitate was collected and was dried under vacuum to afford 1-(cyclopropylmethyl)-1H-benzo[d]imidazol-2-amine (0.138 g, 66.4% yield) as a red/brown solid. $^1$H NMR (400 MHz, DMSO-$d_6$) δ 7.17 (dt, J=7.6, 0.7 Hz, 1H), 7.12 (d, J=7.4 Hz, 1H), 6.97-6.84 (m, 2H), 6.34 (s, 2H), 3.91 (d, J=7.0 Hz, 2H), 2.73-2.54 (m, 1H), 1.27-1.15 (m, 1H), 0.50-0.37 (m, 4H). LCMS m/z=188.1 (M+H).+

Example 7 was prepared through a BOP coupling of the product of step 1 and intermediate 7 (9.6 mg, 32.8% yield). $^1$H NMR (500 MHz, DMSO-$d_6$) δ 8.48-8.04 (m, 2H), 7.96-7.74 (m, 2H), 7.66-7.48 (m, 3H), 7.34 (br d, J=16.9 Hz, 2H), 7.30-6.85 (m, 3H), 4.00 (br s, 2H), 3.69 (br s, 2H), 1.23 (br s, 2H), 0.43 (brd s, 4H). LCMS m/z=476.1 (M+H).+ HPLC purity >92% with retention time 1.38 min. [method B]

Example 8. 2-(2-fluoro-4-(2-((7-methoxy-[1,2,4]triazolo[1,5-a]pyridin-2-yl)amino)-2-oxoethyl)phenoxy)nicotinamide

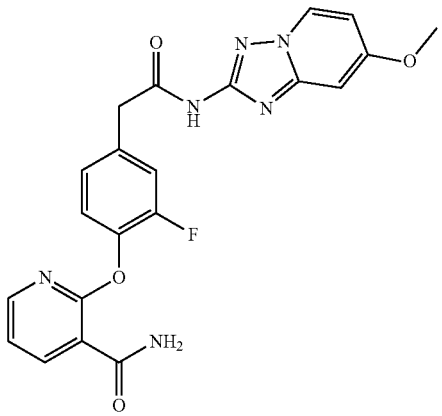 [SMILES: COc1ccn2nc(NC(=O)Cc3ccc(Oc4ncccc4C(N)=O)c(F)c3)nc2c1]

Step 1. To intermediate 2 (0.25 g, 0.86 mmol) and 7-methoxy-[1,2,4]triazolo[1,5-a]pyridin-2-amine (0.14 g, 0.86 mmol) was added THF (3 mL) and pyridine (0.21 mL, 2.6 mmol). After 24 h, the solvents were evaporated and the residue was purified via silica gel chromatography, eluting with DCM/0-100% EtOAc, then DCM/10% MeOH to afford 2-(4-((3-cyanopyridin-2-yl)oxy)-3-fluorophenyl)-N-(7-methoxy-[1,2,4]triazolo[1,5-a]pyridin-2-yl)acetamide (35 mg, 9.7% yield) as a tan solid. $^1$H NMR (400 MHz, CD$_3$OD) δ 8.38-8.28 (m, 2H), 8.27-8.17 (m, 2H), 7.34-7.18 (m, 5H), 4.00-3.89 (m, 2H), 3.34 (s, 3H). LCMS m/z=419.0 (M+H).$^+$ Example 8. The product of step 1 was hydrolyzed as described for intermediate 5 followed by reverse phase HPLC purification (14 mg, 28.9% yield) as a white solid. $^1$H NMR (400 MHz, DMSO-d$_6$) δ 10.96 (br s, 1H), 8.67 (d, J=7.5 Hz, 1H), 8.30-8.15 (m, 2H), 7.86-7.81 (m, 1H), 7.80-7.71 (m, 1H), 7.45-7.30 (m, 2H), 7.27-7.16 (m, 2H), 7.09 (d, J=2.4 Hz, 1H), 6.78 (dd, J=7.5, 2.6 Hz, 1H), 3.90 (s, 3H), 3.88-3.67 (m, 2H). LCMS m/z=436.9 (M+H).$^+$ HPLC purity >95% with retention time 6.07 min. [method C]

Example 9. 2-(4-(2-((6-bromoimidazo[1,2-a]pyridin-2-yl)amino)-2-oxoethyl)-2-chlorophenoxy)nicotinamide

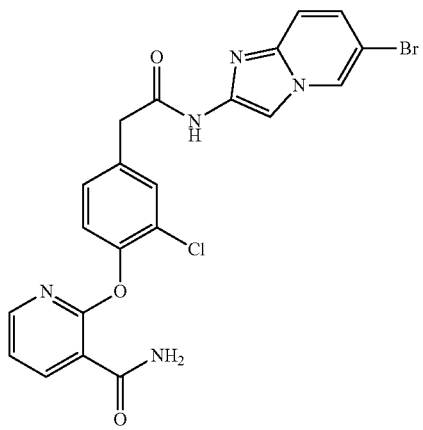 [SMILES: NC(=O)c1cccnc1Oc1ccc(CC(=O)Nc2cn3cc(Br)ccc3n2)cc1Cl]

Example 9 was prepared through a BOP coupling, as described in example 1, of intermediate 7 and 6-bromoimidazo[1,2-a]pyridin-2-amine, and the residue was purified by reverse phase HPLC to afford the desired product (2.6 mg, 1.1% yield). $^1$H NMR (500 MHz, DMSO-d$_6$) δ 8.89 (br s, 1H), 8.21 (dd, J=7.4, 1.7 Hz, 1H), 8.19-8.13 (m, 1H), 8.10 (s, 1H), 7.84 (br s, 1H), 7.79 (br s, 1H), 7.56 (s, 1H), 7.43 (d, J=9.4 Hz, 1H), 7.41-7.28 (m, 3H), 7.24 (dd, J=7.4, 4.9 Hz, 1H), 3.76 (s, 2H). LCMS m/z=500-501.9 (M+H).$^+$ HPLC purity >95% with retention time 1.20 min. [method B]

Example 10. 2-(2-chloro-4-(2-((1-methyl-1H-pyrazolo[3,4-b]pyridin-3-yl)amino)-2-oxoethyl)phenoxy)nicotinamide

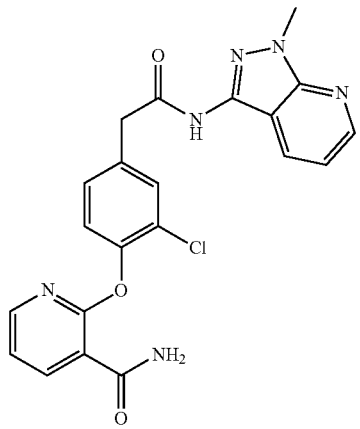 [SMILES: Cn1nc(NC(=O)Cc2ccc(Oc3ncccc3C(N)=O)c(Cl)c2)c2cccnc21]

Step 1. Intermediate 4 (28 mg, 0.097 mmol) was coupled to 1-methyl-1H-pyrazolo[3,4-b]pyridin-3-amine (14 mg, 0.097 mmol) using BOP as described for example 1 to afford 2-(3-chloro-4-((3-cyanopyridin-2-yl)oxy)phenyl)-N-(1-methyl-1H-pyrazolo[3,4-b]pyridin-3-yl)acetamide which was used without further purification. LCMS m/z=419.0 (M+H).$^+$ Step 2. To the intermediate from step 1 was added excess K$_2$CO$_3$ (0.054 g, 0.39 mmol), DMSO (0.3 mL) and 30% H$_2$O$_2$ (0.040 mL, 0.39 mmol). After 72 h, the reaction mixture was quenched by the addition of aq NaSO$_3$, filtered and purified by reverse phase HPLC to afford Example 10 (8 mg, 10% yield). $^1$H NMR (500 MHz, DMSO-d$_6$) δ 11.04 (s, 1H), 8.53 (br d, J=4.0 Hz, 1H), 8.39 (br d, J=7.9 Hz, 1H), 8.22 (dd, J=7.5, 1.7 Hz, 1H), 8.17 (dd, J=4.7, 1.7 Hz, 1H), 7.81 (br s, 1H), 7.77 (br s, 1H), 7.59 (s, 1H), 7.48-7.31 (m, 2H), 7.24 (dd, J=7.3, 4.9 Hz, 1H), 7.15 (dd, J=8.2, 4.3 Hz, 1H), 3.98 (s, 3H), 3.83 (s, 2H). LCMS m/z=437.1 (M+H).$^+$ HPLC purity >99% with retention time 1.23 min. [method B]

Examples 11, 12, 14 and 16 were Prepared as Described Following the General Procedure for Example 1

| Ex # | Structure | Name | HNMR | LCMS (M + H)+ | HPLC retention time (min) |
|---|---|---|---|---|---|
| 11 | 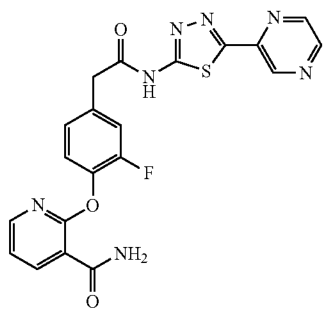 [SMILES: NC(=O)c1cccnc1Oc1ccc(CC(=O)Nc2nnc(-c3cnccn3)s2)cc1F] | 2-(2-fluoro-4-(2-oxo-2-((5-(pyrazin-2-yl)-1,3,4-thiadiazol-2yl)amino)ethyl)phenoxy) nicotinamide | ¹H NMR (500 MHz, DMSO-d₆) δ 9.41 (s, 1H), 8.76 (s, 2H), 8.21 (dd, J = 7.4, 1.8 Hz, 1H), 8.18 (dd, J = 4.7, 1.7 Hz, 1H), 7.72 (br s, 1H), 7.65 (br s, 1H), 7.41-7.33 (m, 2H), 7.27-7.21 (m, 2H), 3.96 (s, 2H), 3.31 (s, 1H) | 452.0 | 1.11 Method B |
| 12 | 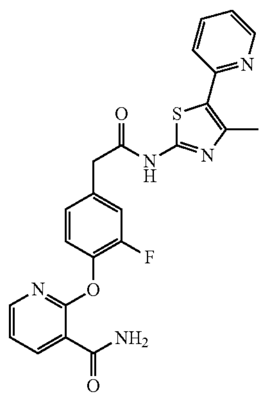 [SMILES: Cc1nc(NC(=O)Cc2ccc(Oc3ncccc3C(N)=O)c(F)c2)sc1-c1ccccn1] | 2-(2-fluoro-4-(2-((4-methyl-5-(pyridin-2-yl)thiazol-2-yl)amino)-2-oxoethyl)phenoxy)nicotinamide | ¹H NMR (500 MHz, DMSO-d₆) δ 8.57 (br d, J = 4.2 Hz, 1H), 8.22 (dd, J = 7.4, 1.8 Hz, 1H), 8.19 (dd, J = 4.8, 1.8 Hz, 1H), 7.84 (td, J = 7.8, 1.6 Hz, 1H), 7.71 (br s, 1H), 7.65 (br s, 1H and brd d, J = 8.0 Hz, 1H), 7.39-7.31 (m, 2H), 7.28-7.21 (m, 4H), 3.85 (s, 2H), 2.57 (s, 3H). | 463.9 | 1.27 Method B |
| 14 | 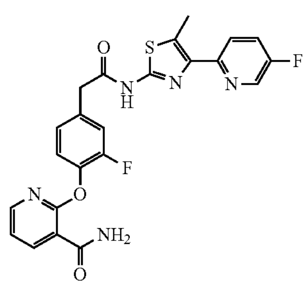 [SMILES: Cc1sc(NC(=O)Cc2ccc(Oc3ncccc3C(N)=O)c(F)c2)nc1-c1ccc(F)cn1] | 2-(2-fluoro-4-(2-((4-(5-fluoropyridin-2-yl)-5-methylthiazol-2-yl)amino)-2-oxoethyl)phenoxy)nicotinamide | ¹H NMR (500 MHz, DMSO-d₆) δ 8.61 (d, J = 2.7 Hz, 1H), 8.22-8.17 (m, 2H), 8.00 (dd, J = 8.9, 4.6 Hz, 1H), 7.85-7.76 (m, 3H), 7.40-7.31 (m, 3H), 7.27-7.19 (m, 2H), 3.84 (s, 2H), 2.69 (s, 3H). ). | 482.0 | 1.61 Method A |
| 16 | 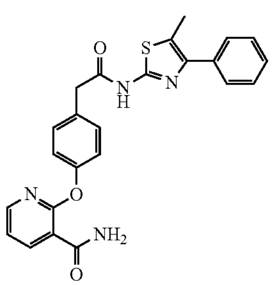 [SMILES: Cc1sc(NC(=O)Cc2ccc(Oc3ncccc3C(N)=O)cc2)nc1-c1ccccc1] | 2-(4-(2-((5-methyl-4-phenylthiazol-2-yl)amino)-2-oxoethyl)phenoxy) nicotinamide | ¹H NMR (500 MHz, DMSO-d₆) δ 8.21-8.11 (m, 2H), 7.79 (br s, 1H), 7.75 (br s, 1H), 7.64 (br d, J = 7.6 Hz, 2H), 7.45 (br t, J = 7.6 Hz, 2H), 7.38 (br d, J = 8.2 Hz, 2H), 7.37-7.29 (m, 1H), 7.21 (dd, J = 7.2, 5.0 Hz, 1H), 7.15 (br d, J = 8.5 Hz, 2H), 3.78 (s, 2H), 3.36 (s, 1H), 2.46 (s, 3H). | 445.0 | 1.75 Method B |

Example 13. 2-(2-fluoro-4-(2-((4-(6-fluoropyridin-2-yl)-5-methylthiazol-2-yl)amino)-2-oxoethyl)phenoxy)nicotinamide

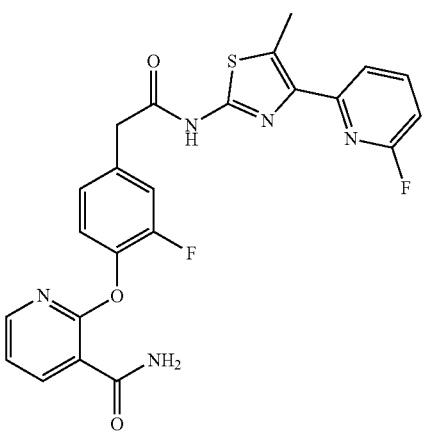 [SMILES: Cc1sc(NC(=O)Cc2ccc(Oc3ncccc3C(N)=O)c(F)c2)nc1-c1cccc(F)n1]

Step 1. To 6-fluoropicolinic acid (980 mg, 6.95 mmol) was in DCM (50 mL) was added DMF (50 µL, 0.65 mmol), followed by dropwise addition of oxalyl chloride (650 µL, 7.43 mmol). After 1.2 h, N,O-dimethylhydroxylamine HCl (1.05 g, 10.8 mmol) was added and the reaction mixture was cooled to 0° C. Pyridine (2.6 mL, 32 mmol) was added and the reaction mixture was allowed to warm to room temperature and stir 72 h. The reaction mixture was quenched by the addition of water and the layers were partitioned. The aqueous phase was extracted with dichloromethane and the combined organic layer was washed with brine, dried ($MgSO_4$), filtered and concentrated under reduced pressure to afford 6-fluoro-N-methoxy-N-methylpicolinamide (1.09 g, 85.0% yield) as a clear pale yellow oil. $^1$H NMR (500 MHz, $CD_3Cl$) δ 7.88 (q, J=7.8 Hz, 1H), 7.56 (br. s., 1H), 7.02 (dd, J=8.2, 2.4 Hz, 1H), 3.79 (br. s., 3H), 3.37 (br. s., 3H). LCMS m/z=185.0 (M+H).$^+$ Step 2. To a 0° C. solution of 6-fluoro-N-methoxy-N-methylpicolinamide (1.23 g, 6.68 mmol) in THF (40 mL) was dropwise added $CH_3CH_2MgBr$ (9 ml, 30 mmol). After 1.5 h at 0° C. the reaction mixture was carefully quenched by the addition of aqueous $NH_4Cl$. The layers were partitioned and the aqueous layer was extracted with $Et_2O$. The combined organic layer was washed with brine, dried ($MgSO_4$), filtered and concentrated under reduced pressure to dryness. The residue was purified via silica gel chromatography using hexanes to 30% EtOAc as eluents. 1-(6-Fluoropyridin-2-yl)propan-1-one (684 mg, 66.9% yield) was obtained as clear colorless oil. $^1$H NMR (500 MHz, $CD_3Cl$) δ 7.86-8.05 (m, 2H), 7.12 (ddd, J=5.6, 3.1, 2.9 Hz, 1H), 3.16 (q, J=7.3 Hz, 2H), 1.19 (t, J=7.3 Hz, 3H). LCMS m/z=154.0 (M+H).$^+$ Step 3. To 1-(6-fluoropyridin-2-yl)propan-1-one (680 mg, 4.44 mmol) in AcOH (30 mL, 524 mmol), warmed to 90° C., was added $Br_2$ (230 µL, 4.46 mmol). After 15 min, the reaction mixture was concentrated in vacuo. To the residue was added aq. $NaHCO_3$. The aqueous layer was extracted with $Et_2O$. The combined organic layer was washed with brine, dried ($MgSO_4$), filtered and concentrated to dryness to afford 2-bromo-1-(6-fluoropyridin-2-yl)propan-1-one (1.01 g, 98.0% yield) as clear pale yellow oil. $^1$H NMR (500 MHz, $CD_3Cl$) δ 7.88-8.05 (m, 2H), 7.17 (dd, J=7.8, 2.6 Hz, 1H), 5.85 (q, J=6.7 Hz, 1H), 1.88 (d, J=6.7 Hz, 3H).

Step 4. To 2-bromo-1-(6-fluoropyridin-2-yl)propan-1-one (1.00 g, 4.31 mmol) in EtOH (30 mL) was added thiourea (335 mg, 4.40 mmol). The reaction mixture was warmed to 80° C. for 16 h. After cooling to room temperature, the solvent volume was reduced under vacuum and the remaining mixture was placed in the freezer for 2 h. The precipitated solids were filtered off and washed with $Et_2O$. The solid was suspended in water and $NH_4OH$ was added. The aqueous layer was extracted with $Et_2O$. The combined organic layer was washed with brine, dried ($MgSO_4$), filtered and concentrated to dryness to afford 4-(6-fluoropyridin-2-yl)-5-methylthiazol-2-amine (760 mg, 84% yield) as an off-white solid. $^1$H NMR (500 MHz, DMSO-d6) δ 7.98 (q, J=8.3 Hz, 1H), 7.78 (dd, J=7.6, 2.4 Hz, 1H), 6.99 (dd, J=8.1, 2.6 Hz, 1H), 6.89 (s, 2H), 2.61 (s, 3H). LCMS m/z=209.7 (M+H).$^+$ Example 13 (3.4 mg, 5.05% yield) was obtained through BOP coupling as described in example 1 substituting 4-(6-fluoropyridin-2-yl)-5-methylthiazol-2-amine (23.8 mg, 0.114 mmol) for 7-methoxy-4,5-dihydronaphtho[1,2-d]thiazol-2-amine. $^1$H NMR (500 MHz, DMSO-$d_6$) δ 12.45 (br s, 1H), 8.24-8.17 (m, 2H), 8.08 (q, J=8.2 Hz, 1H), 7.89 (br d, J=7.6 Hz, 1H), 7.83 (br s, 1H), 7.81-7.77 (m, 1H), 7.44-7.31 (m, 2H), 7.27-7.21 (m, 2H), 7.10 (dd, J=8.1, 2.0 Hz, 1H), 3.86 (s, 2H), 2.73 (s, 3H). LCMS m/z=482.0 (M+H).$^+$ HPLC purity 100% with retention time 1.72 min. [method B]

Example 15. 2-(4-(2-(benzo[d]thiazol-2-ylamino)-2-oxoethyl)-2-fluorophenoxy)nicotinamide

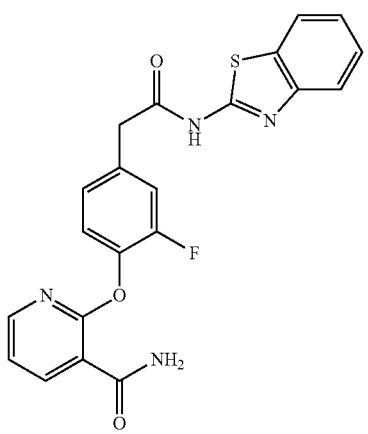 [SMILES: NC(=O)c1cccnc1Oc1ccc(CC(=O)Nc2nc3ccccc3s2)cc1F]

Example 15 (0.6 mg, 2.2% yield) was made from intermediate 8 by dehalogenation during a Suzuki reaction that involved 1,3-dimethyl-4-(4,4,5,5-tetramethyl-1,3,2-dioxaborolan-2-yl)-1H-pyrazole. $^1$H NMR (500 MHz, DMSO-$d_6$) δ 8.25-8.15 (m, 2H), 7.88 (br d, J=7.6 Hz, 1H), 7.83 (br s, 1H), 7.79 (br s, 1H), 7.66 (br d, J=8.2 Hz, 1H), 7.45-7.31 (m, 3H), 7.27-7.14 (m, 3H), 3.82 (s, 2H). LCMS m/z=422.8 (M+H).$^+$ HPLC purity >97% with retention time 1.48 min. [method A]

Example 17. 2-(2-fluoro-4-(2-((4-(1-methyl-2-oxo-1,2-dihydropyridin-4-yl)thiazol-2-yl)amino)-2-oxoethyl)phenoxy)nicotinamide

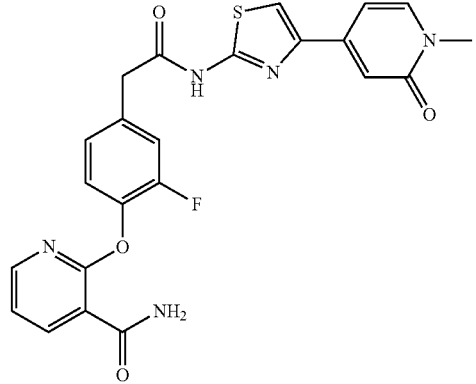 [SMILES: Cn1ccc(-c2csc(NC(=O)Cc3ccc(Oc4ncccc4C(N)=O)c(F)c3)n2)cc1=O]

Step 1. To a suspension of intermediate 1 (1.0 g, 3.7 mmol) in DCE (10 mL) was added SOCl$_2$ (2.7 mL, 37 mmol) and the reaction mixture was heated to 50° C. After 1 h, the solvents were removed under reduced pressure and THF (10 ml), 4-bromothiazol-2-amine (0.70 g, 4.0 mmol), and DIEA (2 mL, 11 mmol) were added. After 24 h, the solvents were removed under reduced pressure and residue was purified via silica gel chromatography to afford (1.1 g, 71% yield) of N-(4-bromothiazol-2-yl)-2-(4-((3-cyanopyridin-2-yl)oxy)-3-fluorophenyl)acetamide as a brown solid. LCMS(ESI) m/z: 432.7-434.7 (M+H).$^+$ $^1$H NMR (400 MHz, CD$_3$OD) δ 8.32 (dd, J=5.0, 1.9 Hz, 1H), 8.27 (dd, J=7.6, 1.9 Hz, 1H), 7.39-7.25 (m, 4H), 7.08 (s, 1H), 3.90 (s, 2H).

Step 2. N-(4-bromothiazol-2-yl)-2-(4-((3-cyanopyridin-2-yl)oxy)-3-fluorophenyl)acetamide (1.0 g, 2.3 mmol) was oxidized in a similar manner as intermediate 5 to afford 2-(4-(2-((4-bromothiazol-2-yl)amino)-2-oxoethyl)-2-fluorophenoxy)nicotinamide, HCl (0.98 g, 87% yield). LCMS (ESI) (ESI) m/z: 450.9-452.9 (M+H).$^+$ $^1$H NMR (400 MHz, DMSO-$d_6$) δ 12.72 (s, 1H), 8.24-8.17 (m, 2H), 7.87-7.81 (m, 1H), 7.80-7.73 (m, 1H), 7.45-7.30 (m, 3H), 7.25 (dd, J=7.4, 5.0 Hz, 1H), 7.21 (dd, J=8.8, 1.1 Hz, 1H), 3.86 (s, 2H)

Step 3. Example 17 (2.4 mg, 4.0% yield) was prepared from the product of step 2 via a Suzuki cross coupling manner as previously described for example 4. $^1$H NMR (500 MHz, DMSO-$d_6$) δ 8.26-8.11 (m, 2H), 7.92 (s, 1H), 7.83 (br s, 1H), 7.79 (br s, 1H), 7.74 (d, J=7.3 Hz, 1H), 7.43-7.31 (m, 2H), 7.27-7.18 (m, 2H), 6.91 (s, 1H), 6.74 (br d, J=7.0 Hz, 1H), 3.84 (s, 2H), 3.41 (s, 3H). LCMS m/z=480.1 (M+H).$^+$ HPLC purity 94% with retention time 1.10 min. [method B]

Example 18. 2-(2-fluoro-4-(2-oxo-2-((4-(2-oxo-1,2-dihydropyridin-4-yl)thiazol-2-yl)amino)ethyl)phenoxy)nicotinamide

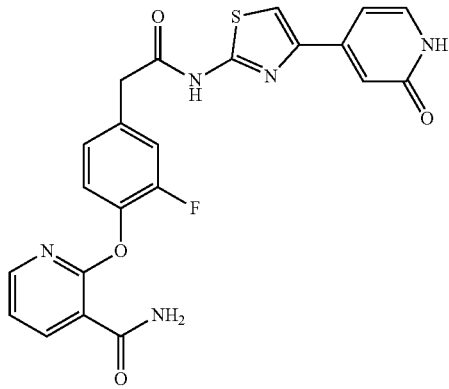 [SMILES: NC(=O)c1cccnc1Oc1ccc(CC(=O)Nc2nc(-c3cc[nH]c(=O)c3)cs2)cc1F]

Step 1. To 4-bromopyridin-2(1H)-one (0.90 g, 5.2 mmol) in dioxane (10 mL) was added 5,5,5',5'-tetramethyl-2,2'-bi(1,3,2-dioxaborinane) (1.3 g, 5.7 mmol), potassium acetate (1.5 g, 16 mmol). The reaction mixture was degassed with N$_2$ for 15 min. and PdCl$_2$(dppf)DCM was added (0.21 g, 0.26 mmol) and the reaction mixture was heated to 90° C. for 24 h. The reaction mixture was partitioned with water (20 mL) and ethyl acetate (50 mL). The aqueous layer was extracted with ethyl acetate (2×20 mL). The combined organic layers were washed with brine (15 mL) and dried (MgSO$_4$), filtered and concentrated under reduced pressure to afford 4-(5,5-dimethyl-1,3,2-dioxaborinan-2-yl)pyridin-2(1H)-one as a dark oil LCMS m/z=208 (M+H).$^+$ Step 2. Example 18 (3.7 mg, 6.0% yield) was prepared from the product of step 2 in same manner as described for example 17 using 4-(5,5-dimethyl-1,3,2-dioxaborinan-2-yl)pyridin-2(1H)-one. $^1$H NMR (500 MHz, DMSO-$d_6$) δ 8.29-8.13 (m, 2H), 7.85 (s, 1H), 7.71 (br s, 1H), 7.66 (br s, 1H), 7.46-7.28 (m, 3H), 7.27-7.04 (m, 2H), 6.84 (s, 1H), 6.68 (br d, J=6.7 Hz, 1H), 3.83 (s, 2H), 2.99 (s, 1H). LCMS m/z=465.9 (M+H).$^+$ HPLC purity 96% with retention time 1.04 min. [method A]

Example 19. methyl (4-(2-(2-(4-((3-carbamoylpyridin-2-yl)oxy)-3-fluorophenyl)acetamido)-5-methylthiazol-4-yl)pyridin-2-yl)carbamate

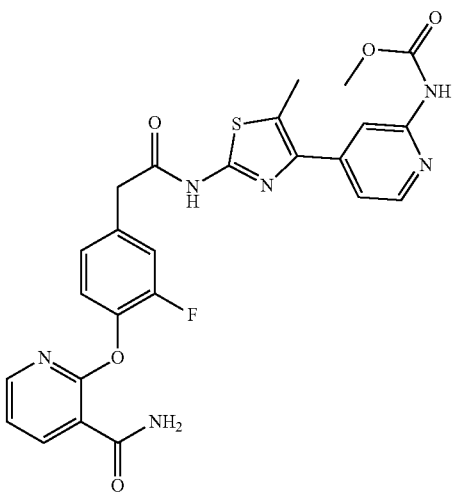 [SMILES: COC(=O)Nc1cc(-c2nc(NC(=O)Cc3ccc(Oc4ncccc4C(N)=O)c(F)c3)sc2C)ccn1]

Step 1. To intermediate 1 (0.3 g, 1 mmol) in THF (2 mL) was added 4-bromo-5-methylthiazol-2-amine (0.2 g, 1 mmol) and pyridine (0.3 mL, 3 mmol) and the reaction mixture was stirred for 18 h. The reaction mixture was concentrated under reduced pressure and the residue was purified via silica gel chromatography to afford N-(4-bromo-5-methylthiazol-2-yl)-2-(4-((3-cyanopyridin-2-yl)oxy)-3-fluorophenyl)acetamide (0.46 g, 99% yield). LCMS(ESI) m/z: 444-446.8 (M+H).+ 1H NMR (400 MHz, DMSO-d6) δ 12.54 (s, 1H), 8.47 (dd, J=7.5, 2.0 Hz, 1H), 8.43-8.36 (m, 1H), 7.45-7.32 (m, 3H), 7.23 (dd, J=8.3, 1.0 Hz, 1H), 3.85 (s, 2H), 2.27 (s, 3H).

Step 2. A mixture of 2-(dicycloxhexylphosphino)-2',4',6'-triisopropylbiphenyl (0.13 g, 0.27 mmol), KOAc (4 g, 40 mmol), 2nd generation xphos precatalyst (0.1 g, 0.1 mmol), methyl (4-chloropyridin-2-yl)carbamate (2.5 g, 13 mmol) and hypodiboric acid (1.8 g, 20 mmol) in EtOH (130 mL) was degassed three times via vacuum/N2 fill cycle. The reaction mixture was heated at 80° C. for 3 h. The solvent was removed via vacuum and the solid was suspended with mixture of methanol and DCM. The suspension was filtered and the filtrate was concentrated to give (2-((methoxycarbonyl)amino)pyridin-4-yl)boronic acid as a yellow solid. LCMS(ESI) m/z: 197.1 (M+H).+

Step 3. Example 19 (1 mg, 3% yield) was prepared from the product of step 2 in a similar manner as example 4 using N-(4-bromo-5-methylthiazol-2-yl)-2-(4-((3-cyanopyridin-2-yl)oxy)-3-fluorophenyl)acetamide and (2-((methoxycarbonyl)amino)pyridin-4-yl)boronic acid. 1H NMR (500 MHz, DMSO-d6) δ 8.30 (d, J=5.2 Hz, 1H), 8.21 (br d, J=4.0 Hz, 2H), 8.19 (s, 1H), 7.83 (br s, 1H), 7.79 (br s, 1H), 7.39-7.31 (m, 3H), 7.27-7.23 (m, 1H), 7.21 (br d, J=8.2 Hz, 1H), 3.91 (s, 1H), 3.77 (br s, 2H), 3.70 (s, 3H), 2.56 (s, 3H), 1.65 (s, 1H). LCMS m/z=537.1 (M+H).+ HPLC purity 98% with retention time 1.46 min. [method A]

Example 20. 2-(2-fluoro-4-(2-((5-methyl-4-(1-methyl-6-oxo-1,6-dihydropyridin-3-yl)thiazol-2-yl)amino)-2-oxoethyl)phenoxy)nicotinamide

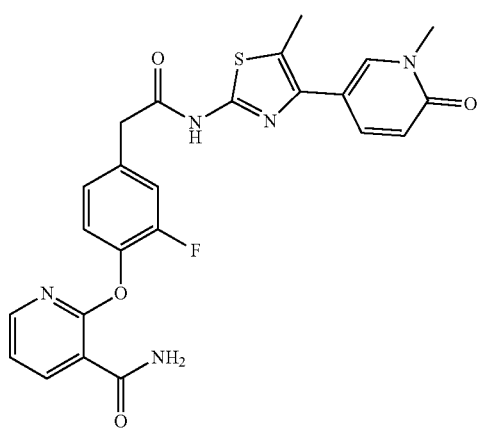 [SMILES: Cc1sc(NC(=O)Cc2ccc(Oc3ncccc3C(N)=O)c(F)c2)nc1-c1ccc(=O)n(C)c1]

Step 1. To 5-bromo-1-methylpyridin-2(1H)-one (0.75 g, 3.9 mmol) in dioxane was added 5,5,5',5'-tetramethyl-2,2'-bi(1,3,2-dioxaborinane) (1.0 g, 4.4 mmol), KOAc (1.2 g, 12 mmol). The reaction mixture was degassed with N2, then PdCl2(dppf)-DCM (0.16 g, 0.19 mmol) was added and the reaction mixture was heated to 90° C. for 18 h. The reaction mixture was allowed to cool, filtered and partitioned with water (20 mL) and EtOAc (50 mL). The aqueous layer was extracted with EtOAc (2×20 mL). The combined organic layers were washed with brine (15 mL) and dried (MgSO4), filtered and concentrated under reduced pressure to afford 5-(5,5-dimethyl-1,3,2-dioxaborinan-2-yl)-1-methylpyridin-2(1H)-one (0.67 g, 76% yield) as a dark oil. LCMS m/z=222 (M+H).+

Step 2. Example 20 (1.8 mg, 5.0% yield) was prepared from the product of step 1 in a similar manner used for example 4 using 5-(5,5-dimethyl-1,3,2-dioxaborinan-2-yl)-1-methylpyridin-2(1H)-one and N-(4-bromo-5-methylthiazol-2-yl)-2-(4-((3-cyanopyridin-2-yl)oxy)-3-fluorophenyl)acetamide. 1H NMR (500 MHz, DMSO-d6) δ 8.21 (br d, J=7.5 Hz, 1H), 8.18 (br d, J=2.9 Hz, 1H), 7.89 (br s, 1H), 7.73 (br dd, J=9.3, 2.3 Hz, 2H), 7.63 (br s, 1H), 7.41-7.29 (m, 2H), 7.24 (dd, J=7.3, 5.0 Hz, 1H), 7.21 (br d, J=8.2 Hz, 1H), 6.48 (d, J=9.3 Hz, 1H), 3.81 (s, 2H), 3.51 (s, 3H), 2.42 (s, 3H), 1.25 (br s, 1H). LCMS m/z=494.2 (M+H).+ HPLC purity 92% with retention time 1.20 min. [method A]

Example 21. 2-(4-(2-((4-(1-(difluoromethyl)-6-oxo-1,6-dihydropyridin-3-yl)-5-methylthiazol-2-yl)amino)-2-oxoethyl)-2-fluorophenoxy)nicotinamide

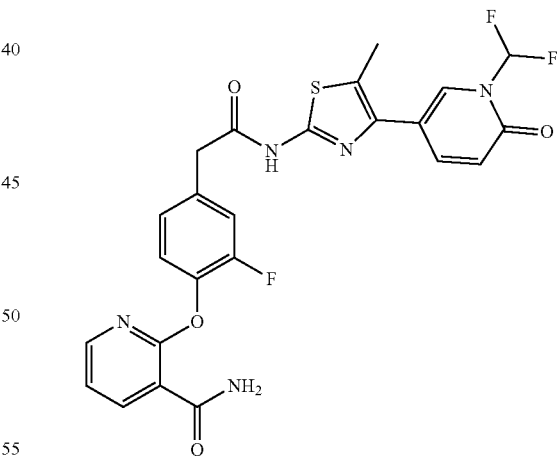

Example 21 (11 mg, 31% yield) was prepared in a similar manner as example 20 substituting 5-bromo-1-(difluoromethyl)pyridin-2(1H)-one for 5-bromo-1-methylpyridin-2(1H)-one. 1H NMR (500 MHz, DMSO-d6) δ 12.27 (br s, 1H), 8.28-8.13 (m, 2H), 7.94-7.85 (m, 3H), 7.71 (br s, 1H), 7.65 (br s, 1H), 7.41-7.30 (m, 2H), 7.28-7.14 (m, 2H), 6.63 (d, J=9.3 Hz, 1H), 3.83 (s, 2H), 2.45 (s, 3H). LCMS m/z=529.9 (M+H).+ HPLC purity 100% with retention time 1.42 min. [method B]

Example 22. 2-(2-chloro-4-(2-((5-methyl-4-(6-methylpyridin-2-yl)thiazol-2-yl)amino)-2-oxoethyl)phenoxy)nicotinamide

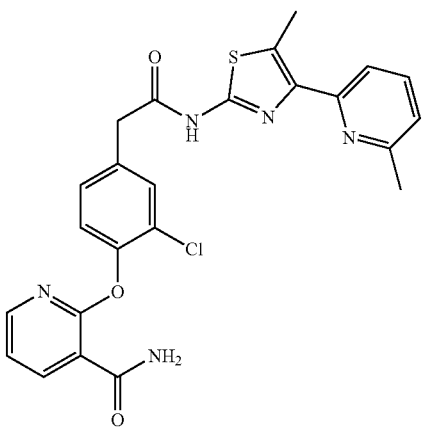 [SMILES: Cc1cccc(-c2nc(NC(=O)Cc3ccc(Oc4ncccc4C(N)=O)c(Cl)c3)sc2C)n1]

Step 1. To 1-(6-methylpyridin-2-yl)propan-1-one (0.3 g, 2 mmol) and AcOH (3 mL), heated to 90° C., was added Br$_2$ (0.1 mL, 2 mmol) in AcOH (1 mL). After 1 h, the solvents were removed under reduced pressure and to the residue was added EtOH (15 mL) and thiourea (0.15 g, 2.0 mmol) and the reaction mixture was heated to 60° C. for 72 h. The solvents were removed under reduced pressure and the residue was partitioned with dil. NH$_4$OH (20 mL) and EtOAc (50 mL). The aqueous layer was extracted with ethyl acetate (2×20 mL). The combined organic layers were washed with brine (15 mL) and dried (MgSO$_4$) to afford 5-methyl-4-(6-methylpyridin-2-yl)thiazol-2-amine (0.3 g, 70% yield) of a tan solid. $^1$H NMR (400 MHz, CDCl$_3$) δ 7.68-7.51 (m, 2H), 7.05 (dd, J=7.3, 1.1 Hz, 1H), 4.91 (br s, 2H), 2.68 (s, 3H), 2.61 (s, 3H). LCMS(ESI) m/z: 206.0 (M+H).$^+$ Step 3. Example 22 (2 mg, 3% yield) was obtained in a similar manner as example 2 using intermediate 7 and 5-methyl-4-(6-methylpyridin-2-yl)thiazol-2-amine. $^1$H NMR (500 MHz, DMSO-d$_6$) δ 12.39 (s, 1H), 8.26-8.20 (m, 1H), 8.20-8.15 (m, 1H), 7.81 (br s, 1H), 7.78-7.72 (m, 3H), 7.57 (s, 1H), 7.31-7.21 (m, 2H), 7.19-7.09 (m, 2H), 3.84 (s, 2H), 2.75 (s, 3H), 2.52 (s, 3H), LCMS m/z=494.0 (M+H).$^+$ HPLC purity 96% with retention time 1.57 min. [method B]

Example 23. 2-(2-chloro-4-(2-((4-cyclobutyl-5-(pyridin-2-yl)thiazol-2-yl)amino)-2-oxoethyl)phenoxy)nicotinamide

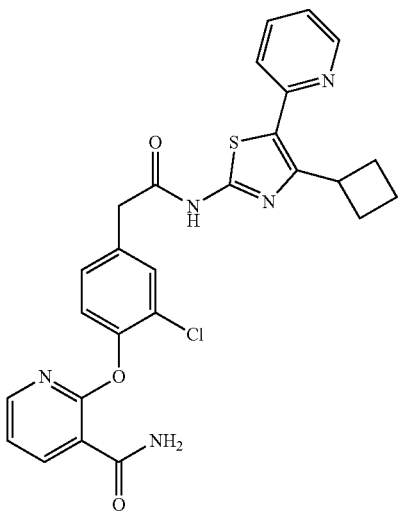 [SMILES: NC(=O)c1cccnc1Oc1ccc(CC(=O)Nc2nc(C3CCC3)c(-c3ccccn3)s2)cc1Cl]

Step 1. 1-cyclobutyl-2-(pyridin-2-yl)ethanone (2.40 g, 13.7 mmol) and NaOAc (1.24 g, 15.1 mmol) were combined and dissolved in AcOH (75 mL). Br$_2$ (0.5 mL, 9 mmol) was added to the reaction mixture in one portion. The reaction mixture was stirred at rt for 20 min., then concentrated under reduced pressure. To the residue was added water and was extracted with EtOAc (2×100 mL). The combined organic extracts were washed twice with aq. NaHCO$_3$, brine, dried (MgSO$_4$), filtered and then concentrated to dryness. The residue was purified by silica gel chromatography using hexanes/EtOAc. 2-Bromo-1-cyclobutyl-2-(pyridin-2-yl)ethanone (2 g, 60% yield) was obtained as pale yellow solid. $^1$H NMR (500 MHz, CDCl$_3$) δ 8.52 (d, J=4.88 Hz, 1H) 7.72 (td, J=7.71, 1.68 Hz, 1H) 7.56 (d, J=7.93 Hz, 1H) 7.23 (dd, J=7.48, 4.73 Hz, 1H) 5.53 (s, 1H) 3.64 (quin, J=8.47 Hz, 1H) 2.18-2.40 (m, 2H) 2.00-2.18 (m, 2H) 1.87-2.00 (m, 1H) 1.74-1.87 (m, 1H). LCMS m/z=254.0, 256.0 (M+H).$^+$ Step 2. To 2-bromo-1-cyclobutyl-2-(pyridin-2-yl)ethanone (2 g, 8 mmol) in EtOH (50 mL), K$_2$CO$_3$ (1.1 g, 8.1 mmol) was added followed by thiourea (0.6 g mg, 8 mmol). The reaction mixture was warmed to 60° C. for 18 h, cooled and the reaction mixture was filtered. The filtrate was concentrated under reduced pressure. To the residue was added water and was extracted with EtOAc (2×100 mL). The combined organic layers were washed with brine, dried (MgSO$_4$), filtered and then concentrated to dryness. The residue was triturated in DCM and hexanes. The solids were filtered off and washed with hexanes to afford 4-cyclobutyl-5-(pyridin-2-yl)thiazol-2-amine (1.3 g, 74% yield) was obtained as tan solid. $^1$H NMR (500 MHz, DMSO-d$_6$) δ 8.65 (s, 0.5H) 8.34-8.56 (m, 1H) 7.59-7.83 (m, 1H) 7.31-7.44 (m, 1H) 7.20 (s, 1.5H) 7.02-7.16 (m, 1H) 4.01 (quin, J=8.62 Hz, 0.4H) 3.91 (quin, J=8.55 Hz, 0.6H) 2.30-2.46 (m, 2H) 2.10-2.30 (m, 2H) 1.94 (spt, J=9.41 Hz, 1H) 1.70-1.87 (m, 1H). LCMS m/z=232.0 (M+H).$^+$ Step 3. Example 23 (5 mg, 7% yield) was obtained in similar manner described for example 2 using intermediate 7 and 4-cyclobutyl-5-(pyridin-2-yl)thiazol-2-amine $^1$H NMR (500 MHz, DMSO-d$_6$) δ 8.55 (br d, J=4.3 Hz, 1H), 8.23 (br d, J=7.4 Hz, 1H), 8.16 (br d, J=3.4 Hz, 1H), 7.83 (t, J=7.7 Hz, 1H), 7.69 (br s, 1H), 7.64 (br s, 1H), 7.55 (s, 1H), 7.50 (d, J=8.0 Hz, 1H), 7.36 (q, J=8.3 Hz, 2H), 7.25 (td, J=8.0, 5.0 Hz, 2H), 4.00 (quin, J=8.3 Hz, 1H), 3.85 (s, 2H), 2.43-2.24 (m, 4H), 2.00 (sxt, J=9.3 Hz, 1H), 1.93-1.81 (m, 1H)

LCMS m/z=520.2 (M+H).$^+$ HPLC purity 95% with retention time 1.91 min. [method A]

The following examples 24-48, were prepared as described following the general procedure used for Example 4

| Ex # | Structure | Name | HNMR | LCMS (M + H)+ | HPLC retention time (min) |
|---|---|---|---|---|---|
| 24 | 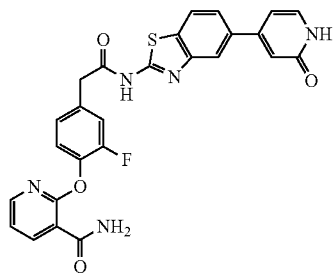 [SMILES: NC(=O)c1cccnc1Oc1ccc(CC(=O)Nc2nc3cc(-c4cc[nH]c(=O)c4)ccc3s2)cc1F] | 2-(2-fluoro-4-(2-oxo-2-((5-(2-oxo-1,2-dihydropyridin-4-yl)benzo[d]thiazol-2-yl)amino)ethyl)phenoxy)nicotinamide | $^1$H NMR (500 MHz, DMSO-d$_6$) δ 8.28-8.16 (m, 2H), 8.10 (br d, J = 8.2 Hz, 1H), 8.06 (s, 1H), 7.84 (br s, 1H), 7.80 (br s, 1H), 7.65 (br d, J = 7.9 Hz, 1H), 7.48 (br d, J = 6.7 Hz, 1H), 7.38 (br d, J = 8.5 Hz, 2H), 7.26 (br d, J = 7.0 Hz, 2H), 6.70 (s, 1H), 6.63 (br d, J = 6.4 Hz, 1H), 3.94 (s, 1H), 3.92 (s, 2H), 2.09 (s, 1H) | 516.1 | 1.23 Method A |
| 25 | 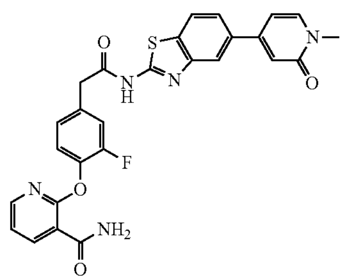 [SMILES: Cn1ccc(-c2ccc3sc(NC(=O)Cc4ccc(Oc5ncccc5C(N)=O)c(F)c4)nc3c2)cc1=O] | 2-(2-fluoro-4-(2-((5-(1-methyl-2-oxo-1,2-dihydropyridin-4-yl)benzo[d]thiazol-2-yl)amino)-2-oxoethyl)phenoxy)nicotinamide | $^1$H NMR (500 MHz, DMSO-d$_6$) δ 8.25-8.17 (m, 2H), 8.13-8.04 (m, 2H), 7.85 (br s, 1H), 7.82 (br s, 1H), 7.80 (d, J = 7.2 Hz, 1H), 7.66 (dd, J = 8.3, 1.5 Hz, 1H), 7.46-7.35 (m, 2H), 7.25 (br dd, J = 7.1, 4.7 Hz, 2H), 6.78 (d, J = 1.7 Hz, 1H), 6.70 (dd, J = 7.1, 1.9 Hz, 1H), 3.93 (s, 2H), 2.55 (s, 3H) | 530.1 | 1.27 Method A |
| 26 | 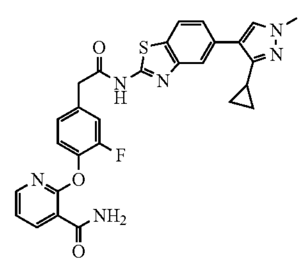 [SMILES: Cn1cc(-c2ccc3sc(NC(=O)Cc4ccc(Oc5ncccc5C(N)=O)c(F)c4)nc3c2)c(C2CC2)n1] | 2-(4-(2-((5-(3-cyclopropyl-1-methyl-1H-pyrazol-4-yl)benzo[d]thiazol-2-yl)amino)-2-oxoethyl)-2-fluorophenoxy)nicotinamide | $^1$H NMR (500 MHz, DMSO-d$_6$) δ 8.27-8.14 (m, 2H), 7.97 (d, J = 8.2 Hz, 1H), 7.91 (s, 2H), 7.86 (br s, 1H), 7.78 (br s, 1H), 7.50 (d, J = 8.2 Hz, 1H), 7.43-7.32 (m, 2H), 7.30-7.21 (m, 2H), 3.91 (s, 2H), 3.77 (s, 3H), 1.99-1.88 (m, 1H), 0.94-0.86 (m, 2H), 0.84-0.77 (m, 2H) | 543.1 | 1.64 Method A |
| 27 | 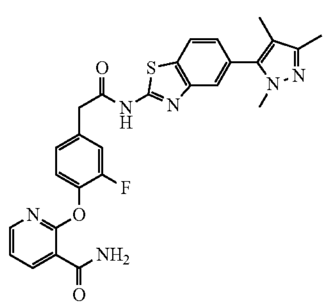 [SMILES: Cc1nn(C)c(-c2ccc3sc(NC(=O)Cc4ccc(Oc5ncccc5C(N)=O)c(F)c4)nc3c2)c1C] | 2-(2-fluoro-4-(2-oxo-2-((5-(1,3,4-trimethyl-1H-pyrazol-5-yl)benzo[d]thiazol-2-yl)amino)ethyl)phenoxy)nicotinamide | $^1$H NMR (500 MHz, DMSO-d$_6$) δ 8.28-8.15 (m, 2H), 8.00 (d, J = 8.2 Hz, 1H), 7.86 (br s, 1H), 7.79 (br s, 1H), 7.59 (s, 1H), 7.46-7.34 (m, 2H), 7.30-7.24 (m, 2H), 7.21 (d, J = 8.2 Hz, 1H), 3.93 (s, 2H), 3.73 (s, 3H), 2.25 (s, 3H), 2.16 (s, 3H) | 531.1 | 1.52 Method A |
| 28 | 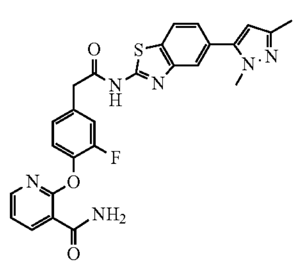 [SMILES: Cc1cc(-c2ccc3sc(NC(=O)Cc4ccc(Oc5ncccc5C(N)=O)c(F)c4)nc3c2)n(C)n1] | 2-(4-(2-((5-(1,3-dimethyl-1H-pyrazol-5-yl)benzo[d]thiazol-2-yl)amino)-2-oxoethyl)-2-fluorophenoxy)nicotinamide | $^1$H NMR (500 MHz, DMSO-d$_6$) δ 8.25-8.12 (m, 2H), 8.04 (d, J = 8.2 Hz, 1H), 7.89 (br s, 1H), 7.79 (br s, 2H), 7.51-7.31 (m, 3H), 7.27-7.10 (m, 2H), 6.24 (s, 1H), 3.88 (br s, 3H), 3.78 (br s, 2H), 2.18 (s, 3H) | 517.1 | 1.54 Method A |

-continued

| Ex # | Structure | Name | HNMR | LCMS (M + H)+ | HPLC retention time (min) |
|---|---|---|---|---|---|
| 29 | 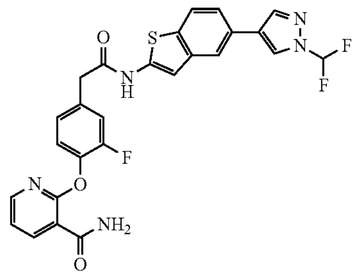 [SMILES: NC(=O)c1cccnc1Oc1ccc(CC(=O)Nc2cc3cc(-c4cnn(C(F)F)c4)ccc3s2)cc1F] | 2-(4-(2-((5-(1-(difluoromethyl)-1H-pyrazol-4-yl)benzo[d]thiazol-2-yl)amino)-2-oxoethyl)-2-fluorophenoxy)nicotinamide | ¹H NMR (400 MHz, DMSO-d₆) δ 12.68 (s, 1H), 8.84 (s, 1H), 8.40 (s, 1H), 8.26-8.17 (m, 2H), 8.12 (d, J = 1.3 Hz, 1H), 8.02 (d, J = 8.6 Hz, 1H), 7.86 (s, 1H), 7.81 (br d, J = 9.7 Hz, 2H), 7.75-7.63 (m, 1H), 7.47-7.34 (m, 2H), 7.29-7.16 (m, 2H), 3.93 (s, 2H) | 539.0 | 1.73 Method A |
| 30 | 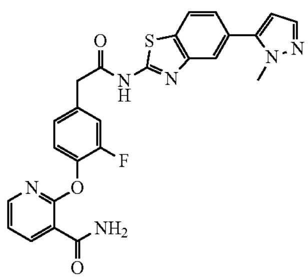 [SMILES: Cn1nccc1-c1ccc2sc(NC(=O)Cc3ccc(Oc4ncccc4C(N)=O)c(F)c3)nc2c1] | 2-(2-fluoro-4-(2-((5-(1-methyl-1H-pyrazol-5-yl)benzo[d]thiazol-2-yl)amino)-2-oxoethyl)phenoxy)nicotinamide | ¹H NMR (500 MHz, DMSO-d₆) δ 8.21 (br d, J = 7.4 Hz, 1H), 8.19 (br d, J = 3.0 Hz, 1H), 8.05 (d, J = 8.2 Hz, 1H), 7.83 (s, 1H), 7.73 (br d, J = 10.2 Hz, 1H), 7.64 (br s, 1H), 7.48 (d, J = 1.7 Hz, 1H), 7.44-7.40 (m, 1H), 7.38-7.32 (m, 2H), 7.24 (dd, J = 7.3, 4.6 Hz, 2H), 6.44 (d, J = 1.7 Hz, 1H), 3.80 (s, 2H), 3.75 (s, 3H) | 503.0 | 1.53 Method A |
| 31 | 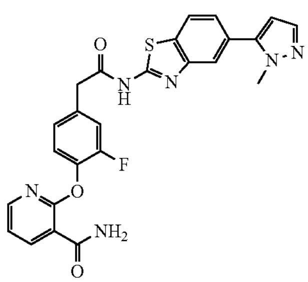 [SMILES: Cn1nccc1-c1ccc2sc(NC(=O)Cc3ccc(Oc4ncccc4C(N)=O)c(F)c3)nc2c1] | 2-(4-(2-((5-(1H-pyrazol-4-yl)benzo[d]thiazol-2-yl)amino)-2-oxoethyl)-2-fluorophenoxy)nicotinamide | ¹H NMR (500 MHz, DMSO-d₆) 8.38-8.01 (m, 4H), 7.97 (s, 1H), 7.91 (br d, J = 8.2 Hz, 1H), 7.82 (br s, 1H), 7.80 (br s, 1H), 7.56 (br d, J = 7.3 Hz, 1H), 7.41-7.32 (m, 2H), 7.29-7.19 (m, 2H), 3.90 (s, 2H), 3.00 (s, 1H) | 489.1 | 1.30 Method A |
| 32 | 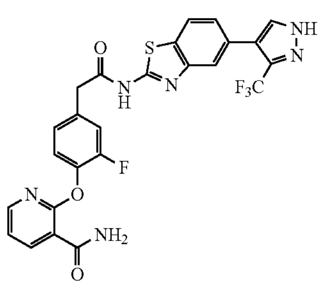 [SMILES: NC(=O)c1cccnc1Oc1ccc(CC(=O)Nc2nc3cc(-c4c[nH]nc4C(F)(F)F)ccc3s2)cc1F] | 2-(2-fluoro-4-(2-oxo-2-((5-(3-(trifluoromethyl)-1H-pyrazol-4-yl)benzo[d]thiazol-2-yl)amino)ethyl)phenoxy)nicotinamide | ¹H NMR (500 MHz, DMSO-d₆) δ 8.29-8.14 (m, 3H), 8.01 (d, J = 8.2 Hz, 1H), 7.86-7.76 (m, 2H), 7.75-7.70 (m, 1H), 7.66-7.60 (m, 1H), 7.43-7.32 (m, 4H), 7.29-7.18 (m, 2H), 3.92 (s, 2H) | 557.1 | 1.57 Method A |
| 33 | 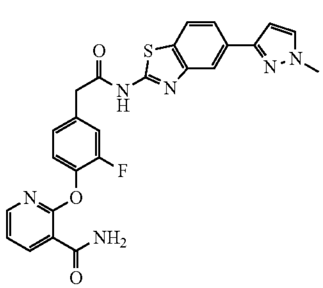 [SMILES: Cn1ccc(-c2ccc3sc(NC(=O)Cc4ccc(Oc5ncccc5C(N)=O)c(F)c4)nc3c2)n1] | 2-(2-fluoro-4-(2-((5-(1-methyl-1H-pyrazol-3-yl)benzo[d]thiazol-2-yl)amino)-2-oxoethyl)phenoxy)nicotinamide | ¹H NMR (500 MHz, DMSO-d₆) δ 8.25-8.20 (m, 1H), 8.20-8.17 (m, 1H), 8.17-8.14 (m, 1H), 7.92-7.88 (m, 3H), 7.77-7.70 (m, 1H), 7.65-7.58 (m, 1H), 7.50 (dd, J = 8.3, 1.2 Hz, 1H), 7.40-7.31 (m, 2H), 7.29-7.18 (m, 2H), 3.90 (s, 2H), 3.87 (s, 3H) | 502.9 | 1.41 Method A |

| Ex # | Structure | Name | HNMR | LCMS (M + H)+ | HPLC retention time (min) |
|---|---|---|---|---|---|
| 34 | 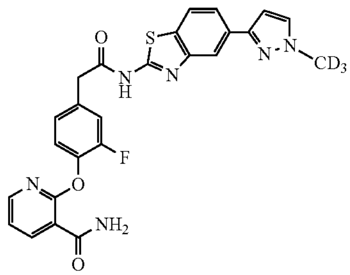 [SMILES: [2H]C([2H])([2H])n1ccc(-c2ccc3sc(NC(=O)Cc4ccc(Oc5ncccc5C(N)=O)c(F)c4)nc3c2)n1] | 2-(2-fluoro-4-(2-((5-(1-(methyl-d3)-1H-pyrazol-3-yl)benzo[d]thiazol-2-yl)amino)-2-oxoethyl)phenoxy)nicotinamide | $^1$H NMR (500 MHz, DMSO-d$_6$) δ 8.22 (s, 1H), 8.21-8.13 (m, 2H), 7.95 (s, 1H), 7.93-7.87 (m, 2H), 7.84 (br s, 1H), 7.80 (br s, 1H), 7.51 (br d, J = 8.8 Hz, 1H), 7.43-7.33 (m, 2H), 7.28-7.19 (m, 2H), 3.90 (s, 2H) | 506.2 | 1.39 Method A |
| 35 | 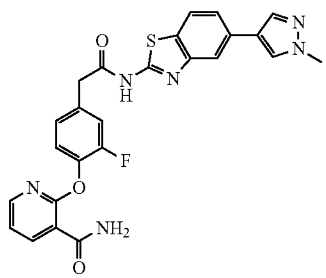 [SMILES: Cn1cc(-c2ccc3sc(NC(=O)Cc4ccc(Oc5ncccc5C(N)=O)c(F)c4)nc3c2)cn1] | 2-(2-fluoro-4-(2-((5-(1-methyl-1H-pyrazol-4-yl)benzo[d]thiazol-2-yl)amino)-2-oxoethyl)phenoxy)nicotinamide | $^1$H NMR (500 MHz, DMSO-d$_6$) δ 8.50-7.98 (m, 4H), 7.97-7.89 (m, 3H), 7.84 (br s, 1H), 7.77 (br s, 1H), 7.53 (br d, J = 9.2 Hz, 1H), 7.41-7.31 (m, 2H), 7.29-7.17 (m, 2H), 3.91 (s, 2H), 3.87 (s, 3H) | 503.1 | 1.42 Method A |
| 36 | 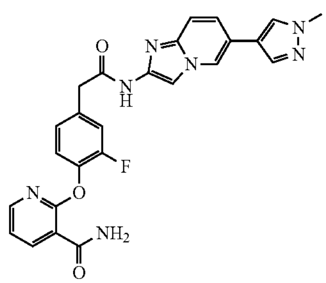 [SMILES: Cn1cc(-c2ccc3nc(NC(=O)Cc4ccc(Oc5ncccc5C(N)=O)c(F)c4)cn3c2)cn1] | 2-(2-fluoro-4-(2-((6-(1-methyl-1H-pyrazol-4-yl)imidazo[1,2-a]pyridin-2-yl)amino)-2-oxoethyl)phenoxy)nicotinamide | $^1$H NMR (500 MHz, DMSO-d$_6$) δ 10.98 (s, 1H), 8.81 (s, 1H), 8.26-8.16 (m, 2H), 8.11 (s, 1H), 8.04 (s, 1H), 7.84 (s, 1H), 7.71 (br s, 1H), 7.66 (br s, 1H), 7.58-7.52 (m, 1H), 7.51-7.47 (m, 1H), 7.41-7.32 (m, 2H), 7.26-7.16 (m, 2H), 3.89 (s, 3H), 3.79 (s, 2H) | 486.1 | 0.90 Method B |
| 37 | 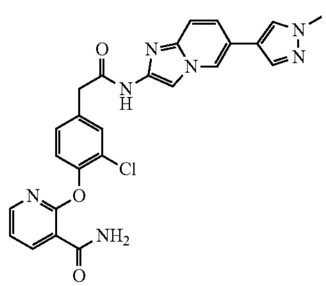 [SMILES: Cn1cc(-c2ccc3nc(NC(=O)Cc4ccc(Oc5ncccc5C(N)=O)c(Cl)c4)cn3c2)cn1] | 2-(2-chloro-4-(2-((6-(1-methyl-1H-pyrazol-4-yl)imidazo[1,2-a]pyridin-2-yl)amino)-2-oxoethyl)phenoxy)nicotinamide | $^1$H NMR (500 MHz, DMSO-d$_6$) δ 10.89 (br s, 1H), 8.77 (s, 1H), 8.24 (br d, J = 7.5 Hz, 1H), 8.17 (br d, J = 4.7 Hz, 1H), 8.09 (s, 1H), 8.03 (s, 1H), 7.83 (s, 1H), 7.68 (br s, 2H), 7.57 (s, 1H), 7.51-7.42 (m, 2H), 7.41-7.32 (m, 2H), 7.27-7.19 (m, 1H), 3.89 (s, 3H), 3.78 (s, 2H) | 502.1 | 0.96 Method B |
| 38 | 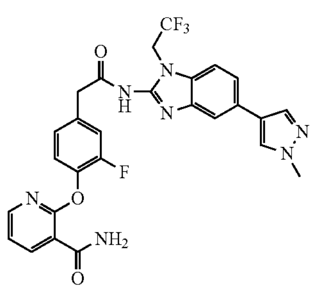 [SMILES: Cn1cc(-c2ccc3c(c2)nc(NC(=O)Cc2ccc(Oc4ncccc4C(N)=O)c(F)c2)n3CC(F)(F)F)cn1] | 2-(2-fluoro-4-(2-((5-(1-methyl-1H-pyrazol-4-yl)-1-(2,2,2-trifluoroethyl)-1H-benzo[d]imidazol-2-yl)amino)-2-oxoethyl)phenoxy)nicotinamide | $^1$H NMR (500 MHz, DMSO-d$_6$) δ 8.21 (br d, J = 7.5 Hz, 1H), 8.18 (br d, J = 4.6 Hz, 1H), 8.02 (br s, 1H), 7.77 (s, 1H), 7.71-7.56 (m, 3H), 7.50-7.42 (m, 1H), 7.41-7.37 (m, 1H), 7.34 (br d, J = 11.8 Hz, 1H), 7.30 (br t, J = 8.3 Hz, 1H), 7.26-7.18 (m, 2H), 5.05 (q, J = 9.3 Hz, 2H), 3.88 (s, 3H), 3.75 (s, 2H) | 568.2 | 1.19 Method A |

| Ex # | Structure | Name | HNMR | LCMS (M + H)+ | HPLC retention time (min) |
|---|---|---|---|---|---|
| 39 | 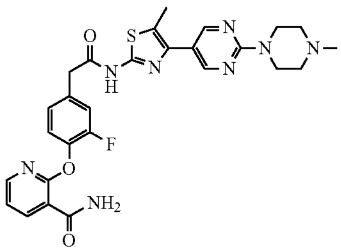 [SMILES: Cc1sc(NC(=O)Cc2ccc(Oc3ncccc3C(N)=O)c(F)c2)nc1-c1cnc(N2CCN(C)CC2)nc1] | 2-(2-fluoro-4-(2-((5-methyl-4-(2-(4-methylpiperazin-1-yl)pyrimidin-5-yl)thiazol-2-yl)amino)-2-oxoethyl)phenoxy)nicotinamide | $^1$H NMR (500 MHz, DMSO-d$_6$) δ 12.40 (br s, 1H), 8.71 (s, 2H), 8.21-8.16 (m, 2H), 7.85 (br s, 1H), 7.78 (br s, 1H), 7.39-7.30 (m, 2H), 7.25 (dd, J = 7.3, 4.9 Hz, 1H), 7.21 (br d, J = 8.9 Hz, 1H), 3.83 (s, 2H), 3.62-3.12 (m, 8H), 2.85 (s, 3H), 2.44 (s, 3H) | 562.9 | 1.11 Method B |
| 40 | 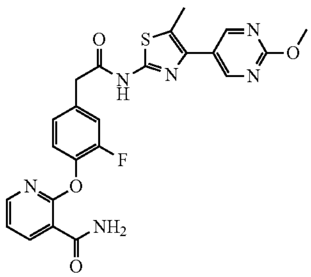 [SMILES: COc1ncc(-c2nc(NC(=O)Cc3ccc(Oc4ncccc4C(N)=O)c(F)c3)sc2C)cn1] | 2-(2-fluoro-4-(2-((4-(2-methoxypyrimidin-5-yl)-5-methylthiazol-2-yl)amino)-2-oxoethyl)phenoxy)nicotinamide | $^1$H NMR (500 MHz, DMSO-d$_6$) δ 12.46 (s, 1H), 8.87 (s, 2H), 8.24-8.13 (m, 2H), 7.83 (br s, 1H), 7.79 (br s, 1H), 7.41-7.32 (m, 2H), 7.29-7.11 (m, 2H), 3.98 (s, 3H), 3.84 (s, 2H), 2.48 (s, 3H) | 494.9 | 1.37 Method A |
| 41 | 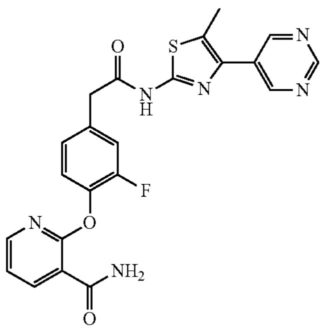 [SMILES: Cc1sc(NC(=O)Cc2ccc(Oc3ncccc3C(N)=O)c(F)c2)nc1-c1cncnc1] | 2-(2-fluoro-4-(2-((5-methyl-4-(pyrimidin-5-yl)thiazol-2-yl)amino)-2-oxoethyl)phenoxy)nicotinamide | $^1$H NMR (500 MHz, DMSO-d$_6$) δ 12.38 (br s, 1H), 9.16 (s, 1H), 9.08 (s, 2H), 8.22 (dd, J = 7.4, 1.6 Hz, 1H), 8.20-8.17 (m, 1H), 7.71 (br s, 1H), 7.66 (br s, 1H), 7.42-7.30 (m, 2H), 7.28-7.18 (m, 2H), 3.86 (s, 2H), 2.51 (s, 3H) | 465.2 | 1.28 Method A |
| 42 | 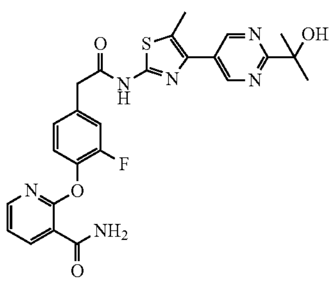 [SMILES: Cc1sc(NC(=O)Cc2ccc(Oc3ncccc3C(N)=O)c(F)c2)nc1-c1cnc(C(C)(C)O)nc1] | 2-(2-fluoro-4-(2-((4-(2-(2-hydroxypropan-2-yl)pyrimidin-5-yl)-5-methylthiazol-2-yl)amino)-2-oxoethyl)phenoxy)nicotinamide | $^1$H NMR (500 MHz, DMSO-d$_6$) δ 12.64-12.28 (m, 1H), 9.15-8.91 (m, 2H), 8.27-8.09 (m, 2H), 7.88 (br s, 1H), 7.78 (br s, 1H), 7.43-7.28 (m, 2H), 7.27-7.07 (m, 2H), 3.78 (s, 2H), 2.98 (s, 1H), 2.57-2.55 (m, 3H), 1.53 (s, 6H) | 523.2 | 1.36 Method A |
| 43 | 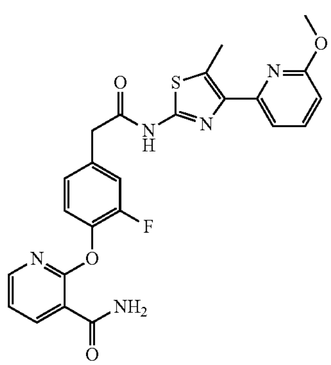 [SMILES: COc1cccc(-c2nc(NC(=O)Cc3ccc(Oc4ncccc4C(N)=O)c(F)c3)sc2C)n1] | 2-(2-fluoro-4-(2-((4-(6-methoxypyridin-2-yl)-5-methylthiazol-2-yl)amino)-2-oxoethyl)phenoxy)nicotinamide | $^1$H NMR (500 MHz, DMSO-d$_6$) δ 12.37 (br s, 1H), 8.38-8.02 (m, 2H), 7.88 (br s, 1H), 7.84-7.69 (m, 2H), 7.57 (br d, J = 7.4 Hz, 1H), 7.44-7.28 (m, 2H), 7.26-7.14 (m, 2H), 6.72 (d, J = 8.2 Hz, 1H), 3.90 (s, 3H), 3.80 (s, 2H), 2.77 (s, 3H) | 494.0 | 1.86 Method B |

| Ex # | Structure | Name | HNMR | LCMS (M + H)+ | HPLC retention time (min) |
|---|---|---|---|---|---|
| 44 | 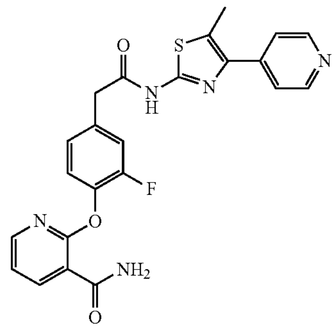 [SMILES: Cc1sc(NC(=O)Cc2ccc(Oc3ncccc3C(N)=O)c(F)c2)nc1-c1ccncc1] | 2-(2-fluoro-4-(2-((5-methyl-4-(pyridin-4-yl)thiazol-2-yl)amino)-2-oxoethyl)phenoxy)nicotinamide | $^1$H NMR (500 MHz, DMSO-d$_6$) δ 12.44 (br s, 1H), 8.25-8.12 (m, 2H), 8.11-7.86 (brd m, 4H??), 7.84 (br s, 1H), 7.76 (br s, 1H), 7.44-7.27 (m, 2H), 7.26-7.12 (m, 2H), 3.82 (s, 2H), 2.55 (s, 3H) | 464.0 | 1.31 Method A |
| 45 | 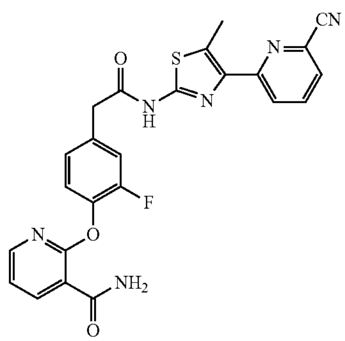 [SMILES: Cc1sc(NC(=O)Cc2ccc(Oc3ncccc3C(N)=O)c(F)c2)nc1-c1cccc(C#N)n1] | 2-(4-(2-((4-(6-cyanopyridin-2-yl)-5-methylthiazol-2-yl)amino)-2-oxoethyl)-2-fluorophenoxy)nicotinamide | $^1$H NMR (500 MHz, DMSO-d$_6$) δ 12.46 (s, 1H), 8.28-8.15 (m, 3H), 8.12 (t, J = 7.9 Hz, 1H), 7.91 (d, J = 7.6 Hz, 1H), 7.84 (br s, 1H), 7.77 (br s, 1H), 7.43-7.29 (m, 2H), 7.28-7.12 (m, 2H), 3.84 (s, 2H), 2.71 (s, 3H) | 489.0 | 1.61 Method A |
| 46 | 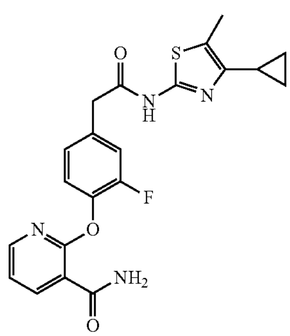 [SMILES: Cc1sc(NC(=O)Cc2ccc(Oc3ncccc3C(N)=O)c(F)c2)nc1C1CC1] | 2-(4-(2-((4-cyclopropyl-5-methylthiazol-2-yl)amino)-2-oxoethyl)-2-fluorophenoxy)nicotinamide | $^1$H NMR (500 MHz, DMSO-d$_6$) δ 8.21 (br d, J = 7.4 Hz, 1H), 8.18 (br d, J = 3.5 Hz, 1H), 7.71 (br s, 1H), 7.64 (br s, 1H), 7.33 (br t, J = 8.2 Hz, 1H), 7.28 (br d, J = 11.4 Hz, 1H), 7.24 (dd, J = 7.1, 5.1 Hz, 1H), 7.18 (br d, J = 8.1 Hz, 1H), 3.76 (s, 2H), 2.32 (s, 3H), 1.98-1.86 (m, 1H), 1.25 (s, 1H), 0.89-0.83 | 427.0 | 1.68 Method B |
| 47 | 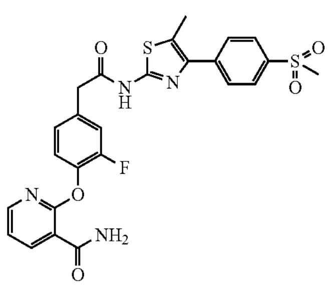 [SMILES: Cc1sc(NC(=O)Cc2ccc(Oc3ncccc3C(N)=O)c(F)c2)nc1-c1ccc(S(C)(=O)=O)cc1] | 2-(2-fluoro-4-(2-((5-methyl-4-(4-(methylsulfonyl)phenyl)thiazol-2-yl)amino)-2-oxoethyl)phenoxy)nicotinamide | $^1$H NMR (500 MHz, DMSO-d$_6$) δ 8.21 (br d, J = 7.6 Hz, 1H), 8.18 (br d, J = 4.0 Hz, 1H), 8.00 (br d, J = 8.2 Hz, 2H), 7.95-7.89 (m, 2H), 7.78-7.69 (m, 1H), 7.66-7.58 (m, 1H), 7.40-7.30 (m, 2H), 7.27-7.16 (m, 2H), 3.84 (s, 2H), 3.38 (br s, 3H), 3.23 (s, 1H), 2.55 (s, 3H) | 541.3 | 1.56 Method B |

| Ex # | Structure | Name | HNMR | LCMS (M + H)+ | HPLC retention time (min) |
|---|---|---|---|---|---|
| 48 | 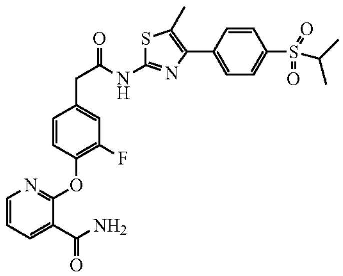 [SMILES: Cc1sc(NC(=O)Cc2ccc(Oc3ncccc3C(N)=O)c(F)c2)nc1-c1ccc(S(=O)(=O)C(C)C)cc1] | 2-(2-fluoro-4-(2-((4-(4-(isopropylsulfonyl)phenyl)-5-methylthiazol-2-yl)amino)-2-oxoethyl)phenoxy)nicotinamide | $^1$H NMR (500 MHz, DMSO-$d_6$) δ 8.20 (br d, J = 7.5 Hz, 1H), 8.16 (br d, J = 3.3 Hz, 1H), 7.97-7.87 (m, 4H), 7.82-7.68 (m, 1H), 7.71-7.52 (m, 1H), 7.38-7.29 (m, 2H), 7.26-7.15 (m, 2H), 3.83 (s, 2H), 3.40 (dt, J = 13.5, 6.7 Hz, 1H), 2.55 (s, 3H), 1.20 (s, 3H), 1.18 (s, 3H) | 568.9 | 1.60 Method A |

Examples 49-105 were prepared following the general procedure used for example 2

| Ex # | Structure | Name | HNMR | LCMS (M + H)+ | HPLC retention time (min) |
|---|---|---|---|---|---|
| 49 | 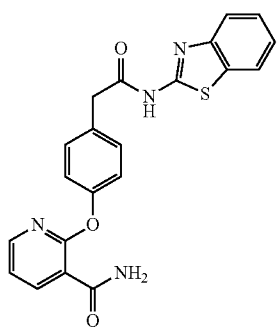 [SMILES: NC(=O)c1cccnc1Oc1ccc(CC(=O)Nc2nc3ccccc3s2)cc1] | 2-(4-(2-(benzo[d]thiazol-2-ylamino)-2-oxoethyl)phenoxy)nicotinamide | $^1$H NMR (500 MHz, DMSO-$d_6$) δ 8.25-8.13 (m, 2H), 7.97 (d, J = 7.9 Hz, 1H), 7.87-7.70 (m, 3H), 7.47-7.35 (m, 3H), 7.30 (t, J = 7.5 Hz, 2H), 7.22-7.11 (m, 3H), 3.86 (s, 2H) | 404.9 | 1.51 Method A |
| 50 | 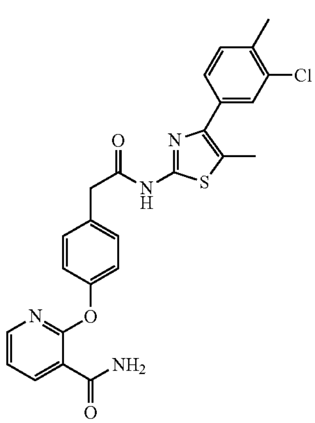 [SMILES: Cc1ccc(-c2nc(NC(=O)Cc3ccc(Oc4ncccc4C(N)=O)cc3)sc2C)cc1Cl] | 2-(4-(2-((4-(3-chloro-4-methylphenyl)-5-methylthiazol-2-yl)amino)-2-oxoethyl)phenoxy)nicotinamide | $^1$H NMR (500 MHz, DMSO-$d_6$) δ 8.20-8.10 (m, 2H), 7.86 (br. s., 1H), 7.75 (br. s., 1H), 7.60 (s, 1H), 7.51-7.45 (m, 2H), 7.37 (d, J = 7.9 Hz, 2H), 7.25-7.17 (m, 1H), 7.13 (d, J = 7.8 Hz, 2H), 3.86 (s, 2H), 3.16 (d, J = 4.4 Hz, 3H), 2.39-2.31 (m, 3H) | 493.0 | 2.04 Method A |

-continued

| Ex # | Structure | Name | HNMR | LCMS (M + H)+ | HPLC retention time (min) |
|---|---|---|---|---|---|
| 51 | 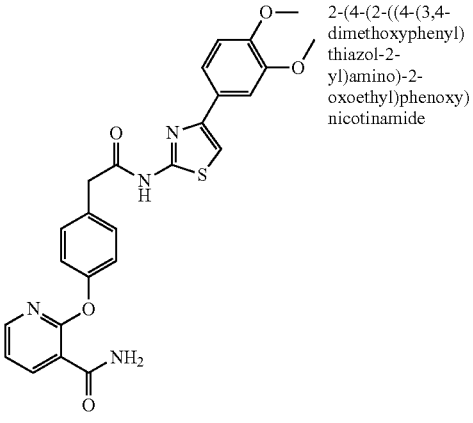 | 2-(4-(2-((4-(3,4-dimethoxyphenyl)thiazol-2-yl)amino)-2-oxoethyl)phenoxy)nicotinamide | ¹H NMR (500 MHz, DMSO-d₆) δ 8.24-8.13 (m, 2H), 7.80 (br. s., 1H), 7.76 (br. s., 1H), 7.50 (s, 1H), 7.45 (s, 1H), 7.40 (d, J = 8.2 Hz, 2H), 7.21 (dd, J = 7.3, 4.9 Hz, 1H), 7.16 (d, J = 8.2 Hz, 2H), 7.01 (d, J = 7.9 Hz, 1H), 3.88-3.69 (m, 7H), 3.38 (s, 1H), 2.55 (s, 1H) | 491.0 | 1.55 Method A |
| 52 | 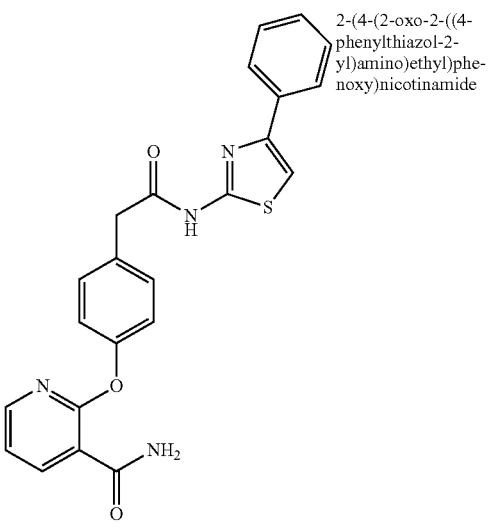 | 2-(4-(2-oxo-2-((4-phenylthiazol-2-yl)amino)ethyl)phenoxy)nicotinamide | ¹H NMR (500 MHz, DMSO-d₆) δ 8.23-8.09 (m, 2H), 7.90 (d, J = 7.7 Hz, 2H), 7.82 (br. s., 1H), 7.78 (br. s., 1H), 7.63 (s, 1H), 7.53-7.35 (m, 4H), 7.35-7.26 (m, 1H), 7.21 (dd, J = 7.2, 5.0 Hz, 1H), 7.16 (d, J = 8.3 Hz, 2H), 3.86 (s, 2H), 3.40 (br. s., 1H) | 430.9 | 1.67 Method A |
| 53 | 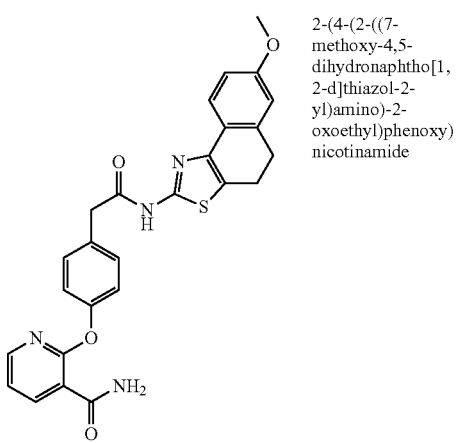 | 2-(4-(2-((7-methoxy-4,5-dihydronaphtho[1,2-d]thiazol-2-yl)amino)-2-oxoethyl)phenoxy)nicotinamide | ¹H NMR (500 MHz, DMSO-d₆) δ 8.23-8.08 (m, 2H), 7.79 (d, J = 15.8 Hz, 2H), 7.58 (d, J = 8.3 Hz, 1H), 7.39 (d, J = 8.2 Hz, 2H), 7.27-7.10 (m, 3H), 6.93-6.78 (m, 2H), 3.84-3.70 (m, 5H), 3.03-2.93 (m, 2H), 2.93-2.83 (m, 2H), 2.55 (s, 1H) | 487.0 | 1.72 Method A |

| Ex # | Structure | Name | HNMR | LCMS (M + H)+ | HPLC retention time (min) |
|---|---|---|---|---|---|
| 54 | 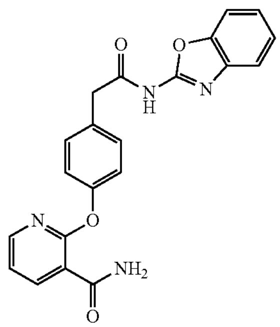 [SMILES: NC(=O)c1cccnc1Oc1ccc(CC(=O)Nc2nc3ccccc3o2)cc1] | 2-(4-(2-(benzo[d]oxazol-2-ylamino)-2-oxoethyl)phenoxy)nicotinamide | $^1$H NMR (500 MHz, DMSO-d$_6$) δ 8.24-8.08 (m, 2H), 7.84 (br. s., 1H), 7.76 (br. s., 1H), 7.56 (t, J = 8.3 Hz, 2H), 7.38 (d, J = 8.2 Hz, 2H), 7.32-7.18 (m, 3H), 7.14 (d, J = 8.2 Hz, 2H), 3.86 (s, 2H), 3.54 (br. s., 1H) | 388.9 | 1.26 Method A |
| 55 | 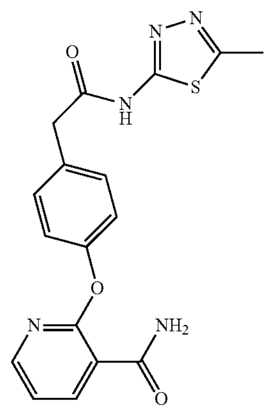 [SMILES: Cc1nnc(NC(=O)Cc2ccc(Oc3ncccc3C(N)=O)cc2)s1] | 2-(4-(2-((5-methyl-1,3,4-thiadiazol-2-yl)amino)-2-oxoethyl)phenoxy)nicotinamide | $^1$H NMR (500 MHz, DMSO-d$_6$) δ 8.23-8.10 (m, 2H), 7.84 (br. s., 1H), 7.76 (br. s., 1H), 7.36 (d, J = 8.2 Hz, 2H), 7.25-7.07 (m, 3H), 3.81 (s, 2H), 2.59 (s, 3H) | 370.3 | 1.07 Method A |
| 56 | 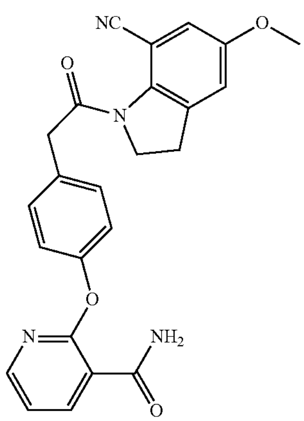 [SMILES: COc1cc(C#N)c2c(c1)CCN2C(=O)Cc1ccc(Oc2ncccc2C(N)=O)cc1] | 2-(4-(2-(7-cyano-5-methoxyindolin-1-yl)-2-oxoethyl)phenoxy)nicotinamide | $^1$H NMR (500 MHz, DMSO-d$_6$) δ 8.20 (d, J = 4.7 Hz, 1H), 8.16 (d, J = 7.2 Hz, 1H), 7.84 (br. s., 1H), 7.76 (br. s., 1H), 7.34 (d, J = 8.2 Hz, 2H), 7.26-7.19 (m, 2H), 7.15 (d, J = 8.2 Hz, 2H), 7.04 (s, 1H), 4.20 (t, J = 7.9 Hz, 2H), 3.94 (s, 3H), 3.76 (s, 2H), 3.11 (t, J = 7.8 Hz, 2H) | 429.3 | 1.39 Method A |
| 57 | 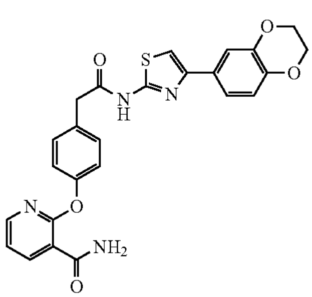 [SMILES: NC(=O)c1cccnc1Oc1ccc(CC(=O)Nc2nc(-c3ccc4c(c3)OCCO4)cs2)cc1] | 2-(4-(2-((4-(2,3-dihydrobenzo[b][1,4]dioxin-6-yl)thiazol-2-yl)amino)-2-oxoethyl)phenoxy)nicotinamide | $^1$H NMR (500 MHz, DMSO-d$_6$) δ 8.16 (d, J = 9.3 Hz, 2H), 7.81 (br. s., 1H), 7.77 (br. s., 1H), 7.47 (s, 1H), 7.44-7.35 (m, 4H), 7.29-7.19 (m, 1H), 7.15 (d, J = 7.7 Hz, 2H), 6.90 (d, J = 8.1 Hz, 1H), 4.27 (s, 4H), 3.80 (s, 2H). | 489.1 | 1.72 Method A |

| Ex # | Structure | Name | HNMR | LCMS (M + H)+ | HPLC retention time (min) |
|---|---|---|---|---|---|
| 58 | 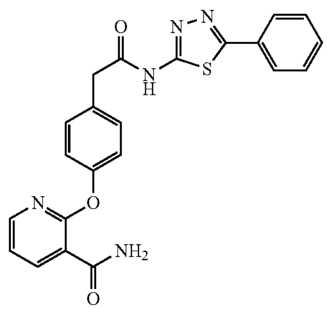 [SMILES: NC(=O)c1cccnc1Oc1ccc(CC(=O)Nc2nnc(-c3ccccc3)s2)cc1] | 2-(4-(2-oxo-2-((5-phenyl-1,3,4-thiadiazol-2-yl)amino)ethyl)phenoxy)nicotinamide | ¹H NMR (500 MHz, DMSO-d₆) δ 8.28-8.11 (m, 2H), 7.93 (d, J = 4.6 Hz, 2H), 7.81 (br. s., 1H), 7.78 (br. s., 1H), 7.53 (br. s., 3H), 7.40 (d, J = 7.7 Hz, 2H), 7.21 (t, J = 5.8 Hz, 1H), 7.17 (d, J = 7.6 Hz, 2H), 3.80 (s, 2H). | 432.1 | 1.59 Method A |
| 59 | 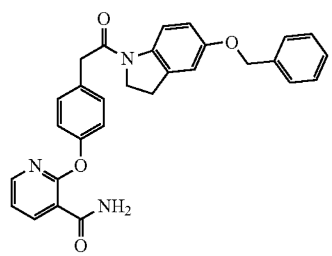 [SMILES: NC(=O)c1cccnc1Oc1ccc(CC(=O)N2CCc3cc(OCc4ccccc4)ccc32)cc1] | 2-(4-(2-(5-(benzyloxy)indolin-1-yl)-2-oxoethyl)phenoxy)nicotinamide | ¹H NMR (500 MHz, DMSO-d₆) δ 8.23-8.11 (m, 2H), 7.97 (d, J = 8.7 Hz, 1H), 7.80 (d, J = 19.2 Hz, 2H), 7.46-7.34 (m, 4H), 7.32 (br. s., 2H), 7.25-7.19 (m, 1H), 7.14 (d, J = 7.9 Hz, 2H), 6.93 (br. s., 1H), 6.80 (d, J = 8.5 Hz, 1H), 5.05 (s, 2H), 4.18 (t, J = 8.3 Hz, 2H), 3.41 (br. s., 1H), 3.14 (t, J = 8.4 Hz, 2H) | 480.1 | 1.59 Method A |
| 60 | 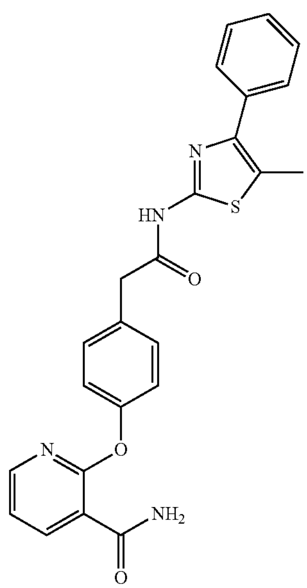 [SMILES: Cc1sc(NC(=O)Cc2ccc(Oc3ncccc3C(N)=O)cc2)nc1-c1ccccc1] | 2-(4-(2-((5-methyl-4-phenylthiazol-2-yl)amino)-2-oxoethyl)phenoxy)nicotinamide | ¹H NMR (500 MHz, DMSO-d₆) δ 8.24-8.12 (m, 2H), 7.79 (br. s., 1H), 7.75 (br. s., 1H), 7.64 (d, J = 7.6 Hz, 2H), 7.45 (t, J = 7.6 Hz, 2H), 7.42-7.32 (m, 3H), 7.21 (d, J = 5.2 Hz, 1H), 7.19-7.07 (m, 2H), 3.80 (s, 2H), 3.46-3.33 (m, 1H), 2.46 (s, 3H) | 445.2 | 1.76 Method A |
| 61 | 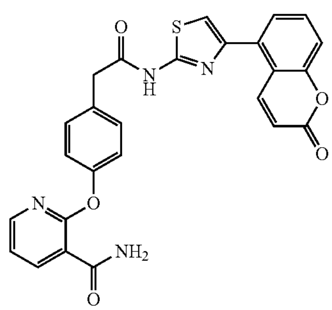 [SMILES: NC(=O)c1cccnc1Oc1ccc(CC(=O)Nc2nc(-c3cccc4oc(=O)ccc34)cs2)cc1] | 2-(4-(2-oxo-2-((4-(2-oxo-2H-chromen-5-yl)thiazol-2-yl)amino)ethyl)phenoxy)nicotinamide | ¹H NMR (500 MHz, DMSO-d₆) δ 8.71 (d, J = 10.1 Hz, 1H), 8.29-8.12 (m, 2H), 7.78 (d, J = 17.1 Hz, 2H), 7.70-7.63 (m, 1H), 7.59 (d, J = 7.6 Hz, 1H), 7.49-7.36 (m, 4H), 7.26-7.18 (m, 1H), 7.15 (d, J = 8.2 Hz, 2H), 6.52 (d, J = 9.8 Hz, 1H), 3.75 (s, 2H) | 498.9 | 1.56 Method A |

| Ex # | Structure | Name | HNMR | LCMS (M + H)+ | HPLC retention time (min) |
|---|---|---|---|---|---|
| 62 | 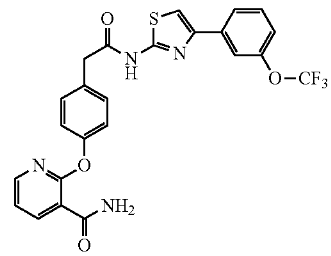 [SMILES: NC(=O)c1cccnc1Oc1ccc(CC(=O)Nc2nc(-c3cccc(OC(F)(F)F)c3)cs2)cc1] | 2-(4-(2-oxo-2-(4-(3-(trifluoromethoxy)phenyl)thiazol-2-yl)amino)ethyl)phenoxy)nicotinamide | $^1$H NMR (500 MHz, DMSO-d$_6$) δ 8.24-8.12 (m, 2H), 7.94 (d, J = 7.9 Hz, 1H), 7.85 (br. s., 1H), 7.80 (s, 2H), 7.74 (br. s., 1H), 7.57 (t, J = 8.1 Hz, 1H), 7.39 (d, J = 8.2 Hz, 2H), 7.32 (d, J = 7.6 Hz, 1H), 7.21 (dd, J = 7.3, 4.9 Hz, 1H), 7.15 (d, J = 8.2 Hz, 2H), 3.82 (s, 2H), 3.40 (br. s., 1H) | 514.9 | 1.96 Method A |
| 63 | 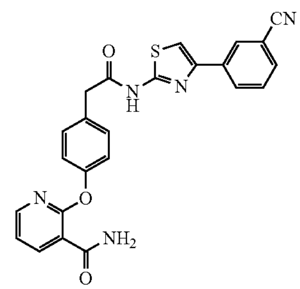 [SMILES: N#Cc1cccc(-c2csc(NC(=O)Cc3ccc(Oc4ncccc4C(N)=O)cc3)n2)c1] | 2-(4-(2-((4-(3-cyanophenyl)thiazol-2-yl)amino)-2-oxoethyl)phenoxy)nicotinamide | $^1$H NMR (500 MHz, DMSO-d$_6$) δ 8.32 (s, 1H), 8.22 (d, J = 7.9 Hz, 1H), 8.19-8.10 (m, 2H), 7.84 (s, 1H), 7.78 (d, J = 7.9 Hz, 2H), 7.74 (br. s., 1H), 7.66 (t, J = 7.8 Hz, 1H), 7.39 (d, J = 8.2 Hz, 2H), 7.21 (dd, J = 7.3, 4.9 Hz, 1H), 7.15 (d, J = 8.2 Hz, 2H), 3.82 (s, 2H), 3.45 (br. s., 1H) | 456.1 | 1.63 Method A |
| 64 | 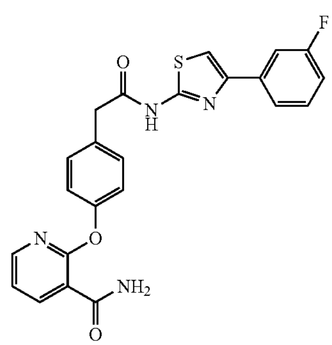 [SMILES: NC(=O)c1cccnc1Oc1ccc(CC(=O)Nc2nc(-c3cccc(F)c3)cs2)cc1] | 2-(4-(2-((4-(3-fluorophenyl)thiazol-2-yl)amino)-2-oxoethyl)phenoxy)nicotinamide | $^1$H NMR (500 MHz, DMSO-d$_6$) δ 8.22-8.11 (m, 2H), 7.86 (br. s., 1H), 7.74 (d, J = 7.8 Hz, 1H), 7.73-7.64 (m, 2H), 7.47 (d, J = 7.2 Hz, 1H), 7.39 (d, J = 7.7 Hz, 2H), 7.25-7.17 (m, 1H), 7.14 (d, J = 7.8 Hz, 2H), 3.76 (br. s., 2H), 3.16 (br. s., 1H) | 449.1 | 1.70 Method A |
| 65 | 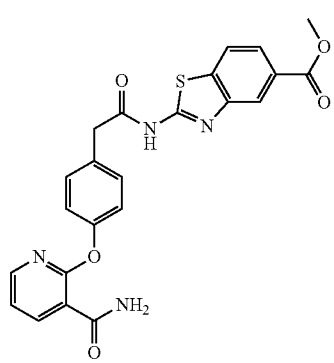 | methyl 2-(2-(4-((3-carbamoylpyridin-2-yl)oxy)phenyl)acetamido)benzo[d]thiazole-5-carboxylate | $^1$H NMR (500 MHz, DMSO-d$_6$) δ 8.55 (s, 1H), 8.23-8.13 (m, 2H), 7.97 (d, J = 8.2 Hz, 1H), 7.79 (br. s., 1H), 7.74 (d, J = 7.9 Hz, 2H), 7.39 (d, J = 8.5 Hz, 2H), 7.26-7.18 (m, 1H), 7.14 (d, J = 8.2 Hz, 2H), 3.86 (s, 3H), 3.83 (s, 2H) | 463.0 | 1.52 Method A |

| Ex # | Structure | Name | HNMR | LCMS (M + H)+ | HPLC retention time (min) |
|---|---|---|---|---|---|
| 66 | 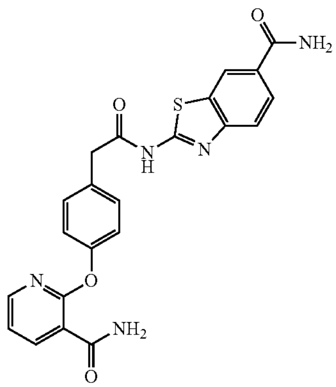 [SMILES: NC(=O)c1ccc2nc(NC(=O)Cc3ccc(Oc4ncccc4C(N)=O)cc3)sc2c1] | 2-(2-(4-((3-carbamoylpyridin-2-yl)oxy)phenyl)acetamido)benzo[d]thiazole-6-carboxamide | $^1$H NMR (500 MHz, DMSO-d$_6$) δ 8.45 (s, 1H), 8.24-8.12 (m, 2H), 7.98 (br. s., 1H), 7.93 (d, J = 8.5 Hz, 1H), 7.79 (br. s., 1H), 7.75 (d, J = 8.2 Hz, 2H), 7.40 (d, J = 8.2 Hz, 2H), 7.33 (br. s., 1H), 7.27-7.18 (m, 1H), 7.16 (d, J = 8.2 Hz, 2H), 3.85 (s, 2H) | 448.1 | 1.14 Method A |
| 67 | 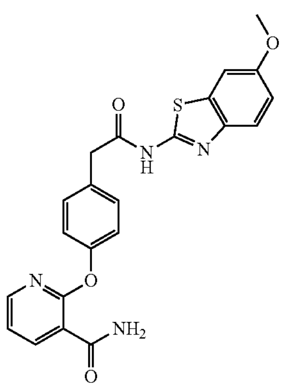 [SMILES: COc1ccc2nc(NC(=O)Cc3ccc(Oc4ncccc4C(N)=O)cc3)sc2c1] | 2-(4-(2-((6-methoxybenzo[d]thiazol-2-yl)amino)-2-oxoethyl)phenoxy)nicotinamide | $^1$H NMR (500 MHz, DMSO-d$_6$) δ 8.25-8.08 (m, 2H), 7.79 (br. s., 1H), 7.75 (br. s., 1H), 7.62 (d, J = 8.9 Hz, 1H), 7.54 (s, 1H), 7.39 (d, J = 8.2 Hz, 2H), 7.26-7.17 (m, 1H), 7.15 (d, J = 8.5 Hz, 2H), 7.02 (d, J = 8.9 Hz, 1H), 3.87-3.71 (m, 5H) | 435.1 | 1.50 Method A |
| 68 | 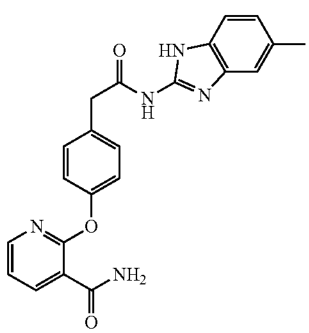 [SMILES: Cc1ccc2[nH]c(NC(=O)Cc3ccc(Oc4ncccc4C(N)=O)cc3)nc2c1] | 2-(4-(2-((5-methyl-1H-benzo[d]imidazol-2-yl)amino)-2-oxoethyl)phenoxy)nicotinamide | $^1$H NMR (500 MHz, DMSO-d$_6$) δ 8.24-8.09 (m, 2H), 7.83 (br. s., 1H), 7.78 (br. s., 1H), 7.42 (d, J = 8.2 Hz, 3H), 7.34 (s, 1H), 7.22-7.14 (m, 3H), 7.07 (d, J = 8.1 Hz, 1H), 3.87 (s, 2H), 2.44-2.35 (m, 3H), 1.23 (s, 2H) | 402.3 | 1.28 Method B |
| 69 | 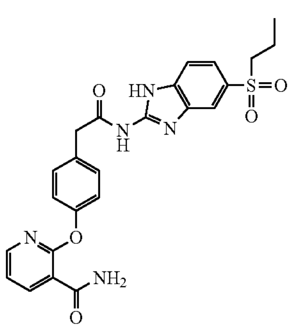 [SMILES: CCCS(=O)(=O)c1ccc2[nH]c(NC(=O)Cc3ccc(Oc4ncccc4C(N)=O)cc3)nc2c1] | 2-(4-(2-oxo-2-((5-(propylsulfonyl)-1H-benzo[d]imidazol-2-yl)amino)ethyl)phenoxy)nicotinamide | $^1$H NMR (500 MHz, DMSO-d$_6$) δ 8.19-8.12 (m, 2H), 7.94 (br. s., 1H), 7.80 (br. s., 1H), 7.75 (br. s., 1H), 7.70-7.62 (m, 1H), 7.62-7.55 (m, 1H), 7.42 (d, J = 8.2 Hz, 2H), 7.24-7.19 (m, 1H), 7.19-7.13 (m, 2H), 3.83 (s, 2H), 3.32-3.17 (m, 2H), 1.63-1.47 (m, 2H), 0.96-0.80 (m, 3H) | 493.9 | 1.32 Method B |

| Ex # | Structure | Name | HNMR | LCMS (M + H)+ | HPLC retention time (min) |
|---|---|---|---|---|---|
| 70 | 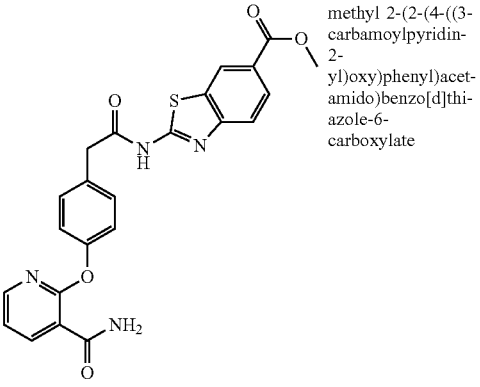 | methyl 2-(2-(4-((3-carbamoylpyridin-2-yl)oxy)phenyl)acetamido)benzo[d]thiazole-6-carboxylate | ¹H NMR (500 MHz, DMSO-d₆) δ 8.61 (d, J = 5.5 Hz, 1H), 8.16 (d, J = 5.5 Hz, 2H), 7.99 (d, J = 6.7 Hz, 1H), 7.84-7.71 (m, 3H), 7.39 (d, J = 7.3 Hz, 2H), 7.27-7.12 (m, 3H), 3.87 (d, J = 6.4 Hz, 5H) | 462.9 | 1.44 Method A |
| 71 | 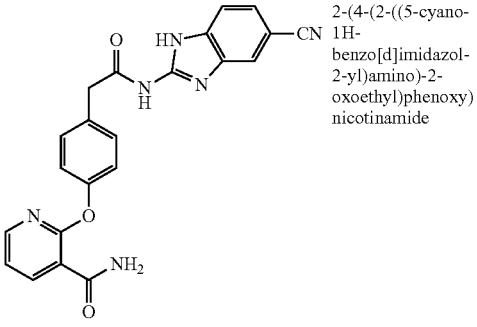 | 2-(4-(2-((5-cyano-1H-benzo[d]imidazol-2-yl)amino)-2-oxoethyl)phenoxy)nicotinamide | ¹H NMR (500 MHz, DMSO-d₆) δ 8.21-8.08 (m, 2H), 7.96-7.88 (m, 1H), 7.82 (br. s., 1H), 7.77 (br. s., 1H), 7.59 (d, J = 8.2 Hz, 1H), 7.50 (d, J = 8.3 Hz, 1H), 7.42 (d, J = 8.2 Hz, 2H), 7.26-7.09 (m, 3H), 3.83 (s, 2H), 3.51-3.39 (m, 2H) | 413.0 | 1.30 Method B |
| 72 | 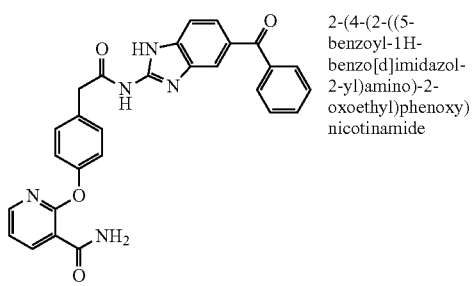 | 2-(4-(2-((5-benzoyl-1H-benzo[d]imidazol-2-yl)amino)-2-oxoethyl)phenoxy)nicotinamide | ¹H NMR (500 MHz, DMSO-d₆) δ 8.22-8.09 (m, 2H), 7.98-7.78 (m, 2H), 7.77-7.69 (m, 3H), 7.69-7.60 (m, 1H), 7.59-7.52 (m, 4H), 7.42 (d, J = 8.2 Hz, 2H), 7.20 (dd, J = 6.9, 5.0 Hz, 1H), 7.15 (d, J = 8.2 Hz, 2H), 3.82 (s, 2H) | 492.05 | 1.40 Method B |
| 73 | 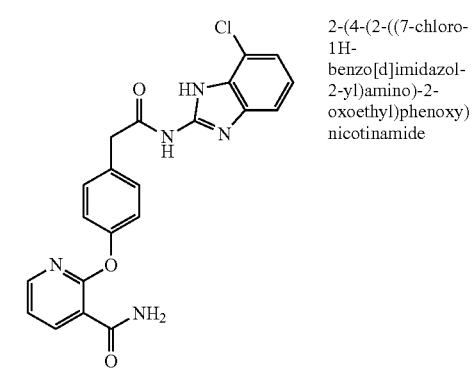 | 2-(4-(2-((7-chloro-1H-benzo[d]imidazol-2-yl)amino)-2-oxoethyl)phenoxy)nicotinamide | ¹H NMR (500 MHz, DMSO-d₆) δ 8.22-8.10 (m, 2H), 7.79 (br. s., 1H), 7.75 (br. s., 1H), 7.42 (d, J = 7.9 Hz, 3H), 7.27-7.13 (m, 4H), 7.11-7.01 (m, 1H), 3.79 (s, 2H), 1.23 (s, 2H) | 422.28 | 1.38 Method A |

| Ex # | Structure | Name | HNMR | LCMS (M + H)+ | HPLC retention time (min) |
|---|---|---|---|---|---|
| 74 | 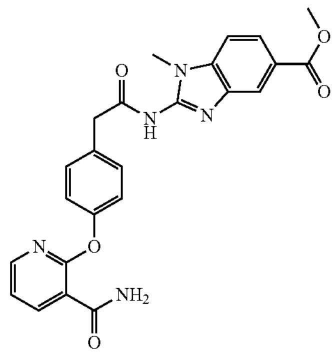 [SMILES: COC(=O)c1ccc2c(c1)nc(NC(=O)Cc1ccc(Oc3ncccc3C(N)=O)cc1)n2C] | methyl 2-(2-(4-((3-carbamoylpyridin-2-yl)oxy)phenyl)acetamido)-1-methyl-1H-benzo[d]imidazole-5-carboxylate | $^1$H NMR (500 MHz, DMSO-d$_6$) δ 8.22-8.17 (m, 1H), 8.15 (br s, 2H), 7.87 (br d, J = 8.2 Hz, 1H), 7.81 (br s, 1H), 7.74 (br s, 1H), 7.65-7.54 (m, 1H), 7.40 (br d, J = 8.2 Hz, 2H), 7.24-7.18 (m, 1H), 7.14 (br s, 2H), 3.85 (s, 3H), 3.60 (s, 3H), 3.57-3.29 (m, 2H), 3.17 (br d, J = 4.9 Hz, 1H) | 459.98 | 0.99 Method B |
| 75 | 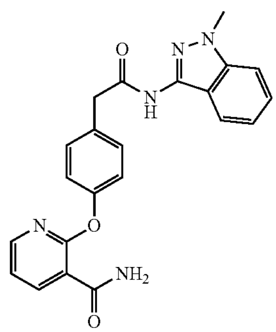 [SMILES: Cn1nc(NC(=O)Cc2ccc(Oc3ncccc3C(N)=O)cc2)c2ccccc21] | 2-(4-(2-((1-methyl-1H-indazol-3-yl)amino)-2-oxoethyl)phenoxy)nicotinamide | $^1$H NMR (500 MHz, DMSO-d$_6$) δ 10.67 (br. s., 1H), 8.28-8.10 (m, 2H), 7.82 (br. s., 1H), 7.75 (d, J = 8.2 Hz, 1H), 7.55 (d, J = 8.5 Hz, 1H), 7.48-7.33 (m, 3H), 7.21 (dd, J = 7.3, 4.9 Hz, 1H), 7.17 (d, J = 8.2 Hz, 2H), 7.06 (t, J = 7.5 Hz, 1H), 3.95 (s, 3H), 3.75 (s, 2H) | 402.2 | 1.20 Method A |
| 76 | 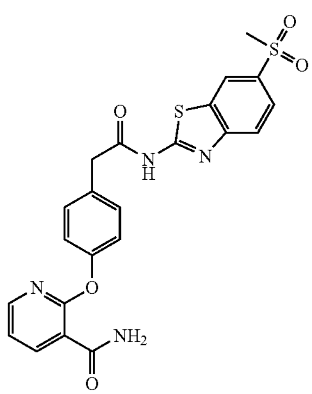 [SMILES: CS(=O)(=O)c1ccc2nc(NC(=O)Cc3ccc(Oc4ncccc4C(N)=O)cc3)sc2c1] | 2-(4-(2-((6-(methylsulfonyl)benzo[d]thiazol-2-yl)amino)-2-oxoethyl)phenoxy)nicotinamide | $^1$H NMR (500 MHz, DMSO-d$_6$) δ 8.64 (s, 1H), 8.23-8.13 (m, 2H), 7.96 (s, 1H), 7.81 (br. s., 1H), 7.76 (br. s., 1H), 7.42 (d, J = 7.9 Hz, 2H), 7.29-7.19 (m, 1H), 7.17 (d, J = 8.2 Hz, 2H), 3.91 (s, 2H), 3.25 (s, 3H) | 483.1 | 1.20 Method B |
| 77 | 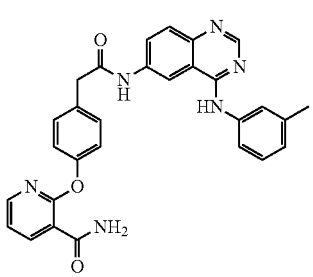 [SMILES: Cc1cccc(Nc2ncnc3ccc(NC(=O)Cc4ccc(Oc5ncccc5C(N)=O)cc4)cc23)c1] | 2-(4-(2-oxo-2-((4-(m-tolylamino)quinazolin-6-yl)amino)ethyl)phenoxy)nicotinamide | $^1$H NMR (500 MHz, DMSO-d$_6$) δ 10.61 (br. s., 1H), 8.65 (br. s., 1H), 8.48 (br. s., 1H), 8.16 (d, J = 4.9 Hz, 2H), 7.94-7.81 (m, 2H), 7.81-7.68 (m, 2H), 7.55 (br. s., 2H), 7.43 (d, J = 8.2 Hz, 2H), 7.31-7.19 (m, 2H), 7.15 (d, J = 8.2 Hz, 2H), 6.95 (d, J = 6.7 Hz, 1H), 3.85 (s, 2H), 2.32 (s, 3H) | 505.3 | 1.21 Method A |

| Ex # | Structure | Name | HNMR | LCMS (M + H)+ | HPLC retention time (min) |
|---|---|---|---|---|---|
| 78 | 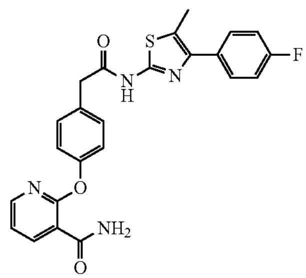 [SMILES: Cc1sc(NC(=O)Cc2ccc(Oc3ncccc3C(N)=O)cc2)nc1-c1ccc(F)cc1] | 2-(4-(2-((4-(4-fluorophenyl)-5-methylthiazol-2-yl)amino)-2-oxoethyl)phenoxy)nicotinamide | ¹H NMR (500 MHz, DMSO-d₆) δ 8.22-8.09 (m, 2H), 7.80 (br. s., 1H), 7.76 (br. s., 1H), 7.73-7.62 (m, 2H), 7.39 (d, J = 8.2 Hz, 2H), 7.28 (t, J = 8.7 Hz, 2H), 7.22-7.17 (m, 1H), 7.16 (d, J = 8.2 Hz, 2H), 3.79 (s, 2H), 2.45 (s, 3H) | 463.2 | 1.74 Method A |
| 79 | 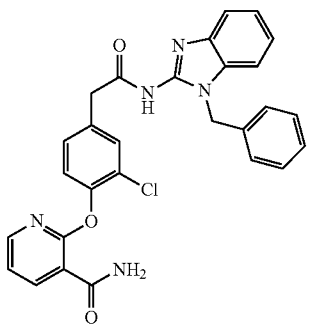 [SMILES: NC(=O)c1cccnc1Oc1ccc(CC(=O)Nc2nc3ccccc3n2Cc2ccccc2)cc1Cl] | 2-(4-(2-((1-benzyl-1H-benzo[d]imidazol-2-yl)amino)-2-oxoethyl)-2-chlorophenoxy)nicotinamide | ¹H NMR (500 MHz, DMSO-d₆) δ 8.26-8.20 (m, 1H), 8.18-8.06 (m, 1H), 7.88-7.80 (m, 1H), 7.78-7.70 (m, 1H), 7.63-7.54 (m, 1H), 7.50-7.47 (m, 1H), 7.44-7.41 (m, 1H), 7.39-7.34 (m, 2H), 7.34-7.27 (m, 3H), 7.27-7.20 (m, 2H), 7.22-7.14 (m, 2H), 7.15-7.04 (m, 1H), 5.38-5.30 (m, 2H), 3.77-3.67 (m, 2H) | 511.9 | 1.83 Method A |
| 80 | 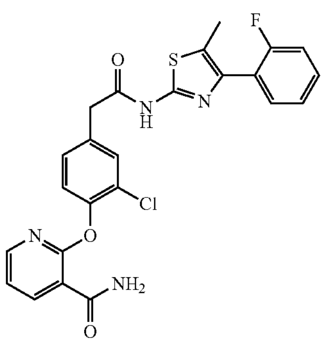 [SMILES: Cc1sc(NC(=O)Cc2ccc(Oc3ncccc3C(N)=O)c(Cl)c2)nc1-c1ccccc1F] | 2-(2-chloro-4-(2-((4-(2-fluorophenyl)-5-methylthiazol-2-yl)amino)-2-oxoethyl)phenoxy)nicotinamide | ¹H NMR (500 MHz, DMSO-d₆) δ 8.27-8.20 (m, 1H), 8.18 (br d, J = 3.1 Hz, 1H), 7.81 (br s, 1H), 7.78 (br s, 1H), 7.56 (s, 1H), 7.53-7.42 (m, 2H), 7.38 (s, 2H), 7.35-7.28 (m, 2H), 7.26-7.17 (m, 1H), 3.83 (s, 2H), 2.27 (s, 3H) | 497.1 | 1.83 Method A |
| 81 | 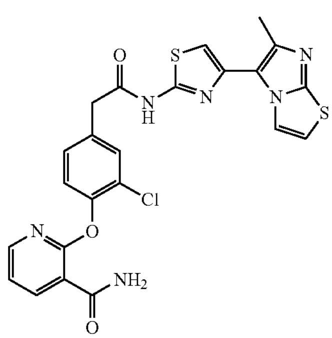 [SMILES: Cc1nc2sccn2c1-c1csc(NC(=O)Cc2ccc(Oc3ncccc3C(N)=O)c(Cl)c2)n1] | 2-(2-chloro-4-(2-((4-(6-methylimidazo[2,1-b]thiazol-5-yl)thiazol-2-yl)amino)-2-oxoethyl)phenoxy)nicotinamide | ¹H NMR (500 MHz, DMSO-d₆) δ 8.32 (d, J = 4.6 Hz, 1H), 8.23 (dd, J = 7.5, 1.7 Hz, 1H), 8.18 (dd, J = 4.7, 1.7 Hz, 1H), 7.82 (br s, 1H), 7.77 (br s, 1H), 7.59 (s, 1H), 7.40 (s, 1H), 7.37 (br d, J = 4.6 Hz, 1H), 7.30 (s, 1H), 7.27-7.20 (m, 1H), 7.13 (s, 1H), 7.03 (s, 1H), 3.91 (s, 2H), 2.49 (s, 3H) | 525.0 | 1.11 Method B |

| Ex # | Structure | Name | HNMR | LCMS (M + H)+ | HPLC retention time (min) |
|---|---|---|---|---|---|
| 82 | 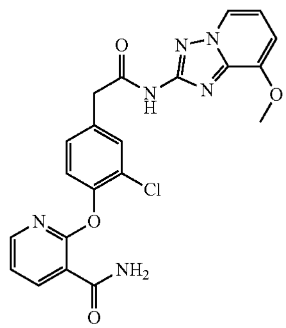 [SMILES: COc1cccn2nc(NC(=O)Cc3ccc(Oc4ncccc4C(N)=O)c(Cl)c3)nc12] | 2-(2-chloro-4-(2-((8-methoxy-[1,2,4]triazolo[1,5-a]pyridin-2-yl)amino)-2-oxoethyl)phenoxy)nicotinamide | $^1$H NMR (500 MHz, DMSO-d$_6$) δ 11.09 (br s, 1H), 8.44 (d, J = 6.4 Hz, 1H), 8.23 (dd, J = 7.5, 1.7 Hz, 1H), 8.20-8.13 (m, 1H), 7.82 (br s, 1H), 7.77 (br s, 1H), 7.57 (s, 1H), 7.38 (s, 2H), 7.25 (dd, J = 7.3, 4.9 Hz, 1H), 7.15-7.08 (m, 1H), 7.08-7.01 (m, 1H), 3.99 (s, 3H), 3.83 (br 2, 2H) | 452.9 | 1.01 Method A |
| 83 | 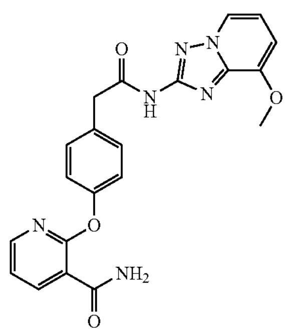 [SMILES: COc1cccn2nc(NC(=O)Cc3ccc(Oc4ncccc4C(N)=O)cc3)nc12] | 2-(4-(2-((8-methoxy-[1,2,4]triazolo[1,5-a]pyridin-2-yl)amino)-2-oxoethyl)phenoxy)nicotinamide | $^1$H NMR (500 MHz, DMSO-d$_6$) δ 11.05 (br s, 1H), 8.43 (d, J = 6.4 Hz, 1H), 8.25-8.13 (m, 2H), 7.80 (br s, 1H), 7.76 (br s, 1H), 7.40 (br d, J = 8.2 Hz, 2H), 7.22 (dd, J = 7.3, 4.9 Hz, 1H), 7.16 (d, J = 8.5 Hz, 2H), 7.12-7.07 (m, 1H), 7.07-6.99 (m, 1H), 3.98 (s, 3H), 3.78 (br s, 2H) | 418.9 | 0.88 Method A |
| 84 | 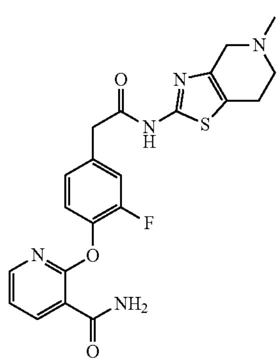 [SMILES: CN1CCc2sc(NC(=O)Cc3ccc(Oc4ncccc4C(N)=O)c(F)c3)nc2C1] | 2-(2-fluoro-4-(2-((5-methyl-4,5,6,7-tetrahydrothiazolo[4,5-c]pyridin-2-yl)amino)-2-oxoethyl)phenoxy)nicotinamide | $^1$H NMR (500 MHz, DMSO-d$_6$) δ 8.29-8.12 (m, 2H), 7.82 (br s, 1H), 7.80 (br s, 1H), 7.46-7.29 (m, 2H), 7.28-7.08 (m, 2H), 3.81 (s, 2H), 3.49 (s, 2H), 2.70 (br d, J = 4.9 Hz, 2H), 2.66 (br d, J = 4.9 Hz, 2H), 2.38 (s, 3H) | 442.1 | 1.04 Method A |
| 85 | 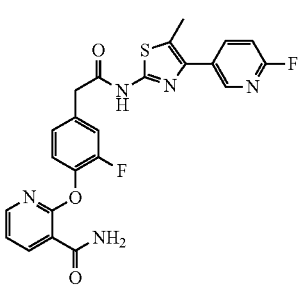 [SMILES: Cc1sc(NC(=O)Cc2ccc(Oc3ncccc3C(N)=O)c(F)c2)nc1-c1ccc(F)nc1] | 2-(2-fluoro-4-(2-((4-(6-fluoropyridin-3-yl)-5-methylthiazol-2-yl)amino)-2-oxoethyl)phenoxy)nicotinamide | $^1$H NMR (500 MHz, DMSO-d$_6$) δ 8.50 (s, 1H), 8.25-8.16 (m, 3H), 7.72 (br s, 1H), 7.65 (br s, 1H), 7.40-7.30 (m, 2H), 7.28-7.17 (m, 3H), 3.89 (s, 1H), 3.83 (s, 2H), 2.48 (s, 3H) | 482.1 | 1.49 Method A |

| Ex # | Structure | Name | HNMR | LCMS (M + H)+ | HPLC retention time (min) |
|---|---|---|---|---|---|
| 86 | 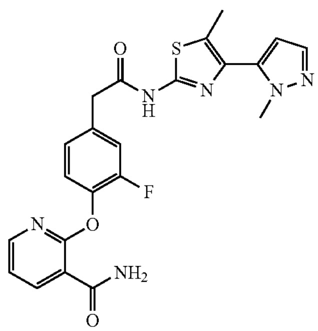 [SMILES: Cc1sc(NC(=O)Cc2ccc(Oc3ncccc3C(N)=O)c(F)c2)nc1-c1ccnn1C] | 2-(2-fluoro-4-(2-((5-methyl-4-(1-methyl-1H-pyrazol-5-yl)thiazol-2-yl)amino)-2-oxoethyl)phenoxy)nicotinamide | ¹H NMR (500 MHz, DMSO-d₆) δ 8.34-8.03 (m, 2H), 7.85 (br s, 1H), 7.78 (br s, 1H), 7.49 (d, J = 1.5 Hz, 1H), 7.40-7.30 (m, 2H), 7.28-7.18 (m, 2H), 6.43 (d, J = 1.8 Hz, 1H), 3.89 (s, 3H), 3.84 (s, 2H), 3.57 (s, 1H), 2.35 (s, 3H) | 466.9 | 1.38 Method A |
| 87 | 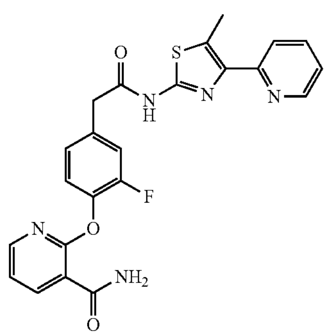 [SMILES: Cc1sc(NC(=O)Cc2ccc(Oc3ncccc3C(N)=O)c(F)c2)nc1-c1ccccn1] | 2-(2-fluoro-4-(2-((5-methyl-4-(pyridin-2-yl)thiazol-2-yl)amino)-2-oxoethyl)phenoxy)nicotinamide | ¹H NMR (500 MHz, DMSO-d₆) δ 8.63 (br d, J = 4.3 Hz, 1H), 8.25-8.15 (m, 2H), 8.00-7.93 (m, 1H), 7.93-7.87 (m, 1H), 7.84 (br s, 1H), 7.79 (br s, 1H), 7.43-7.30 (m, 3H), 7.28-7.18 (m, 3H), 3.85 (s, 2H), 2.73 (s, 3H) | 463.9 | 1.0 Method B |
| 88 | 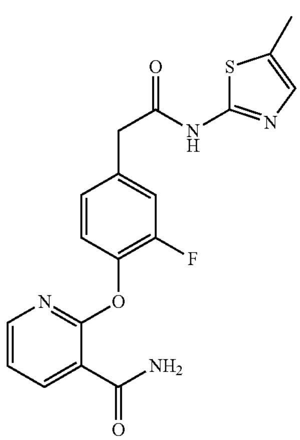 [SMILES: Cc1cnc(NC(=O)Cc2ccc(Oc3ncccc3C(N)=O)c(F)c2)s1] | 2-(2-fluoro-4-(2-((5-methylthiazol-2-yl)amino)-2-oxoethyl)phenoxy)nicotinamide | ¹H NMR (500 MHz, DMSO-d₆) δ 8.28-8.12 (m, 2H), 7.84 (br s, 1H), 7.78 (br s, 1H), 7.40-7.33 (m, 1H), 7.31 (br d, J = 11.3 Hz, 1H), 7.25 (dd, J = 7.3, 4.9 Hz, 1H), 7.20 (br d, J = 8.2 Hz, 1H), 7.14 (s, 1H), 3.83 (s, 2H), 3.53 (s, 1H), 2.33 (s, 3H) | 387.0 | 1.14 Method B |
| 89 | 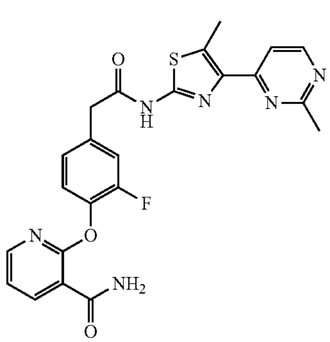 [SMILES: Cc1nccc(-c2nc(NC(=O)Cc3ccc(Oc4ncccc4C(N)=O)c(F)c3)sc2C)n1] | 2-(2-fluoro-4-(2-((5-methyl-4-(2-methylpyrimidin-4-yl)thiazol-2-yl)amino)-2-oxoethyl)phenoxy)nicotinamide | ¹H NMR (500 MHz, DMSO-d₆) δ 12.49 (s, 1H), 8.76 (d, J = 5.5 Hz, 1H), 8.30-8.10 (m, 2H), 7.83 (br s, 1H), 7.80 (br s, 1H), 7.73 (d, J = 5.2 Hz, 1H), 7.48-7.31 (m, 2H), 7.29-7.16 (m, 2H), 3.86 (s, 2H), 2.82 (s, 3H), 2.66 (s, 3H) | 478.9 | 1.20 Method B |

-continued

| Ex # | Structure | Name | HNMR | LCMS (M + H)+ | HPLC retention time (min) |
|---|---|---|---|---|---|
| 90 | 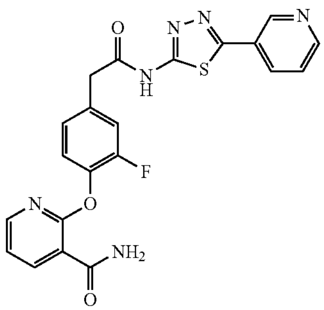 [SMILES: NC(=O)c1cccnc1Oc1ccc(CC(=O)Nc2nnc(-c3cccnc3)s2)cc1F] | 2-(2-fluoro-4-(2-oxo-2-((5-(pyridin-3-yl)-1,3,4-thiadiazol-2-yl)amino)ethyl)phenoxy)nicotinamide | $^1$H NMR (500 MHz, DMSO-d$_6$) δ 9.44-9.03 (m, 1H), 8.98-8.57 (m, 1H), 8.31 (br d, J = 7.8 Hz, 1H), 8.25-8.08 (m, 2H), 7.73 (br s, 1H), 7.65 (br s, 1H), 7.60 (br s, 1H), 7.43-7.32 (m, 2H), 7.28-7.20 (m, 2H), 3.95 (s, 2H), 1.25 (s, 1H) | 451.1 | 1.14 Method A |
| 91 | 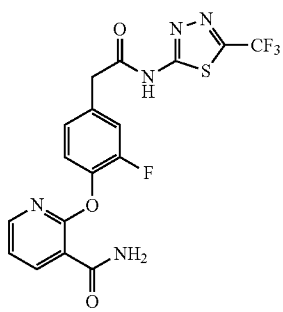 [SMILES: NC(=O)c1cccnc1Oc1ccc(CC(=O)Nc2nnc(C(F)(F)F)s2)cc1F] | 2-(2-fluoro-4-(2-oxo-2-((5-(trifluoromethyl)-1,3,4-thiadiazol-2-yl)amino)ethyl)phenoxy)nicotinamide | $^1$H NMR (500 MHz, DMSO-d$_6$) δ 8.27-8.14 (m, 2H), 7.84 (br s, 1H), 7.79 (br s, 1H), 7.41-7.32 (m, 2H), 7.28-7.15 (m, 2H), 3.97 (br s, 2H), 3.18 (br s, 1H) | 442.0 | 1.50 Method A |
| 92 | 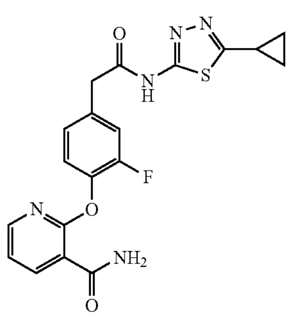 [SMILES: NC(=O)c1cccnc1Oc1ccc(CC(=O)Nc2nnc(C3CC3)s2)cc1F] | 2-(4-(2-((5-cyclopropyl-1,3,4-thiadiazol-2-yl)amino)-2-oxoethyl)-2-fluorophenoxy)nicotinamide | $^1$H NMR (500 MHz, DMSO-d$_6$) δ 12.68 (br s, 1H), 8.32-8.11 (m, 2H), 7.83 (br s, 1H), 7.79 (br s, 1H), 7.45-7.29 (m, 2H), 7.25 (br dd, J = 7.3, 4.9 Hz, 1H), 7.20 (br d, J = 7.9 Hz, 1H), 3.86 (s, 2H), 2.39 (tt, J = 8.4, 4.2 Hz, 1H), 1.17-1.08 (m, 2H), 1.03-0.91 (m, 2H) | 413.8 | 1.18 Method B |
| 93 | 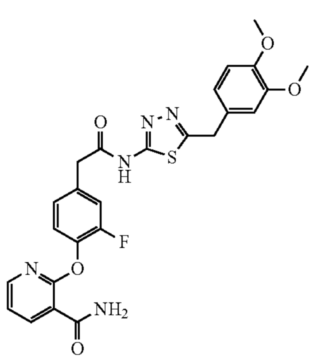 [SMILES: COc1ccc(Cc2nnc(NC(=O)Cc3ccc(Oc4ncccc4C(N)=O)c(F)c3)s2)cc1OC] | 2-(4-(2-((5-(3,4-dimethoxybenzyl)-1,3,4-thiadiazol-2-yl)amino)-2-oxoethyl)-2-fluorophenoxy)nicotinamide | $^1$H NMR (500 MHz, DMSO-d$_6$) δ 8.20 (dd, J = 7.4, 1.6 Hz, 1H), 8.18-8.14 (m, 1H), 7.71 (br s, 1H), 7.64 (br s, 1H), 7.47-7.27 (m, 2H), 7.24 (dd, J = 7.4, 4.9 Hz, 1H), 7.18 (br d, J = 8.2 Hz, 1H), 7.03-6.89 (m, 2H), 6.87-6.71 (m, 1H), 4.25 (s, 2H), 3.85 (s, 2H), 3.74 (s, 6 H), 1.25 (s, 1H) | 524.1 | 1.32 Method A |

| Ex # | Structure | Name | HNMR | LCMS (M + H)+ | HPLC retention time (min) |
|---|---|---|---|---|---|
| 94 | 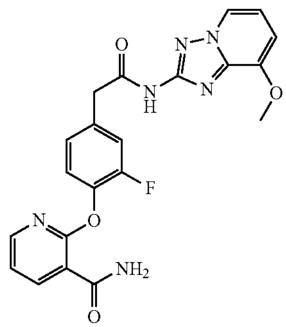 | 2-(2-fluoro-4-(2-((8-methoxy-[1,2,4]triazolo[1,5-a]pyridin-2-yl)amino)-2-oxoethyl)phenoxy)nicotinamide | ¹H NMR (500 MHz, DMSO-d₆) δ 10.91 (br s, 1H), 8.40 (d, J = 6.4 Hz, 1H), 8.21 (dd, J = 7.4, 1.8 Hz, 1H), 8.19 (dd, J = 4.8, 1.8 Hz, 1H), 7.72 (br s, 1H), 7.65 (br s, 1H), 7.46-7.30 (m, 2H), 7.28-7.16 (m, 2H), 7.10-7.06 (m, 1H), 7.06-7.01 (m, 1H), 3.99 (s, 3H), 3.83 (s, 2H) | 437.1 | 0.94 Method A |
| 95 | 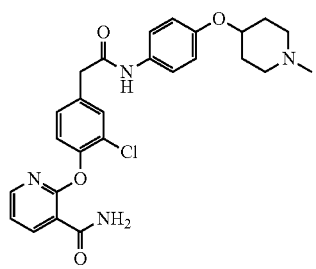 [SMILES: CN1CCC(Oc2ccc(NC(=O)Cc3ccc(Oc4ncccc4C(N)=O)c(Cl)c3)cc2)CC1] | 2-(2-chloro-4-(2-((4-((1-methylpiperidin-4-yl)oxy)phenyl)amino)-2-oxoethyl)phenoxy)nicotinamide | ¹H NMR (500 MHz, DMSO-d₆) δ 10.09 (s, 1H), 8.26-8.20 (m, 1H), 8.18-8.13 (m, 1H), 7.87-7.79 (m, 1H), 7.77 (br s, 1H), 7.54 (s, 1H), 7.50 (d, J = 8.9 Hz, 1H), 7.36 (s, 1H), 7.25 (dd, J = 7.3, 4.9 Hz, 1H), 6.91 (d, J = 8.9 Hz, 1H), 4.30 (br s, 1H), 3.66 (s, 2H), 2.69-2.59 (m, 1H), 2.56 (s, 3H), 2.20 (s, 3H), 1.92 (s, 5H), 1.62 (br d, J = 8.5 Hz, 1H) | 495.3 | 0.95 Method A |
| 96 | 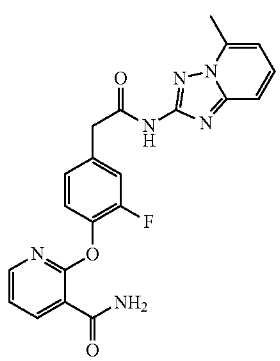 [SMILES: Cc1cccc2nc(NC(=O)Cc3ccc(Oc4ncccc4C(N)=O)c(F)c3)nn12] | 2-(2-fluoro-4-(2-((5-methyl-[1,2,4]triazolo[1,5-a]pyridin-2-yl)amino)-2-oxoethyl)phenoxy)nicotinamide | ¹H NMR (500 MHz, DMSO-d₆) δ 11.11 (br s, 1H), 8.26-8.09 (m, 2H), 7.88 (br s, 1H), 7.78 (br s, 1H), 7.64-7.49 (m, 2H), 7.43-7.31 (m, 2H), 7.26-7.16 (m, 2H), 7.03 (br d, J = 6.3 Hz, 1H), 2.75 (s, 2H), 2.67 (s, 3H) | 421.3 | 1.0 Method A |
| 97 | 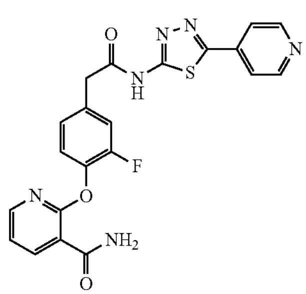 [SMILES: NC(=O)c1cccnc1Oc1ccc(CC(=O)Nc2nnc(-c3ccncc3)s2)cc1F] | 2-(2-fluoro-4-(2-oxo-2-((5-(pyridin-4-yl)-1,3,4-thiadiazol-2-yl)amino)ethyl)phenoxy)nicotinamide | ¹H NMR (400 MHz, DMSO-d₆) δ 13.17 (s, 1H), 8.86-8.71 (m, 2H), 8.30-8.15 (m, 2H), 8.04-7.94 (m, 2H), 7.83 (br s, 1H), 7.80 (br s, 1H), 7.42-7.35 (m, 2H), 7.28-7.23 (m, 2H), 3.97 (s, 2H) | 451.0 | 5.69 Method C |

-continued

| Ex # | Structure | Name | HNMR | LCMS (M + H)+ | HPLC retention time (min) |
|---|---|---|---|---|---|
| 98 | 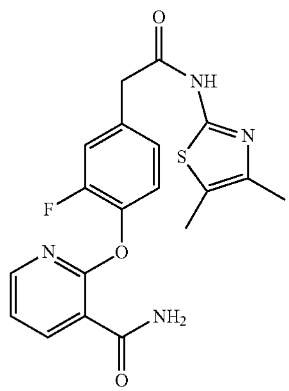 [SMILES: Cc1nc(NC(=O)Cc2ccc(Oc3ncccc3C(N)=O)c(F)c2)sc1C] | 2-(4-(2-((4,5-dimethylthiazol-2-yl)amino)-2-oxoethyl)-2-fluorophenoxy)nicotinamide | ¹H NMR (500 MHz, DMSO-d₆) δ 8.20 (br d, J = 7.5 Hz, 1H), 8.16 (br d, J = 3.7 Hz, 1H), 7.74 (br s, 1H), 7.60 (br s, 1H), 7.37-7.26 (m, 2H), 7.24 (dd, J = 7.4, 4.9 Hz, 1H), 7.18 (br d, J = 8.2 Hz, 1H), 3.76 (s, 2H), 2.21 (s, 3H), 2.14 (s, 3H), 1.23 (s, 1H) | 401.1 | 1.33 Method A |
| 99 | 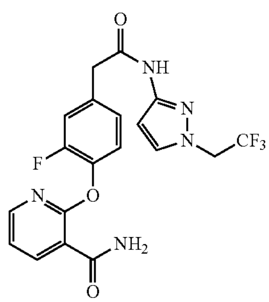 [SMILES: NC(=O)c1cccnc1Oc1ccc(CC(=O)Nc2ccn(CC(F)(F)F)n2)cc1F] | 2-(2-fluoro-4-(2-oxo-2-((1-(2,2,2-trifluoroethyl)-1H-pyrazol-3-yl)amino)ethyl)phenoxy)nicotinamide | ¹H NMR (500 MHz, DMSO-d₆) δ 10.69 (br s, 1H), 8.21 (br d, J = 7.4 Hz, 1H), 8.17 (br d, J = 3.2 Hz, 1H), 7.71 (br d, J = 1.6 Hz, 2H), 7.62 (br s, 1H), 7.38-7.27 (m, 2H), 7.24 (dd, J = 7.3, 5.0 Hz, 1H), 7.19 (br d, J = 8.1 Hz, 1H), 6.59 (br s, 1H), 4.96 (q, J = 9.0 Hz, 2H), 3.68 (s, 2H) | 438.0 | 1.21 Method A |
| 100 | 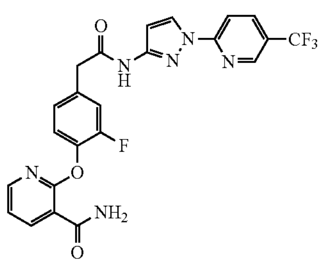 [SMILES: NC(=O)c1cccnc1Oc1ccc(CC(=O)Nc2ccn(-c3ccc(C(F)(F)F)cn3)n2)cc1F] | 2-(2-fluoro-4-(2-oxo-2-((1-(5-(trifluoromethyl)pyridin-2-yl)-1H-pyrazol-3-yl)amino)ethyl)phenoxy)nicotinamide | ¹H NMR (500 MHz, DMSO-d₆) δ 11.18 (s, 1H), 8.85 (s, 1H), 8.60 (d, J = 2.7 Hz, 1H), 8.47-8.33 (m, 1H), 8.24-8.15 (m, 2H), 7.92 (d, J = 8.5 Hz, 1H), 7.83 (br s, 1H), 7.78 (br s, 1H), 7.41-7.29 (m, 2H), 7.27-7.16 (m, 2H), 6.92 (d, J = 2.4 Hz, 1H), 3.75 (s, 2H) | 501.2 | 1.76 Method A |
| 101 | 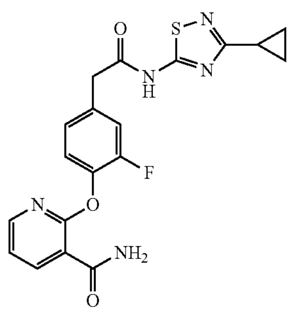 [SMILES: NC(=O)c1cccnc1Oc1ccc(CC(=O)Nc2nc(C3CC3)ns2)cc1F] | 2-(4-(2-((3-cyclopropyl-1,2,4-thiadiazol-5-yl)amino)-2-oxoethyl)-2-fluorophenoxy)nicotinamide | ¹H NMR (500 MHz, DMSO-d₆) δ 8.26-8.13 (m, 2H), 7.83 (br s, 1H), 7.78 (br s, 1H), 7.41-7.28 (m, 2H), 7.25 (dd, J = 7.3, 4.9 Hz, 1H), 7.20 (br d, J = 7.9 Hz, 1H), 3.85 (s, 2H), 3.44 (br s, 1H), 2.44-2.28 (m, 1H), 1.25-1.08 (m, 2H), 1.02-0.84 (m, 2H) | 413.9 | 1.18 Method B |

| Ex # | Structure | Name | HNMR | LCMS (M + H)+ | HPLC retention time (min) |
|---|---|---|---|---|---|
| 102 | 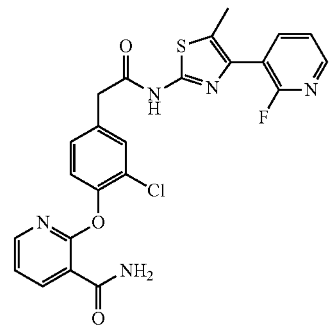 [SMILES: Cc1sc(NC(=O)Cc2ccc(Oc3ncccc3C(N)=O)c(Cl)c2)nc1-c1cccnc1F] | 2-(2-chloro-4-(2-((4-(2-fluoropyridin-3-yl)-5-methylthiazol-2-yl)amino)-2-oxoethyl)phenoxy)nicotinamide | $^1$H NMR (500 MHz, DMSO-d$_6$) δ 12.47 (s, 1H), 8.30 (br d, J = 4.0 Hz, 1H), 8.23 (br d, J = 7.6 Hz, 1H), 8.19 (br d, J = 3.1 Hz, 1H), 8.08 (br t, J = 7.9 Hz, 1H), 7.82 (br s, 1H), 7.77 (br s, 1H), 7.57 (s, 1H), 7.49 (br t, J = 5.3 Hz, 1H), 7.38 (s, 2H), 7.25 (dd, J = 7.5, 5.0 Hz, 1H), 3.84 (s, 2H), 2.31 (s, 3H) | 497.9 | 1.52 Method A |
| 103 | 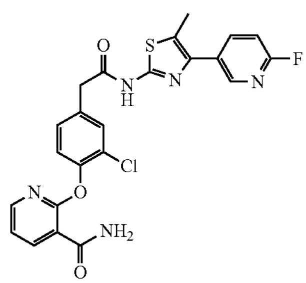 [SMILES: Cc1sc(NC(=O)Cc2ccc(Oc3ncccc3C(N)=O)c(Cl)c2)nc1-c1ccc(F)nc1] | 2-(2-chloro-4-(2-((4-(6-fluoropyridin-3-yl)-5-methylthiazol-2-yl)amino)-2-oxoethyl)phenoxy)nicotinamide | $^1$H NMR (500 MHz, DMSO-d$_6$) δ 12.46 (s, 1H), 8.52 (s, 1H), 8.35-8.15 (m, 3H), 7.82 (br s, 1H), 7.77 (br s, 1H), 7.57 (s, 1H), 7.38 (s, 1H), 7.30 (dd, J = 8.4, 2.6 Hz, 1H), 7.25 (dd, J = 7.3, 4.9 Hz, 1H), 3.85 (s, 2H), 2.49 (s, 3H) | 498.1 | 1.55 Method B |
| 104 | 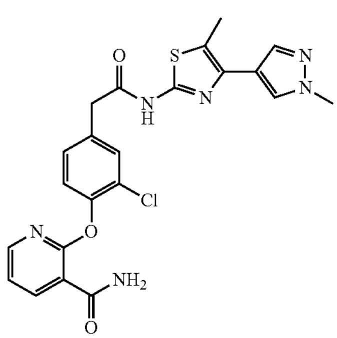 [SMILES: Cc1sc(NC(=O)Cc2ccc(Oc3ncccc3C(N)=O)c(Cl)c2)nc1-c1cnn(C)c1] | 2-(2-chloro-4-(2-((5-methyl-4-(1-methyl-1H-pyrazol-4-yl)thiazol-2-yl)amino)-2-oxoethyl)phenoxy)nicotinamide | $^1$H NMR (500 MHz, DMSO-d$_6$) δ 12.34 (s, 1H), 8.23 (br d, J = 7.3 Hz, 1H), 8.20-8.15 (m, 1H), 7.99 (s, 1H), 7.83 (br s, 1H), 7.77 (br s, 1H), 7.72 (s, 1H), 7.56 (s, 1H), 7.38 (s, 2H), 7.25 (dd, J = 7.5, 5.0 Hz, 1H), 3.90 (s, 3H), 3.82 (s, 2H), 2.41 (s, 3H) | 482.9 | 1.36 Method B |
| 105 | 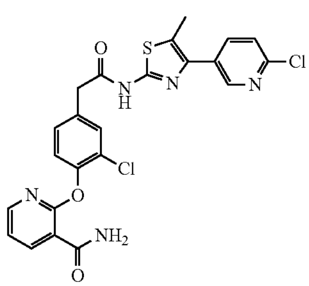 [SMILES: Cc1sc(NC(=O)Cc2ccc(Oc3ncccc3C(N)=O)c(Cl)c2)nc1-c1ccc(Cl)nc1] | 2-(2-chloro-4-(2-((4-(6-chloropyridin-3-yl)-5-methylthiazol-2-yl)amino)-2-oxoethyl)phenoxy)nicotinamide | $^1$H NMR (500 MHz, DMSO-d$_6$) δ 12.50 (s, 1H), 8.71 (d, J = 2.1 Hz, 1H), 8.23 (dd, J = 7.3, 1.5 Hz, 1H), 8.18 (dd, J = 4.9, 1.5 Hz, 1H), 8.11 (dd, J = 8.2, 2.4 Hz, 1H), 7.83 (br s, 1H), 7.77 (br s, 1H), 7.62 (d, J = 8.2 Hz, 1H), 7.57 (s, 1H), 7.39 (s, 2H), 7.25 (dd, J = 7.5, 5.0 Hz, 1H), 3.85 (s, 2H), 2.56 (s, 3H) | 514.1 | 1.68 |

Example 106. 2-(4-(1-((7-methoxy-4,5-dihydronaphtho[1,2-d]thiazol-2-yl)amino)-1-oxopropan-2-yl)phenoxy)nicotinamide

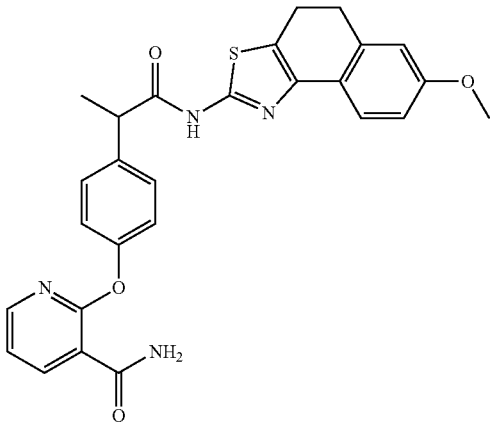 [SMILES: COc1ccc2c(c1)CCc1sc(NC(=O)C(C)c3ccc(Oc4ncccc4C(N)=O)cc3)nc1-2]

Step 1. To methyl 2-(4-hydroxyphenyl)acetate (2.23 g, 13.4 mmol) in DMSO (10 ml) was added methyl 2-(4-hydroxyphenyl)acetate (2.23 g, 13.4 mmol) and K$_2$CO$_3$ (4.08 g, 29.5 mmol) and the reaction mixture was heated to 60° C. for 24 h. Water (25 mL was added and the reaction mixture was extracted with ethylacetate (3×30 mL). The combined organic layers were washed with water (25 mL), then brine (25 mL) and dried (MgSO$_4$), filtered and concentrated under reduced pressure to afford methyl 2-(4-((3-cyanopyridin-2-yl)oxy)phenyl)acetate (2.9 g, 81% yield) as a tan solid; $^1$H NMR (400 MHz, CDCl$_3$) δ 8.34 (dd, J=5.1, 2.0 Hz, 1H), 8.04 (dd, J=7.5, 2.0 Hz, 1H), 7.48-7.37 (m, 2H), 7.23-7.15 (m, 2H), 7.12 (dd, J=7.5, 5.1 Hz, 1H), 3.74 (s, 3H), 3.69 (s, 2H). LCMS(ESI) m/z: 268.9 (M+H).$^+$ Step 2. To methyl 2-(4-((3-cyanopyridin-2-yl)oxy)phenyl)acetate (0.20 g, 0.74 mmol) and iodomethane (0.046 ml, 0.74 mmol) in DMF (3 mL), cooled to 0° C., was added NaH (0.066 g, 1.6 mmol)(60% suspension in oil). After 24 h, the reaction mixture was quenched by the addition of water (10 mL) and extracted with ethyl acetate (3×10 mL). The combined organic layers were washed with brine (15 mL) and dried (MgSO$_4$). Methyl 2-(4-((3-cyanopyridin-2-yl)oxy)phenyl)propanoate (0.149 g) was obtained as a yellow oil and used without further purification in next step. LCMS (ESI) m/z: 282.9 (M+H).$^+$ Step 3. 2-(4-((3-carbamoylpyridin-2-yl)oxy)phenyl)propanoic acid (0.2 g) was obtained from H$_2$O$_2$ oxidation of methyl 2-(4-((3-cyanopyridin-2-yl)oxy)phenyl)propanoate as described for intermediate 5, followed by the addition of LiOH (0.2 g). After 24 h, the reaction mixture was acidified to pH=5 by the addition of 1 N HCl and extracted with ethyl acetate (3×20 mL). The combined organic layers were washed with brine (15 mL) and dried (MgSO$_4$), filtered and concentrated under reduced pressure to afford a white solid. LCMS(ESI) m/z: 286.9 (M+H).$^+$ Example 106 (1.4 mg, 4.5%) was prepared by the coupling of 2-(4-((3-carbamoylpyridin-2-yl)oxy)phenyl)propanoic acid and 7-methoxy-4,5-dihydronaphtho[1,2-d]thiazol-2-amine in a similar manner as described for example 1. $^1$H NMR (500 MHz, DMSO-d$_6$) δ 8.15 (br. s., 2H), 7.94-7.81 (m, 1H), 7.80-7.70 (m, 1H), 7.67-7.51 (m, 1H), 7.42 (d, J=7.7 Hz, 2H), 7.24-7.15 (m, 1H), 7.14 (d, J=7.7 Hz, 2H), 6.85 (br. s., 2H), 4.41-4.30 (m, 1H), 4.08-3.95 (m, 1H), 2.92 (d, J=7.3 Hz, 2H), 2.90-2.80 (m, 2H), 1.45 (d, J=6.6 Hz, 3H) one Me under solvent. LCMS m/z=500.9 (M+H).$^+$ HPLC purity 95.9% with retention time 1.91 min. [method A]

Example 107. 2-(4-(2-((5-(2-hydroxy-2-methylpropoxy)benzo[d]thiazol-2-yl)amino)-2-oxoethyl)phenoxy)nicotinamide

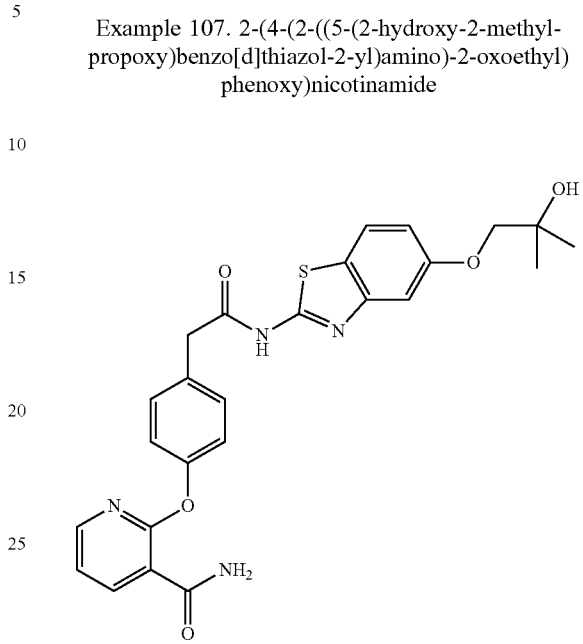

Example 107 (3.3 mg, 6.8% yield) was prepared in a similar manner as example 3 substituting intermediate 6 for intermediate 5. $^1$H NMR (500 MHz, DMSO-d$_6$) δ 8.23-8.11 (m, 2H), 7.82 (d, J=8.5 Hz, 2H), 7.78 (br. s., 1H), 7.40 (d, J=8.2 Hz, 2H), 7.27 (s, 1H), 7.25-7.19 (m, 1H), 7.16 (d, J=8.2 Hz, 2H), 6.96 (d, J=8.6 Hz, 1H), 4.69 (br. s., 1H), 3.85 (s, 2H), 3.78 (s, 2H), 1.23 (s, 6H). LCMS m/z=493.0 (M+H).$^+$ HPLC purity 100% with retention time 1.39 min. [method B]

Example 108. 2-(4-(2-((7-(2-hydroxy-2-methylpropoxy)-4,5-dihydronaphtho[1,2-d]thiazol-2-yl)amino)-2-oxoethyl)phenoxy)nicotinamide

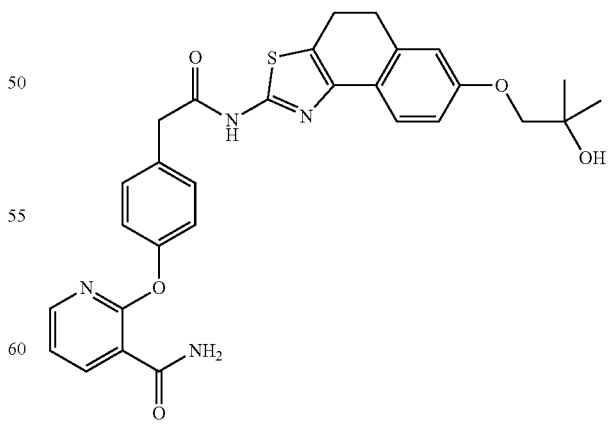

Step 1. To 7-methoxy-4,5-dihydronaphtho[1,2-d]thiazol-2-amine, hydrobromide (0.22 g, 0.70 mmol) stirred in DCM (5 ml) was added BBr$_3$ (0.702 ml, 0.702 mmol). After 72 h, The reaction mixture was cooled to 0° C., quenched by the addition of aqueous K₂CO₃ and MeOH, filtered and concentrated under reduced pressure and purified by silica gel chromatography using DCM/0-10% MeOH as eluents to afford 2-amino-4,5-dihydronaphtho[1,2-d]thiazol-7-ol (0.22 g) as a light brown solid. LCMS(ESI) m/z: 218.8 (M+H).⁺

Step 2. 1-((2-Amino-4,5-dihydronaphtho[1,2-d]thiazol-7-yl)oxy)-2-methylpropan-2-ol (0.12 g, 61%) was prepared from 2-amino-4,5-dihydronaphtho[1,2-d]thiazol-7-ol in a similar manner as described in example 3. ¹H NMR (400 MHz, CDCl3) δ 7.66-7.62 (m, 1H), 6.87-6.79 (m, 2H), 4.91 (br. s., 2H), 3.84 (s, 2H), 3.07-2.97 (m, 2H), 2.90-2.82 (m, 2H), 2.44-2.24 (m, 1H), 1.38 (s, 6H), LCMS(ESI) m/z: 290.9 (M+H).⁺

Example 108 (4.3 mg, 8.4%) was obtained via the coupling of 1-((2-amino-4,5-dihydronaphtho[1,2-d]thiazol-7-yl)oxy)-2-methylpropan-2-ol and 2-(4-((3-carbamoylpyridin-2-yl)oxy)phenyl)acetic acid as described in example 2. ¹H NMR (500 MHz, DMSO-d₆) δ 8.20-8.10 (m, 2H), 7.84 (br. s., 1H), 7.76 (br. s., 1H), 7.56 (d, J=8.3 Hz, 1H), 7.38 (d, J=8.2 Hz, 2H), 7.25-7.18 (m, 1H), 7.14 (d, J=8.2 Hz, 2H), 6.90-6.83 (m, 1H), 6.86-6.78 (m, 1H), 4.78 (br. s., 1H), 3.00-2.91 (m, 2H), 2.90-2.81 (m, 2H), 1.27-1.16 (m, 7H), peaks hidden under water peak. LCMS m/z=545.1 (M+H).⁺ HPLC purity 99% with retention time 1.59 min. [method B]

Example 109. 2-(4-(2-((6-(2-hydroxy-2-methylpropoxy)benzo[d]thiazol-2-yl)amino)-2-oxoethyl)phenoxy)nicotinamide

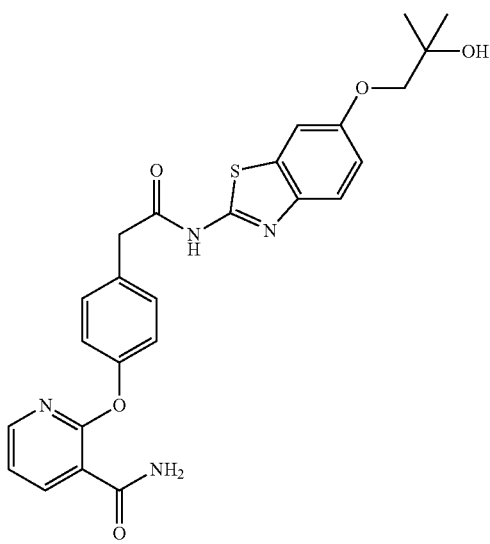 [SMILES: CC(C)(O)COc1ccc2nc(NC(=O)Cc3ccc(Oc4ncccc4C(N)=O)cc3)sc2c1]

Example 109 (5.2 mg, 11%) was prepared as previously described for example 3 by substituting intermediate 6 for intermediate 5. ¹H NMR (500 MHz, DMSO-d₆) δ 8.23-8.12 (m, 2H), 7.79 (br. s., 1H), 7.75 (br. s., 1H), 7.63 (d, J=8.8 Hz, 1H), 7.54 (s, 1H), 7.39 (d, J=8.2 Hz, 2H), 7.21 (br. s., 1H), 7.20-7.11 (m, 2H), 7.04 (d, J=8.8 Hz, 1H), 3.83 (s, 2H), 3.75 (s, 2H), 1.27-1.15 (m, 8H); LCMS m/z=493.0 (M+H),⁺ HPLC purity 97% with retention time 1.32 min. [method B]

Example 110. 2-(2-fluoro-4-(2-((7-(2-hydroxy-2-methylpropoxy)-[1,2,4]triazolo[1,5-a]pyridin-2-yl)amino)-2-oxoethyl)phenoxy)nicotinamide

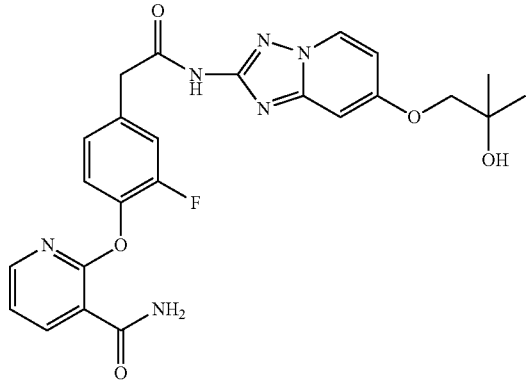 [SMILES: CC(C)(O)COc1ccn2nc(NC(=O)Cc3ccc(Oc4ncccc4C(N)=O)c(F)c3)nc2c1]

Step 1. To 7-methoxy-[1,2,4]triazolo[1,5-a]pyridin-2-amine (0.23 g, 1.4 mmol) in AcOH (3 mL) was added 48% HBr (1.5 mL) and the reaction mixture was heated to 100° C. for 48 h. The solvents were removed under reduced pressure and the residue was azeotroped with toluene (2×10 mL) to afford amino-[1,2,4]triazolo[1,5-a]pyridin-7-ol, hydrobromide (0.30 g, 36% yield) brown solid. LCMS m/z=151.1 (M+H).⁺

Step 2. 1-((2-amino-[1,2,4]triazolo[1,5-a]pyridin-7-yl)oxy)-2-methylpropan-2-ol (23 mg, 23% yield) was prepared from amino-[1,2,4]triazolo[1,5-a]pyridin-7-ol hydrobromide in a similar manner as described for example 3. ¹H NMR (400 MHz, CD₃OD) δ 8.55 (d, J=7.5 Hz, 1H), 7.19 (d, J=2.6 Hz, 1H), 7.12 (dd, J=7.4, 2.8 Hz, 1H), 4.04 (s, 2H), 3.34 (dt, J=3.3, 1.7 Hz, 1H), 1.37 (s, 6H). LCMS m/z=223.1 (M+H).⁺

Step 3. Example 110 (7.0 mg, 12% yield) was obtained in a similar manner as described for example 8 using the intermediate 2 and 1-((2-amino-[1,2,4]triazolo[1,5-a]pyridin-7-yl)oxy)-2-methylpropan-2-ol. ¹H NMR (500 MHz, DMSO-d₆) δ 10.95 (br s, 1H), 8.65 (br s, 1H), 8.27-8.14 (m, 2H), 7.82 (br s, 1H), 7.78 (br s, 1H), 7.44-7.29 (m, 2H), 7.28-7.17 (m, 2H), 7.06 (br s, 1H), 6.78 (br d, J=7.3 Hz, 1H), 4.75 (s, 1H), 3.86 (s, 2H), 3.39 (s, 2H), 1.23 (s, 6H). LCMS m/z=495.3 (M+H).⁺ HPLC purity 99% with retention time 1.05 min. [method A]

Example 111. 2-(4-(2-((1-(2,2-difluoroethyl)-1H-benzo[d]imidazol-2-yl)amino)-2-oxoethyl)-2-fluorophenoxy)nicotinamide

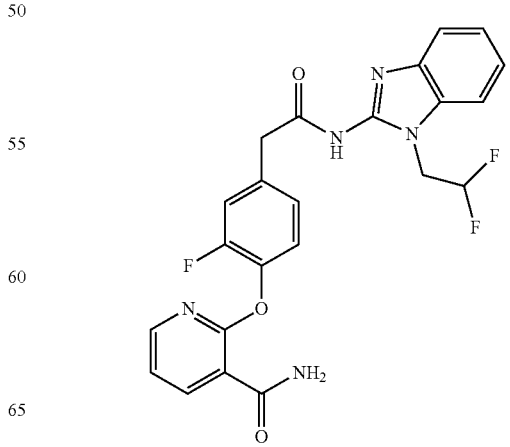

Step 1. To intermediate 5 (0.8 g, 3 mmol) in MeOH (25 ml) was added excess thionyl chloride (1.5 ml, 21 mmol). After 24 h, the reaction mixture was concentrated under reduced pressure and purified by silica gel chromatography using hexane/EtOAc as eluents to afford (0.30 g, 35%) methyl 2-(4-((3-carbamoylpyridin-2-yl)oxy)-3-fluorophenyl)acetate LCMS(ESI) m/z: 304.8 (M+H).⁺

Step 2. To 1-(2,2-difluoroethyl)-1H-benzo[d]imidazol-2-amine (15 mg, 0.076 mmol) and methyl 2-(4-((3-carbamoylpyridin-2-yl)oxy)-3-fluorophenyl)acetate (28 mg, 0.091 mmol) in toluene (2 ml) was added trimethylaluminum (0.11 ml, 0.23 mmol). After 5 minutes, the reaction mixture was heated under microwave irradiation at 120° C. for 30 min. The reaction mixture was concentrated and quenched by the addition of TFA and purified by reverse phase HPLC to afford (1.9 mg, 4.1%) of example 111.

¹H NMR (500 MHz, DMSO-d₆) δ 8.18 (d, J=7.2 Hz, 2H), 7.83 (d, J=11.2 Hz, 2H), 7.66-7.44 (m, 2H), 7.44-7.12 (m, 6H), 4.69-4.55 (m, 2H), 3.71 (br. s., 2H). LCMS m/z=470.1 (M+H).⁺ HPLC purity 100% with retention time 1.19 min. [method B]

Example 112. 2-(2-chloro-4-(2-((5-(2-hydroxy-2-methylpropoxy)benzo[d]thiazol-2-yl)amino)-2-oxoethyl)phenoxy)nicotinamide

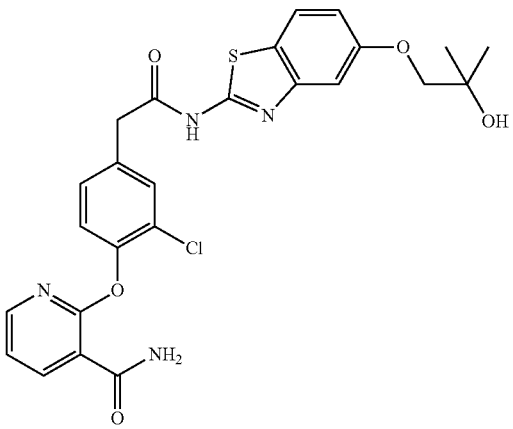 [SMILES: CC(C)(O)COc1ccc2sc(NC(=O)Cc3ccc(Oc4ncccc4C(N)=O)c(Cl)c3)nc2c1]

Example 112 (4 mg, 7% yield) was made in a similar manner as example 108 by substituting intermediate 4 for intermediate 5. ¹H NMR (500 MHz, DMSO-d₆) δ 8.39-8.07 (m, 2H), 7.79 (br d, J=12.8 Hz, 2H), 7.64 (br d, J=8.9 Hz, 1H), 7.56 (br d, J=13.1 Hz, 1H), 7.38 (s, 2H), 7.24 (br dd, J=7.2, 5.0 Hz, 1H), 7.05 (br d, J=8.5 Hz, 1H), 4.03-3.84 (m, 2H), 3.76 (s, 2H), 1.21 (s, 6H), LCMS m/z=526.9 (M+H).⁺ HPLC purity 100% with retention time 1.45 min. [method A]

Example 113. 2-(2-chloro-4-(2-((7-(2-hydroxy-2-methylpropoxy)-4,5-dihydronaphtho[1,2-d]thiazol-2-yl)amino)-2-oxoethyl)phenoxy)nicotinamide

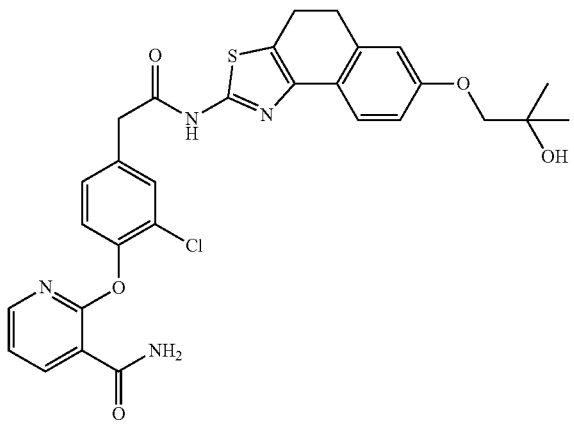 [SMILES: CC(C)(O)COc1ccc2c(c1)CCc1sc(NC(=O)Cc3ccc(Oc4ncccc4C(N)=O)c(Cl)c3)nc1-2]

Example 113 (2 mg, 3% yield) was made in a similar manner as example 108 by substituting 1-((2-amino-4,5-dihydronaphtho[1,2-d]thiazol-7-yl)oxy)-2-methylpropan-2-ol for 1-((2-aminobenzo[d]thiazol-5-yl)oxy)-2-methylpropan-2-ol. ¹H NMR (500 MHz, DMSO-d₆) δ 8.39-8.07 (m, 2H), 7.79 (br d, J=12.8 Hz, 2H), 7.64 (br d, J=8.9 Hz, 1H), 7.56 (br d, J=13.1 Hz, 1H), 7.38 (s, 2H), 7.24 (br dd, J=7.2, 5.0 Hz, 1H), 7.05 (br d, J=8.5 Hz, 1H), 4.03-3.84 (m, 2H), 3.76 (s, 2H), 1.21 (s, 6H), LCMS m/z=579.2 (M+H).⁺ HPLC purity 100% with retention time 1.69 min. [method A]

Example 114. 2-(2-fluoro-4-(2-(6-(2-hydroxy-2-methylpropoxy)indolin-1-yl)-2-oxoethyl)phenoxy)nicotinamide

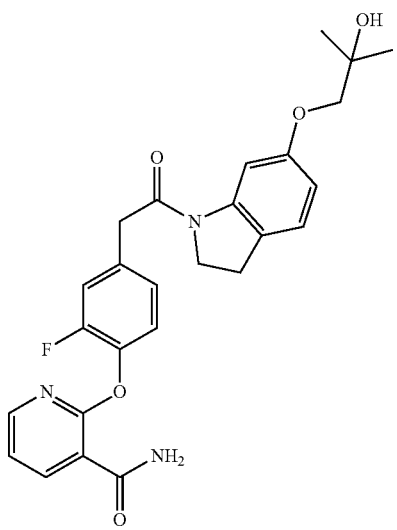 [SMILES: CC(C)(O)COc1ccc2c(c1)N(C(=O)Cc1ccc(Oc3ncccc3C(N)=O)c(F)c1)CC2]

Step 1. tert-Butyl 6-(2-hydroxy-2-methylpropoxy)indoline-1-carboxylate (0.12 g, 0.40 mmol, 94% yield) was obtained as a clear oil in a similar manner as described in example 3 substituting tert-butyl 6-hydroxyindoline-1-carboxylate for 2-aminobenzo[d]thiazol-5-ol). ¹H NMR (400 MHz, CDCl₃) δ 7.65-7.45 (m, 1H), 7.04 (d, J=8.1 Hz, 1H), 6.52 (dd, J=8.1, 2.4 Hz, 1H), 4.07-3.94 (m, 2H), 3.82 (s, 2H), 3.04 (t, J=8.6 Hz, 2H), 2.16 (br. s., 1H), 1.59 (br. s., 9H), 1.35 (s, 6H), LCMS(ESI) m/z: 308.1 (M+H).⁺

Step 2. To tert-butyl 6-(2-hydroxy-2-methylpropoxy)indoline-1-carboxylate (0.12 g, 0.40 mmol) in DCM was added excess 4N HCl in dioxane (5 mL) and stirred 24 h. The reaction mixture was concentrated under reduced pressure to afford 1-(indolin-6-yloxy)-2-methylpropan-2-ol, HCl (98 mg, 100% yield) as a dark film. LCMS(ESI) m/z: 208.1 (M+H).⁺

Step 3. 1-(Indolin-6-yloxy)-2-methylpropan-2-ol, HCl was coupled to 2-(4-((3-carbamoylpyridin-2-yl)oxy)-3-fluorophenyl)acetic acid, HCl as described in example 3 to afford example 114 (4 mg, 11% yield). ¹H NMR (500 MHz, DMSO-d₆) δ 8.23-8.13 (m, 2H), 7.88 (br. s., 1H), 7.79 (br. s., 1H), 7.71 (s, 1H), 7.33 (t, J=8.2 Hz, 1H), 7.29-7.20 (m, 2H), 7.13 (dd, J=19.1, 8.2 Hz, 2H), 6.57 (dd, J=8.2, 2.1 Hz, 1H), 4.20 (t, J=8.4 Hz, 2H), 3.95-3.86 (m, 2H), 3.21-3.03 (m, 2H), 1.17 (s, 6H). LCMS m/z=480.3 (M+H).⁺ HPLC purity 100% with retention time 1.48 min. [method A]

Example 115. 2-(2-chloro-4-(2-((5-methoxybenzo[d]thiazol-2-yl)amino)-2-oxoethyl)phenoxy)nicotinamide

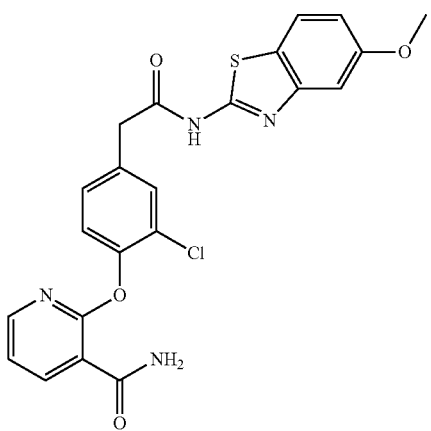 [SMILES: COc1ccc2sc(NC(=O)Cc3ccc(Oc4ncccc4C(N)=O)c(Cl)c3)nc2c1]

To intermediate 4 (28 mg g, 0.090 mmol) and 5-methoxybenzo[d]thiazol-2-amine (17 mg, 0.090 mmol) was added 1 ml DCM followed by pyridine (7.8 μl, 0.090 mmol) and POCl₃ (9 μl, 0.09 mmol). After stirring 24 h, the solvents were removed under reduced pressure and the residue was partitioned with sat. NaHCO₃ (2 mL) and EtOAc (3 mL). The aqueous layer was extracted with EtOAc (2 mL). The combined organic layers were concentrated under reduced pressure and to the residue was added excess K₂CO₃ (54 mg, 0.38 mmol), a few flakes of MgO and DMSO (0.3 ml). To the reaction mixture was added H₂O₂ (0.040 ml, 0.38 mmol). After stirring 24 h, the reaction mixture was quenched by the addition of aq sodium bisulfite (2 mL) and extracted with EtOAc (3×2 mL). The solvents were removed under reduced pressure and the residue was purified by reverse phase HPLC to afford (3.1 mg, 5.0% yield) of example 115. ¹H NMR (500 MHz, DMSO-d₆) δ 8.22 (d, J=7.6 Hz, 1H), 8.16 (d, J=5.3 Hz, 1H), 7.87-7.73 (m, 3H), 7.57 (s, 1H), 7.38 (s, 2H), 7.33-7.20 (m, 2H), 6.94 (dd, J=8.7, 2.3 Hz, 1H), 3.89 (d, J=3.1 Hz, 3H), 3.82 (s, 2H). LCMS m/z=496.1 (M+H).⁺ HPLC purity 100% with retention time 1.55 min. [method B]

Example 116. 2-(2-chloro-4-(2-((7-methoxy-4,5-dihydronaphtho[1,2-d]thiazol-2-yl)amino)-2-oxoethyl)phenoxy)nicotinamide

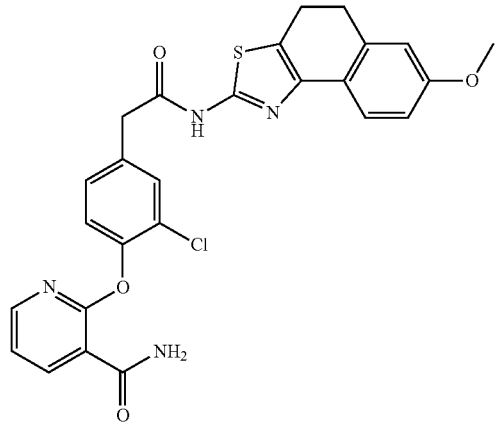 [SMILES: COc1ccc2c(c1)CCc1sc(NC(=O)Cc3ccc(Oc4ncccc4C(N)=O)c(Cl)c3)nc1-2]

Example 116 (4.3 mg, 7.2% yield) was prepared in a similar manner as described for example 115 by substituting 7-methoxy-4,5-dihydronaphtho[1,2-d]thiazol-2-amine, HBr for 5-methoxybenzo[d]thiazol-2-amine. ¹H NMR (500 MHz, DMSO-d₆) δ 8.28-8.12 (m, 2H), 7.87-7.73 (m, 2H), 7.60-7.50 (m, 2H), 7.41-7.28 (m, 2H), 7.28-7.15 (m, 1H), 6.96-6.60 (m, 2H), 3.84 (s, 2H), 3.70 (s, 3H), 3.06-2.93 (m, 2H), 2.93-2.82 (m, 2H). LCMS m/z=521.1 (M+H).⁺ HPLC purity 100% with retention time 1.87 min. [method B]

Example 117. 2-(2-methoxy-4-(2-((5-methoxybenzo[d]thiazol-2-yl)amino)-2-oxoethyl)phenoxy)nicotinamide

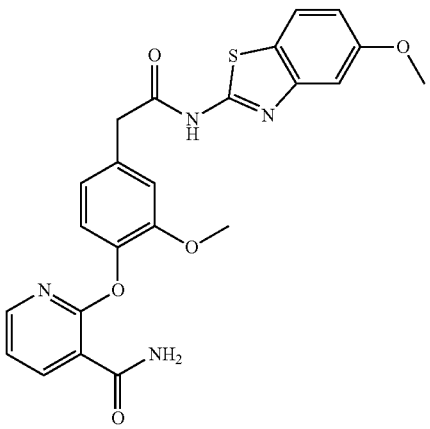 [SMILES: COc1ccc2sc(NC(=O)Cc3ccc(Oc4ncccc4C(N)=O)c(OC)c3)nc2c1]

Step 1 To 2-chloronicotinonitrile (0.31 g, 2.2 mmol) in DMSO (2 ml) was added ethyl 2-(4-hydroxy-3-methoxyphenyl)acetate (0.50 g, 2.2 mmol) and K₂CO₃ (0.70 g, 4.9 mmol) and the reaction mixture was heated to 60° C. for 24 h. The cooled reaction mixture was diluted with water and the resultant solid was collected and dried under vacuum to afford ethyl 2-(4-((3-cyanopyridin-2-yl)oxy)-3-methoxyphenyl)acetate (55 mg, 79% yield) as a brown solid. LCMS (ESI) m/z: 313.1 (M+H).+ 1H NMR (400 MHz, CDCl3) δ 8.30 (dd, J=5.1, 2.0 Hz, 1H), 8.01 (dd, J=7.5, 2.0 Hz, 1H), 7.16 (d, J=8.1 Hz, 1H), 7.08 (dd, J=7.6, 5.0 Hz, 1H), 7.01 (d, J=1.8 Hz, 1H), 6.96 (dd, J=7.9, 2.0 Hz, 1H), 4.21 (q, J=7.1 Hz, 2H), 3.77 (s, 3H), 3.65 (s, 2H), 1.38-1.27 (m, 3H).

Step 2. To ethyl 2-(4-((3-cyanopyridin-2-yl)oxy)-3-methoxyphenyl)acetate (50 mg, 0.16 mmol) and 5-methoxybenzo[d]thiazol-2-amine (0.032 g, 0.18 mmol) in toluene (2 ml) was added Me3Al (0.24 ml, 0.48 mmol). After 5 minutes, the reaction mixture was heated under microwave irradiation at 120° C. for 30 min. The reaction mixture was quenched by the addition of 1N HCl (2 mL), extracted with EtOAc (3×2 mL) and the organic layers were washed with sat'd NaHCO3 and concentrated under reduced pressure to afford 2-(4-((3-cyanopyridin-2-yl)oxy)-3-methoxyphenyl)-N-(5-methoxybenzo[d]thiazol-2-yl)acetamide LCMS(ESI) m/z: 447.1 (M+H).+

Step 3. 2-(4-((3-cyanopyridin-2-yl)oxy)-3-methoxyphenyl)-N-(5-methoxybenzo[d]thiazol-2-yl)acetamide was converted to the carboxamide 117 as described in example 115 and purified by reverse phase HPLC to afford example 117 (2.3 mg, 2.3% yield). 1H NMR (500 MHz, DMSO-d6) δ 8.20 (dd, J=7.6, 1.8 Hz, 1H), 8.14 (d, J=5.4 Hz, 1H), 7.82 (d, J=8.5 Hz, 1H), 7.80-7.77 (m, 1H), 7.70 (br s, 1H), 7.28 (d, J=2.1 Hz, 1H), 7.22-7.13 (m, 3H), 7.04-6.88 (m, 2H), 3.88-3.78 (m, 5H), 3.68 (s, 3H) LCMS m/z=465.1 (M+H).+ HPLC purity 95% with retention time 1.49 min. [method A]

Example 118. 2-(4-(2-((5-(2-hydroxy-2-methylpropoxy)benzo[d]thiazol-2-yl)amino)-2-oxoethyl)-2-methoxyphenoxy)nicotinamide

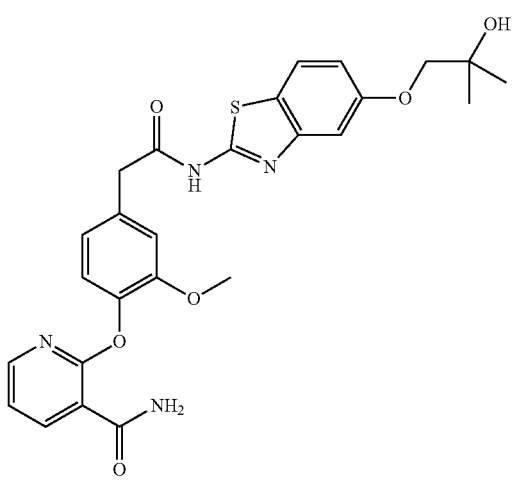 [SMILES: COc1cc(CC(=O)Nc2nc3cc(OCC(C)(C)O)ccc3s2)ccc1Oc1ncccc1C(N)=O]

Example 118 (2.6 mg 4.0% yield) was prepared in a similar manner as described for example 115 by substituting 1-((2-aminobenzo[d]thiazol-5-yl)oxy)-2-methylpropan-2-ol (example 3, step 1) for 5-methoxybenzo[d]thiazol-2-amine. 1H NMR (500 MHz, DMSO-d6) δ 8.20 (br d, J=7.4 Hz, 1H), 8.14 (br d, J=3.0 Hz, 1H), 7.82 (br s, 1H), 7.71 (br s, 1H), 7.64 (d, J=8.8 Hz, 1H), 7.55 (d, J=2.2 Hz, 1H), 7.25 (br s, 1H), 7.23-7.13 (m, 3H), 7.05 (br dd, J=8.7, 2.4 Hz, 1H), 6.97 (br d, J=8.0 Hz, 1H), 3.83 (s, 2H), 3.75 (s, 2H), 3.68 (s, 3H), 3.57 (br s, 1H), 3.17 (s, 1H), 1.21 (s, 6H). LCMS m/z=522.9 (M+H).+ HPLC purity 95% with retention time 1.42 min. [method B]

Example 119. 2-(2-bromo-4-(2-((7-methoxy-[1,2,4]triazolo[1,5-a]pyridin-2-yl)amino)-2-oxoethyl)phenoxy)nicotinamide

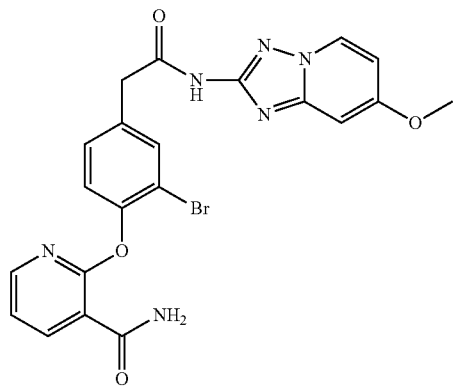 [SMILES: COc1ccn2nc(NC(=O)Cc3ccc(Oc4ncccc4C(N)=O)c(Br)c3)nc2c1]

Step 1. To 2-chloronicotinonitrile (3.4 g, 24 mmol) in DMSO (20 ml) was added 2-(3-bromo-4-hydroxyphenyl)acetic acid (5.6 g, 24 mmol) and K2CO3 (7.4 g, 53 mmol) and reaction mixture was heated to 80° C. for 24 h. The cooled reaction mixture was diluted with water, acidified with HCl, filtered to afford 2-(3-bromo-4-((3-cyanopyridin-2-yl)oxy)phenyl)acetic acid (7.8 g, 96% yield) as a tan solid. 1H NMR (400 MHz, CDCl3) δ 8.32 (dd, J=5.0, 1.9 Hz, 1H), 8.07 (dd, J=7.5, 2.0 Hz, 1H), 7.66 (d, J=2.0 Hz, 1H), 7.38 (dd, J=8.3, 2.1 Hz, 1H), 7.26 (d, J=8.1 Hz, 1H), 7.15 (dd, J=7.6, 5.0 Hz, 1H), 3.71 (s, 2H). LCMS(ESI) m/z: 333-334.9 (M+H).+

Step 2. To a suspension of 2-(3-bromo-4-((3-cyanopyridin-2-yl)oxy)phenyl)acetic acid (0.8 g, 2.5 mmol) in DCE (5 ml) was added thionyl chloride (1.8 ml, 24 mmol) and the reaction mixture was heated to 50° C. for 3 h. The reaction mixture was concentrated under reduced pressure to afford 2-(3-bromo-4-((3-cyanopyridin-2-yl)oxy)phenyl)acetyl chloride (0.88 g, 100% yield) as a tan solid. LCMS(ESI) m/z: 346-348.9 (M+H)*for Me ester.

Step 3. Example 119 (1.8 mg, 3.0% yield) was prepared in a similar manner as described for example 8 by using 2-(3-bromo-4-((3-cyanopyridin-2-yl)oxy)phenyl)acetyl chloride and 7-methoxy-[1,2,4]triazolo[1,5-a]pyridin-2-amine. 1H NMR (500 MHz, DMSO-d6) δ 11.06-10.88 (m, 1H), 8.62 (br d, J=6.7 Hz, 1H), 8.23 (dd, J=7.5, 1.7 Hz, 1H), 8.16 (dd, J=4.6, 1.5 Hz, 1H), 7.81 (br s, 1H), 7.75 (br s, 1H), 7.69 (s, 1H), 7.48-7.38 (m, 1H), 7.33 (d, J=8.2 Hz, 1H), 7.24 (dd, J=7.3, 4.9 Hz, 1H), 7.06 (br s, 1H), 6.77 (br d, J=7.0 Hz, 1H), 3.88 (s, 2H), 3.56 (s, 3H), LCMS m/z=496.7 (M+H).+ HPLC purity 98% with retention time 1.03 min. [method A]

Example 120. 2-(4-(2-((1-(2,2-difluoroethyl)-5-methoxy-1H-benzo[d]imidazol-2-yl)amino)-2-oxoethyl)-2-fluorophenoxy)nicotinamide

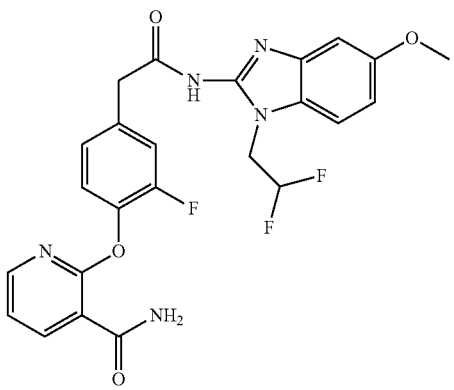 [SMILES: COc1ccc2c(c1)nc(NC(=O)Cc1ccc(Oc3ncccc3C(N)=O)c(F)c1)n2CC(F)F]

Step 1. To 5-methoxy-1H-benzo[d]imidazol-2-amine (0.34 g, 2.1 mmol) and 1,1-difluoro-2-iodoethane (0.4 g, 2 mmol) in DMF (5 ml), cooled to 0° C., was added NaH (0.17 g, 4.2 mmol) in oil and the reaction mixture was stirred at rt. After 72 h, the reaction mixture was quenched by the addition of water (20 mL) and extracted with ethyl acetate (3×30 mL). The combined organic layers were washed with brine (15 mL) and dried (MgSO$_4$). The residue was purified by silica gel chromatography, eluting with DCM/0-10% MeOH to afford 0.2 g of a brown foam as a mixture of isomers. LCMS(ESI) m/z: 228.0 (M+H).$^+$ Purification of a 160 mg sample of this isomer mixture by SFC afforded 1-(2,2-difluoroethyl)-5-methoxy-1H-benzo[d]imidazol-2-amine (27 mg, 25% yield) and 1-(2,2-difluoroethyl)-6-methoxy-1H-benzo[d]imidazol-2-amine (58 mg, 51% yield).

Step 2. To a suspension of intermediate 1 (2.2 g, 8.1 mmol) in DCE (16 ml) was added SOCl$_2$ (5.9 ml, 81 mmol) and the reaction mixture was heated to 50° C. The reaction turned clear and was stirred for 1 h. The solvents were removed under reduced pressure to afford 2-(4-((3-cyanopyridin-2-yl)oxy)-3-fluorophenyl)acetyl chloride (2.3 g, 98% yield) as a white solid.

Step 3. To 2-(4-((3-cyanopyridin-2-yl)oxy)-3-fluorophenyl)acetyl chloride (33 mg, 0.11 mmol) in THF (2 mL) and pyridine (28 μL, 0.34 mmol) was added 1-(2,2-difluoroethyl)-5-methoxy-1H-benzo[d]imidazol-2-amine (26 mg, 0.11 mmol) and the reaction mixture was stirred at rt for 24 h. The reaction mixture was concentrated under reduced pressure and the residue was oxidized as described in example 115 to afford example 120 (2.8 mg, 3.8% yield); $^1$H NMR (500 MHz, DMSO-d$_6$) δ 8.29-8.13 (m, 2H), 7.79-7.69 (m, 1H), 7.67-7.58 (m, 1H), 7.48-7.38 (m, 1H), 7.36-7.29 (m, 2H), 7.27-7.19 (m, 2H), 7.16 (br s, 1H), 6.86 (br d, J=8.8 Hz, 1H), 6.55-6.19 (m, 2H), 4.64-4.56 (m, 2H), 3.81 (s, 3H), 3.78 (s, 2H). LCMS m/z=500.1 (M+H).$^+$ HPLC purity 95% with retention time 1.18 min. [method B]

Examples 121-131 were prepared as described following the general procedure used for example 8 or example 9 and intermediate 8

| Ex# | Structure | Name | HNMR | LCMS (M + H)$^+$ | HPLC retention time (min) |
|---|---|---|---|---|---|
| 121 | 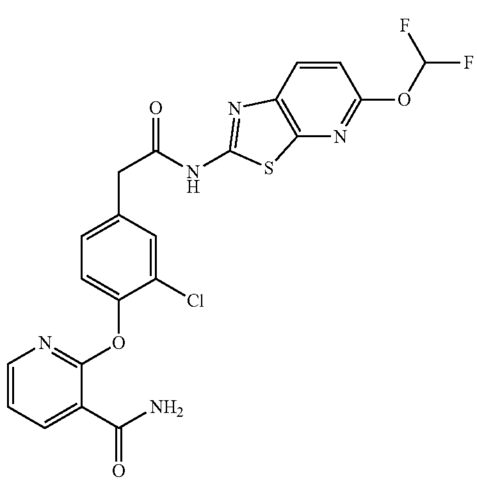 [SMILES: NC(=O)c1cccnc1Oc1ccc(CC(=O)Nc2nc3ccc(OC(F)F)nc3s2)cc1Cl] | 2-(2-chloro-4-(2-((5-(difluoromethoxy)thiazolo[5,4-b]pyridin-2-yl)amino)-2-oxoethyl)phenoxy)nicotinamide | $^1$H NMR (500 MHz, DMSO-d$_6$) δ 8.30-8.14 (m, 3H), 7.91 (s, 1H), 7.82 (br s, 1H), 7.77 (s, 1H), 7.67-7.52 (m, 1H), 7.39 (s, 2H), 7.25 (dd, J = 7.5, 5.0 Hz, 1H), 7.19 (d, J = 8.5 Hz, 1H), 3.94 (s, 2H) | 506.2 | 1.67 Method B |

| Ex# | Structure | Name | HNMR | LCMS (M + H)+ | HPLC retention time (min) |
|---|---|---|---|---|---|
| 122 | 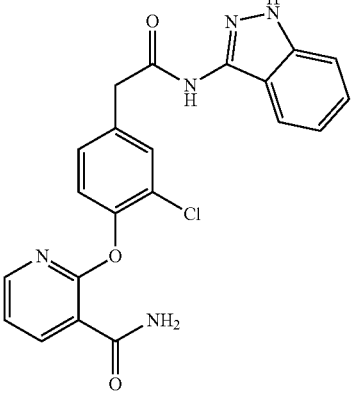 | 2-(4-(2-((1H-indazol-3-yl)-amino)-2-oxoethyl)-2-chlorophenoxy)-nicotinamide | $^1$H NMR (500 MHz, DMSO-d$_6$) δ 10.66 (s, 1H), 8.22 (d, J = 7.6 Hz, 1H), 8.18 (d, J = 5.3 Hz, 1H), 7.88-7.69 (m, 3H), 7.60 (s, 1H), 7.48-7.30 (m, 4H), 7.24 (dd, J = 7.5, 5.0 Hz, 1H), 7.05 (br t, J = 7.5 Hz, 1H), 3.80 (s, 2H). | 422.1 | 1.16 Method A |
| 123 | 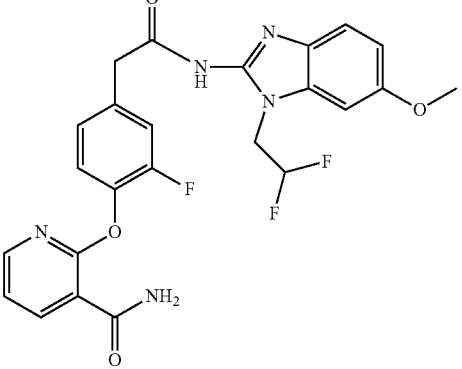 | 2-(4-(2-((1-(2,2-difluoroethyl)-6-methoxy-1H-benzo-[d]imidazol-2-yl)-amino)-2-oxoethyl)-2-fluorophenoxy)-nicotinamide | $^1$H NMR (500 MHz, DMSO-d$_6$) δ 8.37-8.04 (m, 3H), 7.83 (br s, 1H), 7.80-7.72 (m, 1H), 7.42 (br d, J = 8.9 Hz, 1H), 7.37-7.30 (m, 2H), 7.26-7.20 (m, 2H), 7.09 (d, J = 2.1 Hz, 1H), 6.87 (dd, J = 8.9, 1.8 Hz, 1H), 6.49-6.15 (m, 1H), 4.62-4.52 (m, 2H), 3.90 (s, 2H), 3.77 (s, 3H) | 500.0 | 1.50 Method A |
| 124 | 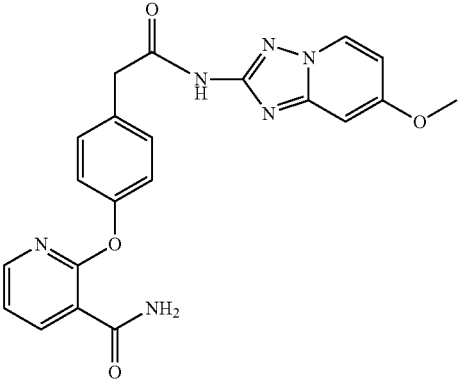 [SMILES: COc1ccn2nc(NC(=O)Cc3ccc(Oc4ncccc4C(N)=O)cc3)nc2c1] | 2-(4-(2-((7-methoxy-[1,2,4]-triazolo[1,5-a]-pyridin-2-yl)-amino)-2-oxo-ethyl)phenoxy)-nicotinamide | $^1$H NMR (500 MHz, DMSO-d$_6$) δ 11.07-10.88 (m, 1H), 8.62 (d, J = 7.3 Hz, 1H), 8.25-8.07 (m, 2H), 7.81 (br s, 1H), 7.74 (br s, 1H), 7.38 (br d, J = 8.5 Hz, 2H), 7.21 (dd, J = 7.3, 4.9 Hz, 1H), 7.14 (br d, J = 8.5 Hz, 2H), 7.06 (br d, J = 2.4 Hz, 1H), 6.77 (dd, J = 7.5, 2.6 Hz, 1H), 3.88 (s, 2H), 3.50 (s, 3H) | 419.0 | 0.99 Method A |

-continued

| Ex# | Structure | Name | HNMR | LCMS (M + H)+ | HPLC retention time (min) |
|---|---|---|---|---|---|
| 125 | 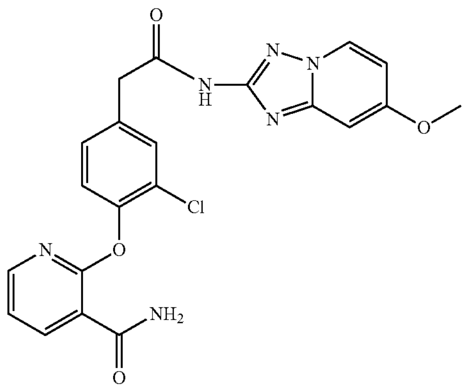 [SMILES: COc1ccn2nc(NC(=O)Cc3ccc(Oc4ncccc4C(N)=O)c(Cl)c3)nc2c1] | 2-(2-chloro-4-(2-((7-methoxy-[1,2,4]triazolo-[1,5-a]pyridin-2-yl)amino)-2-oxoethyl)phenoxy)-nicotinamide | $^1$H NMR (500 MHz, DMSO-$d_6$) δ 10.99 (br s, 1H), 8.59 (d, J = 7.6 Hz, 1H), 8.21 (dd, J = 7.5, 1.7 Hz, 1H), 8.15 (dd, J = 4.7, 1.7 Hz, 1H), 7.78 (br s, 2H), 7.53 (s, 1H), 7.41-7.30 (m, 2H), 7.23 (dd, J = 7.3, 4.9 Hz, 1H), 7.05 (d, J = 2.1 Hz, 1H), 6.77 (dd, J = 7.5, 2.6 Hz, 1H), 3.87 (s, 2H), 3.63 (s, 3H) | 452.8 | 1.01 Method A |
| 126 | 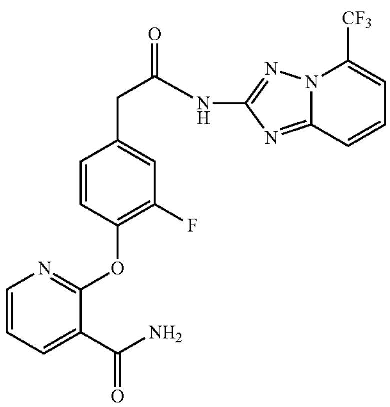 [SMILES: NC(=O)c1cccnc1Oc1ccc(CC(=O)Nc2nc3cccc(C(F)(F)F)n3n2)cc1F] | 2-(2-fluoro-4-(2-oxo-2-((5-(trifluoro-methyl)-[1,2,4]-triazolo[1,5-a]-pyridin-2-yl)amino)-ethyl)phenoxy)-nicotinamide | $^1$H NMR (500 MHz,) δ 8.26 (d, J = 7.8 Hz, 1H), 8.25 (d, J = 4.9 Hz, 1H), 7.83 (dd, J = 7.9, 7.5 Hz, 1H), 7.65 (d, J =7.9 Hz, 1H), 7.52 (dq, J = 7.5, 4.0 Hz, 1H), 7.19 (dd, J = 9.0, 8.4 Hz, 1H), 7.16 (d, J = 12.0 Hz, 1H), 7.13 (d, J = 8.4 Hz, 1H), 6.84 (dd, J = 7.8, 4.9 Hz, 1H), 3.86 (s, 2H) | 474.9 | 1.18 Method A |
| 127 | 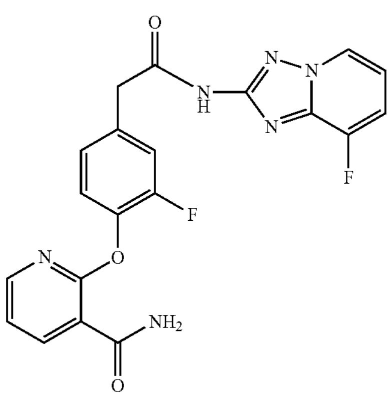 [SMILES: NC(=O)c1cccnc1Oc1ccc(CC(=O)Nc2nc3c(F)cccn3n2)cc1F] | 2-(2-fluoro-4-(2-((8-fluoro-[1,2,4]-triazolo[1,5-a]-pyridin-2-yl)amino)-2-oxoethyl)phenoxy)-nicotinamide | $^1$H NMR (500 MHz, DMSO-$d_6$) δ 11.28 (br s, 1H), 8.77 (br d, J = 6.7 Hz, 1H), 8.27-8.13 (m, 2H), 7.82 (br s, 1H), 7.79 (br s, 1H), 7.66-7.56 (m, 1H), 7.41-7.30 (m, 2H), 7.24 (br t, J = 8.4 Hz, 2H), 7.16-7.02 (m, 1H), 3.83 (br s, 2H) | 424.9 | 0.99 Method A |
| 128 | 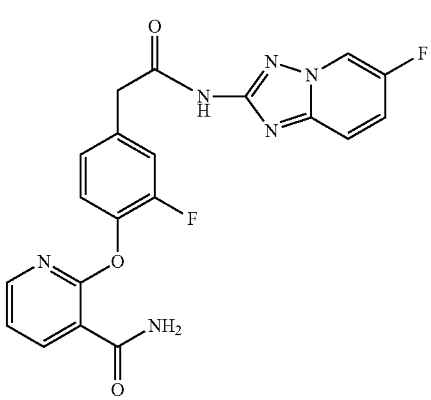 [SMILES: NC(=O)c1cccnc1Oc1ccc(CC(=O)Nc2nc3ccc(F)cn3n2)cc1F] | 2-(2-fluoro-4-(2-((6-fluoro-[1,2,4]-triazolo[1,5-a]-pyridin-2-yl)amino)-2-oxoethyl)phenoxy)-nicotinamide | $^1$H NMR (500 MHz, DMSO-$d_6$) δ 9.24 (br s, 1H), 8.60-8.32 (m, 1H), 8.28-8.12 (m, 2H), 7.82 (br s, 1H), 7.80 (br s, 1H), 7.77 (br d, J = 6.7 Hz, 1H), 7.40-7.31 (m, 2H), 7.28-7.19 (m, 2H), 3.83 (br s, 2H), 1.25 (br s, 1H) | 425.1 | 1.05 Method A |

| Ex# | Name | HNMR | LCMS (M + H)+ | HPLC retention time (min) |
|---|---|---|---|---|
| 129 | 2-(2-fluoro-4-(2-oxo-2-((6-(trifluoromethyl)-[1,2,4]triazolo-[1,5-a]pyridin-2-yl)amino)ethyl)-phenoxy)nicotinamide | $^1$H NMR (500 MHz, DMSO-$d_6$) δ 9.55 (s, 1H), 8.39-8.11 (m, 2H), 8.01-7.90 (m, 1H), 7.90-7.87 (m, 1H), 7.83 (br s, 1H), 7.78 (br s, 1H), 7.41-7.31 (m, 2H), 7.24 (br t, J = 8.2 Hz, 2H), 3.90 (s, 1H), 3.85 (br s, 2H) | 475.1 | 1.22 Method A |
| 130 | 2-(4-(2-((6,7-dimethyl-[1,2,4]-triazolo[1,5-a]-pyridin-2-yl)-amino)-2-oxoethyl)-2-fluorophenoxy)-nicotinamide | $^1$H NMR (500 MHz, DMSO-$d_6$) δ 8.62 (s, 1H), 8.36-8.10 (m, 2H), 7.83 (br s, 1H), 7.79 (br s, 1H), 7.48 (s, 1H), 7.40-7.29 (m, 2H), 7.26-7.12 (m, 2H), 3.80 (br s, 2H), 2.36 (s, 3H), 2.27 (s, 3H), 1.25 (s, 1H) | 435.2 | 1.04 Method A |
| 131 | 2-(4-(2-((5,6-dimethyl-[1,2,4]-triazolo[1,5-a]-pyridin-2-yl)-amino)-2-oxoethyl)-2-fluorophenoxy)-nicotinamide | $^1$H NMR (500 MHz, DMSO-$d_6$) δ 8.21 (br d, J = 7.4 Hz, 1H), 8.18 (br d, J = 3.9 Hz, 1H), 7.72 (br s, 1H), 7.66-7.57 (m, 1H), 7.53-7.47 (m, 1H), 7.47-7.43 (m, 1H), 7.39-7.30 (m, 2H), 7.23 (br t, J = 8.5 Hz, 2H), 3.84 (br s, 2H), 2.66 (s, 3H), 2.36 (s, 3H), 1.66 (br s, 1H) | 435.0 | 1.08 Method A |
| 132 | 2-(2-fluoro-4-(2-oxo-2-((7-(trifluoromethyl)-[1,2,4]-triazolo[1,5-a]-pyridin-2-yl)amino)-ethyl)phenoxy)-nicotinamide | H NMR (500 MHz, DMSO-$d_6$) δ 11.38 (br s, 1H), 9.10 (br d, J =7.0 Hz, 1H), 8.27 (s, 1H), 8.24-8.17 (m, 2H), 7.91-7.84 (m, 1H), 7.81 (br s, 1H), 7.46 (br d, J = 7.0 Hz, 1H), 7.43-7.33 (m, 2H), 7.27 (br t, J = 8.1 Hz, 2H), 3.93 (s, 2H) | 474.9 | 1.19 Method B |

| Ex# | Structure | Name | HNMR | LCMS (M + H)+ | HPLC retention time (min) |
|---|---|---|---|---|---|
| 133 | 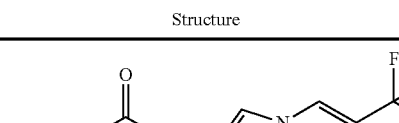 | 2-(2-fluoro-4-(2-oxo-2-((6-(trifluoromethyl)imidazo[1,2-a]pyridin-2-yl)amino)ethyl)phenoxy)nicotinamide | ¹H NMR (500 MHz, DMSO-d₆) δ 11.16 (s, 1H), 9.22 (s, 1H), 8.25 (s, 1H), 8.18 (br t, J = 6.9 Hz, 2H), 7.83 (br s, 1H), 7.78 (br s, 1H), 7.63 (d, J =9.5 Hz, 1H), 7.46 (br d, J =9.5 Hz, 1H), 7.38-7.30 (m, 2H), 7.26-7.17 (m, 2H), 3.78 (s, 2H) | 474.1 | 1.35 Method B |

Example 134. 2-(4-(2-((7-bromo-[1,2,4]triazolo[1,5-a]pyridin-2-yl)amino)-2-oxoethyl)-2-fluorophenoxy)nicotinamide

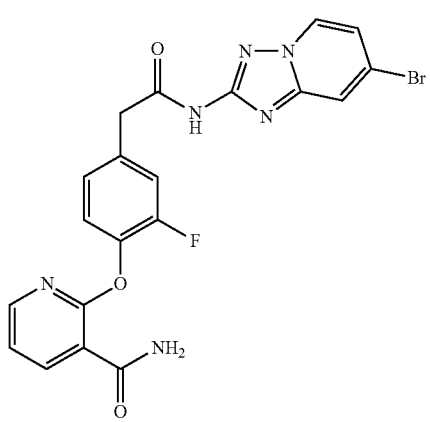 [SMILES: NC(=O)c1cccnc1Oc1ccc(CC(=O)Nc2nc3cc(Br)ccn3n2)cc1F]

2-(4-(2-((7-bromo-[1,2,4]triazolo[1,5-a]pyridin-2-yl)amino)-2-oxoethyl)-2-fluorophenoxy)nicotinamide 134 (0.17 g, 30%) was made by the coupling of intermediate 2 with 7-bromo-[1,2,4]triazolo[1,5-a]pyridin-2-amine, followed by H₂O₂ oxidation as described for intermediate 8. ¹H NMR (400 MHz, DMSO-d₆) δ 11.18 (br s, 1H), 8.96-8.69 (m, 1H), 8.40-8.15 (m, 3H), 8.07 (d, J=2.0 Hz, 1H), 7.82 (br s, 1H), 7.80 (br s, 1H), 7.35-7.31 (m, 2H), 7.27-7.23 (m, 2H), 3.83 (br s, 2H), LCMS m/z=487.1 (M+H).⁺ HPLC purity 96% with retention time 1.12 min. [method A]

Examples 135-137 were prepared following the general procedure used for Example 4

| Ex# | Structure | Name | HNMR | LCMS (M + H)+ | HPLC retention time (min) |
|---|---|---|---|---|---|
| 135 | 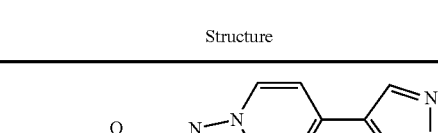 | 2-(4-(2-((7-(1-(difluoromethyl)-1H-pyrazol-4-yl)-[1,2,4]triazolo[1,5-a]pyridin-2-yl)amino)-2-oxoethyl)-2-fluorophenoxy)nicotinamide | ¹H NMR (500 MHz, DMSO-d₆) δ 8.80 (d, J = 7.0 Hz, 1H), 8.29-8.14 (m, 3H), 7.83 (br s, 1H), 7.79 (br s, 1H), 7.62 (s, 1H), 7.45-7.31 (m, 2H), 7.28-7.14 (m, 3H), 3.91 (s, 3 H), 3.83 (s, 2H), 2.55 (s, 1H), 2.41 (s, 3H) | 523.1 | 1.05 Method A |

| Ex# | Structure | Name | HNMR | LCMS (M + H)+ | HPLC retention time (min) |
|---|---|---|---|---|---|
| 136 | 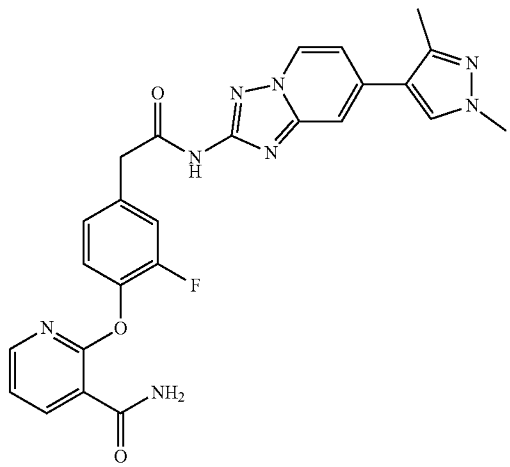 [SMILES: Cc1nn(C)cc1-c1ccn2nc(NC(=O)Cc3ccc(Oc4ncccc4C(N)=O)c(F)c3)nc2c1] | 2-(4-(2-((7-(1,3-dimethyl-1H-pyrazol-4-yl)-[1,2,4]-triazolo[1,5-a]pyridin-2-yl)amino)-2-oxoethyl)-2-fluorophen-oxy)nicotin-amide | 1H NMR (500 MHz, DMSO-d$_6$) δ 8.80 (d, J = 7.0 Hz, 1H), 8.29-8.14 (m, 3H), 7.83 (br s, 1H), 7.79 (br s, 1H), 7.62 (s, 1H), 7.45-7.31 (m, 2H), 7.28-7.14 (m, 3H), 3.91 (s, 3 H), 3.83 (s, 2H), 2.55 (s, 1H), 2.41 (s, 3H) | 501.1 | 1.0 Method A |
| 137 | 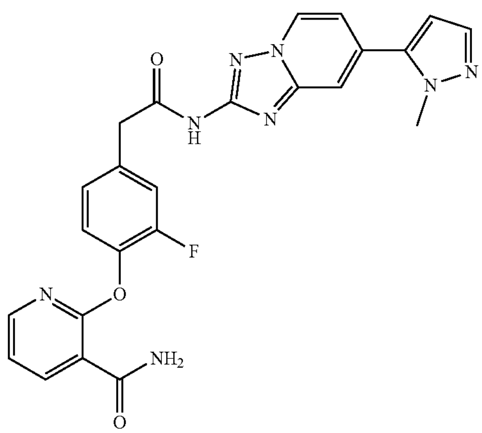 [SMILES: Cn1nccc1-c1ccn2nc(NC(=O)Cc3ccc(Oc4ncccc4C(N)=O)c(F)c3)nc2c1] | 2-(2-fluoro-4-(2-((7-(1-methyl-1H-pyrazol-5-yl)-[1,2,4]-triazolo[1,5-a]pyridin-2-yl)amino)-2-oxoethyl)-phenoxy) nicotinamide | $^1$H NMR (500 MHz, DMSO-d$_6$) δ 11.16 (br s, 1H), 8.96 (d, J = 7.0 Hz, 1H), 8.32-8.14 (m, 2H), 7.91 (s, 1H), 7.83 (br s, 1H), 7.80 (br s, 1H), 7.56 (d, J = 1.5 Hz, 1H), 7.45-7.29 (m, 3H), 7.28-7.13 (m, 2H), 6.68 (d, J = 1.5 Hz, 1H), 4.00 (s, 3H), 3.85 (br s, 2H) | 486.9 | 0.98 Method A |

Example 138. 2-(2-fluoro-4-(2-((6-(1-methyl-1H-pyrazol-5-yl)-[1,2,4]triazolo[1,5-a]pyridin-2-yl)amino)-2-oxoethyl)phenoxy)nicotinamide

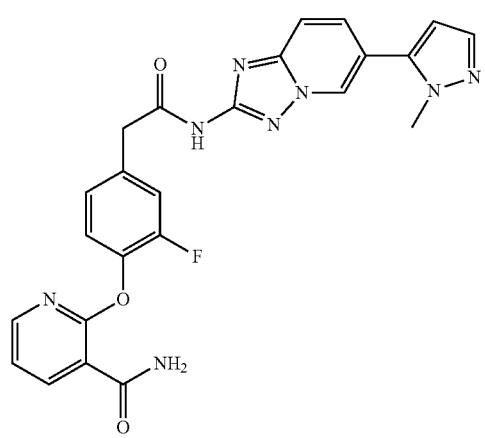 [SMILES: Cn1nccc1-c1ccc2nc(NC(=O)Cc3ccc(Oc4ncccc4C(N)=O)c(F)c3)nn2c1]

Step 1. 2-(4-(2-((6-bromo-[1,2,4]triazolo[1,5-a]pyridin-2-yl)amino)-2-oxoethyl)-2-fluorophenoxy)nicotinamide (28 mg, 7.0% yield) was made using a similar procedure as example 134 substituting 6-bromo-[1,2,4]triazolo[1,5-a]pyridin-2-amine for 7-bromo-[1,2,4]triazolo[1,5-a]pyridin-2-amine. LCMS m/z=485-488.1 (M+H).+

Step 2. Example 138 (1.4 mg, 4.0% yield) was made using a Suzuki reaction with 2-(4-(2-((6-bromo-[1,2,4]triazolo[1,5-a]pyridin-2-yl)amino)-2-oxoethyl)-2-fluorophenoxy)nicotinamide and 1-methyl-5-(4,4,5,5-tetramethyl-1,3,2-dioxaborolan-2-yl)-1H-pyrazole as described in example 4. $^1$H NMR (500 MHz, DMSO-d$_6$) δ 9.15 (s, 1H), 8.27-8.15 (m, 2H), 7.87 (s, 1H), 7.85-7.81 (m, 3H), 7.54 (d, J=1.5 Hz, 1H), 7.42-7.31 (m, 2H), 7.28-7.15 (m, 2H), 6.57 (d, J=1.5 Hz, 1H), 3.93 (s, 3H), 3.91 (s, 2H), 2.56 (s, 1H). LCMS m/z=486.9 (M+H).+ HPLC purity 96% with retention time 0.98 min. [method A]

Example 139. 2-(4-(2-((8-(difluoromethoxy)-[1,2,4]triazolo[1,5-a]pyridin-2-yl)amino)-2-oxoethyl)-2-fluorophenoxy)nicotinamide

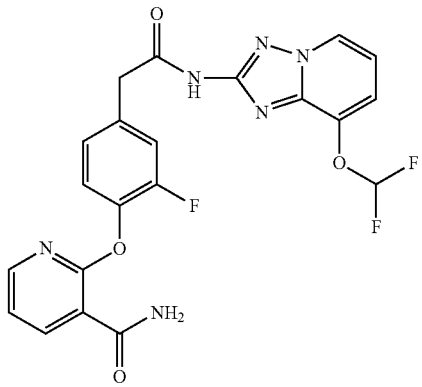 [SMILES: NC(=O)c1cccnc1Oc1ccc(CC(=O)Nc2nc3c(OC(F)F)cccn3n2)cc1F]

Step 1. To 3-(difluoromethoxy)pyridin-2-amine (0.20 g, 1.2 mmol) in dioxane (2 mL) was added O-ethyl carbonisothiocyanatidate (0.16 mL, 1.4 mmol), after 2 h, EtOH (3 mL), hydroxylamine hydrochloride (0.4 g, 6 mmol) and DIEA (0.7 mL, 4 mmol) were added and the reaction mixture was heated to 60° C. After 48 h, a white solid was filtered off and the filtrate was concentrated, extracted with EtOAc, washed with brine and dried (MgSO$_4$). The 8-(difluoromethoxy)-[1,2,4]triazolo[1,5-a]pyridin-2-amine was collected (0.25 g) and was used without further purification. $^1$H NMR (400 MHz, DMSO-d$_6$) δ 9.43 (br s, 2H), 8.48 (dd, J=6.7, 1.0 Hz, 1H), 7.72-7.40 (m, 1H), 7.38-7.22 (m, 1H), 6.87 (dd, J=7.9, 6.6 Hz, 1H).

Step 2. Example 139 (5.6 mg, 9.5% yield) was prepared by coupling 8-(difluoromethoxy)-[1,2,4]triazolo[1,5-a]pyridin-2-amine and intermediate 2 followed by oxidation as described in intermediate 8. $^1$H NMR (500 MHz, DMSO-d$_6$) δ 11.30 (br s, 1H), 8.78 (d, J=6.7 Hz, 1H), 8.25-8.13 (m, 2H), 7.84 (br s, 1H), 7.79 (br s, 1H), 7.54-7.46 (m, 2H), 7.43-7.32 (m, 2H), 7.28-7.20 (m, 2H), 7.15 (t, J=7.3 Hz, 1H), 3.83 (br s, 2H). LCMS m/z=473.0 (M+H).$^+$ HPLC purity 99% with retention time 1.08 min. [method B]

Example 140. 2-(2-fluoro-4-(2-oxo-2-((6-(trifluoromethoxy)-[1,2,4]triazolo[1,5-a]pyridin-2-yl)amino)ethyl)phenoxy)nicotinamide

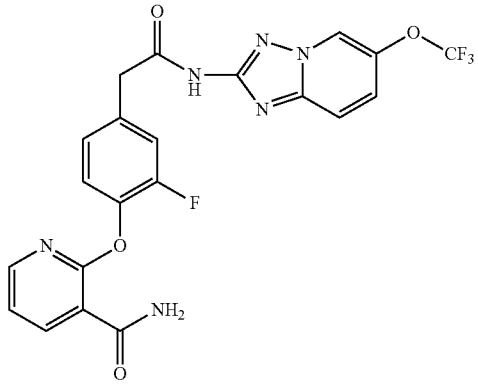 [SMILES: NC(=O)c1cccnc1Oc1ccc(CC(=O)Nc2nc3ccc(OC(F)(F)F)cn3n2)cc1F]

Example 140 (2.2 mg, 3.5% yield) was prepared using the same procedure as example 139 by substituting 5-(trifluoromethoxy)pyridin-2-amine in step-1 for 3-(difluoromethoxy)pyridin-2-amine. $^1$H NMR (500 MHz, DMSO-d$_6$) δ 9.29 (br s, 1H), 8.21 (br d, J=7.4 Hz, 1H), 8.18 (br d, J=3.6 Hz, 1H), 7.87-7.72 (m, 3H), 7.71 (br s, 1H), 7.63 (br s, 1H), 7.36-7.30 (m, 2H), 7.26-7.20 (m, 2H), 3.85 (br s, 2H). LCMS m/z=491.0 (M+H).$^+$ HPLC purity 97% with retention time 1.40 min. [method A]

Example 141 2-(2-fluoro-4-(2-oxo-2-((8-(trifluoromethyl)-[1,2,4]triazolo[1,5-a]pyridin-2-yl)amino)ethyl)phenoxy)nicotinamide

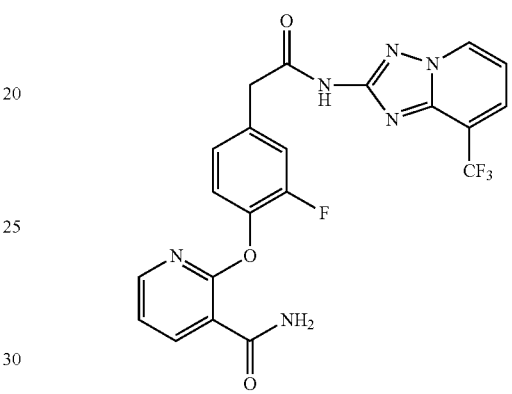

Example 141 (3.5 mg, 5.7% yield) was prepared using the same procedure as example 139 by substituting 3-(trifluoromethyl)pyridin-2-amine in step-1 for 3-(difluoromethoxy)pyridin-2-amine. $^1$H NMR (500 MHz, DMSO-d$_6$) δ 11.50 (br s, 1H), 9.17 (br d, J=6.4 Hz, 1H), 8.33-8.16 (m, 2H), 8.14 (br d, J=7.0 Hz, 1H), 7.85 (br s, 1H), 7.81 (br s, 1H), 7.48-7.34 (m, 2H), 7.31 (br t, J=7.0 Hz, 1H), 7.26 (br d, J=7.0 Hz, 2H), 3.93 (br s, 2H). LCMS m/z=475.0 (M+H).$^+$ HPLC purity 96% with retention time 1.17 min. [method B]

Example 142. 2-(2-fluoro-4-(2-((7-fluoro-[1,2,4]triazolo[1,5-a]pyridin-2-yl)amino)-2-oxoethyl)phenoxy)nicotinamide

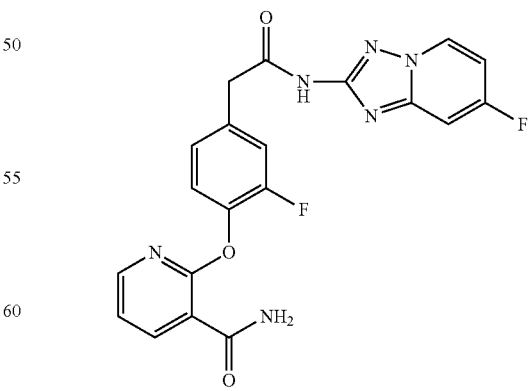

Example 142 (0.6 mg, 1% yield) was prepared using the same procedure as example 139 by substituting 4-fluoropyridin-2-amine in step-1 for 3-(difluoromethoxy)pyridin- 2-amine. ¹H NMR (500 MHz, DMSO-d₆) δ 10.01 (s, 1H), 9.04-8.79 (m, 1H), 8.21 (br d, J=7.5 Hz, 1H), 8.19 (br d, J=4.6 Hz, 1H), 7.70 (br s, 1H), 7.64 (br s, 1H), 7.57 (dd, J=9.1, 2.3 Hz, 1H), 7.38-7.29 (m, 2H), 7.28-7.18 (m, 2H), 7.14 (td, J=7.7, 2.5 Hz, 1H), 3.85 (br s, 2H). LCMS m/z=425.1 (M+H).⁺ HPLC purity 97% with retention time 0.93 min. [method A]

Example 143. 2-(4-(2-((7-(benzyloxy)-[1,2,4]triazolo[1,5-a]pyridin-2-yl)amino)-2-oxoethyl)-2-fluorophenoxy)nicotinamide

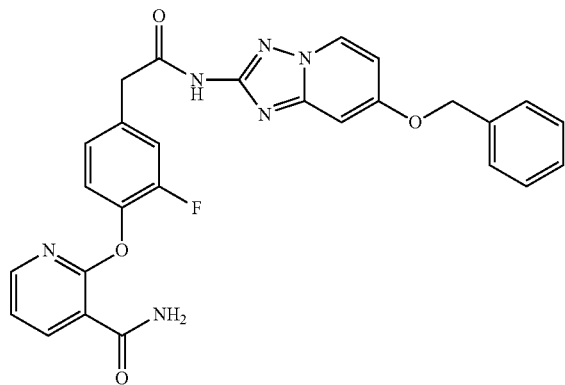 [SMILES: NC(=O)c1cccnc1Oc1ccc(CC(=O)Nc2nc3cc(OCc4ccccc4)ccn3n2)cc1F]

Example 143 (1.3 mg, 2% yield) was prepared via a similar procedure as example 139 by substituting 4-(benzyloxy)pyridin-2-amine in step-1 for 3-(difluoromethoxy)pyridin-2-amine. ¹H NMR (500 MHz, DMSO-d₆) δ 8.70 (br d, J=7.3 Hz, 1H), 8.26-8.16 (m, 2H), 7.84 (br s, 1H), 7.81 (br s, 1H), 7.53 (br d, J=7.3 Hz, 2H), 7.45 (br t, J=7.3 Hz, 2H), 7.44-7.31 (m, 4H), 7.30-7.17 (m, 3H), 6.86 (br dd, J=7.0, 2.1 Hz, 1H), 5.27 (s, 2H), 3.93 (s, 2H). LCMS m/z=513.2 (M+H).⁺ HPLC purity 94% with retention time 1.45 min. [method B]

Example 144. 2-(4-(2-((1-(cyclopropylmethyl)-6-(1-methyl-1H-pyrazol-4-yl)-1H-benzo[d]imidazol-2-yl)amino)-2-oxoethyl)-2-fluorophenoxy)nicotinamide

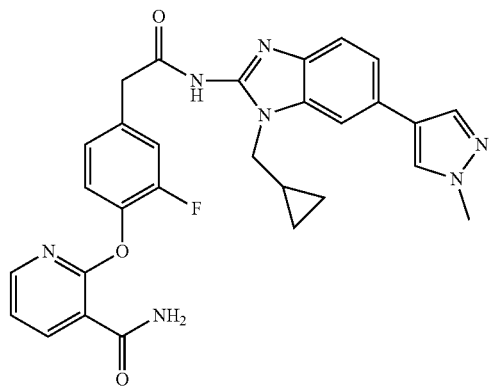 [SMILES: Cn1cc(-c2ccc3nc(NC(=O)Cc4ccc(Oc5ncccc5C(N)=O)c(F)c4)n(CC4CC4)c3c2)cn1]

Step 1. To 4-bromo-2-fluoro-1-nitrobenzene (0.60 g, 2.5 mmol) in THF (2 mL), cooled to 0° C., was added cyclopropylmethanamine (0.19 g, 2.7 mmol) and DIEA (0.5 mL, 3.0 mmol). The reaction mixture was stirred at rt for 18 h. The reaction mixture was concentrated under reduced pressure and the residue dissolved in acetone (3 mL)/water (1.5 mL), cooled to 0° C., and slowly added NH₄Cl (0.70 g, 12 mmol) and zinc (1.6 g, 25 mmol). The zinc was filtered off, acetone was concentrated under reduced pressure. The aqueous layer was partitioned with EtOAc (50 mL). The aqueous layer was extracted with EtOAc (2×20 mL). The combined organic layers were washed with brine (15 mL) and dried (Na₂SO₄). The residue was purified via silica gel chromatography and eluted with DCM/0-10% MeOH to afford 5-bromo-N1-(cyclopropylmethyl)benzene-1,2-diamine (0.40 g, 67% yield) as a dark oil. ¹H NMR (400 MHz, CDCl₃) δ 6.88-6.71 (m, 1H), 6.60 (d, J=8.1 Hz, 1H), 6.33 (br d, J=7.7 Hz, 1H), 3.79-3.40 (m, 1H), 3.08-2.84 (m, 2H), 1.13-0.99 (m, 1H), 0.71-0.54 (m, 2H), 0.40-0.12 (m, 2H).

Step 2. 5-Bromo-N1-(cyclopropylmethyl)benzene-1,2-diamine (0.40 g, 1.7 mmol) and cyanic bromide (0.26 g, 2.5 mmol) were stirred in MeOH (6.6 ml)/H2O (1.6 ml) for 18 h. The solvents were reduced under reduced pressure and then quenched by the addition of ammonium hydroxide. After dilution with water a dark brown solid was filtered off to afford 6-bromo-1-(cyclopropylmethyl)-1H-benzo[d]imidazol-2-amine (0.36 g, 83% yield). LCMS(ESI) m/z: 265-267.9 (M+H).⁺ ¹H NMR (400 MHz, DMSO-d₆) δ 7.41 (t, J=1.1 Hz, 1H), 7.05 (d, J=1.1 Hz, 2H), 6.53 (s, 2H), 3.92 (d, J=7.0 Hz, 2H), 1.32-1.12 (m, 1H), 0.63-0.25 (m, 4H).

Step 3. Intermediate 5 was coupled with 6-bromo-1-(cyclopropylmethyl)-1H-benzo[d]imidazol-2-amine as described in example 2 to afford 2-(4-(2-((6-bromo-1-(cyclopropylmethyl)-1H-benzo[d]imidazol-2-yl)amino)-2-oxoethyl)-2-fluorophenoxy)nicotinamide (72 mg, 36% yield) as an orange solid. LCMS(ESI) m/z: 537-539.9 (M+H).⁺

Step 4. Example 144 (4.0 mg, 21% yield) was made in a similar manner as example 4. ¹H NMR (500 MHz, DMSO-d₆) δ 8.39-8.08 (m, 4H), 7.91 (s, 1H), 7.80 (br s, 2H), 7.72 (br s, 1H), 7.42 (br s, 2H), 7.37-7.27 (m, 2H), 7.23 (br d, J=8.5 Hz, 2H), 4.03 (br d, J=7.6 Hz, 2H), 3.88 (s, 3H), 3.69 (s, 2H), 1.33 (m, 1H), 0.47 (br s, 4H). LCMS m/z=540.1 (M+H).⁺ HPLC purity 99% with retention time 1.19 min. [method B]

Example 145. 2-(4-(2-((1-(cyclopropylmethyl)-6-(dimethylphosphoryl)-1H-benzo[d]imidazol-2-yl)amino)-2-oxoethyl)-2-fluorophenoxy)nicotinamide

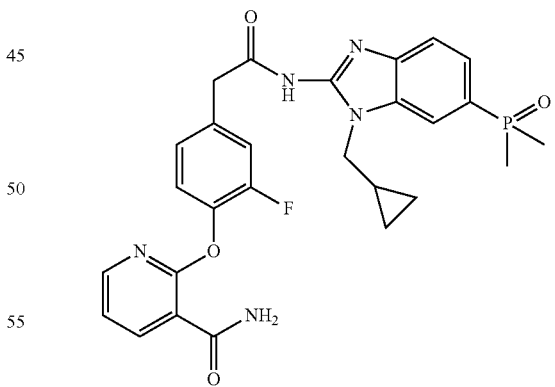

2-(4-(2-((6-Bromo-1-(cyclopropylmethyl)-1H-benzo[d]imidazol-2-yl)amino)-2-oxoethyl)-2-fluorophenoxy)nicotinamide (32 mg, 0.060 mmol), dimethylphosphine oxide (46.mg, 0.60 mmol), and TEA (25 μL, 0.18 mmol) were combined in acetonitrile (2.3 mL) and degassed with a stream of N₂. After purging for 5 min., (Ph₃P)₄Pd (O) (7 mg, 6 μmol) was added and the reaction mixture was heated under microwave irradiation at 120° C. for 40 min. The reaction mixture was allowed to cool, filtered and purified by reverse phase HPLC to afford example 145 (14 mg, 35% yield). ¹H NMR (500 MHz, DMSO-d₆) δ 8.21 (br d, J=7.4 Hz, 1H), 8.18 (br s, 1H), 7.86 (br d, J=10.7 Hz, 1H), 7.70 (br s, 1H), 7.66 (br s, 1H), 7.59 (br d, J=5.8 Hz, 2H), 7.44-7.28 (m, 2H), 7.23 (br d, J=5.4 Hz, 2H), 4.05 (br s, 2H), 3.96-3.64 (m, 2H), 2.55 (s, 1H), 1.71 (s, 3H), 1.69 (s, 3H), 1.30 (br s, 1H), 0.47 (br d, J=7.6 Hz, 3H), 0.32 (br s, 1H), LCMS m/z=536.1 (M+H).⁺ HPLC purity 100% with retention time 1.09 min. [method A]

The following examples 146-150 were prepared following the general procedure used for example 145

| Ex# | Structure | Name | HNMR | LCMS (M + H)⁺ | HPLC retention time (min) |
|---|---|---|---|---|---|
| 146 | 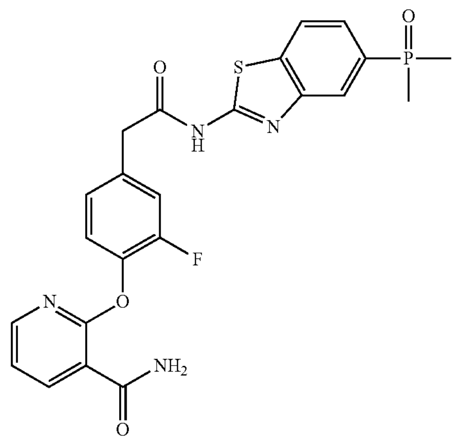 [SMILES: CP(C)(=O)c1ccc2sc(NC(=O)Cc3ccc(Oc4ncccc4C(N)=O)c(F)c3)nc2c1] | 2-(4-(2-((5-(dimethyl)-phosphoryl)benzo[d]-thiazol-2-yl)amino)-2-oxoethyl)-2-fluoro-phenoxy)nicotinamide | ¹H NMR (500 MHz, DMSO-d₆) δ 8.30-8.17 (m, 3H), 8.17-8.05 (m, 2H), 7.71 (br s, 1H), 7.66 (br d, J = 8.1 Hz, 2H), 7.43-7.32 (m, 2H), 7.28-7.19 (m, 2H), 3.94 (br s, 2H), 1.73 (s, 3H), 1.70 (s, 3H) | 499.1 | 1.04 Method A |
| 147 | 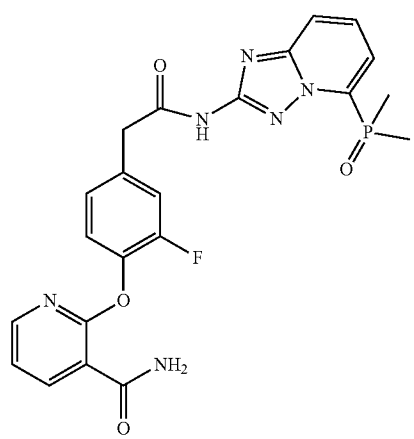 [SMILES: CP(C)(=O)c1cccc2nc(NC(=O)Cc3ccc(Oc4ncccc4C(N)=O)c(F)c3)nn12] | 2-(4-(2-((5-dimethyl-phosphoryl)-[1,2,4]-triazolo[1,5-a]-pyridin-2-yl)amino)-2-oxoethyl)-2-fluoro-phenoxy)nicotinamide | ¹H NMR (500 MHz, DMSO-d₆) δ 11.11 (s, 1H), 8.29-8.14 (m, 2H), 7.90 (br d, J = 8.8 Hz, 1H), 7.79 (br t, J = 8.0 Hz, 1H), 7.70 (br s, 1H), 7.68-7.63 (m, 1H), 7.60 (br t, J = 7.9 Hz, 1H), 7.43-7.29 (m, 2H), 7.26-7.17 (m, 2H), 3.88 (br s, 2H), 1.96 (s, 3H), 1.93 (s, 3H) | 483.1 | 0.80 Method B |
| 148 | 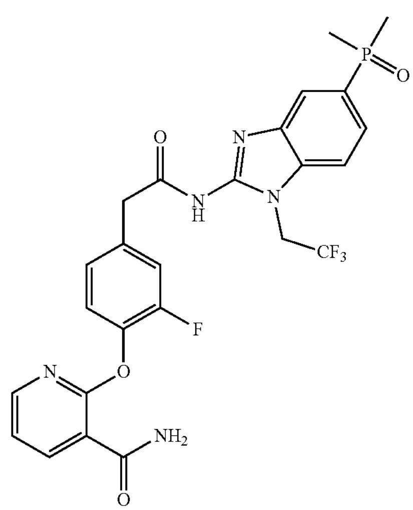 [SMILES: CP(C)(=O)c1ccc2c(c1)nc(NC(=O)Cc1ccc(Oc3ncccc3C(N)=O)c(F)c1)n2CC(F)(F)F] | 2-(4-(2-((5-(dimethyl-phosphoryl)-1-(2,2,2-trifluoroethyl)-1H-benzo[d]imidazol-2-yl)amino)-2-oxoethyl)-2-fluorophenoxy)-nicotinamide | ¹H NMR (500 MHz, DMSO-d₆) δ 8.21 (br d, J = 7.4 Hz, 1H), 8.18 (br d, J = 3.1 Hz, 1H), 7.95 (br d, J = 11.6 Hz, 1H), 7.71 (br s, 2H), 7.69-7.59 (m, 2H), 7.40-7.30 (m, 2H), 7.26-7.15 (m, 2H), 5.24-5.07 (m, 2H), 3.82 (br s, 2H), 1.92 (s, 1H), 1.70 (s, 3H), 1.67 (s, 3H) | 564.1 | 1.16 Method A |

| Ex# | Structure | Name | HNMR | LCMS (M + H)+ | HPLC retention time (min) |
|---|---|---|---|---|---|
| 149 | 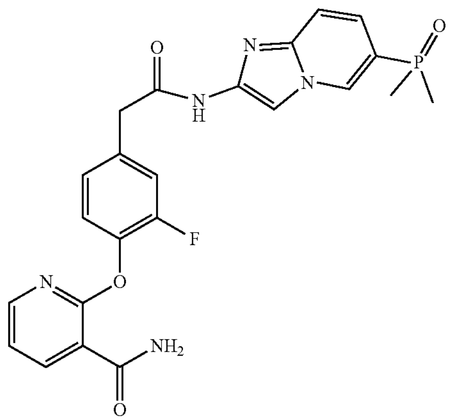 [SMILES: CP(C)(=O)c1ccc2nc(NC(=O)Cc3ccc(Oc4ncccc4C(N)=O)c(F)c3)cn2c1] | 2-(4-(2-((6-(dimethyl-phosphoryl)imidazo-[1,2-a]pyridin-2-yl)-amino)-2-oxoethyl)-2-fluorophenoxy)-nicotinamide | $^1$H NMR (500 MHz, DMSO-d$_6$) δ 10.94 (s, 1H), 8.89 (d, J = 9.4 Hz, 1H), 8.41-8.07 (m, 3H), 7.71 (br s, 1H), 7.65 (br s, 1H), 7.53 (br d, J = 8.2 Hz, 1H), 7.48-7.40 (m, 1H), 7.37-7.29 (m, 2H), 7.26-7.17 (m, 2H), 3.78 (s, 2H), 1.73 (s, 3H), 1.70 (s, 3H) | 482.0 | 0.74 Method B |
| 150 | 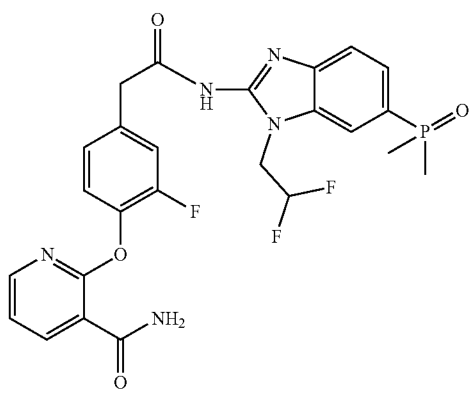 [SMILES: CP(C)(=O)c1ccc2nc(NC(=O)Cc3ccc(Oc4ncccc4C(N)=O)c(F)c3)n(CC(F)F)c2c1] | 2-(4-(2-((1-(2,2-difluoroethyl)-6-(dimethylphosphoryl)-1H-benzo[d]imidazol-2-yl)amino)-2-oxo-ethyl)-2-fluoro-phenoxy)nicotinamide | $^1$H NMR (500 MHz, DMSO-d$_6$) δ 8.22-8.15 (m, 2H), 7.83 (br s, 1H), 7.79 (br s, 1H), 7.69-7.58 (m, 2H), 7.38-7.33 (m, 2H), 7.26-7.21 (m, 4H), 6.55-6.27 (m, 1H), 4.69 (br t, J = 14.3 Hz, 2H), 3.94-3.71 (m, 2H), 1.71 (s, 3H), 1.68 (s, 3H) | 546.2 | 0.95 Method B |

Example 151. 2-(2-fluoro-4-(2-((5-methyl-4-(6-methylpyridin-2-yl)thiazol-2-yl)amino)-2-oxoethyl)phenoxy)nicotinamide

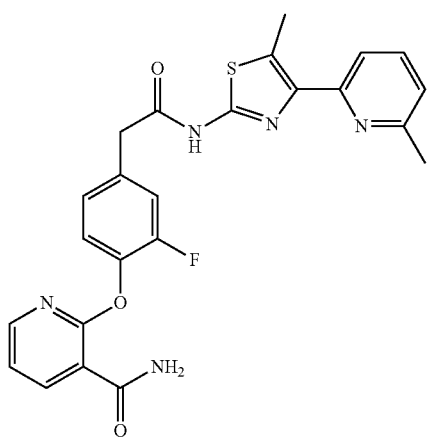 [SMILES: Cc1cccc(-c2nc(NC(=O)Cc3ccc(Oc4ncccc4C(N)=O)c(F)c3)sc2C)n1]

Step 1. To 1-(6-methylpyridin-2-yl)propan-1-one (0.30 g, 2.0 mmol) and AcOH (3 mL), heated to 90° C., was added Br$_2$ (0.10 mL, 2.0 mmol) in AcOH (1 mL). After 1 h, the solvents were removed under reduced pressure and EtOH (15 mL) and thiourea (0.15 g, 2.01 mmol) were added and the reaction mixture was heated to 60° C. for 72 h. The solvents were removed under reduced pressure and residue was partitioned with 0.1 M NH$_4$OH (20 mL) and EtOAc (50 mL). The aqueous layer was extracted with EtOAc (2×20 mL). The combined organic layers were washed with brine (15 mL) and dried (MgSO$_4$), filtered and concentrated to afford 5-methyl-4-(6-methylpyridin-2-yl)thiazol-2-amine (0.30 g, 74% yield) as a tan solid. $^1$H NMR (400 MHz, CDCl$_3$) δ 7.68-7.51 (m, 2H), 7.05 (dd, J=7.3, 1.1 Hz, 1H), 4.91 (br s, 2H), 2.68 (s, 3H), 2.61 (s, 3H). LCMS(ESI) m/z: 206.0 (M+H).+

Step 2. Example 151 (6 mgs, 8% yield) was made using BOP to couple intermediate 5 and 5-methyl-4-(6-methylpyridin-2-yl)thiazol-2-amine as described in example 2. $^1$H NMR (500 MHz, DMSO-d$_6$) δ 12.38 (s, 1H), 8.28-8.13 (m, 2H), 7.83 (br s, 1H), 7.79 (br s, 1H), 7.77-7.66 (m, 2H), 7.48-7.31 (m, 2H), 7.30-7.20 (m, 2H), 7.16 (br d, J=6.7 Hz, 1H), 2.84 (s, 2H), 2.75 (s, 3H), 2.50 (s, 3H), LCMS m/z=478.1 (M+H).$^+$ HPLC purity 95% with retention time 1.62 min. [method A]

Example 152. Preparation 2-(4-(2-((1-(cyclobutylmethyl)-1H-benzo[d]imidazol-2-yl)amino)-2-oxoethyl)-2-fluorophenoxy)nicotinamide

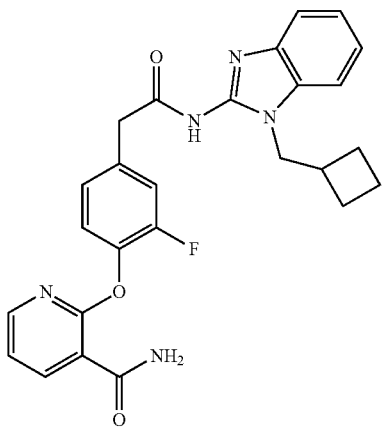 [SMILES: NC(=O)c1cccnc1Oc1ccc(CC(=O)Nc2nc3ccccc3n2CC2CCC2)cc1F]

Step 1. KOH (105 mg, 1.88 mmol) and (bromomethyl)cyclobutane (0.21 mL, 1.9 mmol) were added to a solution of 2-aminobenzimidazole (250 mg, 1.87 mmol) in acetone (10 mL) and heated at 60° C. for 8 h and then allowed to cool to rt. After stirring for 48 hr, the solvent was evaporated under reduced pressure. The residue was dissolved in EtOAc, washed with water, brine, dried over Na$_2$SO$_4$, filtered, and concentrated under reduced pressure. The residue was purified by normal phase chromatography (100% DCM to 10% MeOH/90% DCM) to give 1-(cyclobutylmethyl)-1H-benzo[d]imidazol-2-amine. $^1$H NMR (400 MHz, DMSO-d6) δ 7.17-7.05 (m, 2H), 6.93-6.81 (m, 2H), 6.33 (s, 2H), 4.00 (d, J=7.3 Hz, 2H), 2.80-2.66 (m, 1H), 1.92-1.75 (m, 6H). LCMS m/z=202.0 (M+H).$^+$ Step 2. Intermediate 2 (72 mg, 0.25 mmol) was added to a solution of 1-(cyclobutylmethyl)-1H-benzo[d]imidazol-2-amine (50 mg, 0.20 mmol) and pyridine (60 µl, 0.70 mmol) in THF at 0° C. The reaction mixture was allowed to come to rt. After stirring 18 h, the reaction mixture was diluted with EtOAc and washed with water, brine, dried over sodium sulfate, filtered, and concentrated under reduced pressure. The residue was purified by normal phase chromatography (100% DCM to 10% MeOH/90% DCM) to give a tan solid. The nitrile was hydrolyzed to the primary amide in a similar manner as described in example 8 to afford example 152 (25 mg, 17%) as white solid. $^1$H NMR (500 MHz, DMSO-d6) δ 8.21-8.15 (m, 2H), 7.84-7.76 (m, 2H), 7.72-7.62 (m, 1H), 7.61-7.55 (m, 1H), 7.42-7.29 (m, 4H), 7.24 (dd, J=7.4, 5.0 Hz, 2H), 4.29 (br s, 2H), 3.89 (br s, 2H), 2.80 (dt, J=15.1, 7.5 Hz, 1H), 1.95-1.88 (m, 2H), 1.87-1.77 (m, 4H). LCMS m/z=474.0 (M+H).$^+$ HPLC purity: 98% with retention time 8.37 min. [method C].

Example 153. 2-(2-fluoro-4-(2-((1-isopropyl-1H-benzo[d]imidazol-2-yl)amino)-2-oxoethyl)-phenoxy)nicotinamide

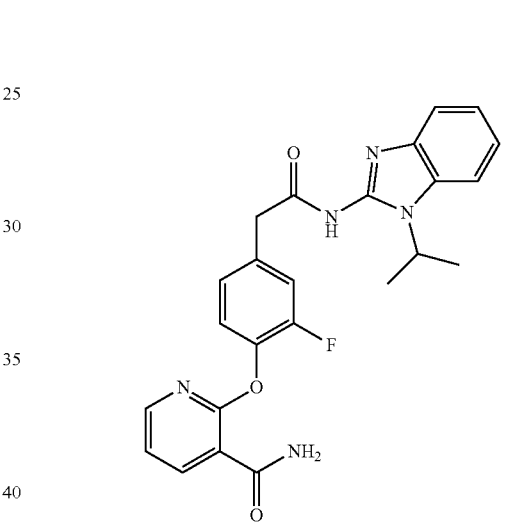

Step 1. 1-Isopropyl-1H-benzo[d]imidazol-2-amine (110 mg, 34%) was prepared in a similar manner as described for step 1 of example 152 by replacing (bromomethyl)cyclobutane with 2-bromopropane. LCMS m/z=176.1 (M+H).$^+$ Step 2. 2-(2-fluoro-4-(2-((1-isopropyl-1H-benzo[d]imidazol-2-yl)amino)-2-oxoethyl)-phenoxy)nicotinamide 153 (49 mg, 13%) was prepared in a similar manner as example 152 by replacing 1-(cyclobutylmethyl)-1H-benzo[d]imidazol-2-amine with 1-isopropyl-1H-benzo[d]imidazol-2-amine. $^1$H NMR (500 MHz, DMSO-d6) δ 8.20-8.16 (m, 2H), 7.84-7.77 (m, 3H), 7.62 (br s, 1H), 7.39-7.30 (m, 4H), 7.26-7.22 (m, 2H), 5.04-4.96 (m, 1H), 3.96-3.88 (m, 2H), 1.59 (s, 3H), 1.58 (s, 3H). LCMS m/z=448.0 (M+H).$^+$ HPLC purity: 93% with retention time 7.49 min. [method C].

The examples 154-177 were prepared following the general procedure used for Example 152.

| Ex# | Structure | Name | HNMR | LCMS (M + H)+ | HPLC retention time (min) |
|---|---|---|---|---|---|
| 154 | 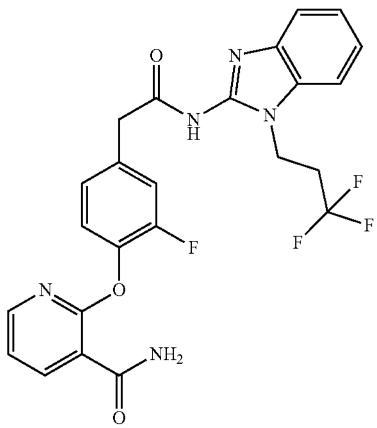 [SMILES: NC(=O)c1cccnc1Oc1ccc(CC(=O)Nc2nc3ccccc3n2CCC(F)(F)F)cc1F] | 2-(2-fluoro-4-(2-oxo-2-((1-(3,3,3-trifluoropropyl)-1H-benzo[d]-imidazol-2-yl)-amino)ethyl)-phenoxy)nicotin-amide | ¹H NMR (500 MHz, DMSO-d₆) δ 8.20-8.13 (m, 2H), 7.77 (br s, 2H), 7.53 (br s, 2H), 7.35-7.19 (m, 6H), 4.40 (br s, 2H), 3.84-3.74 (m, 2H), 2.87-2.77 (m, 2H) | 502.1 | 8.10 Method C |
| 155 | 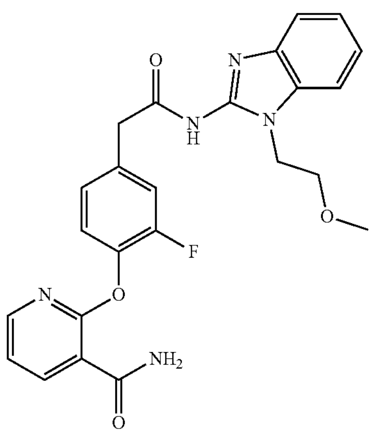 [SMILES: COCCn1c(NC(=O)Cc2ccc(Oc3ncccc3C(N)=O)c(F)c2)nc2ccccc21] | 2-(2-fluoro-4-(2-((1-(2-methoxyethyl)-1H-benzo[d]-imidazol-2-yl)-amino)-2-oxo-ethyl)phenoxy)-nicotinamide | ¹H NMR (500 MHz,DMSO-d₆) δ 8.23-8.14 (m, 2H), 7.74-7.59 (m, 2H), 7.60-7.53 (m, 2H), 7.36-7.21 (m, 7H), 4.38 (br t, J = 5.3 Hz, 2H), 3.84 (s, 2H), 3.70-3.65 (m, 2H) | 464.2 | 1.34 Method A |
| 156 | 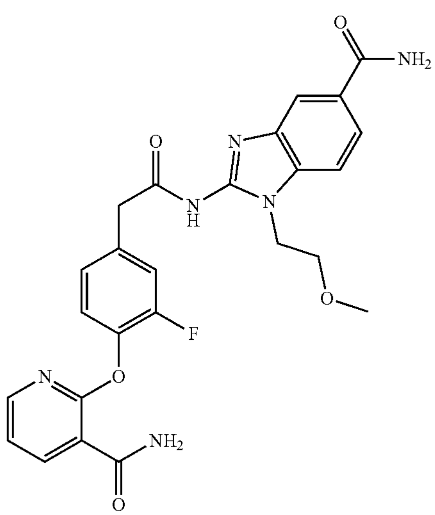 [SMILES: COCCn1c(NC(=O)Cc2ccc(Oc3ncccc3C(N)=O)c(F)c2)nc2cc(C(N)=O)ccc21] | 2-(2-(4-((3-carbamoyl-pyridin-2-yl)oxy)-3-fluorophenyl)-acetamido)-1-(2-methoxyethyl)-1H-benzo[d]-imidazole-5-carboxamide | ¹H NMR (500 MHz, DMSO-d₆) δ 8.26-8.14 (m, 2H), 8.03 (br s, 1H), 7.77 (br d, J = 8.3 Hz, 1H), 7.73-7.61 (m, 2H), 7.52 (br d, J = 8.0 Hz, 1H), 7.36-7.29 (m, 2H), 7.27-7.19 (m, 2H), 4.28 (br t, J = 4.9 Hz, 2H), 3.85-3.68 (m, 2H), 3.64 (br s, 1H), 3.35-3.28 (m, 1H), 3.22-3.13 (m, 1H), 2.56-2.53 (m, 3H) | 507.1 | 1.03 Method A |

| Ex# | Structure | Name | HNMR | LCMS (M + H)+ | HPLC retention time (min) |
|---|---|---|---|---|---|
| 157 | 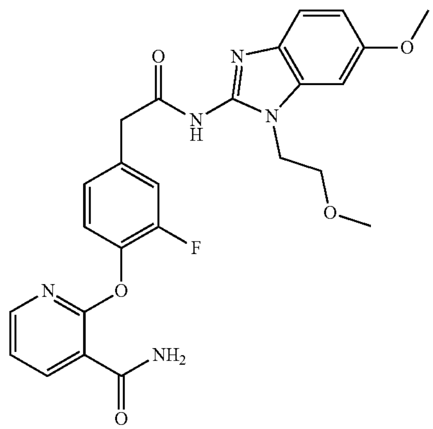 [SMILES: COCCn1c(NC(=O)Cc2ccc(Oc3ncccc3C(N)=O)c(F)c2)nc2ccc(OC)cc21] | 2-(2-fluoro-4-(2-((6-methoxy-1-(2-methoxyethyl)-1H-benzo[d]-imidazol-2-yl)-amino)-2-oxo-ethyl)phenoxy)-nicotinamide | $^{1}$H NMR (500 MHz, DMSO-$d_6$) δ 8.21-8.13 (m, 2H), 7.80 (br d, J = 13.1 Hz, 2H), 7.44-7.30 (m, 3H), 7.25-7.19 (m, 2H), 7.13 (s, 1H), 6.89-6.79 (m, 1H), 4.39-4.21 (m, 2H), 3.84-3.77 (m, 4H), 3.73-3.49 (m, 2H), 3.23-3.17 (m, 2H) | 494.1 | 1.38 Method A |
| 158 | 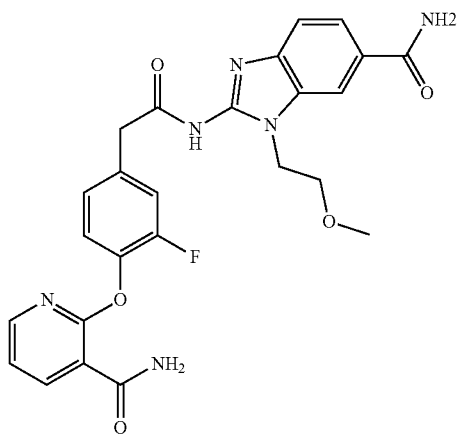 [SMILES: COCCn1c(NC(=O)Cc2ccc(Oc3ncccc3C(N)=O)c(F)c2)nc2ccc(C(N)=O)cc21] | 2-(2-(4-((3-carbamoyl-pyridin-2-yl)oxy)-3-fluorophenyl)-acetamido)-1-(2-methoxyethyl)-1H-benzo[d]-imidazole-6-carboxamide | $^{1}$H NMR (500 MHz, DMSO-$d_6$) δ 8.19-8.14 (m, 2H), 8.06-8.00 (m, 1H), 7.96 (br s, 1H), 7.82-7.72 (m, 3H), 7.36-7.29 (m, 3H), 7.25-7.19 (m, 2H), 4.30 (br t, J = 5.0 Hz, 2H), 3.79-3.63 (m, 2H), 3.26-3.17 (m, 1H), 2.56-2.53 (m, 3H) | 507.2 | 1.02 Method B |
| 159 | 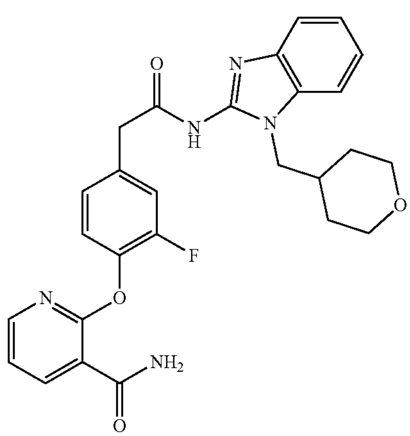 [SMILES: NC(=O)c1cccnc1Oc1ccc(CC(=O)Nc2nc3ccccc3n2CC2CCOCC2)cc1F] | 2-(2-fluoro-4-(2-oxo-2-((1-((tetra-hydro-2H-pyran-4-yl)methyl)-1H-benzo[d]imidazol-2-yl)amino)ethyl)-phenoxy)nicotin-amide | $^{1}$H NMR (500 MHz, DMSO-$d_6$) δ 8.23-8.14 (m, 2H), 7.67 (br s, 2H), 7.55-7.48 (m, 2H), 7.38-7.30 (m, 2H), 7.27-7.18 (m, 4H), 4.00 (br d, J = 7.2 Hz, 2H), 3.81-3.73 (m, 4H), 3.20-3.10 (m, 1H), 1.40-1.24 (m, 4H) | 504.3 | 1.44 Method A |

| Ex# | Structure | Name | HNMR | LCMS (M + H)+ | HPLC retention time (min) |
|---|---|---|---|---|---|
| 160 | 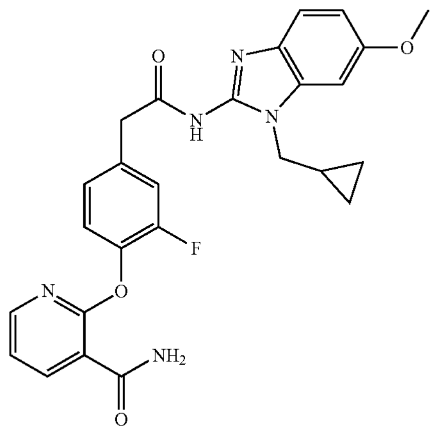 [SMILES: COc1ccc2nc(NC(=O)Cc3ccc(Oc4ncccc4C(N)=O)c(F)c3)n(CC3CC3)c2c1] | 2-(4-(2-((1-(cyclopropyl-methyl)-6-methoxy-1H-benzo[d]-imidazol-2-yl)-amino)-2-oxoethyl)-2-fluorophenoxy)-nicotinamide | $^1$H NMR (500 MHz, DMSO-$d_6$) δ 8.23-8.15 (m, 2H), 7.73-7.59 (m, 2H), 7.41 (d, J = 8.7 Hz, 1H), 7.35-7.28 (m, 2H), 7.25-7.19 (m, 2H), 7.15-7.11 (m, 1H), 6.82 (br d, J = 8.6 Hz, 1H), 3.99 (br d, J = 6.9 Hz, 2H), 3.85-3.79 (m, 3H), 3.77-3.69 (m, 2H), 1.29-1.20 (m, 1H), 0.48-0.36 (m, 4H) | 490.3 | 1.68 Method A |
| 161 | 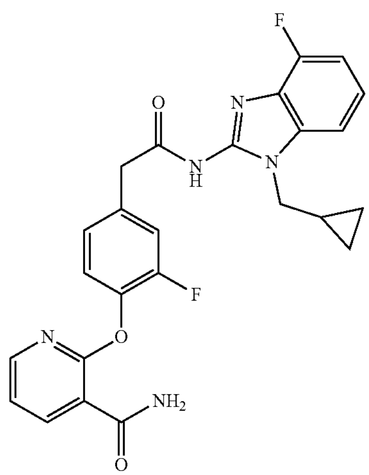 [SMILES: NC(=O)c1cccnc1Oc1ccc(CC(=O)Nc2nc3c(F)cccc3n2CC2CC2)cc1F] | 2-(4-(2-((1-(cyclopropyl-methyl)-4-fluoro-1H-benzo[d]-imidazol-2-yl)-amino)-2-oxoethyl)-2-fluorophenoxy)-nicotinamide | $^1$H NMR (500 MHz, DMSO-$d_6$) δ 8.21-8.14 (m, 2H), 7.88-7.81 (m, 1H), 7.80-7.74 (m, 1H), 7.44 (d, J = 7.9 Hz, 1H), 7.39-7.31 (m, 2H), 7.27-7.16 (m, 3H), 7.06-6.98 (m, 1H), 3.96-3.88 (m, 2H), 3.82 (br s, 1H), 3.58-3.46 (m, 2H), 1.17-1.07 (m, 1H), 0.43-0.37 (m, 2H), 0.30-0.23 (m, 2H) | 478.2 | 1.68 Method A |
| 162 | 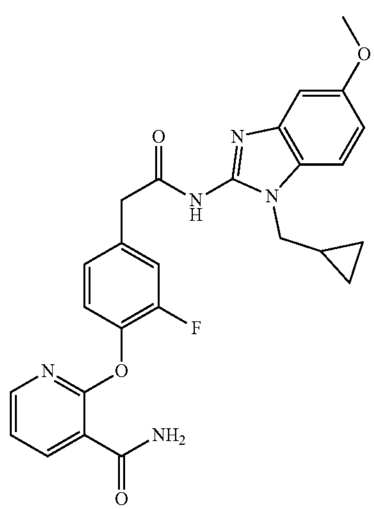 [SMILES: COc1ccc2c(c1)nc(NC(=O)Cc1ccc(Oc3ncccc3C(N)=O)c(F)c1)n2CC1CC1] | 2-(4-(2-((1-(cyclopropyl-methyl)-5-methoxy-1H-benzo[d]-imidazol-2-yl)-amino)-2-oxoethyl)-2-fluorophenoxy)-nicotinamide | $^1$H NMR (500 MHz, DMSO-$d_6$) δ 8.20-8.14 (m, 2H), 7.80 (br d, J = 12.5 Hz, 2H), 7.57 (br d, J = 8.9 Hz, 1H), 7.38-7.31 (m, 2H), 7.25-7.20 (m, 2H), 7.13 (br d, J = 2.1 Hz, 1H), 6.94 (br d, J = 7.6 Hz, 1H), 4.09 (br d, J = 6.4 Hz, 2H), 3.88-3.81 (m, 2H), 3.78 (s, 3H), 1.23 (br d, J = 7.0 Hz, 1H), 0.50-0.44 (m, 2H), 0.44-0.37 (m, 2H) | 490.2 | 1.25 Method B |

-continued

| Ex# | Structure | Name | HNMR | LCMS (M + H)+ | HPLC retention time (min) |
|---|---|---|---|---|---|
| 163 | 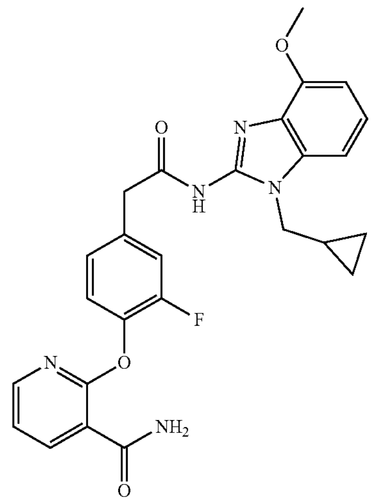 [SMILES: COc1cccc2c1nc(NC(=O)Cc1ccc(Oc3ncccc3C(N)=O)c(F)c1)n2CC1CC1] | 2-(4-(2-((1-(cyclopropylmethyl)-4-methoxy-1H-benzo[d]imidazol-2-yl)amino)-2-oxoethyl)-2-fluorophenoxy)-nicotinamide | No NMR by SCP | 490.3 | 1.29 Method A |
| 164 | 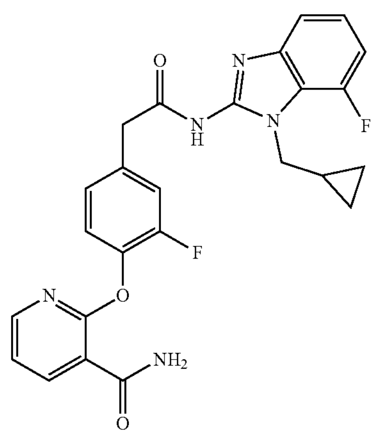 [SMILES: NC(=O)c1cccnc1Oc1ccc(CC(=O)Nc2nc3cccc(F)c3n2CC2CC2)cc1F] | 2-(4-(2-((1-(cyclopropylmethyl)-7-fluoro-1H-benzo[d]imidazol-2-yl)amino)-2-oxoethyl)-2-fluorophenoxy)nicotinamide | $^1$H NMR (500 MHz, DMSO-$d_6$) δ 8.22-8.18 (m, 1H), 8.16 (br d, J = 3.5 Hz, 1H), 7.74-7.68 (m, 1H), 7.67-7.61 (m, 1H), 7.35-7.28 (m, 2H), 7.26-7.15 (m, 4H), 7.07 (br dd, J = 11.6, 8.4 Hz, 1H), 4.01 (br s, 2H), 3.48-3.30 (m, 2H), 1.27-1.21 (m, 1H), 0.48-0.30 (m, 4H) | 478.1 | 1.43 Method B |
| 165 | 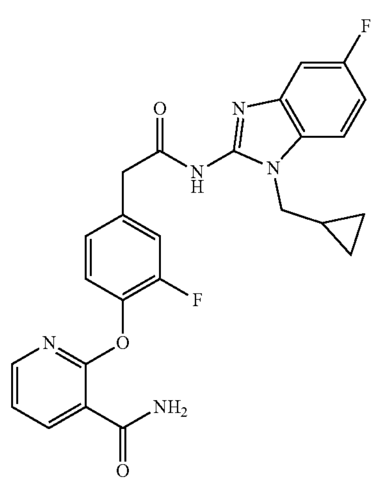 [SMILES: NC(=O)c1cccnc1Oc1ccc(CC(=O)Nc2nc3cc(F)ccc3n2CC2CC2)cc1F] | 2-(4-(2-((1-cyclopropylmethyl)-5-fluoro-1H-benzo[d]imidazol-2-yl)amino)-2-oxoethyl)-2-fluorophenoxy)nicotinamide | $^1$H NMR (500 MHz, DMSO-$d_6$) δ 8.22-8.12 (m, 2H), 7.82 (s, 1H), 7.77 (s, 1H), 7.62-7.50 (m, 1H), 7.39-7.25 (m, 3H), 7.26-7.17 (m, 2H), 7.12-7.05 (m, 1H), 4.02-3.90 (m, 2H), 3.45-3.36 (m, 2H), 1.25-1.21 (m, 1H), 0.48-0.24 (m, 4H) | 478.2 | 1.66 Method A |

| Ex# | Structure | Name | HNMR | LCMS (M + H)+ | HPLC retention time (min) |
|---|---|---|---|---|---|
| 166 | 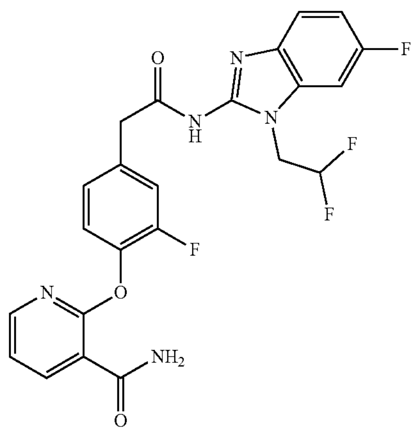 [SMILES: NC(=O)c1cccnc1Oc1ccc(CC(=O)Nc2nc3ccc(F)cc3n2CC(F)F)cc1F] | 2-(4-(2-((1-(2,2-difluoroethyl)-6-fluoro-1H-benzo[d]imidazol-2-yl)amino)-2-oxoethyl)-2-fluorophenoxy)nicotinamide | $^1$H NMR (500 MHz, DMSO-$d_6$) δ 8.23-8.12 (m, 2H), 7.78-7.50 (m, 3H), 7.47-7.40 (m, 1H), 7.36-7.28 (m, 2H), 7.26-7.18 (m, 2H), 7.10-7.00 (m, 1H), 6.47-6.20 (m, 1H), 4.64-4.54 (m, 2H), 3.91-3.65 (m, 2H) | 488.2 | 1.52 Method A |
| 167 | 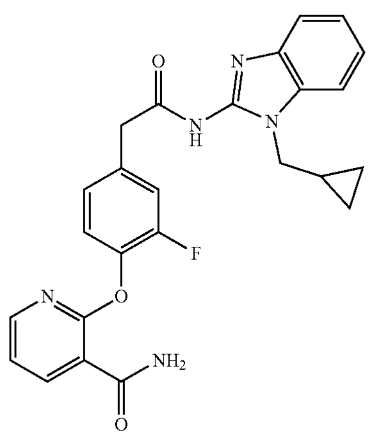 [SMILES: NC(=O)c1cccnc1Oc1ccc(CC(=O)Nc2nc3ccccc3n2CC2CC2)cc1F] | 2-(4-(2-((1-(cyclopropylmethyl)-1H-benzo[d]imidazol-2-yl)amino)-2-oxoethyl)-2-fluorophenoxy)nicotinamide | $^1$H NMR (500 MHz, DMSO-$d_6$) δ 8.19-8.13 (m, 2H), 7.84-7.80 (m, 1H), 7.80-7.76 (m, 1H), 7.68-7.63 (m, 1H), 7.60-7.55 (m, 1H), 7.38-7.28 (m, 4H), 7.25-7.20 (m, 2H), 4.13 (br d, J = 7.0 Hz, 2H), 3.90-3.82 (m, 2H), 1.30-1.21 (m, 1H), 0.50-0.40 (m, 4H) | 460.3 | 1.68 Method A |
| 168 | 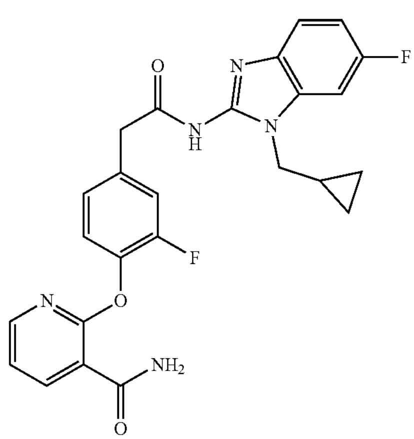 [SMILES: NC(=O)c1cccnc1Oc1ccc(CC(=O)Nc2nc3ccc(F)cc3n2CC2CC2)cc1F] | 2-(4-(2-((1-(cyclopropylmethyl)-6-fluoro-1H-benzo[d]imidazol-2-yl)amino)-2-oxoethyl)-2-fluorophenoxy)nicotinamide | $^1$H NMR (500 MHz, DMSO-$d_6$) δ 8.19-8.13 (m, 2H), 7.84-7.79 (m, 1H), 1H (br s, 1H), 7.58-7.51 (m, 2H), 7.36-7.30 (m, 2H), 7.25-7.19 (m, 2H), 7.15-7.04 (m, 1H), 4.04-3.96 (m, 2H), 3.86-3.74 (m, 1H), 1.25-1.16 (m, 1H), 0.46-0.40 (m, 2H), 0.39-0.34 (m, 2H) | 478.2 | 1.64 Method A |

-continued

| Ex# | Structure | Name | HNMR | LCMS (M + H)+ | HPLC retention time (min) |
|---|---|---|---|---|---|
| 169 | 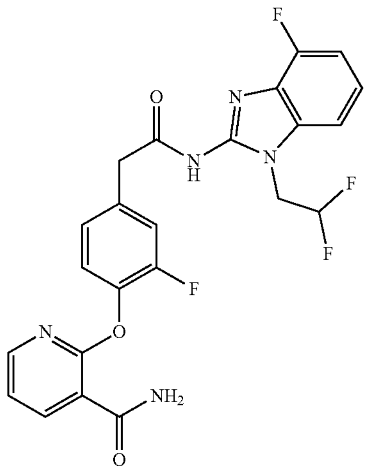 [SMILES: NC(=O)c1cccnc1Oc1ccc(CC(=O)Nc2nc3c(F)cccc3n2CC(F)F)cc1F] | 2-(4-(2-((1-(2,2-difluoroethyl)-4-fluoro-1H-benzo[d]-imidazol-2-yl)-amino)-2-oxo-ethyl)-2-fluoro-phenoxy)nicotin-amide | $^{1}$H NMR (500 MHz, DMSO-$d_6$) δ 8.20-8.16 (m, 2H), 7.85-7.81 (m, 1H), 7.80-7.75 (m, 1H), 7.43 (br d, J = 7.9 Hz, 1H), 7.39-7.32 (m, 2H), 7.28-7.21 (m, 3H), 7.06 (dd, J = 10.5, 8.4 Hz, 1H), 6.48-6.23 (m, 1H), 4.69-4.60 (m, 2H), 3.90-3.79 (m, 2H) | 488.2 | 1.42 Method A |
| 170 | 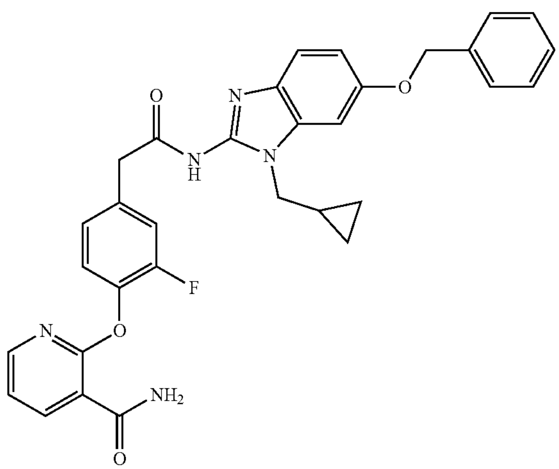 [SMILES: NC(=O)c1cccnc1Oc1ccc(CC(=O)Nc2nc3ccc(OCc4ccccc4)cc3n2CC2CC2)cc1F] | 2-(4-(2-((6-(benzyloxy)-1-(cyclo-propylmethyl)-1H-benzo[d]-imidazol-2-yl)-amino)-2-oxo-ethyl)-2-fluoro-phenoxy)nicotin-amide | $^{1}$H NMR (500 MHz, DMSO-$d_6$) δ 8.22-8.11 (m, 2H), 7.80 (br d, J = 12.8 Hz, 2H), 7.50-7.17 (m, 1H), 6.94-6.83 (m, 1H), 5.18-5.07 (m, 2H), 4.00-3.85 (m, 2H), 1.25-1.11 (m, 1H), 0.44-0.28 (m, 4H) | 566.2 | 1.98 Method A |
| 171 | 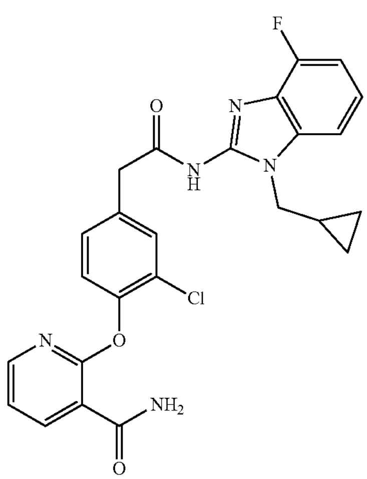 | 2-(2-chloro-4-(2-((1-(cyclo-propylmethyl)-4-fluoro-1H-benzo[d]-imidazol-2-yl)-amino)-2-oxo-ethyl)phenoxy)-nicotinamide | $^{1}$H NMR (500 MHz, DMSO-$d_6$) δ 8.23-8.19 (m, 1H), 8.17-8.13 (m, 1H), 7.83-7.78 (m, 1H), 7.78-7.73 (m, 1H), 7.59-7.54 (m, 1H), 7.46-7.42 (m, 1H), 7.41-7.36 (m, 2H), 7.26-7.19 (m, 2H), 7.05-6.98 (m, 1H), 3.97-3.89 (m, 2H), 3.87-3.75 (m, 2H), 1.16-1.08 (m, 1H), 0.45-0.39 (m, 2H), 0.30-0.25 (m, 2H) | 494.0 | 1.64 Method A |

| Ex# | Structure | Name | HNMR | LCMS (M + H)+ | HPLC retention time (min) |
|---|---|---|---|---|---|
| 172 | 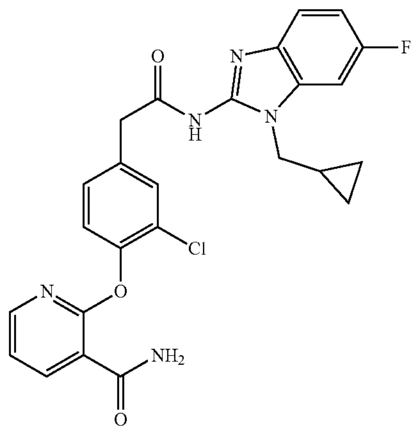 [SMILES: NC(=O)c1cccnc1Oc1ccc(CC(=O)Nc2nc3ccc(F)cc3n2CC2CC2)cc1Cl] | 2-(2-chloro-4-(2-((1-(cyclopropyl-methyl)-6-fluoro-1H-benzo[d]-imidazol-2-yl)-amino)-2-oxo-ethyl)phenoxy)-nicotinamide | $^1$H NMR (500 MHz, DMSO-$d_6$) δ 8.20 (br d, J = 6.4 Hz, 1H), 8.14 (br d, J = 3.7 Hz, 1H), 7.82-7.78 (m, 1H), 7.77-7.74 (m, 1H), 7.54 (br d, J =9.5 Hz, 3H), 7.35 (br d, J = 4.3 Hz, 2H), 7.23 (dd, J = 7.3, 4.9 Hz, 1H), 7.07 (br s, 1H), 4.01-3.92 (m, 2H), 3.81-3.73 (m, 2H), 1.21 (br s, 1H), 0.47-0.42 (m, 2H), 0.36 (br s, 2H) | 494.2 | 1.78 Method A |
| 173 | 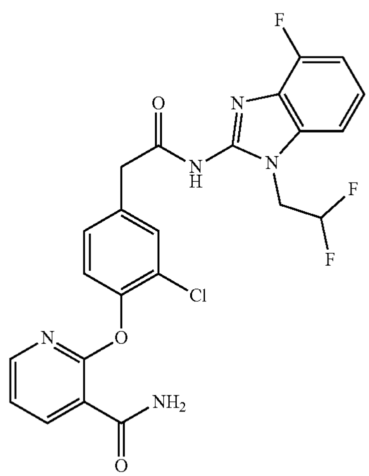 | 2-(2-chloro-4-(2-((1-(2,2-difluoro-ethyl)-4-fluoro-1H-benzo[d]-imidazol-2-yl)-amino)-2-oxo-ethyl)phenoxy)-nicotinamide | $^1$H NMR (500 MHz, DMSO-$d_6$) δ 8.23-8.20 (m, 1H), 8.18-8.14 (m, 1H), 7.81-7.74 (m, 2H), 7.58-7.54 (m, 1H), 7.44-7.40 (m, 1H), 7.38 (s, 2H), 7.28-7.21 (m, 2H), 7.10-7.02 (m, 1H), 6.47-6.22 (m, 1H), 4.69-4.60 (m, 2H), 3.87 (br d, J = 9.5 Hz, 2H), 3.49-3.44 (m, 1H) | 504.2 | 1.44 Method B |
| 174 | 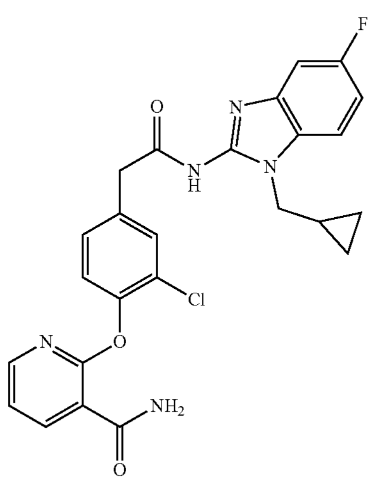 [SMILES: NC(=O)c1cccnc1Oc1ccc(CC(=O)Nc2nc3cc(F)ccc3n2CC2CC2)cc1Cl] | 2-(2-chloro-4-(2-((1-(cyclo-propylmethyl)-5-fluoro-1H-benzo[d]-imidazol-2-yl)-amino)-2-oxo-ethyl)phenoxy)-nicotinamide | $^1$H NMR (500 MHz, DMSO-$d_6$) δ 8.24-8.19 (m, 1H), 8.17-8.13 (m, 1H), 7.84-7.79 (m, 1H), 7.78-7.71 (m, 1H),7.57-7.49 (m, 2H), 7.40-7.27 (m, 3H), 7.26-7.19 (m, 1H), 7.11-7.03 (m, 1H), 4.04-3.91 (m, 2H), 1.23-1.12 (m, 1H), 0.47-0.26 (m, 4H) | 494.0 | 1.66 Method A |

-continued

| Ex# | Structure | Name | HNMR | LCMS (M + H)+ | HPLC retention time (min) |
|---|---|---|---|---|---|
| 175 | 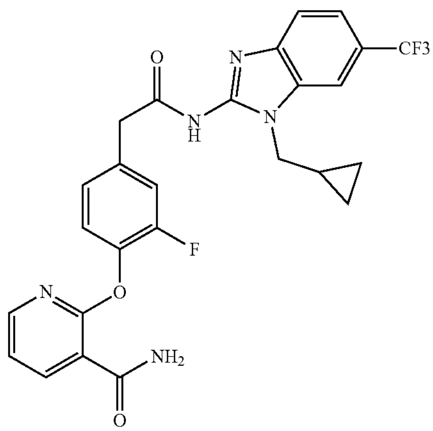 [SMILES: NC(=O)c1cccnc1Oc1ccc(CC(=O)Nc2nc3ccc(C(F)(F)F)cc3n2CC2CC2)cc1F] | 2-(4-(2-((1-(cyclopropyl-methyl)-6-(trifluoro-methyl)-1H-benzo[d]-imidazol-2-yl)amino)-2-oxoethyl)-2-fluorophenoxy)-nicotinamide | $^1$H NMR (500 MHz, DMSO-$d_6$) δ 8.18 (br d, J = 7.6 Hz, 2H), 8.08-8.01 (m, 1H), 7.95-7.91 (m, 1H), 7.83-7.73 (m, 3H), 7.55-7.49 (m, 1H), 7.40-7.27 (m, 2H), 7.24-7.18 (m, 2H), 4.08-4.03 (m, 2H), 1.31-1.09 (m, 1H), 0.46-0.38 (m, 3H), 0.31-0.24 (m, 1H) | 528.2 | 1.65 Method B |
| 176 | 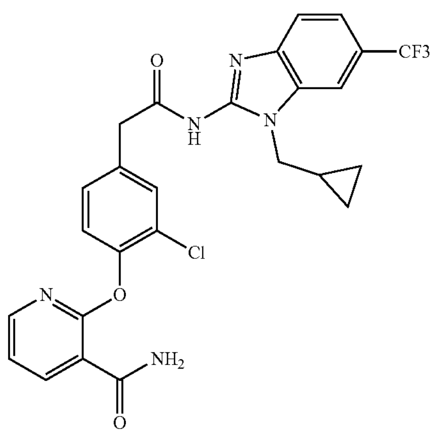 [SMILES: NC(=O)c1cccnc1Oc1ccc(CC(=O)Nc2nc3ccc(C(F)(F)F)cc3n2CC2CC2)cc1Cl] | 2-(2-chloro-4-(2-((1-(cyclo-propylmethyl)-6-(trifluoro-methyl)-1H-benzo[d]-imidazol-2-yl)-amino)-2-oxo-ethyl)phenoxy)-nicotinamide | $^1$H NMR (500 MHz, DMSO-$d_6$) δ 8.23-8.19 (m, 1H), 8.16-8.11 (m, 1H), 8.01-7.92 (m, 1H), 7.83-7.75 (m, 2H), 7.72-7.63 (m, 1H), 7.56-7.50 (m, 2H), 7.36 (br s, 2H), 7.25-7.19 (m, 1H), 4.09-4.00 (m, 2H), 3.61-3.49 (m, 1H), 1.25-1.15 (m, 1H), 0.46-0.26 (m, 4H) | 544.1 | 1.98 Method A |
| 177 | 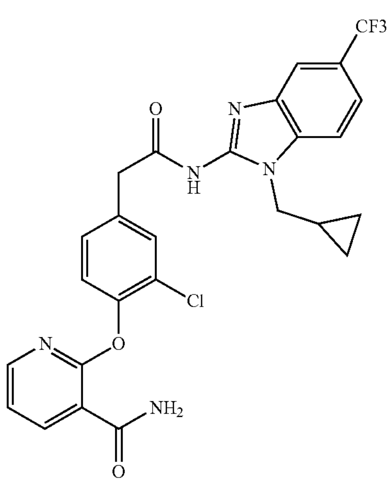 [SMILES: NC(=O)c1cccnc1Oc1ccc(CC(=O)Nc2nc3cc(C(F)(F)F)ccc3n2CC2CC2)cc1Cl] | 2-(2-chloro-4-(2-((1-(cyclo-propylmethyl)-5-(trifluoro-methyl)-1H-benzo[d]-imidazol-2-yl)-amino)-2-oxo-ethyl)phenoxy)-nicotinamide | $^1$H NMR (500 MHz, DMSO-$d_6$) δ 8.23-8.19 (m, 1H), 8.16-8.13 (m, 1H), 7.81-7.71 (m, 3H), 7.58-7.54 (m, 2H), 7.36 (br d, J = 5.5 Hz, 2H), 7.23 (dd, J = 7.3, 4.9 Hz, 1H), 4.02 (br d, J = 7.0 Hz, 2H), 1.25-1.19 (m, 1H), 0.47-0.30 (m, 4H) | 544.1 | 1.76 Method B |

149

Example 178. 2-(4-(2-((1-(cyclopropylmethyl)-6-(2-hydroxy-2-methylpropoxy)-1H-benzo[d]imidazol-2-yl)amino)-2-oxoethyl)-2-fluorophenoxy)nicotinamide

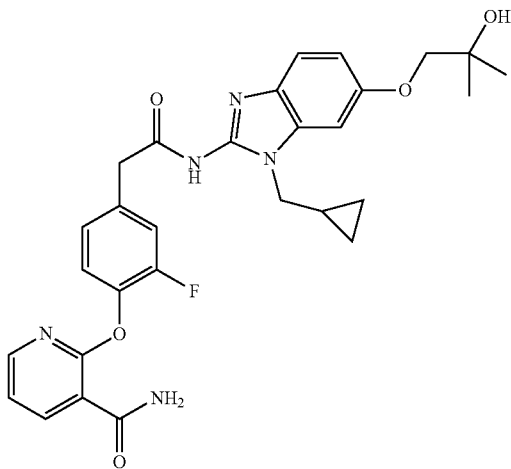 [SMILES: CC(C)(O)COc1ccc2nc(NC(=O)Cc3ccc(Oc4ncccc4C(N)=O)c(F)c3)n(CC3CC3)c2c1]

Step 1. A mixture of 3-fluoro-4-nitrophenol (1.0 g, 6.4 mmol), (bromomethyl)benzene (0.80 mL, 7.0 mmol), K$_2$CO$_3$ (2.6 g, 19 mmol), and TBAI (16 mg, 0.050 mmol) were added to DMF (15 mL) and stirred at rt. After stirring 18 h, water (75 mL) was added and the resulting solids collected by vacuum filtration, washed with water, and dried to give 4-(benzyloxy)-2-fluoro-1-nitrobenzene as a yellow solid (1.5 g, 95%). $^1$H NMR (500 MHz, DMSO-d$_6$) δ 8.16 (t, J=9.1 Hz, 1H), 7.51-7.45 (m, 2H), 7.45-7.40 (m, 2H), 7.39-7.35 (m, 1H), 7.28 (dd, J=13.6, 2.6 Hz, 1H), 7.08-7.03 (m, 1H), 5.30-5.26 (m, 2H). LCMS m/z=248.1 (M+H).$^+$ Step 2. 4-(Benzyloxy)-2-fluoro-1-nitrobenzene (869 mg, 3.52 mmol), cyclopropylmethanamine (250 mg, 3.52 mmol), and Cs$_2$CO$_3$ (1.1 g, 3.5 mmol) were added to ACN (15 mL) and irradiated at 120° C. for 15 min. The reaction mixture was concentrated under reduced pressure and the residue partitioned between in EtOAc and water. The organic layer was washed with brine, dried over sodium sulfate, filtered, and concentrated. The intermediate was dissolved in EtOH (30 mL) and treated with NH$_4$Cl (0.90 g, 18 mmol) in water (15 mL). The solution was warmed to 60° C. before adding Zn (3.4 g, 53 mmol). After 2 h, the mixture was allowed to cool to rt, filtered through a plug of Celite, and washed with EtOAc. The organic layer was washed with water, brine, and dried over Na$_2$SO$_4$. The residue was purified by normal phase chromatography to give the desired product (396 mg, 42%). LCMS m/z=269.1 (M+H).$^+$ Step 3. To a solution of 5-(benzyloxy)-N1-(cyclopropylmethyl)benzene-1,2-diamine (0.40 g, 1.5 mmol) in MeOH (6 ml) and Water (1.5 ml), cyanic bromide (0.171 g, 1.62 mmol) was added and stirred at rt. After 18 h, the reaction mixture was adjusted to pH=9 by addition of conc. NH$_4$OH and diluted with water (75 mL). The resulting solid was collected and dried via vacuum filtration to give 6-(benzyloxy)-1-(cyclopropylmethyl)-1H-benzo[d]imidazol-2-amine as a reddish-orange solid. LCMS m/z=294.0 (M+H).$^+$ Step 4. To a solution of 6-(benzyloxy)-1-(cyclopropylmethyl)-1H-benzo[d]imidazol-2-amine (200 mg, 0.682 mmol) in THF (15 mL), TEA (0.095 mL, 0.68 mmol) and BOC-anhydride (0.24 mL, 1.0 mmol) were added. After stirring for 18 h, the reaction was diluted with water and extracted with EtOAc (3×). The combined organic layer was washed with brine, dried over Na$_2$SO$_4$, filtered and concentrated under reduced pressure. The residue was dissolved in EtOH, treated with Pd/C (145 mg), and subjected to a hydrogen atmosphere (55 psi). After 2 h, the suspension was filtered through a plug of Celite and filtrate concentrated to give tert-butyl (1-(cyclopropylmethyl)-6-hydroxy-1H-benzo[d]imidazol-2-yl)carbamate (150 mg, 71%). LCMS m/z=304.1 (M+H).$^+$ Step 5. tert-Butyl (1-(cyclopropylmethyl)-6-(2-hydroxy-2-methylpropoxy)-1H-benzo[d]imidazol-2-yl)carbamate was made in a similar manner as step 1 of example 3 from tert-butyl (1-(cyclopropylmethyl)-6-hydroxy-1H-benzo[d]imidazol-2-yl)carbamate The material was carried forward to next reaction without further purification. LCMS m/z=376.1 (M+H).$^+$ Step 6. tert-Butyl (1-(cyclopropylmethyl)-6-(2-hydroxy-2-methylpropoxy)-1H-benzo[d]imidazol-2-yl)carbamate (24 mg, 0.060 mmol) was dissolved in HCl (4.0 M in dioxane) (320 µl, 1.28 mmol) and stirred at rt. After 1 h, additional HCl (4.0 M in dioxane) (320 µl, 1.28 mmol) and a drop of HCl (conc.) was added and stirring continued. After stirring for a total of 6 h, the reaction mixture was concentrated under reduced pressure and placed under high vacuum for 14 h. 1-((2-Amino-1-(cyclopropylmethyl)-1H-benzo[d]imidazol-6-yl)oxy)-2-methylpropan-2-ol, HCl salt was carried forward to the next reaction without further purification. LCMS m/z=276.1 (M+H).$^+$ Step 7. 2-(4-(2-((1-(cyclopropylmethyl)-6-(2-hydroxy-2-methylpropoxy)-1H-benzo[d]imidazol-2-yl)amino)-2-oxoethyl)-2-fluorophenoxy)nicotinamide example 178 (4.9 mg, 11%) was prepared in a similar manner as example 152 by replacing 1-(cyclobutylmethyl)-1H-benzo[d]imidazol-2-amine with 1-((2-amino-1-(cyclopropylmethyl)-1H-benzo[d]imidazol-6-yl)oxy)-2-methylpropan-2-ol HCl salt. $^1$H NMR (500 MHz, DMSO-d6) δ 8.18-8.12 (m, 2H), 7.87-7.82 (m, 1H), 7.78-7.74 (m, 1H), 7.49 (d, J=8.9 Hz, 1H), 7.36-7.31 (m, 2H), 7.29-7.26 (m, 1H), 7.25-7.21 (m, 2H), 6.96 (br d, J=8.9 Hz, 1H), 4.19-4.12 (m, 2H), 3.91-3.87 (m, 1H), 3.80-3.76 (m, 1H), 1.29-1.16 (m, 8H), 0.52-0.39 (m, 4H). LCMS m/z=548.3 (M+H).$^+$ HPLC purity: 96% with retention time 1.54 min. [method A].

What is claimed is:

1. A compound of Formula (I):

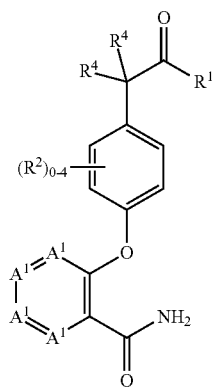

or a pharmaceutically acceptable salt thereof, wherein
- $A^1$, at each occurrence, is independently selected from $CR^3$ and N; provided that $A^1$ is not all $CR^3$ and that no more than two $A^1$ variables are N;
- $R^1$ is $NR^5R^5$;
- $R^2$, at each occurrence, is independently selected from halogen, $C_{1-6}$ alkyl, $C_{1-4}$ alkoxy, $C_{1-4}$ alkylthio, $C_{1-4}$ haloalkyl, —OH, —$CH_2OH$, —$OCH_2F$, —$OCHF_2$, —$OCF_3$, CN, —$NH_2$, —$NH(C_{1-4}$ alkyl), —$N(C_{1-4}$ alkyl)$_2$, —$CO_2H$, —$CH_2CO_2H$, —$CO_2(C_{1-4}$ alkyl), —$CO(C_{1-4}$ alkyl), —$CH_2NH_2$, —$CONH_2$, —CONH ($C_{1-4}$ alkyl), —$CON(C_{1-4}$ alkyl)$_2$, —$OCH_2CO_2H$, —$NHCO(C_{1-4}$ alkyl), —$NHCO_2(C_{1-4}$ alkyl), —$NHSO_2(C_{1-4}$ alkyl), —$SO_2NH_2$, —C(=NH)$NH_2$, carbocycle, and heterocycle, wherein said alkyl, alkoxy, alkylthio, haloalkyl, carbocycle, and heterocycle are substituted with 0-4 $R^9$;
- $R^3$, at each occurrence, is independently selected from H, halogen, $C_{1-6}$ alkyl, $C_{1-4}$ alkoxy, $C_{1-4}$ alkylthio, $C_{1-4}$ haloalkyl, —$CH_2OH$, —$OCH_2F$, —$OCHF_2$, —$OCF_3$, CN, —$NH_2$, —$NH(C_{1-4}$ alkyl), —$N(C_{1-4}$ alkyl)$_2$, —$CO_2H$, —$CH_2CO_2H$, —$CO_2(C_{1-4}$ alkyl), —$CO(C_{1-4}$ alkyl), —$CH_2NH_2$, —$CONH_2$, —$CONH(C_{1-4}$ alkyl), —$CON(C_{1-4}$ alkyl)$_2$, —$OCH_2CO_2H$, —$NHCO(C_{1-4}$ alkyl), —$NHCO_2(C_{1-4}$ alkyl), —$NHSO_2(C_{1-4}$ alkyl), —$SO_2NH_2$, —C(=NH)$NH_2$, carbocycle, and heterocycle, wherein said alkyl, alkoxy, alkylthio, haloalkyl, carbocycle, and heterocycle are substituted with 0-4 $R^9$;
- $R^4$, at each occurrence, is independently selected from H and $C_{1-4}$ alkyl;
- $R^5$, at each occurrence, is independently selected from H, —$(CR^6R^6)_n$—$C_{3-10}$ carbocycle, and —$(CR^6R^6)_n$—4-15 membered heterocycle comprising carbon atoms and 1-4 heteroatoms selected from N, $NR^8$, O, and $S(O)_p$, wherein said alkyl, carbocycle and heterocycle are substituted with 1-4 $R^7$;
- alternatively, $R^5$ and $R^5$ are taken together with the nitrogen atom to which they are attached to form 4- to 15-membered heterocycle substituted with 1-4 $R^7$;
- $R^6$, at each occurrence, is independently selected from H and $C_{1-4}$ alkyl;
- $R^7$, at each occurrence, is independently selected from H, =O, $NO_2$, halogen, $C_{1-4}$ alkyl, $C_{1-4}$ alkoxy, CN, OH, $CF_3$, —$(CH_2)_n$—$CO_2H$, —$(CH_2)_n$—$CO_2(C_{1-4}$ alkyl), —$(CH_2)_n$—$NR^8R^8$, —NHCO($C_{1-4}$ alkyl), —$NHCOCF_3$, —$NHCO_2(C_{1-4}$ alkyl), —$NHCO_2(CH_2)_2O(C_{1-4}$ alkyl), —$NHCO_2(CH_2)_3O(C_{1-4}$ alkyl), —$NHCO_2(CH_2)_2OH$, —$NHCO_2(CH_2)_2NH_2$, —$NHCO_2(CH_2)_2N(C_{1-4}$ alkyl)$_2$, —$NHCO_2CH_2CO_2H$, —$CH_2NHCO_2(C_{1-4}$ alkyl), —NHC(O)$NR^8R^8$, —$NHSO_2(C_{1-4}$ alkyl), —$SO_2NH_2$, —$SO_2NH(C_{1-4}$ alkyl), —$SO_2N(C_{1-4}$ alkyl)$_2$, —$SO_2NH(CH_2)_2OH$, —$SO_2NH(CH_2)_2O(C_{1-4}$ alkyl), —$(CH_2)_n$—$CONR^8R^8$, —O($CH_2)_n$-carbocycle, —O($CH_2)_n$-heterocycle, —NHCO-carbocycle, —NHCO-heterocycle, —$(CH_2)_n$-carbocycle, and —$(CH_2)_n$-heterocycle comprising carbon atoms and 1-4 heteroatoms selected from N, $NR^8$, O, and $S(O)_p$, wherein said alkyl, alkenyl, alkynyl, alkoxyl, carbocycle, and heterocycle are substituted with 0-4 $R^9$;
- $R^8$, at each occurrence, is independently selected from H, $C_{1-4}$ alkyl, $C_{2-4}$ alkenyl, $C_{2-4}$ alkynyl, —$(CH_2)_n$—C(O)$C_{1-4}$alkyl, —$(CH_2)_n$—C(O)carbocycle, —$(CH_2)_n$—C(O)heterocycle, —$(CH_2)_n$—C(O)$NR^aR^a$, —$(CH_2)_n$—C(O)O-alkyl, —$(CH_2)_n$—C(O)O-carbocycle, —$(CH_2)_n$—C(O)O-heterocycle, —$(CH_2)_n$—$SO_2$alkyl, —$(CH_2)_n$ $SO_2$carbocycle, —$(CH_2)_n$—$SO_2$heterocycle, —$(CH_2)_n$—$SO_2NR^aR^a$, —$(CH_2)_n$-carbocycle, and —$(CH_2)_n$-heterocycle, wherein said alkyl, carbocycle, and heterocycle are substituted with 0-4 $R^9$;
- alternatively, $R^8$ and $R^8$ are taken together with the nitrogen atom to which they are attached to form 4- to 10-membered heterocycle substituted with 0-4 $R^9$;
- $R^9$, at each occurrence, is independently selected from halogen, OH, $NO_2$, $CHF_2$, $CF_3$, $C_{1-4}$ alkyl, $C_{1-4}$ alkoxy, $CH_2OH$, $CO(C_{1-4}$ alkyl), $CO_2H$, $CO_2(C_{1-4}$ alkyl), —$(CH_2)_n$$NR^aR^a$, —$(CH_2)_n$$CONR^aR^a$, —O($CH_2)_n$carbocycle, —O($CH_2)_n$heterocycle, —O($CH_2)_n$$NR^aR^a$, —$(CR^{10}R^{10})_n$— 4-10 membered heterocycle, wherein said alkyl, alkoxyl, carbocycle, and heterocycle are substituted with 0-4 $R^b$;
- $R^{10}$ is selected from H and $C_{1-4}$ alkyl;

R$^a$, at each occurrence, is independently selected from H, C$_{1-4}$ alkyl, —(CH$_2$)$_n$OH, CO(C$_{1-4}$ alkyl), COCF$_3$, CO$_2$(C$_{1-4}$ alkyl), —CONH$_2$, —CONH—C$_{1-4}$ alkylene-CO$_2$(C$_{1-4}$ alkyl), C$_{1-4}$ alkylene-CO$_2$(C$_{1-4}$ alkyl), R$^c$, CO$_2$R$^c$, and CONHR$^c$; alternatively, R$^a$ and R$^a$ are taken together with the nitrogen atom to which they are attached to form 4- to 10-membered heterocycle, wherein said alkyl, alkylene, and heterocycle are substituted with 0-4 R$^b$;

R$^b$, at each occurrence, is independently selected from =O, OH, halogen, C$_{1-4}$ alkyl, C$_{1-4}$ alkoxy, OCF$_3$, NH$_2$, NO$_2$, N(C$_{1-4}$ alkyl)$_2$, CO(C$_{1-4}$ alkyl), CO(C$_{1-4}$ haloalkyl), CO$_2$(C$_{1-4}$ alkyl), CONH$_2$, —CONH(C$_{1-4}$ alkyl), —CON(C$_{1-4}$ alkyl)$_2$, —CONH—C$_{1-4}$ alkylene-O(C$_{1-4}$ alkyl), —CONH—C$_{1-4}$ alkylene-N(C$_{1-4}$ alkyl)$_2$, —CONH—C$_{1-4}$ alkylene-N(C$_{1-4}$ alkyl)$_2$, —C$_{1-4}$ alkylene-O—P(O)(OH)$_2$, —NHCO$_2$(C$_{1-4}$ alkyl), —R$^c$, COR$^c$, CO$_2$R$^c$, and CONHR$^c$;

R$^c$, at each occurrence, is independently selected from —(CH$_2$)$_n$—C$_{3-6}$ cycloalkyl, —(CH$_2$)$_n$-phenyl, and —(CH$_2$)$_n$-5- to 6-membered heterocycle containing carbon atoms and 1-4 heteroatoms selected from the group consisting of: N, NH, N(C$_{1-4}$ alkyl), O, and S(O)$_p$; wherein each ring moiety is substituted with 0-2 R$^d$;

R$^d$, at each occurrence, is independently selected from =O, halogen, —OH, C$_{1-4}$ alkyl, NH$_2$, NH(C$_{1-4}$ alkyl), N(C$_{1-4}$ alkyl)$_2$, C$_{1-4}$ alkoxy, and —NHCO(C$_{1-4}$ alkyl), and heterocycle containing carbon atoms and 1-4 heteroatoms selected from the group consisting of: N, NH, N(C$_{1-4}$ alkyl), O, and S(O)$_p$;

n, at each occurrence, is independently selected from 0, 1, 2, 3, and 4; and p, at each occurrence, is independently selected from 0, 1, and 2.

2. The compound of claim 1, having Formula (II):

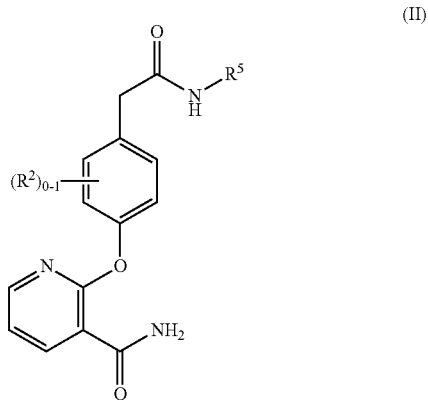

(II)

or a pharmaceutically acceptable salt thereof, wherein
R$^2$ is independently selected from halogen and C$_{1-6}$ alkyl;
R$^5$ is a 4-15 membered heterocycle comprising carbon atoms and 1-4 heteroatoms selected from N, NR$^8$, O, and S(O)$_p$, wherein said heterocycle is substituted with 1-4 R$^7$;

R$^7$, at each occurrence, is independently selected from H, =O, NO$_2$, halogen, C$_{1-4}$ alkyl, C$_{1-4}$ alkoxy, CN, OH, CF$_3$, —(CH$_2$)$_n$—CO$_2$H, —(CH$_2$)$_n$—CO$_2$(C$_{1-4}$ alkyl), —(CH$_2$)$_n$—NR$^8$R$^8$, —NHCO(C$_{1-4}$ alkyl), —NHCOCF$_3$, —NHCO$_2$(C$_{1-4}$ alkyl), —NHCO$_2$(CH$_2$)$_2$O(C$_{1-4}$ alkyl), —NHCO$_2$(CH$_2$)$_3$O(C$_{1-4}$ alkyl), —NHCO$_2$(CH$_2$)$_2$OH, —NHCO$_2$(CH$_2$)$_2$NH$_2$, —NHCO$_2$(CH$_2$)$_2$N(C$_{1-4}$ alkyl)$_2$, —NHCO$_2$CH$_2$CO$_2$H, —CH$_2$NHCO$_2$(C$_{1-4}$ alkyl), —NHC(O)NR$^8$R$^8$, —NHSO$_2$(C$_{1-4}$ alkyl), —SO$_2$NH$_2$, —SO$_2$NH(C$_{1-4}$ alkyl), —SO$_2$N(C$_{1-4}$ alkyl)$_2$, —SO$_2$NH(CH$_2$)$_2$OH, —SO$_2$NH(CH$_2$)$_2$O(C$_{1-4}$ alkyl), —(CH$_2$)$_n$—CONR$^8$R$^8$, —O(CH$_2$)$_n$-carbocycle, —O(CH$_2$)$_n$-heterocycle, —NHCO-carbocycle, —NHCO-heterocycle, —(CH$_2$)$_n$-carbocycle, and —(CH$_2$)$_n$-heterocycle comprising carbon atoms and 1-4 heteroatoms selected from N, NR$^8$, O, and S(O)$_p$, wherein said alkyl, alkenyl, alkynyl, alkoxy, carbocycle, and heterocycle are substituted with 0-4 R$^9$;

R$^8$, at each occurrence, is independently selected from H, C$_{1-4}$ alkyl, C(O)C$_{1-4}$alkyl, —(CH$_2$)$_n$C(O)NR$^a$R$^a$, C(O)O-alkyl, SO$_2$alkyl, SO$_2$NR$^a$R$^a$, —(CH$_2$)$_n$-carbocycle, and —(CH$_2$)$_n$-heterocycle, wherein said alkyl, carbocycle, and heterocycle are substituted with 0-4 R$^9$;

R$^9$, at each occurrence, is independently selected from halogen, OH, NO$_2$, CHF$_2$, CF$_3$, C$_{1-4}$ alkyl, C$_{1-4}$ alkoxy, CH$_2$OH, CO$_2$H, CO$_2$(C$_{1-4}$ alkyl), CONH$_2$, —(CH$_2$)$_n$NR$^a$R$^a$, —(CH$_2$)$_n$CONR$^a$R$^a$, —O(CH$_2$)$_n$heterocycle, —O(CH$_2$)$_{(2-4)}$NR$^a$R$^a$, —(CH$_2$)$_n$— 4-10 membered heterocycle, wherein said alkyl, alkoxyl, carbocycle, and heterocycle are substituted with 0-4 R$^b$;

R$^a$, at each occurrence, is independently selected from H, C$_{1-4}$ alkyl, —(CH$_2$)$_n$OH, CO(C$_{1-4}$ alkyl), COCF$_3$, CO$_2$(C$_{1-4}$ alkyl), —CONH$_2$, —CONH—C$_{1-4}$ alkylene-CO$_2$(C$_{1-4}$ alkyl), C$_{1-4}$ alkylene-CO$_2$(C$_{1-4}$ alkyl), R$^c$, CO$_2$R$^c$, and CONHR$^c$; alternatively, R$^a$ and R$^a$ are taken together with the nitrogen atom to which they are attached to form 4- to 10-membered heterocycle, wherein said alkyl, alkylene, and heterocycle are substituted with 0-4 R$^b$;

R$^b$, at each occurrence, is independently selected from =O, halogen, C$_{1-4}$ alkyl, C$_{1-4}$ alkoxy, OCF$_3$, NH$_2$, NO$_2$, N(C$_{1-4}$ alkyl)$_2$, CO(C$_{1-4}$ alkyl), CO(C$_{1-4}$ haloalkyl), CO$_2$(C$_{1-4}$ alkyl), CONH$_2$, —CONH(C$_{1-4}$ alkyl), —CON(C$_{1-4}$ alkyl)$_2$, —CONH—C$_{1-4}$ alkylene-O(C$_{1-4}$ alkyl), —CONH—C$_{1-4}$ alkylene-N(C$_{1-4}$ alkyl)$_2$, —CONH—C$_{1-4}$ alkylene-N(C$_{1-4}$ alkyl)$_2$, —C$_{1-4}$ alkylene-O—P(O)(OH)$_2$, —NHCO$_2$(C$_{1-4}$ alkyl), —R$^c$, COR$^c$, CO$_2$R$^c$, and CONHR$^c$;

R$^c$, at each occurrence, is independently selected from —(CH$_2$)$_n$—C$_{3-6}$ cycloalkyl, —(CH$_2$)$_n$-phenyl, and —(CH$_2$)$_n$-5- to 6-membered heterocycle containing carbon atoms and 1-4 heteroatoms selected from the group consisting of: N, NH, N(C$_{1-4}$ alkyl), O, and S(O)$_p$; wherein each ring moiety is substituted with 0-2 R$^d$;

R$^d$, at each occurrence, is independently selected from =O, halogen, —OH, C$_{1-4}$ alkyl, NH$_2$, NH(C$_{1-4}$ alkyl), N(C$_{1-4}$ alkyl)$_2$, C$_{1-4}$ alkoxy, and —NHCO(C$_{1-4}$ alkyl), and heterocycle containing carbon atoms and 1-4 heteroatoms selected from the group consisting of: N, NH, N(C$_{1-4}$ alkyl), O, and S(O)$_p$;

n, at each occurrence, is independently selected from 0, 1, 2, 3, and 4;

p, at each occurrence, is independently selected from 0, 1, and 2.

3. The compound of claim 2, or a pharmaceutically acceptable salt thereof, wherein
R$^2$ is independently selected from F, Cl, and Br;
R$^5$ is selected from

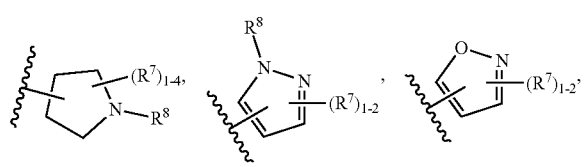

-continued
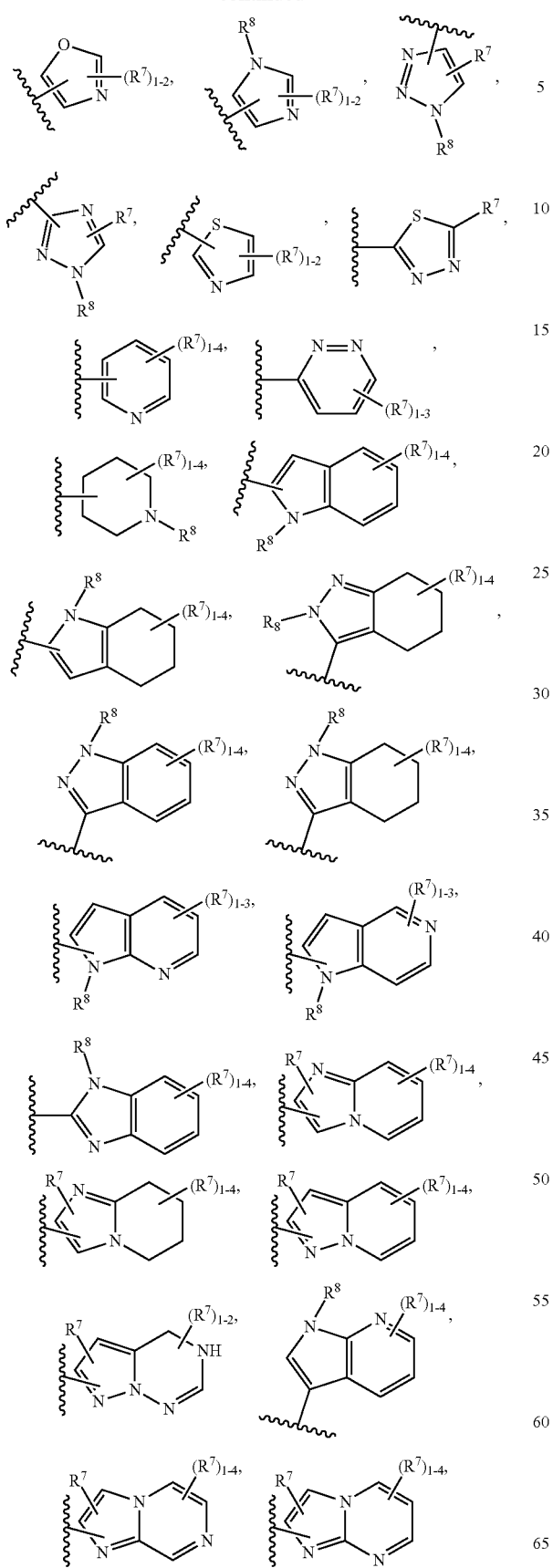
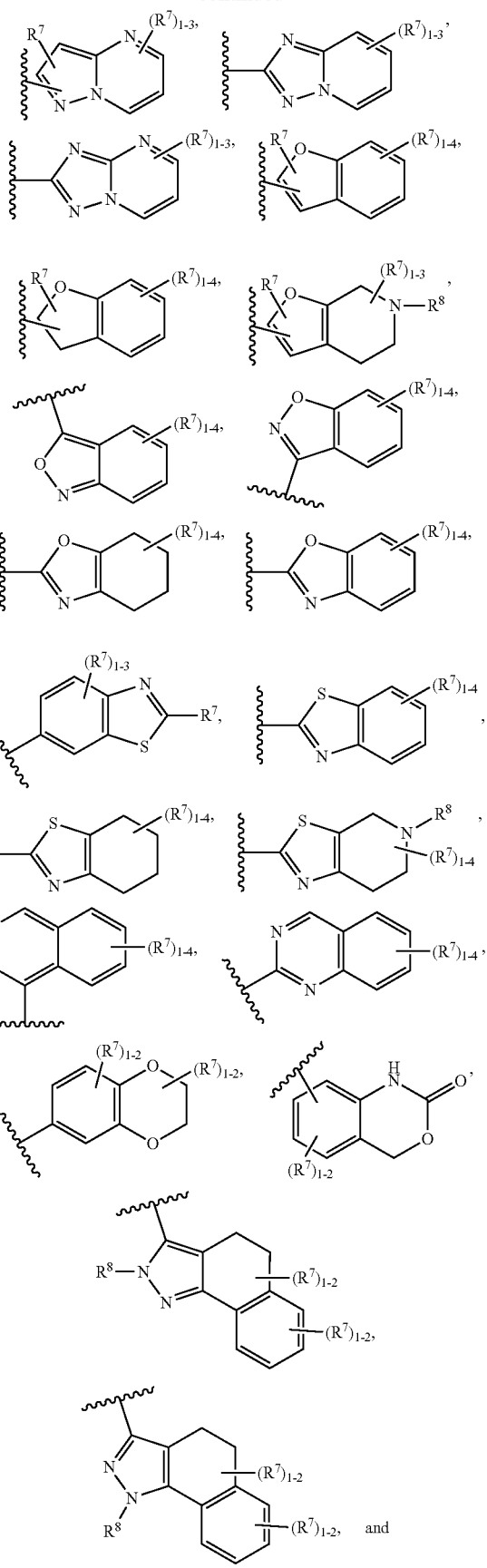

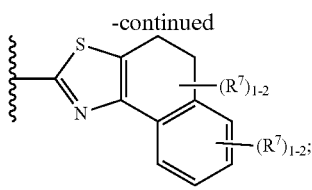

R⁷, at each occurrence, is independently selected from H, =O, halogen, $C_{1-4}$ alkyl, $C_{1-4}$ alkoxy, CN, OH, $CF_3$, $-(CH_2)_n-CO_2H$, $-(CH_2)_n-CO_2(C_{1-4}$ alkyl), $-(CH_2)_n-NR^8R^8$, $-NHCO(C_{1-4}$ alkyl), $-NHCOCF_3$, $-NHCO_2(C_{1-4}$ alkyl), $-NHCO_2(CH_2)_2O(C_{1-4}$ alkyl), $-NHCO_2(CH_2)_3O(C_{1-4}$ alkyl), $-NHCO_2(CH_2)_2OH$, $-NHCO_2(CH_2)_2NH_2$, $-NHCO_2(CH_2)_2N(C_{1-4}$ alkyl)$_2$, $-NHCO_2CH_2CO_2H$, $-CH_2NHCO_2(C_{1-4}$ alkyl), $-NHC(O)NR^8R^8$, $-NHSO_2(C_{1-4}$ alkyl), $-SO_2NH_2$, $-SO_2NH(C_{1-4}$ alkyl), $-SO_2N(C_{1-4}$ alkyl)$_2$, $-SO_2NH(CH_2)_2OH$, $-SO_2NH(CH_2)_2O(C_{1-4}$ alkyl), $-(CH_2)_n-CONR^8R^8$, $-O(CH_2)_n$-carbocycle, $-O(CH_2)_n$-heterocycle, $-NHCO$-carbocycle, $-NHCO$-heterocycle, $-(CH_2)_n$-carbocycle, and $-(CH_2)_n$-heterocycle comprising carbon atoms and 1-4 heteroatoms selected from N, $NR^8$, O, and $S(O)_p$, wherein said alkyl, alkenyl, alkynyl, alkoxy, carbocycle, and heterocycle are substituted with 0-4 $R^9$;

R⁸, at each occurrence, is independently selected from H, $C_{1-4}$ alkyl, $-(CH_2)_n$-carbocycle, and $-(CH_2)_n$-heterocycle, wherein said alkyl, carbocycle, and heterocycle are substituted with 0-4 $R^9$; and R⁹, at each occurrence, is independently selected from halogen, OH, $NO_2$, $CHF_2$, $CF_3$, $C_{1-4}$ alkyl, $C_{1-4}$ alkoxy, $CH_2OH$, $CO_2H$, $CO_2(C_{1-4}$ alkyl), $CONH_2$, $-(CH_2)_nNH_2$, $-(CH_2)_nCONH_2$, $-O(CH_2)_n$heterocycle, $-O(CH_2)_{(2-4)}NH_2$, $-(CH_2)_n$-4-10 membered heterocycle.

4. The compound of claim 3, or a pharmaceutically acceptable salt thereof, wherein
$R^2$ is independently selected from F and Cl;
$R^5$ is selected from

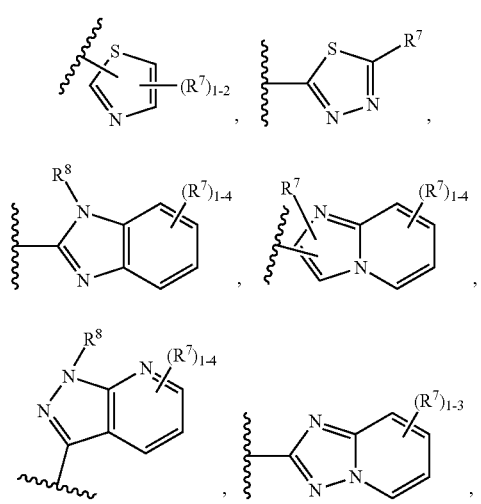

R⁷, at each occurrence, is independently selected from H, halogen, $C_{1-4}$ alkyl, $C_{1-4}$ alkoxy, a carbocycle, and a heterocycle comprising carbon atoms and 1-4 heteroatoms selected from N, $NR^8$, O, and $S(O)_p$, wherein said alkyl, alkenyl, alkynyl, alkoxy, carbocycle, and heterocycle are substituted with 0-4 $R^9$;

R⁸, at each occurrence, is independently selected from H, $C_{1-4}$ alkyl, and $-(CH_2)_n-C_{3-6}$cycloalkyl; and R⁹, at each occurrence, is independently selected from halogen, OH, $CHF_2$, $CF_3$, $C_{1-4}$ alkyl, $C_{1-4}$ alkoxy, $CH_2OH$, $CO_2H$, $CO_2(C_{1-4}$ alkyl), and $CONH_2$.

5. The compound of claim 4, or a pharmaceutically acceptable salt thereof, wherein $R^7$, at each occurrence, is independently selected from H, F, Cl, Br, Me, Et, OMe, OEt, $OCH_2C(CH_2)_2OH$,

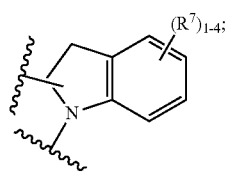

R⁹, at each occurrence, is independently selected from F, Cl, Br, OH, $CHF_2$, $CF_3$, $C_{1-4}$ alkyl, and $C_{1-4}$ alkoxy.

6. The compound of claim 1, or a pharmaceutically acceptable salt thereof, wherein
$R^5$ and $R^5$ are taken together with the nitrogen atom to which they are attached to form and $R^7$ is selected from H, CN, $C_{1-4}$ alkyl substituted with 0-4 $R^9$, $C_{1-4}$ alkoxy substituted with 0-4 $R^9$; and $R^9$ is selected from halogen, OH, $C_{3-6}$ cycloalkyl, phenyl, and heterocycle.

7. A compound having Formula (III):

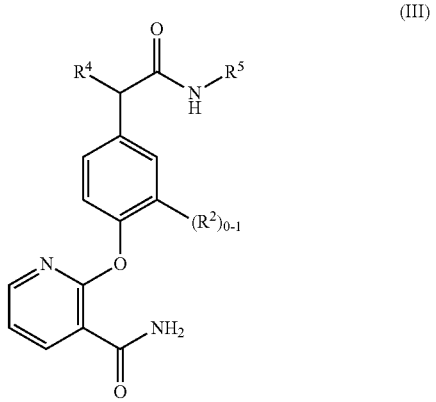

or a pharmaceutically acceptable salt thereof, wherein
$R^2$ is selected from F, Cl, Br, and $OC_{1-4}$ alkyl;
$R^4$ is selected from H and $C_{1-4}$ alkyl;
$R^5$ is selected from

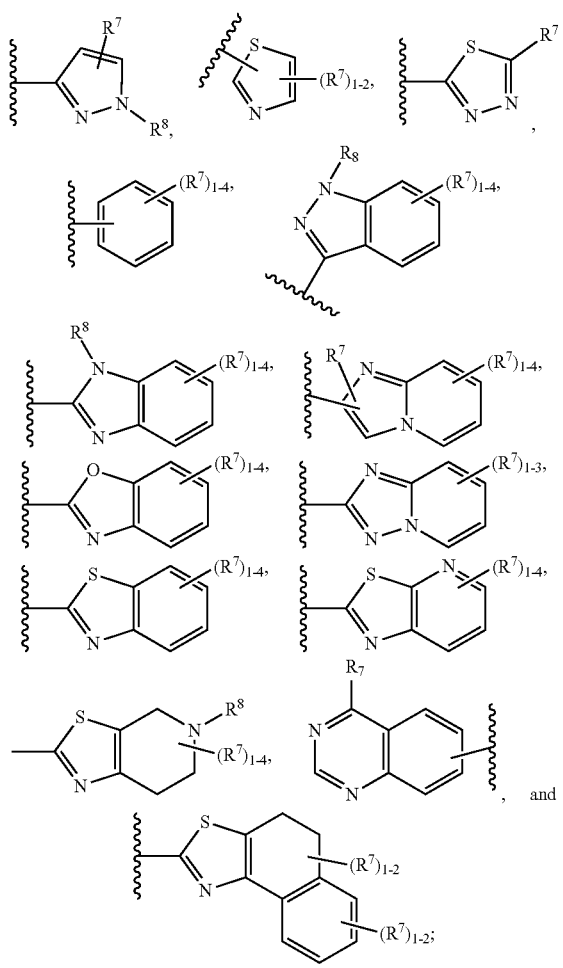

$R^7$, at each occurrence, is independently selected from H, =O, $NO_2$, halogen, $C_{1-4}$ alkyl, $C_{1-4}$ alkoxy, CN, OH, $CF_3$, —$(CH_2)_n$—CO($C_{1-4}$ alkyl), —$(CH_2)_n$—$CO_2$H, —$(CH_2)_n$—$CO_2(C_{1-4}$ alkyl), —$(CH_2)_n$—$NR^8R^8$, —NHCO($C_{1-4}$ alkyl), —$NHCOCF_3$, —$NHCO_2(C_{1-4}$ alkyl), —$NHCO_2(CH_2)_2O(C_{1-4}$ alkyl), —$NHCO_2(CH_2)_3O(C_{1-4}$ alkyl), —$NHCO_2(CH_2)_2OH$, —$NHCO_2(CH_2)_2NH_2$, —$NHCO_2(CH_2)_2N(C_{1-4}$ alkyl)$_2$, —$NHCO_2CH_2CO_2H$, —$CH_2NHCO_2(C_{1-4}$ alkyl), —NHC(O)$NR^8R^8$, —$NHSO_2(C_{1-4}$ alkyl), —P(=O)($C_{1-3}$ alkyl)$_2$, —$SO_2C_{1-4}$ alkyl, —$SO_2NH_2$, —$SO_2NH(C_{1-4}$ alkyl), —$SO_2N(C_{1-4}$ alkyl)$_2$, —$SO_2NH(CH_2)_2OH$, —$SO_2NH(CH_2)_2O(C_{1-4}$ alkyl), —$(CH_2)_n$—$CONR^8R^8$, —$O(CH_2)_n$-carbocycle, —$O(CH_2)_n$-heterocycle, —NHCO-carbocycle, —NHCO-heterocycle, —CO-carbocycle, —CO-heterocycle, —$(CH_2)_n$-carbocycle, and —$(CH_2)_n$-heterocycle comprising carbon atoms and 1-4 heteroatoms selected from N, $NR^8$, O, and $S(O)_p$, wherein said alkyl, alkenyl, alkynyl, alkoxyl, carbocycle, and heterocycle are substituted with 0-4 $R^9$;

$R^8$, at each occurrence, is independently selected from H, $C_{1-4}$ alkyl, $C_{2-4}$ alkenyl, $C_{2-4}$ alkynyl, —$(CH_2)_n$—C(O)$C_{1-4}$alkyl, —$(CH_2)_n$—C(O)carbocycle, —$(CH_2)_n$—C(O)heterocycle, —$(CH_2)_n$—C(O)$NR^aR^a$, —$(CH_2)_n$—C(O)O-alkyl, —$(CH_2)_n$—C(O)O-carbocycle, —$(CH_2)_n$—C(O)O-heterocycle, —$(CH_2)_n$—$SO_2$alkyl, —$(CH_2)_n$ $SO_2$carbocycle, —$(CH_2)_n$—$SO_2$heterocycle, —$(CH_2)_n$—$SO_2NR^aR^a$, —$(CH_2)_n$-carbocycle, and —$(CH_2)_n$-heterocycle, wherein said alkyl, carbocycle, and heterocycle are substituted with 0-4 $R^9$;

alternatively, $R^8$ and $R^8$ are taken together with the nitrogen atom to which they are attached to form 4- to 10-membered heterocycle substituted with 0-4 $R^9$;

$R^9$, at each occurrence, is independently selected from halogen, OH, $NO_2$, $CHF_2$, CN, $CF_3$, $C_{1-4}$ alkyl, $C_{1-4}$ alkoxy, $CH_2OH$, $CO(C_{1-4}$ alkyl), $CO_2H$, $CO_2(C_{1-4}$ alkyl), —$(CH_2)_nNR^aR^a$, —$(CH_2)_nCONR^aR^a$, —$O(CH_2)_n$carbocycle, —$O(CH_2)_n$heterocycle, —$O(CH_2)_nNR^aR^a$, $NR^aCO_2(C_{1-4}$ alkyl), $S(O)_pC_{1-4}$ alkyl, —$(CR^{10}R^{10})_n$-carbocycle, —$(CR^{10}R^{10})_n$— 4-10 membered heterocycle, wherein said alkyl, alkoxyl, carbocycle, and heterocycle are substituted with 0-4 $R^b$;

$R^{10}$ is selected from H and $C_{1-4}$ alkyl;

$R^a$, at each occurrence, is independently selected from H, $C_{1-4}$ alkyl, —$(CH_2)_nOH$, $CO(C_{1-4}$ alkyl), $COCF_3$, $CO_2(C_{1-4}$ alkyl), —$CONH_2$, —CONH—$C_{1-4}$ alkylene-$CO_2(C_{1-4}$ alkyl), $C_{1-4}$ alkylene-$CO_2(C_{1-4}$ alkyl), $R^c$, $CO_2R^c$, and $CONHR^c$; alternatively, $R^a$ and $R^a$ are taken together with the nitrogen atom to which they are attached to form 4- to 10-membered heterocycle, wherein said alkyl, alkylene, and heterocycle are substituted with 0-4 $R^b$;

$R^b$, at each occurrence, is independently selected from =O, OH, halogen, $C_{1-4}$ alkyl, $C_{1-4}$ alkoxy, $OCF_3$, $NH_2$, $NO_2$, $N(C_{1-4}$ alkyl)$_2$, $CO(C_{1-4}$ alkyl), $CO(C_{1-4}$ haloalkyl), $CO_2(C_{1-4}$ alkyl), $CONH_2$, —CONH($C_{1-4}$ alkyl), —CON($C_{1-4}$ alkyl)$_2$, —CONH—$C_{1-4}$ alkylene-O($C_{1-4}$ alkyl), —CONH—$C_{1-4}$ alkylene-N($C_{1-4}$ alkyl)$_2$, —CONH—$C_{1-4}$ alkylene-N($C_{1-4}$ alkyl)$_2$, —$C_{1-4}$ alkylene-O—P(O)(OH)$_2$, —$NHCO_2(C_{1-4}$ alkyl), —$R^c$, $COR^c$, $CO_2R^c$, and $CONHR^c$;

$R^c$, at each occurrence, is independently selected from —$(CH_2)_n$—$C_{3-6}$ cycloalkyl, —$(CH_2)_n$-phenyl, and —$(CH_2)_n$-5- to 6-membered heterocycle containing carbon atoms and 1-4 heteroatoms selected from the group consisting of: N, NH, N($C_{1-4}$ alkyl), O, and $S(O)_p$; wherein each ring moiety is substituted with 0-2 $R^d$;

$R^d$, at each occurrence, is independently selected from =O, halogen, —OH, $C_{1-4}$ alkyl, $NH_2$, $NH(C_{1-4}$ alkyl), $N(C_{1-4}$ alkyl)$_2$, $C_{1-4}$ alkoxy, and —NHCO($C_{1-4}$ alkyl), and heterocycle containing carbon atoms and 1-4 heteroatoms selected from the group consisting of: N, NH, $N(C_{1-4}$ alkyl), O, and $S(O)_p$;

n, at each occurrence, is independently selected from 0, 1, 2, 3, and 4; and p, at each occurrence, is independently selected from 0, 1, and 2.

8. The compound of claim 7, or a pharmaceutically acceptable salt thereof, wherein
$R^2$ is selected from F, Cl, and $OCH_3$;
$R^5$ is selected from

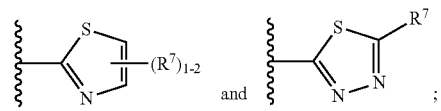

$R^7$ is selected from H, $C_{1-3}$alkyl substituted with halogen,

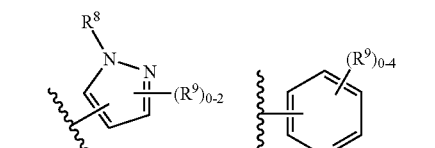

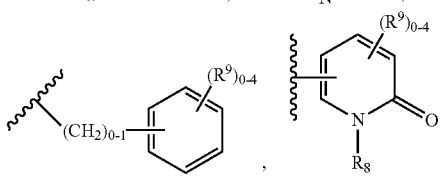

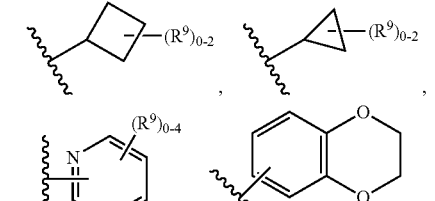

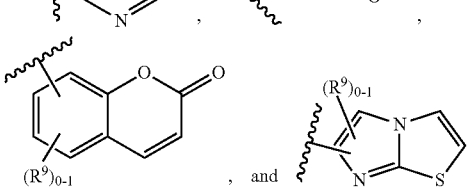

$R^8$ is selected from H and $C_{1-3}$alkyl optionally substituted with halogen;
$R^9$ is selected from F, Cl, CN, $C_{1-4}$ alkyl substituted with 0-2 $R^b$, $C_{1-3}$ alkoxy, $C_{3-6}$ cycloalkyl, $NHCOOC_{1-4}$ alkyl, $SO_2C_{1-4}$ alkyl, and

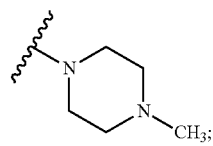

and
$R^b$, at each occurrence, is independently selected from OH and halogen.

9. The compound of claim 7, or a pharmaceutically acceptable salt thereof, wherein
$R^2$ is independently selected from F, Cl, and $OCH_3$;
$R^5$ is selected from

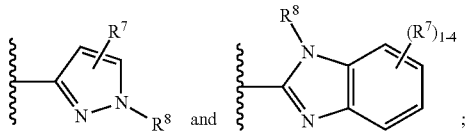

$R^7$ is selected from H, F, Cl, Br, $C_{1-3}$ alkyl substituted with 0-4 $R^9$, $C_{1-3}$ alkoxy substituted with 0-4 $R^9$, CN, $CO_2C_{1-4}$ alkyl, P(=O)($C_{1-3}$ alkyl)$_2$, $SO_2C_{1-4}$ alkyl,

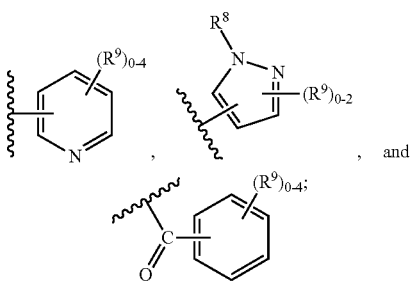

$R^8$ is selected from H and $C_{1-3}$ alkyl substituted with 0-4 $R^9$;
$R^9$ is selected from halogen, OH, CN, $C_{1-3}$ alkyl substituted with 0-4 $R^b$, $C_{1-3}$ alkoxy substituted with 0-4 $R^b$, $CO_2(C_{1-4}$ alkyl), $CONH_2$, $NHCO_2(C_{1-3}$ alkyl), $C_{3-6}$ cycloalkyl, phenyl, and heterocycle; and
$R^b$, at each occurrence, is independently selected from OH and halogen.

10. The compound of claim 7, or a pharmaceutically acceptable salt thereof, wherein
$R^2$ is independently selected from F, Cl, and $OCH_3$;
$R^5$ is selected from

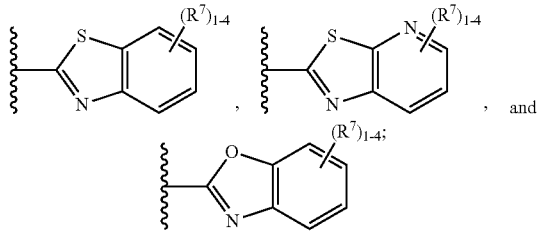

$R^7$ is selected from H, CN, $C_{1-3}$ alkyl substituted with 0-4 $R^9$, $C_{1-3}$ alkoxy substituted with 0-4 $R^9$, $CO_2C_{1-4}$ alkyl, $CONH_2$, P(=O)($C_{1-3}$ alkyl)$_2$, $SO_2C_{1-3}$ alkyl,

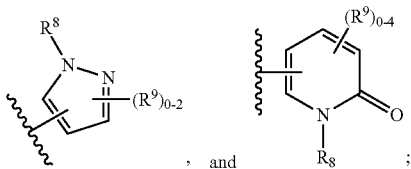

$R^8$ is selected from H and $C_{1-3}$ alkyl substituted with 0-4 $R^9$;

$R^9$ is selected from halogen, OH, CN, $C_{1-3}$ alkyl substituted with 0-4 $R^b$; $C_{1-3}$ alkoxy substituted with 0-4 $R^b$, $CO_2(C_{1-4}$ alkyl), $CONH_2$, $NHCO_2(C_{1-3}$ alkyl), $C_{3-6}$ cycloalkyl, phenyl, and heterocycle; and $R^b$, at each occurrence, is independently selected from OH and halogen.

11. The compound of claim 7 or a pharmaceutically acceptable salt thereof, wherein
$R^2$ is selected from F, Cl, and $OCH_3$;
$R^5$ is

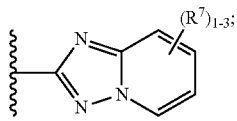

$R^7$ is selected from H, F, Cl, Br, CN, $C_{1-3}$ alkyl substituted with 0-4 $R^9$, $C_{1-3}$ alkoxy substituted with 0-4 $R^9$, $CO_2C_{1-4}$ alkyl, $CONH_2$, $P(=O)(C_{1-3}$ alkyl$)_2$, $SO_2C_{1-3}$ alkyl, and

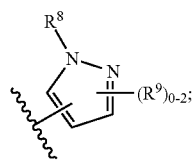

$R^8$ is selected from H and $C_{1-3}$ alkyl substituted with 0-4 $R^9$;

$R^9$ is selected from halogen, OH, CN, $C_{1-3}$ alkyl substituted with 0-4 $R^b$; $C_{1-3}$ alkoxy substituted with 0-4 $R^b$, $CO_2(C_{1-4}$ alkyl), $CONH_2$, $NHCO_2(C_{1-3}$ alkyl), $C_{3-6}$ cycloalkyl, phenyl, and heterocycle; and $R^b$, at each occurrence, is independently selected from OH and halogen.

12. A pharmaceutical composition comprising one or more compounds according to claim 1 and a pharmaceutically acceptable carrier or diluent.

13. A compound according to claim 1, wherein the compound is selected from 2-(2-fluoro-4-(2-((7-methoxy-4,5-dihydronaphtho[1,2-d]thiazol-2-yl)amino)-2-oxoethyl)phenoxy)nicotinamide;

2-(4-(2-((5-methoxybenzo[d]thiazol-2-yl)amino)-2-oxoethyl)phenoxy) nicotinamide;

2-(2-fluoro-4-(2-((5-(2-hydroxy-2-methylpropoxy)benzo[d]thiazol-2-yl)amino)-2-oxoethyl)phenoxy)nicotinamide;

2-(4-(2-((5-(1,3-dimethyl-1H-pyrazol-4-yl)benzo[d]thiazol-2-yl)amino)-2-oxoethyl)-2-fluorophenoxy)nicotinamide;

2-(4-(2-((5-(3,5-dimethyl-1H-pyrazol-4-yl)benzo[d]thiazol-2-yl)amino)-2-oxoethyl)-2-fluorophenoxy)nicotinamide;

2-(2-fluoro-4-(2-((5-(1-methyl-3-(trifluoromethyl)-1H-pyrazol-5-yl)benzo[d]thiazol-2-yl)amino)-2-oxoethyl)phenoxy)nicotinamide 2-(2-chloro-4-(2-((1-(cyclopropylmethyl)-1H-benzo[d]imidazol-2-yl)amino)-2-oxoethyl)phenoxy)nicotinamide;

2-(2-fluoro-4-(2-((7-methoxy-[1,2,4]triazolo[1,5-a]pyridin-2-yl)amino)-2-oxoethyl)phenoxy)nicotinamide;

2-(4-(2-((6-bromoimidazo[1,2-a]pyridin-2-yl)amino)-2-oxoethyl)-2-chlorophenoxy)nicotinamide;

2-(2-chloro-4-(2-((1-methyl-1H-pyrazolo[3,4-b]pyridin-3-yl)amino)-2-oxoethyl)phenoxy)nicotinamide;

2-(2-fluoro-4-(2-oxo-2-((5-(pyrazin-2-yl)-1,3,4-thiadiazol-2yl)amino)ethyl)phenoxy) nicotinamide;

2-(2-fluoro-4-(2-((4-methyl-5-(pyridin-2-yl)thiazol-2-yl)amino)-2-oxoethyl)phenoxy)nicotinamide;

2-(2-fluoro-4-(2-((4-(5-fluoropyridin-2-yl)-5-methylthiazol-2-yl)amino)-2-oxoethyl)phenoxy)nicotinamide;

2-(4-(2-((5-methyl-4-phenylthiazol-2-yl)amino)-2-oxoethyl)phenoxy) nicotinamide;

2-(2-fluoro-4-(2-((4-(6-fluoropyridin-2-yl)-5-methylthiazol-2-yl)amino)-2-oxoethyl)phenoxy)nicotinamide;

2-(4-(2-(benzo[d]thiazol-2-ylamino)-2-oxoethyl)-2-fluorophenoxy)nicotinamide;

2-(2-fluoro-4-(2-((4-(1-methyl-2-oxo-1,2-dihydropyridin-4-yl)thiazol-2-yl)amino)-2-oxoethyl)phenoxy) nicotinamide;

2-(2-fluoro-4-(2-oxo-2-((4-(2-oxo-1,2-dihydropyridin-4-yl)thiazol-2-yl)amino)ethyl)phenoxy)nicotinamide;

methyl (4-(2-(2-(4-((3-carbamoylpyridin-2-yl)oxy)-3-fluorophenyl)acetamido)-5-methylthiazol-4-yl)pyridin-2-yl)carbamate;

2-(2-fluoro-4-(2-((5-methyl-4-(1-methyl-6-oxo-1,6-dihydropyridin-3-yl)thiazol-2-yl)amino)-2-oxoethyl)phenoxy)nicotinamide;

2-(4-(2-((4-(1-(difluoromethyl)-6-oxo-1,6-dihydropyridin-3-yl)-5-methylthiazol-2-yl)amino)-2-oxoethyl)-2-fluorophenoxy)nicotinamide;

2-(2-chloro-4-(2-((5-methyl-4-(6-methylpyridin-2-yl)thiazol-2-yl)amino)-2-oxoethyl)phenoxy)nicotinamide;

2-(2-chloro-4-(2-((4-cyclobutyl-5-(pyridin-2-yl)thiazol-2-yl)amino)-2-oxoethyl)phenoxy)nicotinamide;

2-(2-fluoro-4-(2-oxo-2-((5-(2-oxo-1,2-dihydropyridin-4-yl)benzo[d]thiazol-2-yl)amino)ethyl)phenoxy)nicotinamide;

2-(2-fluoro-4-(2-((5-(1-methyl-2-oxo-1,2-dihydropyridin-4-yl)benzo[d]thiazol-2-yl)amino)-2-oxoethyl)phenoxy)nicotinamide;

2-(4-(2-((5-(3-cyclopropyl-1-methyl-1H-pyrazol-4-yl)benzo[d]thiazol-2-yl)amino)-2-oxoethyl)-2-fluorophenoxy)nicotinamide;

2-(2-fluoro-4-(2-oxo-2-((5-(1,3,4-trimethyl-1H-pyrazol-5-yl)benzo[d]thiazol-2-yl)amino)ethyl)phenoxy)nicotinamide;

2-(4-(2-((5-(1,3-dimethyl-1H-pyrazol-5-yl)benzo[d]thiazol-2-yl)amino)-2-oxoethyl)-2-fluorophenoxy)nicotinamide;

2-(4-(2-((5-(1-(difluoromethyl)-1H-pyrazol-4-yl)benzo[d]thiazol-2-yl)amino)-2-oxoethyl)-2-fluorophenoxy) nicotinamide;

2-(2-fluoro-4-(2-((5-(1-methyl-1H-pyrazol-5-yl)benzo[d]thiazol-2-yl)amino)-2-oxoethyl)phenoxy)nicotinamide;

2-(4-(2-((5-(1H-pyrazol-4-yl)benzo[d]thiazol-2-yl)amino)-2-oxoethyl)-2-fluorophenoxy)nicotinamide;

2-(2-fluoro-4-(2-oxo-2-((5-(3-(trifluoromethyl)-1H-pyrazol-4-yl)benzo[d]thiazol-2-yl)amino)ethyl)phenoxy) nicotinamide;

2-(2-fluoro-4-(2-((5-(1-methyl-1H-pyrazol-3-yl)benzo[d]thiazol-2-yl)amino)-2-oxoethyl)phenoxy)nicotinamide;

2-(2-fluoro-4-(2-((5-(1-(methyl-d3)-1H-pyrazol-3-yl)benzo[d]thiazol-2-yl)amino)-2-oxoethyl)phenoxy) nicotinamide;

2-(2-fluoro-4-(2-((5-(1-methyl-1H-pyrazol-4-yl)benzo[d]thiazol-2-yl)amino)-2-oxoethyl)phenoxy)nicotinamide;

2-(2-fluoro-4-(2-((6-(1-methyl-1H-pyrazol-4-yl)imidazo[1,2-a]pyridin-2-yl)amino)-2-oxoethyl)phenoxy)nicotinamide;

2-(2-chloro-4-(2-((6-(1-methyl-1H-pyrazol-4-yl)imidazo[1,2-a]pyridin-2-yl)amino)-2-oxoethyl)phenoxy)nicotinamide;

2-(2-fluoro-4-(2-((5-(1-methyl-1H-pyrazol-4-yl)-1-(2,2,2-trifluoroethyl)-1H-benzo[d]imidazol-2-yl)amino)-2-oxoethyl)phenoxy)nicotinamide;

2-(2-fluoro-4-(2-((5-methyl-4-(2-(4-methylpiperazin-1-yl)pyrimidin-5-yl)thiazol-2-yl)amino)-2-oxoethyl)phenoxy)nicotinamide;

2-(2-fluoro-4-(2-((4-(2-methoxypyrimidin-5-yl)-5-methylthiazol-2-yl)amino)-2-oxoethyl)phenoxy)nicotinamide;

2-(2-fluoro-4-(2-((5-methyl-4-(pyrimidin-5-yl)thiazol-2-yl)amino)-2-oxoethyl)phenoxy)nicotinamide;

2-(2-fluoro-4-(2-((4-(2-(2-hydroxypropan-2-yl)pyrimidin-5-yl)-5-methylthiazol-2-yl)amino)-2-oxoethyl)phenoxy)nicotinamide;

2-(2-fluoro-4-(2-((4-(6-methoxypyridin-2-yl)-5-methylthiazol-2-yl)amino)-2-oxoethyl)phenoxy)nicotinamide;

2-(2-fluoro-4-(2-((5-methyl-4-(pyridin-4-yl)thiazol-2-yl)amino)-2-oxoethyl)phenoxy)nicotinamide;

2-(4-(2-((4-(6-cyanopyridin-2-yl)-5-methylthiazol-2-yl)amino)-2-oxoethyl)-2-fluorophenoxy)nicotinamide;

2-(4-(2-((4-cyclopropyl-5-methylthiazol-2-yl)amino)-2-oxoethyl)-2-fluorophenoxy)nicotinamide;

2-(2-fluoro-4-(2-((5-methyl-4-(4-(methylsulfonyl)phenyl)thiazol-2-yl)amino)-2-oxoethyl)phenoxy)nicotinamide;

2-(2-fluoro-4-(2-((4-(4-(isopropylsulfonyl)phenyl)-5-methylthiazol-2-yl)amino)-2-oxoethyl)phenoxy)nicotinamide;

2-(4-(2-(benzo[d]thiazol-2-ylamino)-2-oxoethyl)phenoxy)nicotinamide;

2-(4-(2-((4-(3-chloro-4-methylphenyl)-5-methylthiazol-2-yl)amino)-2-oxoethyl)phenoxy)nicotinamide;

2-(4-(2-((4-(3,4-dimethoxyphenyl)thiazol-2-yl)amino)-2-oxoethyl)phenoxy)nicotinamide;

2-(4-(2-oxo-2-((4-phenylthiazol-2-yl)amino)ethyl)phenoxy)nicotinamide;

2-(4-(2-((7-methoxy-4,5-dihydronaphtho[1,2-d]thiazol-2-yl)amino)-2-oxoethyl)phenoxy)nicotinamide;

2-(4-(2-(benzo[d]oxazol-2-ylamino)-2-oxoethyl)phenoxy)nicotinamide;

2-(4-(2-((5-methyl-1,3,4-thiadiazol-2-yl)amino)-2-oxoethyl)phenoxy)nicotinamide;

2-(4-(2-(7-cyano-5-methoxyindolin-1-yl)-2-oxoethyl)phenoxy)nicotinamide;

2-(4-(2-((4-(2,3-dihydrobenzo[b][1,4]dioxin-6-yl)thiazol-2-yl)amino)-2-oxoethyl)phenoxy)nicotinamide;

2-(4-(2-oxo-2-((5-phenyl-1,3,4-thiadiazol-2-yl)amino)ethyl)phenoxy)nicotinamide;

2-(4-(2-(5-(benzyloxy)indolin-1-yl)-2-oxoethyl)phenoxy)nicotinamide;

2-(4-(2-((5-methyl-4-phenylthiazol-2-yl)amino)-2-oxoethyl)phenoxy)nicotinamide;

2-(4-(2-oxo-2-((4-(2-oxo-2H-chromen-5-yl)thiazol-2-yl)amino)ethyl)phenoxy)nicotinamide;

2-(4-(2-oxo-2-((4-(3-(trifluoromethoxy)phenyl)thiazol-2-yl)amino)ethyl)phenoxy)nicotinamide;

2-(4-(2-((4-(3-cyanophenyl)thiazol-2-yl)amino)-2-oxoethyl)phenoxy)nicotinamide;

2-(4-(2-((4-(3-fluorophenyl)thiazol-2-yl)amino)-2-oxoethyl)phenoxy)nicotinamide;

methyl 2-(2-(4-((3-carbamoylpyridin-2-yl)oxy)phenyl)acetamido)benzo[d]thiazole-5-carboxylate;

2-(2-(4-((3-carbamoylpyridin-2-yl)oxy)phenyl)acetamido)benzo[d]thiazole-6-carboxamide;

2-(4-(2-((6-methoxybenzo[d]thiazol-2-yl)amino)-2-oxoethyl)phenoxy)nicotinamide;

2-(4-(2-((5-methyl-1H-benzo[d]imidazol-2-yl)amino)-2-oxoethyl)phenoxy)nicotinamide;

2-(4-(2-oxo-2-((5-(propylsulfonyl)-1H-benzo[d]imidazol-2-yl)amino)ethyl)phenoxy)nicotinamide;

methyl 2-(2-(4-((3-carbamoylpyridin-2-yl)oxy)phenyl)acetamido)benzo[d]thiazole-6-carboxylate;

2-(4-(2-((5-cyano-1H-benzo[d]imidazol-2-yl)amino)-2-oxoethyl)phenoxy)nicotinamide;

2-(4-(2-((5-benzoyl-1H-benzo[d]imidazol-2-yl)amino)-2-oxoethyl)phenoxy)nicotinamide;

2-(4-(2-((7-chloro-1H-benzo[d]imidazol-2-yl)amino)-2-oxoethyl)phenoxy)nicotinamide;

methyl 2-(2-(4-((3-carbamoylpyridin-2-yl)oxy)phenyl)acetamido)-1-methyl-1H-benzo[d]imidazole-5-carboxylate;

2-(4-(2-((1-methyl-1H-indazol-3-yl)amino)-2-oxoethyl)phenoxy)nicotinamide;

2-(4-(2-((6-(methylsulfonyl)benzo[d]thiazol-2-yl)amino)-2-oxoethyl)phenoxy)nicotinamide;

2-(4-(2-oxo-2-((4-(m-tolylamino)quinazolin-6-yl)amino)ethyl)phenoxy)nicotinamide;

2-(4-(2-((4-(4-fluorophenyl)-5-methylthiazol-2-yl)amino)-2-oxoethyl)phenoxy)nicotinamide, 2-(4-(2-((1-benzyl-1H-benzo[d]imidazol-2-yl)amino)-2-oxoethyl)-2-chlorophenoxy)nicotinamide;

2-(2-chloro-4-(2-((4-(2-fluorophenyl)-5-methylthiazol-2-yl)amino)-2-oxoethyl)phenoxy)nicotinamide;

2-(2-chloro-4-(2-((4-(6-methylimidazo[2,1-b]thiazol-5-yl)thiazol-2-yl)amino)-2-oxoethyl)phenoxy)nicotinamide;

2-(2-chloro-4-(2-((8-methoxy-[1,2,4]triazolo[1,5-a]pyridin-2-yl)amino)-2-oxoethyl)phenoxy)nicotinamide;

2-(4-(2-((8-methoxy-[1,2,4]triazolo[1,5-a]pyridin-2-yl)amino)-2-oxoethyl)phenoxy)nicotinamide;

2-(2-fluoro-4-(2-((5-methyl-4,5,6,7-tetrahydrothiazolo[4,5-c]pyridin-2-yl)amino)-2-oxoethyl)phenoxy)nicotinamide;

2-(2-fluoro-4-(2-((4-(6-fluoropyridin-3-yl)-5-methylthiazol-2-yl)amino)-2-oxoethyl)phenoxy)nicotinamide;

2-(2-fluoro-4-(2-((5-methyl-4-(1-methyl-1H-pyrazol-5-yl)thiazol-2-yl)amino)-2-oxoethyl)phenoxy)nicotinamide;

2-(2-fluoro-4-(2-((5-methyl-4-(pyridin-2-yl)thiazol-2-yl)amino)-2-oxoethyl)phenoxy)nicotinamide;

2-(2-fluoro-4-(2-((5-methylthiazol-2-yl)amino)-2-oxoethyl)phenoxy)nicotinamide;

2-(2-fluoro-4-(2-((5-methyl-4-(2-methylpyrimidin-4-yl)thiazol-2-yl)amino)-2-oxoethyl)phenoxy)nicotinamide;

2-(2-fluoro-4-(2-oxo-2-((5-(pyridin-3-yl)-1,3,4-thiadiazol-2-yl)amino)ethyl)phenoxy)nicotinamide;

2-(2-fluoro-4-(2-oxo-2-((5-(trifluoromethyl)-1,3,4-thiadiazol-2-yl)amino)ethyl)phenoxy)nicotinamide;

2-(4-(2-((5-cyclopropyl-1,3,4-thiadiazol-2-yl)amino)-2-oxoethyl)-2-fluorophenoxy)nicotinamide;

2-(4-(2-((5-(3,4-dimethoxybenzyl)-1,3,4-thiadiazol-2-yl)amino)-2-oxoethyl)-2-fluorophenoxy)nicotinamide;

2-(2-fluoro-4-(2-((8-methoxy-[1,2,4]triazolo[1,5-a]pyridin-2-yl)amino)-2-oxoethyl)phenoxy)nicotinamide;
2-(2-chloro-4-(2-((4-((1-methylpiperidin-4-yl)oxy)phenyl)amino)-2-oxoethyl)phenoxy)nicotinamide;
2-(2-fluoro-4-(2-((5-methyl-[1,2,4]triazolo[1,5-a]pyridin-2-yl)amino)-2-oxoethyl)phenoxy)nicotinamide;
2-(2-fluoro-4-(2-oxo-2-((5-(pyridin-4-yl)-1,3,4-thiadiazol-2-yl)amino)ethyl)phenoxy)nicotinamide;
2-(4-(2-((4,5-dimethylthiazol-2-yl)amino)-2-oxoethyl)-2-fluorophenoxy)nicotinamide,
2-(2-fluoro-4-(2-oxo-2-((1-(2,2,2-trifluoroethyl)-1H-pyrazol-3-yl)amino)ethyl)phenoxy)nicotinamide;
2-(2-fluoro-4-(2-oxo-2-((1-(5-(trifluoromethyl)pyridin-2-yl)-1H-pyrazol-3-yl)amino)ethyl)phenoxy)nicotinamide;
2-(4-(2-((3-cyclopropyl-1,2,4-thiadiazol-5-yl)amino)-2-oxoethyl)-2-fluorophenoxy)nicotinamide;
2-(2-chloro-4-(2-((4-(2-fluoropyridin-3-yl)-5-methylthiazol-2-yl)amino)-2-oxoethyl)phenoxy)nicotinamide;
2-(2-chloro-4-(2-((4-(6-fluoropyridin-3-yl)-5-methylthiazol-2-yl)amino)-2-oxoethyl)phenoxy)nicotinamide;
2-(2-chloro-4-(2-((5-methyl-4-(1-methyl-1H-pyrazol-4-yl)thiazol-2-yl)amino)-2-oxoethyl)phenoxy)nicotinamide;
2-(2-chloro-4-(2-((4-(6-chloropyridin-3-yl)-5-methylthiazol-2-yl)amino)-2-oxoethyl)phenoxy)nicotinamide;
2-(4-(1-((7-methoxy-4,5-dihydronaphtho[1,2-d]thiazol-2-yl)amino)-1-oxopropan-2-yl)phenoxy)nicotinamide;
2-(4-(2-((5-(2-hydroxy-2-methylpropoxy)benzo[d]thiazol-2-yl)amino)-2-oxoethyl)phenoxy)nicotinamide;
2-(4-(2-((7-(2-hydroxy-2-methylpropoxy)-4,5-dihydronaphtho[1,2-d]thiazol-2-yl)amino)-2-oxoethyl)phenoxy)nicotinamide;
2-(4-(2-((6-(2-hydroxy-2-methylpropoxy)benzo[d]thiazol-2-yl)amino)-2-oxoethyl)phenoxy)nicotinamide;
2-(2-fluoro-4-(2-((7-(2-hydroxy-2-methylpropoxy)-[1,2,4]triazolo[1,5-a]pyridin-2-yl)amino)-2-oxoethyl)phenoxy)nicotinamide;
2-(4-(2-((1-(2,2-difluoroethyl)-1H-benzo[d]imidazol-2-yl)amino)-2-oxoethyl)-2-fluorophenoxy)nicotinamide;
2-(2-chloro-4-(2-((5-(2-hydroxy-2-methylpropoxy)benzo[d]thiazol-2-yl)amino)-2-oxoethyl)phenoxy)nicotinamide;
2-(2-chloro-4-(2-((7-(2-hydroxy-2-methylpropoxy)-4,5-dihydronaphtho[1,2-d]thiazol-2-yl)amino)-2-oxoethyl)phenoxy)nicotinamide;
2-(2-fluoro-4-(2-(6-(2-hydroxy-2-methylpropoxy)indolin-1-yl)-2-oxoethyl)phenoxy)nicotinamide;
2-(2-chloro-4-(2-((5-methoxybenzo[d]thiazol-2-yl)amino)-2-oxoethyl)phenoxy)nicotinamide;
2-(2-chloro-4-(2-((7-methoxy-4,5-dihydronaphtho[1,2-d]thiazol-2-yl)amino)-2-oxoethyl)phenoxy)nicotinamide;
2-(2-methoxy-4-(2-((5-methoxybenzo[d]thiazol-2-yl)amino)-2-oxoethyl)phenoxy)nicotinamide;
2-(4-(2-((5-(2-hydroxy-2-methylpropoxy)benzo[d]thiazol-2-yl)amino)-2-oxoethyl)-2-methoxyphenoxy)nicotinamide;
2-(2-bromo-4-(2-((7-methoxy-[1,2,4]triazolo[1,5-a]pyridin-2-yl)amino)-2-oxoethyl)phenoxy)nicotinamide;
2-(4-(2-((1-(2,2-difluoroethyl)-5-methoxy-1H-benzo[d]imidazol-2-yl)amino)-2-oxoethyl)-2-fluorophenoxy)nicotinamide;
2-(2-chloro-4-(2-((5-(difluoromethoxy)thiazolo[5,4-b]pyridin-2-yl)amino)-2-oxoethyl)phenoxy)nicotinamide;
2-(4-(2-((1H-indazol-3-yl)amino)-2-oxoethyl)-2-chlorophenoxy)nicotinamide;
2-(4-(2-((1-(2,2-difluoroethyl)-6-methoxy-1H-benzo[d]imidazol-2-yl)amino)-2-oxoethyl)-2-fluorophenoxy)nicotinamide;
2-(4-(2-((7-methoxy-[1,2,4]triazolo[1,5-a]pyridin-2-yl)amino)-2-oxoethyl)phenoxy)nicotinamide;
2-(2-chloro-4-(2-((7-methoxy-[1,2,4]triazolo[1,5-a]pyridin-2-yl)amino)-2-oxoethyl)phenoxy)nicotinamide;
2-(2-fluoro-4-(2-oxo-2-((5-(trifluoromethyl)-[1,2,4]triazolo[1,5-a]pyridin-2-yl)amino)ethyl)phenoxy)nicotinamide;
2-(2-fluoro-4-(2-((8-fluoro-[1,2,4]triazolo[1,5-a]pyridin-2-yl)amino)-2-oxoethyl)phenoxy)nicotinamide;
2-(2-fluoro-4-(2-((6-fluoro-[1,2,4]triazolo[1,5-a]pyridin-2-yl)amino)-2-oxoethyl)phenoxy)nicotinamide;
2-(2-fluoro-4-(2-oxo-2-((6-(trifluoromethyl)-[1,2,4]triazolo[1,5-a]pyridin-2-yl)amino)ethyl)phenoxy)nicotinamide;
2-(4-(2-((6,7-dimethyl-[1,2,4]triazolo[1,5-a]pyridin-2-yl)amino)-2-oxoethyl)-2-fluorophenoxy)nicotinamide;
2-(4-(2-((5,6-dimethyl-[1,2,4]triazolo[1,5-a]pyridin-2-yl)amino)-2-oxoethyl)-2-fluorophenoxy)nicotinamide;
2-(2-fluoro-4-(2-oxo-2-((7-(trifluoromethyl)-[1,2,4]triazolo[1,5-a]pyridin-2-yl)amino)ethyl)phenoxy)nicotinamide;
2-(2-fluoro-4-(2-oxo-2-((6-(trifluoromethyl)imidazo[1,2-a]pyridin-2-yl)amino)ethyl)phenoxy)nicotinamide;
2-(4-(2-((7-bromo-[1,2,4]triazolo[1,5-a]pyridin-2-yl)amino)-2-oxoethyl)-2-fluorophenoxy)nicotinamide;
2-(4-(2-((7-(1-(difluoromethyl)-1H-pyrazol-4-yl)-[1,2,4]triazolo[1,5-a]pyridin-2-yl)amino)-2-oxoethyl)-2-fluorophenoxy)nicotinamide;
2-(4-(2-((7-(1,3-dimethyl-1H-pyrazol-4-yl)-[1,2,4]triazolo[1,5-a]pyridin-2-yl)amino)-2-oxoethyl)-2-fluorophenoxy)nicotinamide;
2-(2-fluoro-4-(2-((7-(1-methyl-1H-pyrazol-5-yl)-[1,2,4]triazolo[1,5-a]pyridin-2-yl)amino)-2-oxoethyl)phenoxy)nicotinamide;
2-(2-fluoro-4-(2-((6-(1-methyl-1H-pyrazol-5-yl)-[1,2,4]triazolo[1,5-a]pyridin-2-yl)amino)-2-oxoethyl)phenoxy)nicotinamide;
2-(4-(2-((8-(difluoromethoxy)-[1,2,4]triazolo[1,5-a]pyridin-2-yl)amino)-2-oxoethyl)-2-fluorophenoxy)nicotinamide;
2-(2-fluoro-4-(2-oxo-2-((6-(trifluoromethoxy)-[1,2,4]triazolo[1,5-a]pyridin-2-yl)amino)ethyl)phenoxy)nicotinamide;
2-(2-fluoro-4-(2-oxo-2-((8-(trifluoromethyl)-[1,2,4]triazolo[1,5-a]pyridin-2-yl)amino)ethyl)phenoxy)nicotinamide;
2-(2-fluoro-4-(2-((7-fluoro-[1,2,4]triazolo[1,5-a]pyridin-2-yl)amino)-2-oxoethyl)phenoxy)nicotinamide;
2-(4-(2-((7-(benzyloxy)-[1,2,4]triazolo[1,5-a]pyridin-2-yl)amino)-2-oxoethyl)-2-fluorophenoxy)nicotinamide;
2-(4-(2-((1-(cyclopropylmethyl)-6-(1-methyl-1H-pyrazol-4-yl)-1H-benzo[d]imidazol-2-yl)amino)-2-oxoethyl)-2-fluorophenoxy)nicotinamide;
2-(4-(2-((1-(cyclopropylmethyl)-6-(dimethylphosphoryl)-1H-benzo[d]imidazol-2-yl)amino)-2-oxoethyl)-2-fluorophenoxy)nicotinamide;
2-(4-(2-((5-(dimethylphosphoryl)benzo[d]thiazol-2-yl)amino)-2-oxoethyl)-2-fluorophenoxy)nicotinamide;
2-(4-(2-((5-(dimethylphosphoryl)-[1,2,4]triazolo[1,5-a]pyridin-2-yl)amino)-2-oxoethyl)-2-fluorophenoxy)nicotinamide;

2-(4-(2-((5-(dimethylphosphoryl)-1-(2,2,2-trifluoro-ethyl)-1H-benzo[d]imidazol-2-yl)amino)-2-oxoethyl)-2-fluorophenoxy)nicotinamide;
2-(4-(2-((6-(dimethylphosphoryl)imidazo[1,2-a]pyridin-2-yl)amino)-2-oxoethyl)-2-fluorophenoxy)nicotinamide;
2-(4-(2-((1-(2,2-difluoroethyl)-6-(dimethylphosphoryl)-1H-benzo[d]imidazol-2-yl)amino)-2-oxoethyl)-2-fluorophenoxy)nicotinamide;
2-(2-fluoro-4-(2-((5-methyl-4-(6-methylpyridin-2-yl)thiazol-2-yl)amino)-2-oxoethyl)phenoxy)nicotinamide;
2-(4-(2-((1-(cyclobutylmethyl)-1H-benzo[d]imidazol-2-yl)amino)-2-oxoethyl)-2-fluorophenoxy)nicotinamide;
2-(2-fluoro-4-(2-((1-isopropyl-1H-benzo[d]imidazol-2-yl)amino)-2-oxoethyl)-phenoxy)nicotinamide;
2-(2-fluoro-4-(2-oxo-2-((1-(3,3,3-trifluoropropyl)-1H-benzo[d]-imidazol-2-yl)-amino)ethyl)phenoxy)nicotinamide;
2-(2-fluoro-4-(2-((1-(2-methoxyethyl)-1H-benzo[d]imidazol-2-yl)amino)-2-oxoethyl)-phenoxy)nicotinamide;
2-(2-(4-((3-carbamoylpyridin-2-yl)oxy)-3-fluorophenyl)acetamido)-1-(2-methoxyethyl)-1H-benzo[d]imidazole-5-carboxamide;
2-(2-fluoro-4-(2-((6-methoxy-1-(2-methoxyethyl)-1H-benzo[d]-imidazol-2-yl)amino)-2-oxoethyl)phenoxy)nicotinamide;
2-(2-(4-((3-carbamoylpyridin-2-yl)oxy)-3-fluorophenyl)acetamido)-1-(2-methoxyethyl)-1H-benzo[d]-imidazole-6-carboxamide;
2-(2-fluoro-4-(2-oxo-2-((1-((tetrahydro-2H-pyran-4-yl)methyl)-1H-benzo[d]imidazol-2-yl)amino)ethyl)-phenoxy)nicotinamide;
2-(4-(2-((1-(cyclopropylmethyl)-6-methoxy-1H-benzo[d]-imidazol-2-yl)amino)-2-oxoethyl)-2-fluorophenoxy)nicotinamide;
2-(4-(2-((1-(cyclopropylmethyl)-4-fluoro-1H-benzo[d]imidazol-2-yl)amino)-2-oxoethyl)-2-fluorophenoxy)nicotinamide;
2-(4-(2-((1-(cyclopropylmethyl)-5-methoxy-1H-benzo[d]imidazol-2-yl)amino)-2-oxoethyl)-2-fluorophenoxy)nicotinamide;
2-(4-(2-((1-(cyclopropylmethyl)-4-methoxy-1H-benzo[d]imidazol-2-yl)amino)-2-oxoethyl)-2-fluorophenoxy)nicotinamide;
2-(4-(2-((1-(cyclopropylmethyl)-7-fluoro-1H-benzo[d]imidazol-2-yl)amino)-2-oxoethyl)-2-fluorophenoxy)nicotinamide;
2-(4-(2-((1-(cyclopropylmethyl)-5-fluoro-1H-benzo[d]imidazol-2-yl)amino)-2-oxoethyl)-2-fluorophenoxy)nicotinamide;
2-(4-(2-((1-(2,2-difluoroethyl)-6-fluoro-1H-benzo[d]imidazol-2-yl)amino)-2-oxoethyl)-2-fluorophenoxy)nicotinamide;
2-(4-(2-((1-(cyclopropylmethyl)-1H-benzo[d]imidazol-2-yl)amino)-2-oxoethyl)-2-fluorophenoxy)nicotinamide;
2-(4-(2-((1-(cyclopropylmethyl)-6-fluoro-1H-benzo[d]imidazol-2-yl)amino)-2-oxoethyl)-2-fluorophenoxy)nicotinamide;
2-(4-(2-((1-(2,2-difluoroethyl)-4-fluoro-1H-benzo[d]imidazol-2-yl)amino)-2-oxoethyl)-2-fluorophenoxy)nicotinamide;
2-(4-(2-((6-(benzyloxy)-1-(cyclopropylmethyl)-1H-benzo[d]imidazol-2-yl)amino)-2-oxoethyl)-2-fluorophenoxy)nicotinamide;
2-(2-chloro-4-(2-((1-(cyclopropylmethyl)-4-fluoro-1H-benzo[d]imidazol-2-yl)amino)-2-oxoethyl)phenoxy)nicotinamide;
2-(2-chloro-4-(2-((1-(cyclopropylmethyl)-6-fluoro-1H-benzo[d]imidazol-2-yl)amino)-2-oxoethyl)phenoxy)nicotinamide;
2-(2-chloro-4-(2-((1-(2,2-difluoroethyl)-4-fluoro-1H-benzo[d]imidazol-2-yl)amino)-2-oxoethyl)phenoxy)nicotinamide;
2-(2-chloro-4-(2-((1-(cyclopropylmethyl)-5-fluoro-1H-benzo[d]imidazol-2-yl)amino)-2-oxoethyl)phenoxy)nicotinamide;
2-(4-(2-((1-(cyclopropylmethyl)-6-(trifluoromethyl)-1H-benzo[d]imidazol-2-yl)amino)-2-oxoethyl)-2-fluorophenoxy)nicotinamide;
2-(2-chloro-4-(2-((1-(cyclopropylmethyl)-6-(trifluoromethyl)-1H-benzo[d]imidazol-2-yl)amino)-2-oxoethyl)phenoxy)nicotinamide;
2-(2-chloro-4-(2-((1-(cyclopropylmethyl)-5-(trifluoromethyl)-1H-benzo[d]imidazol-2-yl)amino)-2-oxoethyl)phenoxy)nicotinamide; or
2-(4-(2-((1-(cyclopropylmethyl)-6-(2-hydroxy-2-methylpropoxy)-1H-benzo[d]imidazol-2-yl)amino)-2-oxoethyl)-2-fluorophenoxy)nicotinamide;

or a stereoisomer, a tautomer, or a pharmaceutically acceptable salt thereof.

14. A method for treatment of a disorder selected from the group consisting of angina, atherosclerosis, stroke, cerebrovascular disease, heart failure, coronary artery disease, myocardial infarction, peripheral vascular disease, stenosis, vasospasm, hypertension and pulmonary hypertension, comprising administrating to a patient in need thereof a therapeutically effective amount of a compound according to claim 1.

\* \* \* \* \*